United States Patent
Oltvai et al.

(10) Patent No.: US 9,449,144 B2
(45) Date of Patent: *Sep. 20, 2016

(54) FLUX BALANCE ANALYSIS WITH MOLECULAR CROWDING

(71) Applicant: University of Pittsburgh—Of the Commonwealth System of Higher Education, Pittsburgh, PA (US)

(72) Inventors: Zoltan N. Oltvai, Pittsburgh, PA (US); Alexei Vazquez, Princeton, NJ (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 847 days.

This patent is subject to a terminal disclaimer.

(21) Appl. No.: 13/630,650

(22) Filed: Sep. 28, 2012

(65) Prior Publication Data

US 2013/0095566 A1   Apr. 18, 2013

Related U.S. Application Data

(63) Continuation-in-part of application No. 12/170,852, filed on Jul. 10, 2008, now Pat. No. 9,037,445.

(60) Provisional application No. 61/540,770, filed on Sep. 29, 2011, provisional application No. 60/959,024, filed on Jul. 10, 2007.

(51) Int. Cl.
| | | |
|---|---|---|
| G06G 7/48 | (2006.01) | |
| G06G 7/58 | (2006.01) | |
| G01N 33/48 | (2006.01) | |
| G01N 31/00 | (2006.01) | |
| G06F 19/00 | (2011.01) | |
| G06F 19/12 | (2011.01) | |
| C12M 1/36 | (2006.01) | |

(52) U.S. Cl.
CPC ........... *G06F 19/3437* (2013.01); *G06F 19/12* (2013.01); *C12M 41/48* (2013.01)

(58) Field of Classification Search
None
See application file for complete search history.

(56) References Cited

U.S. PATENT DOCUMENTS

| | | | |
|---|---|---|---|
| 5,930,154 A | 7/1999 | Thalhammer-Reyero | |
| 7,127,379 B2 | 10/2006 | Palsson et al. | |
| 7,734,420 B2 | 6/2010 | Palsson et al. | |
| 7,803,587 B2 * | 9/2010 | Lee et al. | 435/142 |
| 2004/0029149 A1 | 2/2004 | Palsson et al. | |
| 2007/0123386 A1 | 5/2007 | Hasegawa | |

OTHER PUBLICATIONS

Varma et al. (Applied and Environmental Microbiology, 1993, 2465-2473).*

(Continued)

*Primary Examiner* — Larry D Riggs, II
(74) *Attorney, Agent, or Firm* — The Webb Law Firm

(57) ABSTRACT

Methods are provided herein for: calculating cell growth rates in various environments and genetic backgrounds; calculating the order of substrate utilization from a defined growth medium; calculating metabolic flux reorganization in various environments and at various growth rates; and calculating the maximum metabolic rate and optimal metabolite concentrations and enzyme activities by applying a computational optimization method to a kinetic model of a metabolic pathway. The optimization methods use intracellular molecular crowding parameters and/or well as kinetic rates to assist in modeling metabolic activity.

22 Claims, 63 Drawing Sheets

(56) References Cited

OTHER PUBLICATIONS

Uygun et al. (Biotechnology and Bioengineering, 2006, 97(3), 622-637).*
Himes et al., Formyltetrahydrofolate Synthetase II. Characteristics of the Enzyme and the Enzymic Reaction, The Journal of Biological Chemistry, Sep. 1962, 2903-2914, 237-9.
Hochheiser et al., Dynamic Querying for Pattern Identification in Microarray and Genomic Data, 4 pages.
Hofmeyr et al., The reversible Hill equation: how to incorporate cooperative enzymes into metabolic models, Compt Appl Biosci, 1997, vol. 13, No. 4, pp. 377-385.
Hu et al., 13C-Pyruvate Imaging Reveals Alterations in Glycolysis that Precede c-Myc-Induced Tumor Formation and Regression, Cell Metabolism, Jul. 6, 2011, 131-142, 14.
Hynne et al., Full-scale model of glycolysis in *Saccharomyces cerevisiae*, Biophysical Chemistry, 2001, 94, pp. 121-163.
Ibarra et al., *Escherichia coli* K-12 undergoes adaptive evolution to achieve in silico predicted optimal growth, Nature, Nov. 2002, vol. 420, pp. 186-189.
Joyner et al., Endurance exercise performance: the physiology of champions, J Physiol, 2008 35-44, 586.1.
Kang et al., Systematic mutagenesis of the *Escherichia coli* genome, Journal of Bacteriology, Aug. 2004, vol. 186, No. 15, pp. 4921-4930.
Karp et al., HinCyc: A knowledge base of the complete genome and metabolic pathways of H. influenzae, Proc Int Conf Intell Syst Mol Biol, 1996, pp. 116-124.
Karp et al. The EcoCyc and MetaCyc databases, Nucleic.Acids Research, 2000, vol. 28, No. 1, pp. 56-59.
Kiley et al., Oxygen sensing by the global regulator, FNR: the role of the iron-sulfur cluster, FEMS Microbiology Reviews, 1999, 22, pp. 341-352.
Klipp et al., Prediction of temporal gene expression. Metabolic opimization by re-distribution of enzyme activities, Eur J. Biochem., 2002, pp. 5406-5413, 269.
Kolkman et al., Comparative proteome analysis of *Saccharomyces cerevisiae* grown in chemostat cultures limited for glucose or ethanol, Molecular & Cellular Proteomics, 2005, 4, pp. 1-11.
Kruschwitz et al., Expression, Purification, and Characterization of Human Cytosolic Serine Hydroxymethyltransferase, Protein Expression and Purification, 1995, 411-416, 6.
Kushmerick et al., Mammalian skeletal muscle fibers distinguished by contents of phosphocreatine, ATP, and Pi, Proc. Natl. Acad. Sci. USA, Aug. 1992, 7521-7525, 89.
Lee, Calculation of volume fluctuation for globular protein models, Proc Natl Acad Sci USA, Jan. 1983, vol. 80, pp. 622-626.
Lee et al., Fatty acid cycling in human hepatoma cells and the effects of troglitazone, Journal of Biological Chemistry, Aug. 1998, vol. 273, No. 33, pp. 20929-20934.
Lee et al., Isotopomer study of lipogenesis in human hepatoma cells in culture: contribution of carbon and hydrogen atoms from glucose, Analytical Biochemistry, 1995, 226, pp. 100-112.
Lee et al., Mass isotopomer study of glutamine oxidation and synthesis in primary culture of astrocytes, Dev Neurosci, 1996, 18, pp. 469-477.
Lee et al., Mass isotopomer study of the nonoxidative pathways of the pentose cycle with [1,2-13C2]glucose, American Physiological Society, 1998, 274, pp. E843-E851.
Leimer et al., Complete mass spectra of the per-trimethylsilylated amino acids, Journal of Chromatography, 1977, 141, pp. 355-375.
Lemons et al., Quiescent fibroblasts exhibit high metabolic activity, PLoS Biology, Oct. 2010, 1-16, 8-10.
Li et al., Model-based analysis of oligonucleotide arrays: model validation, design issues and standard error application, Genome Biology, 2001, 2(8), research0032.1-0032.11.
Liu et al., Global transcriptional programs reveal a carbon source foraging strategy by *Escherichia coli*, Journal of Biological Chemistry, Apr. 22, 2005, vol. 280, No. 16, pp. 15921-15927.
Locasale et al., Phosphoglycerate dehydrogenase diverts glycolytic flux and contributes to oncogenesis, Nature Genetics, 2011, 869-874, 43.9.
Mahadevan et al., Biophysical Journal, 2002, 83, 1331-1340.
Minton, How can biochemical reactions within cells differ from those in test tubes?, Journal of Cell Science, 2006, 119, pp. 2863-2869.
Minton, Influence of macromolecular crowding upon the stability and state of association of proteins: Predictions and observations, Journal of Pharmaceutical Sciences, Aug. 2005, vol. 94, No. 8, pp. 1668-1675.
Mo et al., A genome-scale, constraint-based approach to systems biology of human metabolism, Molecular Biosystems, 2007, 598-603, 3.
Morrish et al., c-Myc activates multiple metabolic networks to generate substrates for cell cycle entry, Oncogene, Jul. 9, 2009, 2485-2491, 28-27.
Neidhardt et al., Physiology of the Bacterial Cell: A Molecular Approach, 1990, pp. 419-440, Sinauer Associates Inc., Sunderland, Massachusetts.
Nijhout et al., A Mathematical Model of the Folate Cycle New Insights into Folate Homeostasis, The Journal of Biological Chemistry, Dec. 31, 2004, 55008-55016, 279-53.
Ogata et al., KEGG: Kyoto encyclopedia of genes and genomes, Nucleic Acids Research, 1999, vol. 27, No. 1, pp. 29-34.
Paalme et al., The computer-controlled continuous culture of *Escherichia coli* with smooth change of dilution rate (A-stat). Journal of Microbioogical Methods, 1995, 24, pp. 145-153.
Paalme et al., The growth rate control in *Escherichia coli* at near to maximum growth rates: the A-stat approach. Antonie Van Leeuwenhoek, 1997, 71, pp. 217-230.
Parra-Bonilla et al., Critical role for lactate dehydrogenase A in aerobic glycolysis that sustains pulmonary microvascular endothelial cell proliferation, American Journal of Physiology—Lung Cellular and Molecular Physiology, 2010, L513-L522, 299.
Pawelek et al., Methenyltetrahydrofolate Cyclohydrolase is Rate Limiting for the Enzymatic Conversion of 10-Formyltetrahydrofolate to 5,10-Methylenetetrahydrofolate in Bifunctional Dehydrogenase-Cyclohydrolase Enzymes, Biochemistry, 1998, 1109-1115, 37.
Pawelek et al., Channeling efficiency in the bifunctional methylenetetrahydrofolate dehydrogenase/cyclohydrolase domain: the effects of site-directed mutagenesis of NADP binding residues, Biochimica et Biophysica Acta, 2000, 59-68, 1479.
Peng et al., Global metabolic regulation analysis for *Escherichia coli* KI2 based on protein expression by 2-dimensional electrophoresis and enzyme activity measurement, Appl Microbiol Biotechnol, 2003, 61, pp. 163-178.
Peterson, Partitioning large-sample microarray-based gene expression profiles using principal components analysis, Computer Methods and Programs in Biomedicine, 2003, 70, pp. 107-119.
Pinkas-Sarafova et al., Dynamic changes in nicotinamide pyridine dinucleotide content in normal human epidermal keratinocytes and their effect on retinoic acid biosynthesis, Biochemical and Biophysical Research Communications, 2005, 554-564, 336.
Pramanik et al., Stoichiometric model of *Escherichia coli* metabolism: Incorporation of growth-rate dependent biomass composition and mechanistic energy requirements, Biotechnol Bioeng, Apr. 1997, 56, pp. 398-421.
Press et al., Numerical recipes in C: The art of scientific computing, Cambridge: Cambridge University Press, 1993, http://www.nr.com/bookreader_chooser.htm.
Price et al., Genome-scale models of microbial cells: evaluating the consequences of constraints, Nature Reviews, Nov. 2004, vol. 2, pp. 886-897.
Raamsdonk et al., Co-consumption of sugars or ethanol and glucose in a *Saccharomyces cerevisiae* strain deleted in the HXK2 gene, Yeast, 2001, 18, pp. 1023-1033.
Reed et al., an expanded genome-scale model of *Escherichia coli* K-12 (iJR904 GSM/GPR), Genome Biology., 2003, 4, pgs. R54.1-R54.12.

(56) References Cited

OTHER PUBLICATIONS

Reed et al., Genome-scale in silico models of *E. coli* have multiple equivalent phenotypic states: assessment of correlated reaction subsets that comprise network states, Genome Research, 2004, 14, pgs. 1797-1805.

Reiling et al., Mass culture of *Escherichia coli*: medium development for low and high density cultivation of *Escherichia coli* B/r in minimal and complex media, Journal of Biotechnology, 1985, 2, pgs. 191-206.

Savinell et al., Network analysis of intermediary metabolism using linear optimization. I. Development of Mathematical Formalism, J. Theor. Biol., 1992, 421-454, 154.

Savinell et al, Network analysis of intermediary metabolism using linear optimization. II. Interpretation of Hybridoma Cell Metabolism, J. Theor. Biol., 1992, 455-473, 154.

Alcazar et al., Yeast intracellular water determination by thermogravimetry, Journal of Thermal Analysis Calorimetry, 2000, vol. 59, pp. 643-648.

Baev et al., Growth of *Escherichia coli* MG1655 on LB medium: determining metabolic strategy with transcriptional microarrays, Appl Microbiol Biotechnol, 2006, 71, pp. 323-328.

Balazsi et al., Topological units of environmental signal processing in the transcriptional regulatory network of *Escherichia coli*, PNAS, May 31, 2005, vol. 102, No. 22, pp. 7841-7846.

Bar-Joseph et al., Fast optimal leaf ordering for hierarchical clustering, Bioinformatics, 2001, pp. S22-S29.

Barabasi et al., Network biology: understanding the cell's functional organization, Nature Reviews, Feb. 2004, vol. 5, pp. 101-113.

Beard et al., Energy balance for analysis of complex metabolic networks, Biophysical Journal, Jul. 2002, vol. 83, pp. 79-86.

Beg et al., Intracellular crowding defines the mode and sequence of substrate uptake by *Escherichia coli* and constrains its metabolic activity, PNAS,Jul. 31, 2007, vol. 104, No. 31, pp. 12663-12668.

Bismut et al, Glucose contribution to nucleic acid base synthesis in proliferating hepatoma cells: a glycine-biosynthesis-mediated pathway, Biochem J., 1995, 761-767, 308.

Boiteux et al., Design of glycolysis, Phil Trans R Soc Lond B, 1981, 293, pp. 5-22.

Bonarius et al. Flux analysis of underdetermined metabolic networks: The quest for the missing constraints, Trends in Biotechnology, 1997, vol. 15, No. 8, pp. 308-314.

Boros et al., Metabolic profiling of cell growth and death in cancer: applications in drug discovery, DDT, Mar. 2002, vol. 7, No. 6, pp. 364-372.

Brocchieri et al., Protein length in eukaryotic and prokaryotic proteomes, Nucleic Acids Research, 2005, 3390-3400, 33-10.

Brown, Total cell protein concentration as an evolutionary constraint on the metabolic control distribution in cells, J. Theor. Biol., 1991, 153, pp. 195-203.

Buttlaire, Purification and Properties of Formyltetrahydrofolate Synthetase, Methods in Enzymology, 1980, 585-599, 66.

Cardenas-Navia et al., The pervasive presence of fluctuating oxygenation in tumors, Cancer Research, Jul. 15, 2008, 5812-5819, 68-14.

Cascante et al., Modeling of Regulation Glycolysis and Overall Energy Metabolism Under a Systems Biology Approach found in Brain Energetics. Integration of Molecular and Cellular Processes, Handbook of Neurochemistry and Molecular Neurobiology, 2006, pp. 862-872.

Chang et al., Gene expression profiling of *Escherichia coli* growth transitions: an expanded stringent response model, Molecular Microbiology, 2002, 45(2), pp. 289-306.

Chen et al., The Warburg effect and its cancer therapeutic implications, J Bioenerg Biomembr, 2007, 39, pp. 267-274.

Cheng et al., Pyruvate carboxylase is required for glutamine-independent growth of tumor cells, PNAS, May 24, 2011, 8674-8679, 108-21.

Christensen et al., The MTHFD1 p.Arg653Gln Variant Alters Enzyme Function and Increases Risk for Congenital Heart Defects, Human Mutation, 2009, 212-220, 30-2.

Covert et al., Identifying constraints that govern cell behavior: a key to converting conceptual to computational models in biology?, Wiley InterScience, Nov. 2003, pp. 763-772.

Covert et al., Metabolic modeling of microbial strains in silico, Trends in Biochemical Sciences, 2001, vol. 26, No. 3, pp. 179-186.

Covert et al., Transcriptional regulation in constraints-based metabolic models of *Escherichia coli*, Journal of Biological Chemistry, Aug. 2002, vol. 277, No. 31, pp. 28058-28064.

Curthoys et al., Formyltetrahydrofolate Synthetase Binding of folate substrates and kinetics of the reverse reaction, The Journal of Biological Chemistry, Apr. 10, 1972, 1965-1971, 247-7.

Deutscher et al., Multiple knockout analysis of genetic robustness in the yeast metabolic network, Nature Genetics, Sep. 2006, vol. 38, No. 9, pp. 993-998.

Duarte et al., Integrated analysis of metabolic phenotypes in *Saccharomyces cerevisiae*, BMC Genomics, 2004, 5, 11 pages.

Edwards et al., Characterizing the metabolic phenotype: a phenotype phase plane analysis, Biotech Bioeng, 2002, 77, pp. 27-36.

Edwards et al., In silico predictions of *Escherichia coli* metabolic capabilities are consistent with experimental data, Nature Biotechnology, Feb. 2001, vol. 19, pp. 125-130.

Edwards et al., Metabolic flux balance analysis and the in silico analysis of *Es-cherichia coli* K-12 gene deletions, BMC Bioinformatics, 2000,1-1.

Edwards et al., Metabolic flux Balance Analysis, In: (Lee S.Y, Papoutsakis E. T., eds.) Metabolic Engineering: Marcel DekKer, 1999, pp. 13-57.

Edwards et al., Systems properties of the Haemophilus influenzae Rd metabolic genotype, Journal of Bioligical Chemistry, Jun. 1999, vol. 274, No. 25, pp. 17410-17416.

Egli, The ecological and physiological significance of the growth of heterotrophic microorganisms with mixtures of substrates, Advances in Microbial Ecology, 1995, vol. 14, pp. 305-386.

Eichler et al., The role of serine hydroxymethyltransferase in cell proliferation: DNA synthesis from serine following mitogenic stimulation of lymphocytes, Bioscience Reports, 1981, 101-106, 1.

Eisen et al., Cluster analysis and display of genome-wide expression patterns, Proc. Natl. Acad. Sci. USA, Dec. 1998, vol. 95, pp. 14863-14868.

El-Mansi et al., Control of carbon flux to acetate excretion during growth of *Escherichia coli* in batch and continuous cultures, Journal of General Microbiology, 1989, 135, pp. 2875-2883.

Ellis, Macromolecular crowding: obvious but underappreciated, TRENDS in Biochemical Sciences, Oct. 2001, vol. 26, No. 10, pp. 597-604.

Ernst et al., Reconstructing dynamic regulatory maps, Molecular Systems Biology, 2007, 3, article No. 74., pp. 1-13.

Ernst et al., STEM: a tool for the analysis of short time series gene expression data, BMC Bioinformatics, 2006, 7:191, 11 pages.

Feist et al., A genome-scale metabolic reconstruction for *Escherichia coli* K-12 MG1655 that accounts for 1260 ORFs and thermodynamic information, Molecular Systems Biology, 2007, 3, article No. 121., pp. 1-18.

Fischer et al., High-throughput metabolic flux analysis based on gas chromatography-mass spectrometry derived 13C constraints, Analytical Biochemistry, 2004, 325, pp. 308-316.

Fong et al., Metabolic gene-deletion strains of *Escherichia coli* evolve to computationally predicted growth phenotypes, Nature Genetics, Oct. 2004, vol. 36, No. 10, pp. 1056-1058.

Frick et al., Characterization of the metabolic shift between oxidative and fermentative growth in *Saccharomyces cerevisiae* by comparative 13C flux analysis, Microbial Cell Factories, 2005, 4:30, 16 pages.

Glas et al, Quantitative study of mitochondria in rat liver: Dry mass, wet mass, volume, and concentration of solids, The Journal of Cell Biology, Jun. 1, 1966, 507-523, 29.

Gottschalk et al., Imatinib (STI 571)-mediated changes in glucose metabolism in human leukemia BCR-ABL positive cells, Clinical Cancer Research, Oct. 1, 2004, vol. 10, pp. 6661-6668.

Hall et al., Macromolecular crowding: qualitative and semiquantitative successes, quantitative challenges, Biochimica et Biophysica Acta, 2003, 1649, pp. 127-139.

(56) References Cited

OTHER PUBLICATIONS

Harder et al., Strategies of mixed substrate utilization in microorganisms, Phil Trans R Soc Lond B, 1982, 297, pp. 459-480.
Hatzimanikatis et al., Exploring the diversity of complex metabolic networks, Bioinformatics, 2005, vol. 21, No. 8, pp. 1603-1609.
Hatzimanikatis et al., Metabolic networks: enzyme function and metabolite structure, Current Opinion in Structural Biology, 2004, 14, pp. 300-306.
Heinrich et al., The regulation of cellular systems, 1996, Chapman & Hall, New York, http://books.google.com/books?id=LUQSSDViXX0C&printsec=frontcover&source=gbs_ge_summary_r&cad=0#v=onepage&q&f=false.
Henry et al., Genome-scale thermodynamic analysis of Escherichia coli metabolism, Biophysical Journal, Feb. 2006, vol. 90, pp. 1453-1461.
Selkov et al., MPW: the metabolic pathways database, Nucleic Acids Research., 1998, vol. 26, No. 1, pp. 43-45.
Semenza et al., Tumor metabolism: cancer cells give and take lactate, The Journal of Clinical Investigation, 2008, 3835-3837, 118.
Serkova et al., 1H-NMR-based metabolic signatures of mild and severe ischemia/reperfusion injury in rat kidney transplants, Kidney International, 2005, vol. 67, pp. 1142-1151.
Serkova et al., Metabolite concentrations in human term placentae and their changes due to delayed collection after delivery, Placenta, 2003, 24, pp. 227-235.
Shlomi et al., Genome-scale metabolic modeling elucidates the role of proliferative adaptation in causing the Warburg effect, PLoS Computational Biology, Mar. 2011, 1-8, 7-3.
Short et al., T(3) increases mitochondrial ATP production in oxidative muscle despite increased expression of UCP2 and -3, Am J Physiol Endocrinol Metab, 2001, E761-E769, 280.
Subramanian et al., Gene set enrichment analysis: A knowledge-based approach for interpreting genome-wide expression profiles, PNAS, Oct. 25, 2005, 15545-15550, 102-43.
Teusink et al., Can yeast glycolysis be understood in terms of in vitro kinetics of the constituent enzymes? Testing biochemistry. Eur. J. Biochem., 2000, 267, pp. 5313-5329.
Thiele et al., Expanded metabolic reconstruction of Helicobacter pylori (iIT341 GSM/GPR): an in silico genome-scale characterization of single- and double-deletion mutants, Journal of Bacteriology, Aug. 2005, vol. 187, No. 16, pp. 5818-5830.
Trabold et al., Lactate and oxygen constitute a fundamental regulatory mechanism in wound healing, Wound Rep Reg, 2003, 504-509, 11.
Vander Heiden et al., Evidence for an alternative glycolytic pathway in rapidly proliferating cells, Science, Sep. 17, 2010, 1492-1499, 329.
Scheer et al., BRENDA, the enzyme information system in 2011, Nucleic Acids Research, 2011, D670-D676, 39.
Schellenberger et al., BiGG: a Biochemical Genetic and Genomic knowledgebase of large scale metabolic reconstructions, BMC Bioinformatics, 2010, 1-16, 11-213.
Schilling et al., Assessment of the metabolic capabilities of Haemophilus influenzae Rd through a genome-scale pathway analysis, J. Theor Biol., 2000, 203, pp. 249-283.
Schilling et al., The underlying pathway structure of biochemical reaction networks. Proc. Natl. Acad. Sci. USA, Apr. 1998, vol. 95, pp. 4193-4198.
Schomburg et al., BRENDA, Enzyme data and metabolic information, Nucleic Acids Research, 2002, vol. 30, No. 1, pp. 47-49.
Schomburg et al., BRENDA: The enzyme database: updates and major new developments, Nucleic Acids Research, 2004, vol. 32, database issue, pp. D431-D433.
Schuetz et al., Systematic evaluation of objective functions for predicting intracellular fluxes in Escherichia coli, Molecular Systems Biology, 2007, 3, article No. 119., pp. 1-15.

Schulze, Ulrik, "Anaerobic physiology of Saccharomyces cerevisiae", Department of Biotechnology, Technical University of Denmark, 1995, five (5) pages.
Schwerzmann et al., Oxidative capacity of muscle and mitochondria: Correlation of physiological, biochemical, and morphometric characteristics, Proc. Natl. Acad. Sci. USA, Mar. 1989, 1583-1587, 86.
Segre et al., Analysis of optimality in natural and perturbed metabolic networks, PNAS, Nov. 12, 2002, vol. 99, No. 23, pp. 15112-15117.
Selkov et al. A reconstruction of the metabolism of Methanococcus jannaschii from sequence data, Gene, 1997, 197, pp. GC11-GC26.
Van Der Werf et al., Environmental and physiological factors affecting the succinate product ratio during carbohydrate fermentation by Actinobacillus sp. 130Z. Arch Microbiol, 1997, 167, pp. 332-342.
Varma et al., Metabolic flux balancing: Basic concepts, scientific and practical use, Nature Biotechnology, Oct. 1994, vol. 12, pp. 994-998.
Varma et al., Stoichiometric flux balance models quantitatively predict growth and metabolic by-product secretion in wild-type Escherichia coli W3110, Applied and Environmental Microbiology, Oct. 1994, vol. 60, No. 10, pp. 3724-3731.
Vazquez, (APS March Meeting, 2006, Session P7: Physics of Transcriptional Regulatory Networks, full presentation).
Vazquez et al., Impact of limited solvent capacity on metabolic rate, enzyme activities, and metabolite concentrations of S. cerevisiae glycolysis, PLoS Computational Biology, Oct. 2008, vol. 4, issue 10, pp. 1-6.
Vazquez et al., Impact of the solvent capacity constraint on E. coli metabolism, BMC Systems Biology, 2008, 2:7, 10 pages.
Vemuri et al., Increasing NADH oxidation reduces overflow metabolism in Saccharomyces cerevisiae, PNAS, Feb. 13, 2007, vol. 104, No. 7, pp. 2402-2407.
Williams et al., Metabolism of freshly isolated human hair follicles capable of hair elongation: a glutaminolytic, aerobic glycolytic tissue, J Invest Dermatol, 1993, 834-840, 100.
Wise et al., Myc regulates a transcriptional program that stimulates mitochondrial glutaminolysis and leads to glutamine addiction, PNAS, Dec. 2, 2008, 18782-18787, 105-48.
Wolfe, The acetate switch, Microbiology and Molecular Biology Reviews, Mar. 2005, vol. 69, No. 1, pp. 12-50.
Xu et al., Determination of a glucose-dependent futile recycling rate constant from an intraperitoneal glucose tolerance test, Analytical Biochemistry, 2003, 315, pp. 238-246.
Yang et al., Metabolomic assays of the concentration and mass isotopomer distribution of gluconeogenic and citric acid cycle intermediates, Metabolomics, Jun. 2006, vol. 2, No. 2, pp. 85-94.
Zeller et al., An integrated database of genes responsive to the Myc oncogenic transcription factor: identification of direct genomic targets, Genome Biology, 2003, 1-10, 4-R69.
Zhao et al., Global metabolic response of Escherichia coli to gnd or zwf gene-knockout, based on 13C-labeling experiments and the measurement of enzyme activities, Appl Microbiol Biotechnol, 2004, 64, pp. 91-98.
Zhou et al., Universal behavior of the osmotically compressed cell and its analogy to the colloidal glass transition, PNAS Early Edition, 2009, 1-6, 106.
Zimmerman et al., Estimation of macromolecule concentrations and excluded volume effects for the cytoplasm of Escherichia coli, J. Mol. Biol., 1991, 222, pp. 599-620.
Zinn et al., Dual nutrient limited growth: models, experimental observations, and applications, Journal of Biotechnology, Sep. 30, 2004, 113(1-3), pp. 263-279.

* cited by examiner

| Category ID | Category Name | #Genes Category | #Genes Assigned | #Genes Expected | #Genes Enriched | p-value | Corrected p-value |
|---|---|---|---|---|---|---|---|
| GO:0009058 | biosynthetic process | 603 | 230.0 | 108.0 | +122.0 | 2.2E-30 | <0.001 |
| GO:0044249 | cellular biosynthetic process | 562 | 209.0 | 100.6 | +108.4 | 1.9E-32 | <0.001 |
| GO:0044237 | cellular metabolic process | 1729 | 432.0 | 309.6 | +122.4 | 6.1E-24 | <0.001 |
| GO:0044238 | primary metabolic process | 1446 | 375.0 | 258.9 | +116.1 | 1.5E-22 | <0.001 |
| GO:0006412 | translation | 113 | 65.0 | 20.2 | +44.8 | 9.9E-22 | <0.001 |
| GO:0009059 | macromolecule biosynthetic process | 251 | 93.0 | 44.9 | +48.1 | 7.3E-14 | <0.001 |
| GO:0003723 | RNA binding | 96 | 49.0 | 17.2 | +31.8 | 7.8E-14 | <0.001 |
| GO:0005737 | cytoplasm | 224 | 82.0 | 40.1 | +41.9 | 5.5E-12 | <0.001 |
| GO:0005840 | ribosome | 58 | 34.0 | 10.6 | +23.4 | 8.5E-12 | <0.001 |
| GO:0030529 | ribonucleoprotein complex | 62 | 35.0 | 11.1 | +23.9 | 7.2E-12 | <0.001 |
| GO:0003735 | structural constituent of ribosome | 58 | 33.0 | 10.4 | +22.6 | 2.2E-11 | <0.001 |
| GO:0019538 | protein metabolic process | 311 | 101.0 | 55.7 | +45.3 | 6.7E-11 | <0.001 |
| GO:0044267 | cellular protein metabolic process | 307 | 100.0 | 55.0 | +45.0 | 9.8E-11 | <0.001 |
| GO:0044444 | cytoplasmic part | 83 | 40.0 | 14.8 | +25.1 | 1.7E-10 | <0.001 |
| GO:0009165 | nucleotide biosynthetic process | 58 | 31.0 | 10.0 | +21.0 | 2.3E-10 | <0.001 |
| GO:0005515 | protein binding | 347 | 108.0 | 62.1 | +45.9 | 2.4E-10 | <0.001 |
| GO:0043170 | macromolecule metabolic process | 1135 | 271.0 | 203.2 | +67.8 | 9.8E-10 | <0.001 |
| GO:0006139 | nucleobase, nucleoside, nucleotide and nuc... | 691 | 180.0 | 123.7 | +56.3 | 2.5E-9 | <0.001 |
| GO:0044260 | cellular macromolecule metabolic process | 404 | 118.0 | 72.3 | +45.7 | 2.6E-9 | <0.001 |
| GO:0006399 | tRNA metabolic process | 62 | 31.0 | 11.1 | +19.9 | 6.5E-9 | <0.001 |
| GO:0009117 | nucleotide metabolic process | 80 | 36.0 | 14.3 | +21.7 | 1.4E-8 | <0.001 |
| GO:0019843 | rRNA binding | 32 | 20.0 | 5.7 | +14.3 | 2.3E-8 | <0.001 |
| GO:0044424 | intracellular part | 321 | 96.0 | 57.5 | +38.5 | 2.8E-8 | <0.001 |
| GO:0009308 | amine metabolic process | 232 | 75.0 | 41.5 | +33.5 | 3.1E-8 | <0.001 |
| GO:0006520 | amino acid metabolic process | 210 | 69.0 | 37.6 | +31.4 | 5.7E-9 | <0.001 |
| GO:0006164 | purine nucleotide biosynthetic process | 28 | 18.0 | 5.0 | +13.0 | 6.4E-8 | <0.001 |
| GO:0005622 | intracellular | 460 | 130.0 | 85.9 | +44.1 | 6.6E-9 | <0.001 |
| GO:0006163 | purine nucleotide metabolic process | 31 | 19.0 | 5.6 | +13.4 | 9.4E-8 | <0.001 |
| GO:0006519 | amino acid and derivative metabolic process | 219 | 70.0 | 39.2 | +30.8 | 1.0E-7 | <0.001 |
| GO:0009069 | serine family amino acid metabolic process | 26 | 16.0 | 4.7 | +11.3 | 9.5E-7 | <0.001 |

Fig. 8D-1

| | | | | | | |
|---|---|---|---|---|---|---|
| GO:0006807 | nitrogen compound metabolic process | 263 | 780 | 47.1 | +30.9 | 9.5E-7 | <0.001 |
| GO:0019752 | carboxylic acid metabolic process | 304 | 87.0 | 54.4 | +32.6 | 1.2E-6 | <0.001 |
| GO:0016853 | isomerase activity | 97 | 37.0 | 17.4 | +19.6 | 1.5E-6 | <0.001 |
| GO:0009070 | serine family amino acid biosynthetic process | 19 | 13.0 | 3.4 | +9.6 | 1.7E-6 | <0.001 |
| GO:0003676 | nucleic acid binding | 538 | 136.0 | 96.0 | +40.0 | 2.1E-6 | 0.002 |
| GO:0009260 | ribonucleotide biosynthetic process | 22 | 14.0 | 3.9 | +10.1 | 2.4E-6 | 0.002 |
| GO:0006082 | organic acid metabolic process | 309 | 87.0 | 55.3 | +31.7 | 2.5E-6 | 0.002 |
| GO:0016740 | transferase activity | 515 | 130.0 | 92.2 | +37.8 | 4.9E-6 | 0.002 |
| GO:0009259 | ribonucleotide metabolic process | 23 | 14.0 | 4.1 | +9.9 | 5.1E-6 | 0.002 |

Fig. 8D-2

| Category ID | Category Name | #Genes Category | #Genes Assigned | #Genes Expected | #Genes Enriched | p-value | Corrected p-value |
|---|---|---|---|---|---|---|---|
| GO:0009289 | fimbrium | 58 | 21.0 | 5.9 | +15.1 | 8.0E-8 | 0.002 |
| GO:0007155 | cell adhesion | 40 | 16.0 | 4.2 | +11.8 | 1.1E-6 | 0.002 |
| GO:0030288 | outer membrane-bounded periplasmic space | 43 | 13.0 | 4.6 | +8.4 | 3.4E-4 | 0.070 |
| GO:0006814 | sodium ion transport | 17 | 7.0 | 1.8 | +5.2 | 1.1E-3 | 0.198 |
| GO:0032196 | transposition | 40 | 11.0 | 4.2 | +6.8 | 2.3E-3 | 0.376 |
| GO:0006313 | transposition, DNA-mediated | 40 | 11.0 | 4.2 | +6.8 | 2.3E-3 | 0.376 |
| GO:0004553 | hydrolase activity, hydrolyzing O-glycosyl com... | 27 | 8.0 | 2.9 | +5.1 | 5.4E-3 | 0.606 |
| GO:0044460 | flagellum part | 13 | 5.0 | 1.4 | +3.6 | 8.2E-3 | 0.750 |
| GO:0044461 | flagellin-based flagellum part | 13 | 5.0 | 1.4 | +3.6 | 8.2E-3 | 0.750 |
| GO:0044463 | cell projection part | 13 | 5.0 | 1.4 | +3.6 | 8.2E-3 | 0.750 |
| GO:0006310 | DNA recombination | 62 | 13.0 | 6.6 | +6.4 | 0.01 | 0.834 |

Fig. 9C

| Category ID | Category Name | #Genes Category | #Genes Assigned | #Genes Expected | #Genes Enriched | p-value | Corrected p-value |
|---|---|---|---|---|---|---|---|
| GO:0031224 | intrinsic to membrane | 819 | 118.0 | 86.4 | +31.6 | 6.3E-5 | 0.012 |
| GO:0016021 | integral to membrane | 819 | 118.0 | 86.4 | +31.6 | 6.3E-5 | 0.012 |
| GO:0044425 | membrane part | 859 | 122.0 | 90.6 | +31.4 | 8.8E-5 | 0.020 |
| GO:0016020 | membrane | 1017 | 135.0 | 107.3 | +27.7 | 8.3E-4 | 0.158 |
| GO:0015288 | porin activity | 14 | 5.0 | 1.5 | +3.5 | 0.01 | 0.842 |
| GO:0043283 | biopolymer metabolic process | 725 | 94.0 | 76.5 | +17.5 | 0.01 | 0.858 |
| GO:0000160 | two-component signal transduction system (...) | 70 | 14.0 | 7.4 | +6.6 | 0.01 | 0.860 |

Fig. 10C

| Category ID | Category Name | #Genes Category | #Genes Assigned | #Genes Expected | #Genes Enriched | p-value | Corrected p-value |
|---|---|---|---|---|---|---|---|
| GO:0000271 | polysaccharide biosynthetic process | 96 | 15.0 | 5.7 | +9.3 | 4.2E-4 | 0.074 |
| GO:0005976 | polysaccharide metabolic process | 102 | 15.0 | 6.0 | +9.0 | 8.2E-4 | 0.138 |
| GO:0044264 | cellular polysaccharide metabolic process | 102 | 15.0 | 6.0 | +9.0 | 8.2E-4 | 0.126 |
| GO:0043284 | biopolymer biosynthetic process | 104 | 15.0 | 6.1 | +8.9 | 1.0E-3 | 0.174 |
| GO:0043283 | biopolymer metabolic process | 725 | 61.0 | 42.8 | +18.1 | 1.6E-3 | 0.234 |
| GO:0009103 | lipopolysaccharide biosynthetic process | 77 | 11.0 | 4.6 | +6.4 | 5.1E-3 | 0.496 |
| GO:0008653 | lipopolysaccharide metabolic process | 77 | 11.0 | 4.6 | +6.4 | 5.1E-3 | 0.496 |
| GO:0016051 | carbohydrate biosynthetic process | 137 | 16.0 | 8.1 | +7.9 | 6.3E-3 | 0.566 |
| GO:0008610 | lipid biosynthetic process | 126 | 15.0 | 7.4 | +7.6 | 6.8E-3 | 0.582 |
| GO:0032196 | transposition | 40 | 7.0 | 2.4 | +4.6 | 8.0E-3 | 0.632 |
| GO:0006313 | transposition, DNA-mediated | 40 | 7.0 | 2.4 | +4.6 | 8.0E-3 | 0.632 |
| GO:0044255 | cellular lipid metabolic process | 142 | 16.0 | 8.4 | +7.6 | 8.9E-3 | 0.652 |
| GO:0006629 | lipid metabolic process | 147 | 16.0 | 8.7 | +7.3 | 0.01 | 0.758 |

Fig. 11B

| Category ID | Category Name | #Genes Category | #Genes Assigned | #Genes Expected | #Genes Enriched | p-value | Corrected p-value |
|---|---|---|---|---|---|---|---|
| GO:0008652 | amino acid biosynthetic process | 134 | 29.0 | 5.1 | +23.9 | 3.6E-15 | <0.001 |
| GO:0009309 | amine biosynthetic process | 143 | 29.0 | 5.4 | +23.6 | 2.3E-14 | <0.001 |
| GO:0044271 | nitrogen compound biosynthetic process | 143 | 29.0 | 5.4 | +23.6 | 2.3E-14 | <0.001 |
| GO:0006520 | amine acid metabolic process | 210 | 34.0 | 8.0 | +26.0 | 1.1E-13 | <0.001 |
| GO:0006807 | nitrogen compound metabolic process | 263 | 39.0 | 10.0 | +29.0 | 1.3E-13 | <0.001 |
| GO:0006519 | amino acid and derivative metabolic process | 219 | 34.0 | 8.3 | +25.7 | 3.9E-13 | <0.001 |
| GO:0044249 | cellular biosynthetic process | 562 | 56.0 | 21.4 | +34.6 | 7.4E-13 | <0.001 |
| GO:0009308 | amine metabolic process | 232 | 34.0 | 8.8 | +25.2 | 2.2E-12 | <0.001 |
| GO:0009058 | biosynthetic process | 603 | 56.0 | 22.9 | +33.1 | 1.6E-11 | <0.001 |
| GO:0019752 | carboxylic acid metabolic process | 304 | 37.0 | 11.6 | +25.4 | 8.1E-11 | <0.001 |
| GO:0006526 | arginine biosynthetic process | 13 | 9.0 | 0.5 | +8.5 | 8.2E-11 | <0.001 |
| GO:0006082 | organic acid metabolic process | 308 | 37.0 | 11.7 | +25.3 | 1.0E-10 | <0.001 |
| GO:0009084 | glutamine family amino acid biosynthetic pro... | 23 | 11.0 | 0.9 | +10.1 | 1.5E-10 | <0.001 |
| GO:0009064 | glutamine family amino acid metabolic proc... | 46 | 13.0 | 1.7 | +11.3 | 7.2E-9 | <0.001 |
| GO:0006591 | urea cycle intermediate metabolic process | 22 | 9.0 | 0.8 | +8.2 | 4.3E-8 | <0.001 |
| GO:0006525 | arginine metabolic process | 22 | 9.0 | 0.8 | +8.2 | 4.3E-8 | <0.001 |
| GO:0044238 | primary metabolic process | 1446 | 87.0 | 55.0 | +32.0 | 7.0E-8 | <0.001 |
| GO:0044422 | organelle part | 29 | 9.0 | 1.1 | +7.9 | 9.8E-7 | <0.001 |
| GO:0044446 | intracellular organelle part | 29 | 9.0 | 1.1 | +7.9 | 9.8E-7 | <0.001 |
| GO:0006547 | histidine metabolic process | 11 | 6.0 | 0.4 | +5.6 | 1.1E-6 | <0.001 |
| GO:0009075 | histidine family amino acid metabolic process | 11 | 6.0 | 0.4 | +5.6 | 1.1E-6 | <0.001 |
| GO:0009076 | histidine family amino acid biosynthetic proc... | 11 | 6.0 | 0.4 | +5.6 | 1.1E-6 | <0.001 |
| GO:0008105 | histidine biosynthetic process | 11 | 6.0 | 0.4 | +5.6 | 1.1E-6 | <0.001 |
| GO:0006412 | translation | 113 | 16.0 | 4.3 | +11.7 | 4.0E-6 | <0.001 |
| GO:0044237 | cellular metabolic process | 1729 | 91.0 | 65.7 | +25.3 | 2.3E-5 | 0.009 |
| GO:0003735 | structural constituent of ribosome | 58 | 10.0 | 2.2 | +7.8 | 5.1E-5 | 0.012 |
| GO:0005840 | ribosome | 59 | 10.0 | 2.2 | +7.8 | 5.9E-5 | 0.012 |
| GO:0043176 | amine binding | 13 | 5.0 | 0.5 | +4.5 | 7.6E-5 | 0.014 |
| GO:0016597 | amino acid binding | 13 | 5.0 | 0.5 | +4.5 | 7.5E-5 | 0.014 |
| GO:0030529 | ribonucleoprotein complex | 62 | 10.0 | 2.4 | +7.6 | 9.2E-5 | 0.014 |
| GO:0019843 | rRNA binding | 32 | 7.0 | 1.2 | +5.8 | 1.5E-4 | 0.018 |
| GO:0009059 | macromolecule biosynthetic process | 251 | 22.0 | 9.5 | +12.5 | 1.6E-4 | 0.020 |

Fig. 12B

| Carbon source and gene | Functions and reactions catalyzed by enzymes/proteins |
|---|---|
| Glucose | |
| ptsG | Functions |
| | The product of *ptsG* gene (glucose-specific PTS permease) is responsible for uptake of exogenous glucose from the medium, releasing the phosphate ester into the cell cytoplasm in preparation for metabolism, primarily via glycolysis. PtsG/Crr, the glucose-specific PTS permease, belongs to the functional superfamily of the phospho*enol*pyruvate (PEP)-dependent sugar-transporting phosphotransferase system (PTS). The PTS transports and simultaneously phosphorylates its sugar substrates in a process called group translocation. |
| | Reaction |
| | phospho*enol*pyruvate + β-D-glucose$_{[periplasmic\ space]}$ → β-D-glucose 6-phosphate + pyruvate |
| Maltose | |
| malEFGK | Functions |
| | *malKFGE* operon plays the major role in the maltose transport system and it belongs to the ATP-binding cassette (ABC) superfamily of transporters. *malE* is the periplasmic maltose-binding protein, *malF* and *malG* are the integral membrane components of the ABC transporter, and *malK* is the ATP-binding component of the ABC transporter (MalFGK$_2$) |
| | Reactions |
| | maltose$_{[extracellular\ space]}$ ↔ maltose$_{[cytosol]}$ |
| | ATP + maltose$_{[periplasmic\ space]}$ + H$_2$O ↔ ADP + phosphate + maltose$_{[cytosol]}$ |
| malQ | Functions |
| | *malQ* codes for amylomaltase, which is responsible for degrading maltose after transport into the cell (6). The glucose liberated in the degradation reaction is then used in glycolysis. Amylomaltase also recognizes maltotriose and larger maltodextrins (donors), cleaving off the reducing glucose residue and transferring the remaining dextrinyl residue onto the nonreducing end of maltodextrin (acceptors), including maltose and glucose. Amylomaltase thus produces glucose and longer maltodextrins from maltotriose, the smallest donor substrate, as well as from longer linear maltodextrins. |
| | Reaction |
| | H$_2$O + maltose ↔ 2 β-D-glucose |
| | maltotriose + maltose ↔ maltotetraose + β-D-glucose |

Fig. 20-1

| glk | Functions |
|---|---|
| | Under normal conditions, glucokinase plays a minor role in E. coli glucose metabolism. Under anabolic stress the enzyme is required to supplement the levels of glucose 6-phosphate. |
| | Reaction |
| | β-D-glucose + ATP ↔ β-D-glucose 6-phosphate + ADP |
| Galactose | |
| mglABC | Functions |
| | MglABC is a β-methyl galactoside transport system that is a member of the ABC superfamily of transporters. The mglB gene codes for a galactose-binding protein that serves both as the galactose chemoreceptor as well as the recognition component of the β-methyl galactoside transport system, which utilizes the galactose-binding protein; mglC encodes the integral membrane component; and mglA encodes the ATP-binding component of the ABC transporter. |
| | Reaction |
| | ATP + β-D-galactose$_{[periplasmic\ space]}$ + H$_2$O ↔ ADP + phosphate + β-D-galactose$_{[cytosol]}$ |
| galE | Functions |
| | galE codes for UDP-galactose 4-epimerase, which catalyzes a hydride transfer and the interconversion of UDP-galactose and UDP-glucose as part of galactose catabolism. |
| | Reaction |
| | UDP-D-glucose ↔ UDP-galactose |
| galK | Functions |
| | Galactokinase, coded by galK, catalyzes the first step in galactose metabolism. |
| | Reaction |
| | D-galactose + ATP → α-D-galactose 1-phosphate + ADP |
| galT | Functions |
| | galT codes for galactose-1-phosphate uridylyltransferase, which catalyzes an interconversion reaction in galactose catabolism. |
| | Reactions |
| | UDP-D-glucose + α-D-galactose 1-phosphate ↔ α-D-glucose 1-phosphate + UDP-galactose |

Fig. 20-2

| | |
|---|---|
| | α-D-galactose 1-phosphate + UTP ↔ UDP-galactose + diphosphate |
| galP | Functions |
| | GalP is one of two, along with MglABC, major routes for galactose transport into E. coli. 2-Deoxy-D-galactose is a specific substrate for GalP but not for MglABC, and GalP operates by a sugar-proton symport mechanism whereas MglABC does not. |
| | Reaction |
| | $H^+_{[periplasmic\ space]}$ + β-D-galactose$_{[periplasmic\ space]}$ ↔ $H^+_{[cytosol]}$ + β-D-galactose$_{[cytosol]}$ |
| pgm | Functions |
| | pgm codes for phosphoglucose mutase, which catalyzes conversion of glucose 1-phosphate to glucose 6-phosphate. Maximum activity is obtained only in the presence of α-D-glucose 1,6-bisphosphate. This bisphosphate is an intermediate in the reaction, being formed by transfer of a phosphate residue from the enzyme to the substrate, but the dissociation of bisphosphate from the enzyme complex is much slower than the overall isomerization. |
| | Reaction |
| | α-D-glucose 1-phosphate → α-D-glucose 6-phosphate |
| Glycerol | |
| glpK | Function |
| | glpK codes for glycerol kinase, which catalyzes the MgATP-dependent phosphorylation of glycerol to yield sn-glycerol 3-phosphate. This is also the rate-limiting step in glycerol utilization in E. coli. |
| | Reaction |
| | glycerol + ATP → sn-glycerol 3-phosphate + ADP |
| glpF | Function |
| | The glycerol facilitator, GlpF, allows the facilitated diffusion of glycerol into the cell. |
| | Reaction |
| | glycerol$_{[periplasmic\ space]}$ ↔ glycerol$_{[cytosol]}$ |
| gpsA | Functions |
| | gpsA codes for glycerol-3-phosphate dehydrogenase [NAD(P)$^+$], which catalyzes the NAD(P)H-dependent reduction of the glycolytic intermediate dihydroxyacetone phosphate to produce glycerol 3-phosphate |
| | Reaction |

Fig. 20-3

| | |
|---|---|
| | sn-glycerol 3-phosphate + NAD(P)$^+$ ↔ dihydroxyacetone phosphate + NAD(P)H + H$^+$ |
| Lactate | |
| *lldP* | Function |
| | LldP (or LctP) is a lactate/proton symporter responsible for the uptake of L-lactate. The *lldP/lctP* gene is located in a lactate-inducible operon with the *lctD* and *lctR* genes encoding a lactate dehydrogenase and a regulatory protein, respectively. |
| | Reaction |
| | H$^+$[periplasmic space] + lactate[periplasmic space] ↔ H$^+$[cytosol] + lactate[cytosol] |
| *dld* | Function |
| | *dld* codes for D-lactate dehydrogenase. There are three lactate dehydrogenase enzymes in *E. coli* that interconvert pyruvate and lactate. One is an NAD-linked fermentative dehydrogenase. The other two are membrane-bound flavoproteins, each specific for the D- or L-isomer, and are involved in the aerobic respiratory chain of *E. coli*. The D-lactate dehydrogenase is coded for by the *dld* gene, and it is the primary source of energy to drive the active transport of certain sugars and amino acids into the cell. |
| | Reaction |
| | ubiquinone-8 + D-lactate ↔ ubiquinol-8 + pyruvate |
| Acetate | |
| *ackA* | Function |
| | The *ackA* gene product has propionate kinase activity as well as acetate kinase activity. It is unclear whether the two *ack* genes, *ackA* and *ackB*, code for two distinct acetate kinase enzymes or control a single enzyme. Helps in conversion of acetate to acetyl phosphate. The *ackA*-encoded propionate kinase 2 has an important role in propionyl-CoA metabolism. Acetate kinase can also catalyze acetylation of CheY, increasing signal strength for flagellar rotation. |
| | Reactions |

Fig. 20-4

|     |     |
| --- | --- |
|     | ATP + propionate ↔ ADP + propionyl-P<br><br>acetate + ATP ↔ acetylphosphate + ADP |
| *pta* | Function |
|     | *pta* gene codes for phosphate acetyltransferase, which can utilize both acetyl-CoA and propionyl-CoA. |
|     | Reactions |
|     | phosphate + acetyl-CoA ↔ acetylphosphate + CoA<br><br>propionyl-CoA + phosphate ↔ propionyl-P + CoA |
| *acs* | Function |
|     | *acs* gene codes for acetyl-CoA synthetase (ACS). There are two distinct pathways by which *E. coli* converts acetate to acetyl-CoA. ACS catalyzes one of them. It is thought that this ACS pathway functions in a mainly anabolic role, scavenging acetate present in the extracellular medium. ACS also can catalyze acetylation of CheY, increasing signal strength for flagellar rotation. |
|     | Reactions |
|     | CoA + 4-coumarate + ATP → coumaroyl-CoA + diphosphate + AMP<br>CoA + propionate + ATP ↔ propionyl-CoA + diphosphate + AMP<br>CoA + acetate + ATP ↔ acetyl-CoA + diphosphate + AMP |

Fig. 20-5

B – red channel

FLUX BALANCE ANALYSIS WITH MOLECULAR CROWDING

STATEMENT REGARDING FEDERAL FUNDING

This invention was made with government support under Grant No. GM062449, awarded by the National Institutes of Health. The government has certain rights in this invention.

Understanding an organism's metabolism at a system level requires knowledge of the physicochemical constraints limiting its metabolic capabilities under different growth conditions, and the genetic regulatory mechanisms that ultimately allow it to adapt to a changing environment. In some cases there is an obvious connection between an environmental change and the regulatory mechanisms responding to it, an example being a switch from aerobic to anaerobic growth. However, there are constraints leading to less obvious metabolic changes, involving a complex global rearrangement of the cell's metabolism. A key aim of systems biology is to uncover the metabolic constraints determining such complex phenotypic changes, which can be understood only when the system is analyzed at a global scale. In the absence of cell-scale kinetic models, flux balance analysis (FBA) provides experimentally testable predictions on an organism's metabolic flux state, which are based on conservation principles, particularly mass conservation, and metabolic capacity constraints. The impact of local constraints, such as uptake capacities, has been investigated, and capacity constraints over full metabolic pathways have been considered as well.

SUMMARY

The technologies described herein are useful in, without limitation: 1) calculating cell growth rates in various environments and genetic backgrounds; 2) calculating the order of substrate utilization from a defined growth medium; 3) calculating metabolic flux reorganization in various environments and at various growth rates; and 4) calculating the maximum metabolic rate and optimal metabolite concentrations and enzyme activities by applying a computational optimization method to a kinetic model of a metabolic pathway. The methods described herein, including computer-implemented methods and/or apparatus, such as computer-devices embodying/for implementing the methods supercede existing methods and capabilities in several ways. In particular, current flux balance-based modeling approaches have limited ability to predict substrate uptake from the environment. Also, the predictions they generate are based on previous knowledge of the maximum uptake rates in the corresponding medium (the actual variables one aims to predict), and, in contrast to extensive experimental evidence, FBA in itself predicts the simultaneous utilization of all carbon sources from a mixed-substrate growth medium. Using the modeling framework described herein, one can provide superior capabilities to predict cellular metabolism over the existing modeling frameworks.

In one embodiment, provided herein is a method of optimizing one or more biological activities in cells in a cell culture, comprising: calculating one or more optimal cell culture parameters for one or more biological activities in a cell in a cell culture by applying an optimization method to a list of one or more reactions representing or affecting the one or more biological activities, wherein the optimization method uses an intracellular molecular crowding parameter (e.g., employs one or more values, algorithms, formulas, etc., that represent the extent of intracellular crowding or solvent capacity of the cell in calculating an optimal value) for one or more elements of the one or more reactions to calculate a cell culture parameter for the one or more biological activities in the cells. The method further comprises initiating and/or maintaining the one or more optimal cell culture parameter in a culture of the cells. In one embodiment, the cell culture parameter is a concentration of a metabolite in the cell culture, such as a carbon or nitrogen source, including, without limitation, one or more of: glucose, galactose, maltose, lactate, glycerol, an amino acid and a nucleotide. Additional non-limiting examples of a cell culture parameter include: $O_2$, $CO_2$, or $N_2$ levels, pH, buffer capacity, viscosity, degree of agitation (e.g., stirring), cell density, etc. In one non-limiting embodiment the method comprises calculating an order of substrate usage from a growth medium and controlling an order of substrate usage in the culture to achieve the one or more optimal biological activities.

The method may further comprise calculating one or more of a maximum metabolic rate, an optimal metabolite concentration and an enzyme activity by applying a computational optimization method to a kinetic model of a metabolic pathway.

In another embodiment, a method is provided for achieving an optimal function of a biochemical reaction network in a cell. The method comprises: (a) calculating optimal properties of a biochemical reaction network by applying a computational optimization method to a list of reactions representing said biochemical reaction network, wherein the optimization method uses an intracellular molecular crowding parameter for one or more elements of the one or more reactions of the list of reactions to calculate the optimal properties; (b) altering the list of reactions in the biochemical reaction network and re-computing the optimal properties; and (c) repeating (b) until a desired optimal function is reached. The method may further comprise calculating one or more of a maximum metabolic rate, an optimal metabolite concentration and an enzyme activity by applying a computational optimization method to a kinetic model of a metabolic pathway. The method also may further comprise culturing a cell under culture conditions that favor achievement of the optimal function (e.g., the cells are cultured in a manner, based on the calculations, that is calculated to result in achievement of the optimal function, such as growth rate or metabolite (e.g., starting material, intermediate or product of a cellular metabolic process), by-product, secreted product or (e.g., recombinant) protein production). The method may further comprise (d) constructing the genetic makeup of a cell to contain the biochemical reactions which result from (c); (e) placing the cell constructed under (d) in culture under a specified environment to obtain a population of cells; and (f) cultivating the cells as in step (e) for a sufficient period of time and under conditions to allow the cells to evolve to the desired optimal function determined under (c), wherein the biochemical reaction network comprises a comprehensive biochemical reaction network.

According to a further embodiment, provided herein is a computer-implemented method for achieving an optimal function of a biochemical reaction network in cells in a cell culture, including prokaryotic or eukaryotic cells, for example and without limitation, bacterial, fungal (including yeast), mammalian and cancer cells. The method comprises (a) calculating in a computer one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. According to one embodiment, the optimization method further comprises calculating one or more of a maximum metabolic rate, an optimal metabolite concentration and an enzyme activity by applying a computational optimization method to a kinetic model of a metabolic pathway. In an example of an implementation of the method, the method further comprises culturing a cell under culture conditions that favor achievement of the optimal function. Optionally, the method further comprises: (c) constructing the genetic makeup of a cell to contain the biochemical reactions (d) placing the cell constructed under (c) in culture under a specified environment to obtain a population of cells; and (e) cultivating the cells as in step (d) for a sufficient period of time and under conditions to allow the cells to evolve to the desired optimal function determined under (a), wherein the biochemical reaction network comprises a comprehensive biochemical reaction network. In one embodiment, the optimal function is maximizing biomass production. In another, the optimal property is maximal internal yield of ATP. In a further embodiment, the solvent capacity accounts for ribosome density in the cells in the cell culture as a measure of ribosomal-, enzyme associated-, and non-metabolic proteins in the cells or accounts for mitochondria as a subcellular compartment in the cells in the cell culture. According to one embodiment, the method comprises a model of a pathway for ATP generation that involves reactions in the serine biosynthesis, one-carbon metabolism and the glycine cleavage system.

According to another embodiment, also provided is a computer readable medium having stored thereon instructions which, when executed by a processor, cause the processor to implement a process implementing a computer model for achieving an optimal function of a biochemical reaction network in cells in a cell culture. The process comprises: (a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. The computer-readable medium may include in its various embodiments instructions which, when executed by a processor, cause the processor to implement a process implementing a computer model for achieving any method described in this document, including, without limitation, the following: a computer readable medium as described above in which the optimization method further comprises calculating one or more of a maximum metabolic rate, an optimal metabolite concentration and an enzyme activity by applying a computational optimization method to a kinetic model of a metabolic pathway; a computer readable medium as described above wherein the optimal function is maximizing biomass production; a computer readable medium as described above in which the optimal property is maximal internal yield of ATP; a computer readable medium as described above in which the solvent capacity accounts for ribosome density in the cells in the cell culture as a measure of ribosomal-, enzyme associated-, and non-metabolic-proteins in the cells; a computer readable medium as described above in which the solvent capacity accounts for mitochondria as a subcellular compartment in the cells in the cell culture; a computer readable medium as described above in which the cells are human cells; a computer readable medium as described above in which the cells are cancer cells; and a computer readable medium as described above that comprises a model of a pathway for ATP generation that involves reactions in the serine biosynthesis, one-carbon metabolism and the glycine cleavage system.

According to further embodiments, a device is provided that comprises the computer-readable medium described according to any embodiment herein, and a processor for executing the instructions on the computer-readable medium for achieving an optimal function of a biochemical reaction network in cells in a cell culture. As above, the instructions, when executed by a processor, cause the processor to implement a process implementing a computer model for achieving an optimal function of a biochemical reaction network in cells in a cell culture, comprising: (a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. As above, The computer-readable medium may include in its various embodiments instructions which, when executed by a processor, cause the processor to implement a process implementing a computer model for achieving any method described in this document, including, without limitation, the following: a computer readable medium as described above in which the optimization method further comprises calculating one or more of a maximum metabolic rate, an optimal metabolite concentration and an enzyme activity by applying a computational optimization method to a kinetic model of a metabolic pathway; a computer readable medium as described above wherein the optimal function is maximizing biomass production; a computer readable medium as described above in which the optimal property is maximal internal yield of ATP; a computer readable medium as described above in which the solvent capacity accounts for ribosome density in the cells in the cell culture as a measure of ribosomal-, enzyme associated-, and non-metabolic-proteins in the cells; a computer readable medium as described above in which the solvent capacity accounts for mitochondria as a subcellular compartment in the cells in the cell culture; a computer readable medium as described above in which the cells are human cells; a computer readable medium as described above in which the cells are cancer cells; and a computer readable medium as described above that comprises a model of a pathway for ATP generation that involves reactions in the serine biosynthesis, one-carbon metabolism and the glycine cleavage system. The device also may comprise additional components for implementation of the instructions, including, without limitation one or more sensors, such as pH, gas (e.g. $O_2$ or $CO_2$), chemical or temperature sensors, one or more culture vessels, one or more heating elements or cooling elements, reservoirs for storing storing cell culture medium, cell culturing ingredients or an analytical composition (e.g., a composition useful in testing a cell culture parameter) and one or more mechanisms for dispensing the storing cell culture medium, cell culturing ingredients or an analytical composition into a cell culture or other container, such as a cuvette, or for taking and/or analyzing samples from one or more cell culture vessels, including, mechanical, fluidic and robotic mechanisms, a display (e.g., a monitor); one or more analytical devices, such as a spectrophotometer for measuring cell density and/or the results of an analytical assay; and one or more communication subsystems for receiving or transmitting data, including, without limitation wired communication devices, such as Ethernet, modem, FIREWIRE, Universal Serial Bus (USB), and THUNDERBOLT devices, or wireless communication devices such as BLUETOOTH or 802.11g or n protocol devices.

BRIEF DESCRIPTION OF THE DRAWINGS

Comparison of measured metabolic fluxes and in-vitro enzyme activities.

FIG. 9—FIGS. 9A-9B show Cluster 2 (Profiles 5 and 6 from FIG. 7) and FIG. 9C shows GO results.

FIG. 10—FIGS. 10A-10B show Cluster 3 (Profiles 25 and 28 from FIG. 7) and FIG. 10C shows GO results.

FIG. 11—FIG. 11A shows Cluster 4 (Profile 12 from FIG. 7) and FIG. 11B shows GO results.

FIG. 12—FIG. 12A shows Cluster 5 (Profile 42 from FIG. 7) and FIG. 12B shows GO results.

FIG. 15—Comparison between the gene expression profiles and predicted substrate uptake rates.

FIG. 20 is a table showing major functions and reactions catalyzed by the transporters/enzymes encoded by the genes involved in substrate uptake, as shown in FIG. 15

FIG. 27: Selected reactions contributing to ATP generation at different proliferation rates. Contribution of ATP synthase, phosphoglycerate kinase (PGK), pyruvate kinase (PK) and formate-tetrahydrofolate ligase (FTHFL) to ATP generation in cells at low (0.03/day, left) and high (2.52/day, right) proliferation rates. The ATP consumed for cell maintenance (black) is shown as a reference.

FIG. 29A is too large to reproduce, and is broken down into four enlarged parts as shown in FIGS. 29B-29E, corresponding to parts a) through d), respectively in FIG. 29A. The fate of the high glycolysis flux in cells utilizing the alternative glycolysis. The squared panels show the rate of the indicated reaction (vertical axis, in units of mM/min=mmol/min/L) as a function of the proliferation rate (horizontal axis, in units of 1/day). The gray shadow background contains reactions taking place in the mitochondria. Metabolite and enzyme abbreviations: 3-phosphoglycerate (3pg), phosphoglycerate dehydrogenase (PHGDH), 3-phosphohydroxypyruvate (3php), L-glutamate (glu-L), phosphoserine transaminase (PSAT), α-ketoglutarate (aKg), L-phosphoserine (pser-L), phosphoserine phosphatase (PSPH), L-serine (ser-L), tetrahydrofolate (thf), serine hydroxymethyltransferase (SHMT), glycine (gly), 5,10-methylene tetrahydrofolate (mlthf), methylenetetrahydrofolate dehydrogenase (MTHFD), 5,10-methenyltetrahydrofolate (methf), methenyltetrahydrofolate cyclohydrolase (MTHFC), 10-formyltetrahydrofolate (10thf), formate (for), formate-tetrahydrofolate ligase (FTHFL), S-aminomethyldihydrolipoylprotein (alpro), dyhydrolipolprotein (dhlpro), lipoylprotein (lpro), S-aminomethyldihydrolipoamide (alpam), dihydrolipoamide (dhlam), and lipoamide (lpam). glycine-cleavage complex with lipoylprotein (GCCam, GCCbim and GCCcm) and glycine-cleavage complex with lipoamide (GCC2am, GCC2bim and GCC2 cm).

FIG. 31: Transcriptional upregulation of the novel pathway in a Myc-induced tumor. The original is in color, showing red and green colors and is separated into green and red channels for grayscale display.

DETAILED DESCRIPTION

Figure 1:
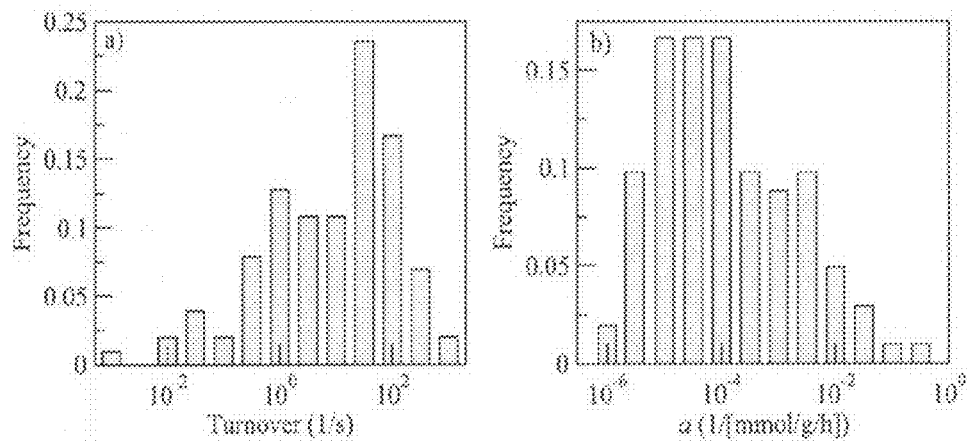
FIG. 1—Estimating the crowding coefficients of *E. coli* metabolic enzymes: (a) Distribution of turnover rates of *E. coli* enzymes as obtained from the BRENDA data base (Schomburg I, Chang A, Schomburg D: BRENDA, enzyme data and metabolic information. *Nucleic Acids Res* 2002, 30:47-49); (b) Distribution of crowding coefficients among a hundred *E. coli* enzymes, as obtained using Eq. 4 in Example 1.

All ranges or numerical values stated herein, whether or not preceded by the term "about" unless stated otherwise are considered to be preceded by the term "about" to account for variations in precision of measurement and functionally equivalent ranges.

As used herein, the terms "comprising," "comprise" or "comprised," and variations thereof, are meant to be open ended. The terms "a" and "an" are intended to refer to one or more.

Methods for conducting flux balance calculations for cell cultures are provided. In one aspect, cytoplasmic molecular crowding (synonymous with solvent capacity) in cells in a cell culture are used in flux balance calculations. In another aspect, reaction kinetics (e.g., enzyme kinetics) parameters of reactions taking place in cells of the cell culture are used along with molecular crowding considerations to conduct flux balance calculations. The methods provided herein are useful in optimizing cell growth conditions and/or one or more reactions in a cell culture system. The methods are useful in research and commercial applications where it is desirable to optimize cell culture conditions with respect to growth rate of cells (e.g., to maximize biomass production), and/or optimizing certain biochemical reactions (including enzymatic and non-enzymatic biochemical reactions) or activities of cells in a culture system. As an example, for production of biomass, with or without consideration of the production of a certain reaction product in the cell, such as sugars, oils, fatty acids, alcohols, polysaccharides, polymers, etc., cell growth can be maximized by optimizing one or more biochemical reactions in the cell by maintaining cell growth conditions within certain tolerances based on the flux balance calculations described herein. Production of certain metabolites by a cell, such as a wild type or mutant cell, can be optimized by the flux balance analysis methods described herein. As an example, production of fatty acids or ethanol can be optimized for biofuel production. Production of product(s) of a recombinantly-modified cell can be optimized by the methods described herein. Metabolic engineering involves the modification by random mutation or by directed methods, such as by recombinant methods, to optimize the production of certain metabolites or products of cellular metabolism. Production of sugars, alcohols, fatty acids, triglycerides, polymers or subunits thereof, or literally any cellular component, including reaction starting materials, intermediates or products, can be optimized using the methods described herein. The methods described herein provide significantly increased accuracy in flux balance calculations as compared to prior methods that do not consider cytoplasmic molecular crowding by itself or with reaction kinetics of biochemical reactions within the cells.

In a flux balance model of cellular metabolism a cell's metabolic network is mathematically represented by the stoichiometric matrix, $S_{mi}$, providing the stoichiometric coefficient of metabolite m (m=1, . . . , M) in reaction i (i= 1, . . . , N) where M and N are the number of metabolites and reactions, respectively. The cell is assumed to be in a steady state, where the concentration of each intracellular metabolite (other than those that constitute the biomass) remains constant in time. Thus, the stationary reaction rates (fluxes) consuming and producing a metabolite should balance, $$\sum_{i=1}^{N} S_{mi} f_i = 0, \quad (1)$$

where, $f_i$ denotes the flux of reaction i. The study of the solution space defined by (1) together with maximum capacity constraints for the uptake rates of extracellular substrates constitutes the basis of 'flux balance analysis' (FBA).

We extend this framework to consider the physical and spatial constraints resulting from the very high intracellular concentration of macromolecules. Given that the enzyme molecules have a finite molar volume $v_i$ we can only fit a finite number of them in a given volume V. Indeed, if n, is the number of moles of the $i^{th}$ enzyme, then $$\sum_{i=1}^{N} v_i n_i \leq V. \quad (2)$$

Equation (2) represents a constraint on the enzyme levels $n_i$, potentially affecting their maximum attainable values and relative abundance. Dividing by cell mass M we can reformulate this constraint in terms of the enzyme concentrations $E_i = n_i/M$ (moles/unit mass), resulting in $$\sum_{i=1}^{N} v_i E_i \leq \frac{1}{C}, \quad (3)$$

where C=M/V≈0.34 g/ml is the *E. coli* cytoplasmic density. Equation (3) imposes a constraint on the maximum attainable enzyme concentrations and, therefore, we refer to it as the enzyme concentration constraint. This constraint is reflected in the metabolic fluxes as well. Indeed, an enzyme concentration $E_i$ results in a flux $f_i = b_i E_i$ over reaction i, where the parameter $b_i$ is determined by the reaction mechanism, kinetic parameters, and metabolite concentrations. Therefore, the enzyme concentration constraint is reflected in the metabolic flux constraint $$\sum_{i=1}^{N} a_i f_i \leq 1, \quad (4)$$

where $a_i = Cv_i/b_i$ [Eq. 5], affecting the maximum attainable fluxes and the flux distribution among different metabolic reactions. From here on, we refer to this mathematical framework as 'flux balance analysis with molecular crowding' (FBAwMC). Furthermore, since the coefficient $a_i$ quantifies the contribution to the overall crowding by reaction i we refer to it as the 'crowding coefficient of reaction i', or simply 'crowding coefficient'.

Accordingly, in one non-limiting aspect, a method of optimizing one or more biological activities (for example and without limitation, a growth rate, production of one or more metabolic products or recombinant proteins) in a cell in a cell culture is provided. The method comprises calculating an optimal cell culture parameter for one or more biological activities in a cell in a cell culture by applying an optimization method to a list of one or more reactions representing or affecting the one or more biological activities, wherein the optimization method uses an intracellular molecular crowding parameter for one or more elements (e.g., enzyme, substrate, cofactor, etc.) of the one or more reactions to calculate an optimal cell culture parameter for the one or more biological activities in the cell; initiating or maintaining the optimal cell culture parameter in a cell culture. A cell culture parameter is a culture condition, for example and without limitation, culture medium composition or physical characteristic of the culture, including without limitation, concentration of, for example, one or more of a carbon source, a nitrogen source, cofactors, salts, buffers, nucleotides, amino acids, oxygen (e.g., $pO_2$) and products and/or byproducts of cellular metabolism, as well as pH, $CO_2$, temperature, cell density, osmolality, viscosity and/or other physical parameter of the culture.

By "initiating or maintaining an optimal cell culture parameter" it is meant that in the culture at its inception, or at any time during cell culture, including at more than one time point, continuously, substantially continuously or for any duration or multiple durations, the "optimal cell culture parameter or parameters are initiate or re-initiated. For instance, at optimal cell culture conditions, a carbon source might be at a specific concentration. The optimal concentration of the carbon source is then periodically tested and, if not at an optimal concentration, additional carbon source is added to the culture to reach the optimal concentration. It should be recognized that the optimal concentration of any given cell culture constituent may change as optimal parameters are re-calculated based on readings of one or more cell culture parameters over time. A person of skill in the art also will recognize that, depending on the culture conditions, the timing, duration and the method of initiating and/or maintaining the cell culture parameter, and/or the method of monitoring the concentration of the metabolite in the culture, the concentration of the metabolite may rise above or below the exact calculated optimal concentration, and that given the practicalities of implementation, a person of skill in the art would recognize that "initiating and maintaining an optimal concentration" means approximating that concentration, as is practicable and acceptable in terms of the desired outcome, such as maximum cell growth or production of a product by the cell.

U.S. Pat. No. 7,127,379 provides one example of how the methods described herein can be implemented (see also, Edwards J. S., et al. (1999) *Journal of Biological Chemistry*, 274(25):17410 16). In that document, flux calculations are used in the implementation of a method for directed evolution of a cell culture. The present methods, including considerations of cytoplasmic cell crowding and/or reaction kinetics, are not only applicable to the evolutionary methods described in that patent, but more generally to optimizing culture conditions with the goal of attaining an optimal, desired outcome.

The methods described herein and steps thereof are typically of such complexity that they are preferably implemented in a computer, and as such, a biochemical reaction network can be designed for implementation in a computer (in silico), e.g., by instructions executed by one or more processors. According to typical embodiments, the methods described herein, including all or substantially all steps thereof are performed in a computer and are therefore considered to be "computer-implemented". Following the design of the reaction network, cell growth and/or production of one or more cellular constituents can be optimized for a genetically modified organism or a wild-type strain that corresponds to the network used for the computer simulations. Organisms may achieve the optimal behavior in a non-unique fashion—that is there may be equivalent optimal solutions.

Thus, in one aspect, methods are provided for determining optimal functions of a comprehensive biochemical reaction network in a living cell with respect to one or more functions of a cell. The method can be performed by representing a listing of the biochemical reactions in the network in a computer; using optimization methods to calculate the optimal properties of the network; altering the list of reactions in the network and re-computing the optimal properties; and repeating the altering step until the desired performance is met. A person of skill in the computer programming arts can design such as system using any of a number of available programming languages and software tools available in the computer programming field, including mathematical modeling and/or object—oriented processes as are available.

In addition to in silico steps, according to one non-limiting embodiment, the methods can further include steps involving culturing a living cell, or a population of cells and optimizing culture conditions to optimize cell growth and/or production of a cellular constituent. In an additional embodiment, these steps include constructing the genetic makeup of a cell to contain the biochemical reactions which result from repeating the altering step until the desired performance are met; placing the cell constructed thereunder in culture under the specified environment; and cultivating the cell for a sufficient period of time and under conditions to allow the cell to evolve to the determined desired performance.

A biochemical reaction network is an interrelated series of biochemical reactions that are part of a biochemical pathway or linked biochemical pathways. Many biochemical reaction networks have been identified such as metabolic reaction networks, catabolic reaction networks, polypeptide and nucleic acid synthesis reaction networks, amino acid synthesis networks, energy metabolism and so forth. Other types of biochemical reaction networks include regulatory networks including cell signaling networks, cell cycle networks, genetic networks involved in regulation of gene expression, such as operon regulatory networks, and actin polymerization networks that generate portions of the cytoskeleton. Most of the major cell functions rely on a network of interactive biochemical reactions.

To implement the methods described herein, the reaction structure of a comprehensive, preferably substantially whole, or most preferably whole biochemical reaction network in an organism to be biochemically designed can be reconstructed for computer simulations. A whole biochemical reaction network includes all of the biochemical reactions of a cell related to a certain biochemical function. For example a whole metabolic reaction network includes essentially all of the biochemical reactions that provide the metabolism of a cell. This is made possible with the advent of whole genome sequencing. Biochemical reaction networks have been worked out for a number of organisms, such as E. coli and S. cerevisiae, as shown in the Examples, below. Metabolic reaction networks exemplify a universal biochemical reaction network found in some form in all living cells. A comprehensive biochemical reaction network is an interrelated group of biochemical reactions that affect a detectable property, and that can be modified in a predictable manner with respect to the effect of such modifications on the detectable property in the context of a living cell. For example, a comprehensive biochemical reaction network can include core reactions that effect the yield of a biomolecule produced by the cell, even though the core reactions include only a portion of the reactions in the whole biochemical reaction network involved in yield of the biomolecule, provided that computational methods can be used to predict the effect of changes in the core biochemical reactions on the yield in a living cell. A substantially whole biochemical reaction network is an interrelated group of biochemical reactions that are responsible for a detectable property of a living cell. Substantially whole biochemical reaction networks include core reactions as well as secondary reactions that have an effect on the detectable property, even though this effect can be relatively minor. Changes in substantially whole biochemical reaction networks can be predicted using computational methods. The methods described herein can also utilize the majority of reactions in a whole biochemical reaction network, rather than a comprehensive, substantially whole, or whole biochemical reaction network.

Optimal properties can be determined using the methods described herein include, for example, glycerol uptake rate, oxygen uptake rate, growth rate, sporulation occurrence and/or rates, rates of scouring of rare elements under nutritionally poor conditions, biomass, and yields of biomolecules such as proteins, amino acids, carbohydrates, fatty acids, alcohols, triglycerides, antibiotics, vitamins, amino acids, and fermentation products. Optimal properties also include, for example, yields of chiral compounds and other low molecular weight compounds. Optimal properties also include, for example, the maximal internal yields of key co-factors, such as energy carrying ATP or redox carrying NADPH and NADH. Optimal properties can also be defined by a cellular engineer to include properties such as flux rates through key reactions in the biochemical reaction network. The methods described herein facilitate achievement of an optimal performance related to one or more of the properties to be achieved, such as a target growth rate or yield of a cellular constituent or other product.

For implementation of the methods described herein, biochemical reactions of a reconstructed biochemical reaction network are represented in a computer by a listing of the biochemical reactions in the reconstructed biochemical reaction network. The listing can be represented in a computer database, for example as a series of tables of a relational database, so that it can be interfaced with computer processes (e.g., functions and/or algorithms that are implemented by software and/or hardware) that represent network simulation and calculation of optimal properties.

The biochemical network reconstruction preferably is of high quality. The process of high quality biochemical reaction network, specifically metabolic reaction network, reconstruction has been established (see, e.g., M. W. Covert, et al. Trends in Biochemical Sciences, 26: 179 186 (2001); Edwards J., et al. BMC Structural Biology, 1(2) (2000a); Edwards J. S., et al., Journal of Biological Chemistry, 274(25):17410 16, (1999), Karp P. D. et al. ISMB 4:116 24, (1996); Karp P. D. et al., Nucleic. Acids Res. 28(1):56 59 (2000); Ogata et al. Nucleic Acids Res. 27(1):29 34 (1999); Schilling C. H. et al. J. Theor. Biol., 203(3): 249 83 (2000); Selkov E. Jr. et al., Nucleic Acids Res., 26(1): 43 45 (1998); and Selkov E. et al., Gene 197(1 2):GC11 26 (1997)). This process typically involves the use of annotated genome sequences, and biochemical and physiological data. These annotated genome sequences and biochemical and physiological data can be found in any useful source. Careful analysis of the reconstructed network is needed to reconcile all the data sources used. Similar methods can be used for the reconstruction of other biochemical reaction networks.

As illustrated in the Examples, below, the reconstructed comprehensive, substantially whole, or whole biochemical reaction network can then be used to determine optimal properties of the comprehensive, substantially whole, or whole biochemical reaction network, or portions thereof, under specified and varying environmental conditions. This determination allows the design of a biochemical reaction network that achieves a desired performance in a specified environment. In one embodiment, this can be combined with steps for constructing the genetic makeup of a cell and cultivating the cell to provide a method for developing a recombinant cell, or a population of cells, that achieves the desired performance.

Optimal properties of the comprehensive, substantially whole, or whole biochemical reaction network, or portion thereof, under a series of specified environments can be determined using computational methods known as optimization methods. Optimization methods are known in the art (see e.g., Edwards J. S., et al., Journal of Biological Chemistry, 274(25):17410 16, (1999)). The optimization methods used in the methods described herein utilize linear and/or no-linear optimization with linear constraints. The optimization with respect to the reaction rates is linear and we can utilize any available package for linear optimization with linear constraints to find the optimal reaction rates. The optimization with respect to the metabolite concentrations in non-linear and we can, for example, utilize simulated annealing or other non-linear optimization packages with linear constraints to find the optimal metabolite concentrations.

The reconstructed metabolic network can be used to perform quantitative simulations of the metabolic flux distribution in a steady state using established methods (see, e.g., Bonarius et al., Trends in Biotechnology, 15(8): 308 14 (1997); Edwards J. S., et al., Metabolic flux Balance Analysis, In: (Lee S. Y., Papoutsakis E. T., eds.) Metabolic Engineering: Marcel Deker. P 13 57 (1999); and Varma A. et al., Bio/Technology 12:994 98 (1994a)). Computer simulations of the metabolic network can be performed under any conditions. Furthermore, any reaction list can be simulated in a computer by changing the parameters describing the environment and the contents of the reaction list.

The metabolic capabilities of a reconstructed metabolic network can be assessed using the established method of flux balance analysis (FBA) (Bonarius et al., (1997); Edwards et al., (1999); and Varma and Palsson (1994a)). FBA is based on the conservation of mass in the metabolic network in a steady state and capacity constraints (maximal fluxes through the reactions) on individual reactions in the network. Additionally, experimentally determined strain specific parameters are also required, the biomass composition (Pramanik J. et al., Biotechnology and Bioengineering, 56(4): 398 421 (1997)) and the maintenance requirements (Varma A. et al., Applied and Environmental Microbiology, 60(10): 3724 31 (1994b)). In addition to the above parameters, cytoplasmic molecular crowding and/or reaction kinetics are constraints placed on individual reactions in the reaction network. These factors are then used to calculate the flux distribution through the reconstructed metabolic network.

More specifically, the definition of these factors leads mathematically to a closed solution space to the equations in which all feasible solutions lie. There are thus many possible solutions (flux distributions) to any problem. The 'best' or optimal solution within the set of all allowable solutions can then be determined using optimization procedures and a stated objective. The optimization procedure used may be linear programming and the objective may be the optimal use of the biochemical reaction network to produce all or some biomass components simultaneously. Non-limiting examples of these optimization procedures are established and have been published (Varma et al. (1994a); Bonarious (1997); and Edwards et al. (1999)). The comparison of the calculated behavior based on the optimal growth objective to the experimental data is favorable in the majority of cases (Varma (1994b); Edwards J. S., et al., Nat Biotechnol., 19(2): 125 30 (2001a); and Edwards, et al. Biotechnol Bioeng. 2002; 77(1):27-36), though, as shown in the examples below, the addition of constraints relating to cytoplasmic molecular crowding and/or reaction kinetics, leads to superior tracking of in silico data to experimental data. In other words, these solution confinement and optimization procedures lead to a prediction of the optimal uses of a biochemical reaction network to support cellular growth and/or desired biological function.

Steady state metabolic flux distributions are mathematically confined to the solution space defined for a given reconstructed metabolic network, where each solution in the solution space corresponds to a particular flux distribution through the network or a particular metabolic phenotype (Edwards and Palsson (1999)). Under a single specified growth condition, the optimal metabolic flux distribution can be determined using linear programming (LP) or other related and/or useful approaches for calculating optimal solutions of such problems.

More specifically, the definition of these factors leads mathematically to a closed solution space to the equations in which all feasible solutions lie. There are thus many possible solutions (flux distributions) to any problem. The 'best' or optimal solution within the set of all allowable solutions can then be determined using optimization procedures and a stated objective. The optimization procedure used may be linear programming and the objective may be the use of the biochemical reaction network such as to produce biomass components at a maximal rate. Non-limiting examples of these optimization procedures are established and have been published (Varma and Palsson (1994a); Bonarious (1997); and Edwards et al. (1999)). The comparison of the calculated behavior based on the optimal growth objective to the experimental data is favorable in the majority of cases (Varma (1994b); Edwards J. S., et al. Nat Biotechnol., 19(2): 125 30 (2001a); and Edwards, et al., Biotechnol Bioeng. 2002; 77(1):27-36), though, as shown in the examples below, the addition of constraints relating to cytoplasmic molecular crowding and/or reaction kinetics, leads to superior tracking of in silico data to experimental data. In other words, these solution confinement and optimization procedures lead to a prediction of the optimal uses of a biochemical reaction network to support cellular growth and/or desired biological function.

The metabolic reconstruction is then used to predict the optimal flux distribution within the given constraints. Using the optimization procedure, the properties of the corresponding actual biochemical reaction network may not be optimal or the same as desired from a practical standpoint. The simulated reconstructed network and its synthesis in an organism may not display the optimal solution desired, also referred to herein as the desired optimal performance or desired optimal function. Lack of optimality may be due to the fact that:

The natural organism with an intact network has never experienced the environmental conditions of interest and never undergone growth competition and selection in this environment, or The wild type network is perturbed from its optimal state by genetic manipulations, through the deletion/addition of a new reaction from/to the network.

The in silico methods described herein are designed to resolve the second cause of lack of optimality, by altering the reactions in the network until a desired performance is achieved. Culturing methods can be used to resolve the first cause of the lack of optimality related to growth competition and selection.

As mentioned above, after calculation of the optimal properties, one or more cellular parameters may be changed, in order to achieve a desired performance, growth, metabolic or production goal. In one instance, a metabolic engineer can alter the reaction list in the network, or an algorithm can be developed that automatically alters one or more reactions in the reaction list to achieve a desired performance. After alteration of one or more growth parameters and/or the biochemical list, optimal properties of this network under given environmental conditions can be calculated. For optimizing performance, this typically involves repeated monitoring of one or more culture parameters, along with repeated calculations based on the latest culture parameters and/or trends. In the context of engineering/evolving a cell, this is an iterative design procedure that may require many different versions of the reaction list until the desired performance is achieved. The desired performance is a qualitative characteristic or quantitative value for a property calculated using an optimization procedure. Many properties for which a desired performance can be achieved are known in the art. For example, a desired performance can be a desired growth rate or a desired yield of a biomolecule such as an enzyme or an antibiotic.

As mentioned above, after calculation of the optimal properties, a metabolic engineer can alter the reaction list in the network, or an algorithm can be developed that automatically alters one or more reactions in the reaction list, to achieve a desired performance. After alteration of the biochemical list, optimal properties of this network under given environmental conditions can be calculated. This is an iterative design procedure that may require many different versions of the reaction list until the desired performance is achieved. The desired performance is a qualitative characteristic or quantitative value for a property calculated using an optimization procedure. Many properties for which a desired performance can be achieved are known in the art. For example, a desired performance can be a desired growth rate or a desired yield of a biomolecule such as an enzyme or an antibiotic.

The optimization method may be carried out using a computer system. The computer system typically includes a processor for executing instructions, a database that provides information regarding one or more biochemical reaction networks of at least one organism; a user interface capable of receiving a selection of one or more biochemical reaction networks for optimization and/or comparison, and capable of receiving a selection of a desired performance; and a process (e.g., software, instructions) for carrying out the optimization method calculations and recalculations. Furthermore, the computer system may include a process for performing biochemical reaction network reconstruction.

The computer system can be a stand-alone computer, a portable computer or PDA, such as a laptop computer or a smart phone, or a conventional network system including a client/server environment and one or more database servers. A number of conventional network systems, including a local area network (LAN) or a wide area network (WAN), and including wireless and/or wired components, are known in the art. Additionally, client/server environments, database servers, and networks are well documented in the technical, trade, and patent literature. For example, the database server can run on an operating system such as UNIX, running a relational database management system, a World Wide Web application, and a World Wide Web Server.

The information in the database may include biomolecular sequence information regarding biomolecules involved in the biochemical reactions of the biochemical reaction network, for example information regarding multiple biomolecular sequences such as genomic sequences. At least some of the genomic sequences can represent open reading frames located along one or more contiguous sequences on each of the genomes of the one or more organisms. The information regarding biochemical reaction networks can include information identifying those biochemical reaction networks to which a biomolecular sequence plays a role and the specific reactions in the biochemical reaction network involving the biomolecule.

The database can include any type of biological sequence information that pertains to biochemical reactions. For example, the database can be a nucleic acid sequence database, including ESTs and/or more preferably full-length sequences, or an amino acid sequence database. The database preferably provides information about a comprehensive, substantially whole, or whole biochemical reaction network. For example, the database can provide information regarding a whole metabolic reaction network. The database can provide nucleic acid and/or amino acid sequences of an entire genome of an organism.

The database can include biochemical and sequence information from any living organism and can be divided into two parts, one for storing sequences and the other for storing information regarding the sequences. For example, the database can provide biochemical reaction information and sequence information for animals (e.g., human, primate, rodent, amphibian, insect, etc.), plants, or microbes. The database may be annotated, such as with information regarding the function, especially the biochemical function, of the biomolecules of the database. The annotations can include information obtained from published reports studying the biochemistry of the biomolecules of the database, such as specific reactions to which a biomolecule is involved, whether the biomolecule is or encodes an enzyme, whether the sequence is a wild-type sequence, etc.

The annotations and sequences of the database can provide sufficient information for a selected biochemical genotype of an organism to be identified. A biochemical genotype is a grouping of all the nucleic acid or amino acid sequences in a selected biochemical process of an organism. For example, a metabolic genotype is a grouping of all the nucleic acid and/or amino acid sequences of proteins involved in metabolism. Methods for identifying metabolic genotypes have been described in the literature (see e.g. Edwards and Palsson 1999).

The database can be a flat file database or a relational database. The database can be an internal database, or an external database that is accessible to users, for example a public biological sequence database, such as GenBank or GenPept. An internal database is a database maintained as a private database, typically maintained behind a firewall, by an enterprise. An external database is located outside an internal database, and is typically maintained by a different entity than an internal database. In one non-limiting embodiment, the methods rely on information stored both in an internal and an external database. In such a system, proprietary information can be maintained in an internal database, but the system also can obtain information from one or more external databases. A number of external public biological sequence databases are available and can be used with the methods described herein. For example, many of the biological sequence databases available from the National Center for Biological Information (NCBI), part of the National Library of Medicine, can be used with the current invention. Other examples of external databases include the Blocks database maintained by the Fred Hutchinson Cancer Research Center in Seattle, and the Swiss-Prot site maintained by the University of Geneva. Additionally, the external databases can include a database providing information regarding biochemical reactions, including databases of published literature references describing and analyzing biochemical reactions. Where a database included in the computer systems of the present invention is a public computer database that does not identify information that is relevant for a particular biochemical reaction network, the computer system either includes a function for performing biochemical reaction network reconstruction, or includes identification of the database entries that pertain to a particular biochemical reaction network. Additionally, there are several databases with biochemical pathway information, these databases include, for non-limiting example, EcoCyc, KEGG, WIT, and EMP. These databases can be used to provide the information to reconstruct the metabolic models.

In addition to the database discussed above, the computer system typically includes a user interface capable of receiving a selection of one or more biochemical reaction networks for optimization and/or comparison, and capable of receiving a selection of an optimal performance. The interface can be a graphic user interface where selections are made using a series of menus, dialog boxes, and/or selectable buttons, for example. The interface typically takes a user through a series of screens beginning with a main screen. The user interface can include links that a user may select to access additional information relating to a biochemical reaction network.

The function of the computer system that carries out the optimization methods typically includes a processing unit that executes a computer program product (process) that includes a computer-readable program code embodied on a computer-readable medium and/or present in a memory function connected to the processing unit. The memory function can be, for example, a disk drive (optical and/or magnetic), Random Access Memory, Read Only Memory, or Flash Memory.

The computer program product, including instructions, that is read and executed by a processing unit of a computer system, includes modules (sub-programs) and processes/functions, such as a computer-readable program code embodied on a computer-readable medium for implementing aspects of the computer program, including, without limitation, functions and algorithms. The program code is capable of interacting with a database, for example, as described above, and typically effects the following steps within the computing system: providing an interface for receiving a selection of a desired performance of the networks; determining the desired optimal properties, displaying the results of the determination, and altering the biochemical reaction network, before recalculating optimal properties of the biochemical reaction network, and repeating the process until a desired performance is achieved. Altering the biochemical reaction network can be performed based on an alteration identified by a user, or can be performed automatically by the program code. The computer program can further provide an identification of database entries that are part of a reconstructed biochemical network, or can perform biochemical reaction network reconstruction. Furthermore, the computer program can provide a function for comparing biochemical reaction networks to identify differences in components and properties. Lastly, the computer program may comprise a process or module for receiving data obtained from a cell culture (automatically or manually) and a process or module for controlling one or more external devices, such as a solenoid valve, for controlling a rate of input into a culture of one or more culture medium constituents, such as water, sugars, oxygen, carbon dioxide, buffers, chelating compounds, etc., or for controlling other physical or chemical parameters of the culture, such as a heating device or stirrer.

The computer-readable program code can be generated, for example, using any well-known compiler that is compatible with a programming language used to write software for carrying out the methods of the current invention. Many programming languages and software programs are known that can be used to write software to perform the computational methods described herein, such as, for example and without limitation MATLAB® (The Mathworks, Inc., Natick, Mass.), or similar software.

As mentioned above, an aspect of the methods described herein can further include steps that involve adaptive evolution of a cultured strain to achieve a desired performance. Virtually any cell can be used with the methods described herein including, for example, a prokaryotic cell, or a eukaryotic cell such as a fungal cell or an animal cell including a cell of an animal cell line. However, a biochemical reaction network of the cell, or the cell of a closely related organism, must be sufficiently characterized to allow a high quality reconstruction of the comprehensive, substantially whole, and/or whole biochemical reaction network in a computer. Preferably, essentially the entire genome of the organism has been sequenced and genes encoding biomolecules, typically proteins, involved in the biochemical reaction network have been identified.

The genetic makeup of a cell can be constructed to contain the biochemical reactions that meet the desired performance to produce a cell with a potential to meet the desired performance. This can be achieved using the indigenous list of reactions in the cell and by adding and subtracting reactions from this list using genetic manipulations to achieve the reaction list capable of achieving the desired performance criteria, identified by the steps performed in silico described above. For example, reactions can be added or subtracted from the list by adding, changing, or deleting all or portions of one or more genes encoding one or more biomolecules involved in the reaction, for example by adding, changing, or deleting protein coding regions of one or more genes or by adding, changing, or deleting regulatory regions of one or more genes. In addition, for example, reactions can be added or subtracted from the list by altering expression of regulatory components (e.g., transcription factors) that effect the expression of one or more biomolecules involved in one or more reactions of the reaction list. The resulting engineered cell may or may not display the optimal properties calculated ahead of time by the in silico methods using the iterative optimization procedure described above.

After a cell has been identified or constructed to have a potential to meet the desired performance, it is placed in culture under a specified environment. The specified environment is determined during the optimization procedure. That is, the optimization procedure calculates properties of the network under various environments, as described above, and identifies the specified environment in which the desired performance is achieved.

In one aspect of the methods described herein, a cell culture is optimized to produce a desired growth rate and/or biomass accumulation, or to produce a specific end-product or products, such as a fatty acid, methanol or ethanol for biofuel production, antibiotic, recombinant protein, sugar, polymer, etc. At the inception of a culture, the methods and computational processes described herein are used to determine optimal cultural parameters, such as optimal metabolite concentration. For instance, glucose may be optimally present in a certain concentration in the culture media in order to optimize growth rates without, for example, harmful accumulation of by-products. In another embodiment, an amino acid may be added to the culture medium, or a culture medium constituent may be limited in order to maximize production of a protein, such as a recombinant protein (for instance, too rapid production of a protein may be counterproductive, resulting in cytoplasmic crowding by the overproduced protein, preventing optimal metabolic activity of the cell and/or optimal function of the cellular processes involved in making the protein, such as limitation of inducers or necessary transcription factors). Culture conditions, such as glucose concentration, $pO_2$, pH, etc., may be monitored occasionally, at fixed time periods, or continuously, and the data input either automatically or manually into a computer program to determine if optimal conditions for the desired outcome are present and, optionally, to determine steps, such as the addition of sugars, $CO_2$, $O_2$, buffers, chelating agents, water, new media, etc., necessary to bring the culture to, or back to, optimal conditions. The computer system may be configured (that is, comprises necessary software, hardware and peripheral components), to automatically bring the cell culture to optimal parameters by automatically adding or removing materials from the cell culture to optimize a desired outcome.

In one example, the cell culture is a continuous culture and a computerized system is used to monitor culture parameters, including, for example and without limitation, temperature, sugar (or other carbon and/or nitrogen source) concentration, pH, $pO_2$, and/or any other relevant parameter or indicator of culture status. The computerized system also contains hardware and computer processes for controlling flow of new culture media into the cell culture; flow of culture media (containing biomass) out of the culture and the addition of one or more culture constituents, such as a carbon source, a nitrogen source, a buffer, $O_2$ or $CO_2$, and/or an amino acid(s) to the culture. A person of skill in the art can readily configure and program such as system.

According to another non-limiting embodiment of the methods described herein, in which a cell is required to adapt to culture conditions, the cells are cultured for a sufficient period of time and under conditions to allow the cells to evolve to the desired performance. That is, adaptive evolution of natural or engineered strains can be carried out as guided by the general optimization methods or procedures. Natural strains that have not experienced a particular environment or genetically altered strains can be analyzed by the network reconstruction and optimization procedures disclosed above. These strains can then be put under a selection pressure consistent with the desired function of the organisms and evolved towards the predetermined performance characteristics. The cells may achieve the desired performance without additional adaptive evolution. That is, the sufficient period of time for culturing the cells, may be immediately after the genetic makeup of the cells is constructed using the methods described herein without the need for further adaptive evolution.

In other words, extended cultivation of a non-optimal or non-evolved strain can be performed to optimize or evolve the metabolic network toward the optimal solution that is achievable under the defined environmental conditions. The practice of this evolutionary process requires on the order of weeks to years to optimize a metabolic network depending on how far it is from the optimal conditions at the beginning of the evolutionary process, and how difficult it is to achieve the necessary changes through random mutation and shifts in regulation of gene expression. This process can be accelerated by the use of chemical mutagens and/or radiation. Additionally, the process can be accelerated by genetically altering the living cell so that it contains the biochemical reactants determined by the in silico method described above, that achieve a desired performance.

Methods are known in the art for culturing cells under specified environmental conditions. For example, if the cell is E. coli, and the desired performance is a desired growth rate, the procedure set out below can be used. This procedure can be readily adapted for use with other bacterial cells and/or other performance criteria. Additionally, the procedures can be readily developed for use with other cell types such as animal cells. For example, the methods can be readily adapted for use with other culturing systems, such as large scales systems in which cells adhere to a culturing vessel. The culturing methods may be adapted for high-throughput analysis, as known in the art.

If a strain needs to be directionally evolved to achieve the desired performance, then following the construction of the metabolic reaction network in the chosen host strain, the cells are typically stored frozen at −80° C. with 30% glycerol. For each adaptive evolutionary process, frozen stocks can be plated on LB agar and grown overnight at 37° C. From the plate, individual colonies can be identified that arose from a single cell. An individual colony can be used to inoculate a liquid culture, known as a pre-culture. Pre-cultures inoculated from a single colony of the respective strain are grown overnight in the defined medium for the subsequent evolutionary process. A pre-culture sample is taken the following day, typically at mid-log phase (in the middle of logarithmic growth) of growth to inoculate the culture conditions that define the environment that the adaptive evolution is to take place. Batch bioreactors or other suitable culture vessels are then initiated. This, typically would be done at 250 mL volumes in micro-carrier spinner flasks inside a temperature controlled incubator on top of a magnetic stir plate, set at suitable, typically high, speed to ensure sufficient aeration and at the optimal growth temperature (37° C. for wild type E. coli) for any given strain. Other frequently used cultivation procedures known in the art can also be used.

After a suitable time period, typically the following day for E. coli (before the culture reaches stationary phase), an aliquot of the culture now in mid-log phase is serially transferred to a new spinner flask containing fresh medium. If the culture is being optimized for growth rate, stationary phase must be avoided to ensure that the selection criterion is growth rate. Then serial transfers are performed at fixed time intervals (typically every 24 hours depending on the growth rate) at mid-log phase and the volume of the inoculum into the new culture vessel can be adjusted accordingly based on the increase in growth rate.

Growth rate is thus monitored frequently, typically on a daily basis in order to determine the proper volume of the inoculum to use for the next serial transfer. This serial cultivation process is repeated sufficiently often to allow the cells to evolve towards its optimal achievable growth under the conditions specified through the medium composition.

The growth and metabolic behavior typically is monitored during the adaptive evolutionary process to determine how the population is evolving over time. At fixed time intervals, typically every few days, the culture is tested for metabolic and growth behavior, by measuring the oxygen uptake rate, substrate uptake rate and the growth rate. The results are then plotted as a data point on the phenotype phase plane. Movement of the so-determined data point towards the line of optimality would indicate evolution towards optimal growth behavior. These measurements of the membrane transport fluxes along with the growth rate are repeated until the cells are observed to be operating their metabolic network such that the data points lie at the optimal conditions. The evolutionary process can then be continued until there is no further increase in the optimal performance, e.g., growth rate. If no further change is observed, then maximal growth rate has been achieved for the given conditions.

Byproduct secretion can be monitored by HPLC or other suitable methods of analytical chemistry to assess changes in metabolism that are implicated in the evolution towards optimal growth behavior. For these studies it typically is imperative to determine a correlation of dry weight vs optical density for the evolved strain since this will be different from the wild type. In addition to monitoring the growth rate and steady state growth, the cultures are inspected for any signs of possible contamination or co-evolution with a mutant subpopulation. Aliquots for each day of culture are kept refrigerated as a backup in the event of any contamination, and the phenotype of the culture is ascertained by plating samples of the culture and inspecting for any differences in colony morphology or different mutants. On a daily basis, the optical density of the culture, time of inoculation, inoculum volume, growth rate, and any signs of contamination, can be logged. Samples are also frozen at −80° C. in 30% glycerol for each day of culture for any possible further use.

According to a further embodiment, provided herein is a computer-implemented method for achieving an optimal function of a biochemical reaction network in cells in a cell culture, including prokaryotic or eukaryotic cells, for example and without limitation, bacterial, fungal (including yeast), mammalian and cancer cells. The method comprises (a) calculating in a computer one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. According to one embodiment, the optimization method further comprises calculating one or more of a maximum metabolic rate, an optimal metabolite concentration and an enzyme activity by applying a computational optimization method to a kinetic model of a metabolic pathway. In an example of an implementation of the method, the method further comprises culturing a cell under culture conditions that favor achievement of the optimal function. Optionally, the method further comprises: (c) constructing the genetic makeup of a cell to contain the biochemical reactions (d) placing the cell constructed under (c) in culture under a specified environment to obtain a population of cells; and (e) cultivating the cells as in step (d) for a sufficient period of time and under conditions to allow the cells to evolve to the desired optimal function determined under (a), wherein the biochemical reaction network comprises a comprehensive biochemical reaction network. In one embodiment, the optimal function is maximizing biomass production. In another, the optimal property is maximal internal yield of ATP. hi a further embodiment, the solvent capacity accounts for ribosome density in the cells in the cell culture as a measure of ribosomal-, enzyme associated-, and non-metabolic proteins in the cells or accounts for mitochondria as a subcellular compartment in the cells in the cell culture. According to one embodiment, the method comprises a model of a pathway for ATP generation that involves reactions in the serine biosynthesis, one-carbon metabolism and the glycine cleavage system.

According to another embodiment, also provided is a computer readable medium having stored thereon instructions which, when executed by a processor, cause the processor to implement a process implementing a computer model for achieving an optimal function of a biochemical reaction network in cells in a cell culture. The process comprises: (a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. The computer-readable medium may include in its various embodiments instructions which, when executed by a processor, cause the processor to implement a process implementing a computer model for achieving any method described in this document, including, without limitation, the following: a computer readable medium as described above in which the optimization method further comprises calculating one or more of a maximum metabolic rate, an optimal metabolite concentration and an enzyme activity by applying a computational optimization method to a kinetic model of a metabolic pathway; a computer readable medium as described above wherein the optimal function is maximizing biomass production; a computer readable medium as described above in which the optimal property is maximal internal yield of ATP; a computer readable medium as described above in which the solvent capacity accounts for ribosome density in the cells in the cell culture as a measure of ribosomal-, enzyme associated-, and non-metabolic-proteins in the cells; a computer readable medium as described above in which the solvent capacity accounts for mitochondria as a subcellular compartment in the cells in the cell culture; a computer readable medium as described above in which the cells are human cells; a computer readable medium as described above in which the cells are cancer cells; and a computer readable medium as described above that comprises a model of a pathway for ATP generation that involves reactions in the serine biosynthesis, one-carbon metabolism and the glycine cleavage system.

According to further embodiments, a device is provided that comprises the computer-readable medium described according to any embodiment herein, and a processor for executing the instructions on the computer-readable medium for achieving an optimal function of a biochemical reaction network in cells in a cell culture. As above, the instructions, when executed by a processor, cause the processor to implement a process implementing a computer model for achieving an optimal function of a biochemical reaction network in cells in a cell culture, comprising: (a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and (b) initiating or maintaining the optimal cell culture parameter in the cell culture to achieve the optimal function of the biochemical reaction network in the cells. As above, The computer-readable medium may include in its various embodiments instructions which, when executed by a processor, cause the processor to implement a process implementing a computer model for achieving any method described in this document, including, without limitation, the following: a computer readable medium as described above in which the optimization method further comprises calculating one or more of a maximum metabolic rate, an optimal metabolite concentration and an enzyme activity by applying a computational optimization method to a kinetic model of a metabolic pathway; a computer readable medium as described above wherein the optimal function is maximizing biomass production; a computer readable medium as described above in which the optimal property is maximal internal yield of ATP; a computer readable medium as described above in which the solvent capacity accounts for ribosome density in the cells in the cell culture as a measure of ribosomal-, enzyme associated-, and non-metabolic-proteins in the cells; a computer readable medium as described above in which the solvent capacity accounts for mitochondria as a subcellular compartment in the cells in the cell culture; a computer readable medium as described above in which the cells are human cells; a computer readable medium as described above in which the cells are cancer cells; and a computer readable medium as described above that comprises a model of a pathway for ATP generation that involves reactions in the serine biosynthesis, one-carbon metabolism and the glycine cleavage system. The device also may comprise additional components for implementation of the instructions, including, without limitation one or more sensors, such as pH, gas (e.g. $O_2$ or $CO_2$), chemical or temperature sensors, one or more culture vessels, one or more heating elements or cooling elements, reservoirs for storing storing cell culture medium, cell culturing ingredients or an analytical composition (e.g., a composition useful in testing a cell culture parameter) and one or more mechanisms for dispensing the storing cell culture medium, cell culturing ingredients or an analytical composition into a cell culture or other container, such as a cuvette, or for taking and/or analyzing samples from one or more cell culture vessels, including, mechanical, fluidic and robotic mechanisms, a display (e.g., a monitor); one or more analytical devices, such as a spectrophotometer for measuring cell density and/or the results of an analytical assay; and one or more communication subsystems for receiving or transmitting data, including, without limitation wired communication devices, such as Ethernet, modem, FIREWIRE, Universal Serial Bus (USB), and THUNDERBOLT devices, or wireless communication devices such as BLUETOOTH or 802.11g or n protocol devices. The computer-readable medium may be located in a device comprising the processor or in communication with a device, such as with one or more external storage media. As would be apparent to those of ordinary skill one or more aspects of the integrated system, such as reaction parameters, might be located remotely and downloaded or otherwise integrated into the system of implementing the methods described herein.

In one embodiment of the implementation of the methods described herein, the methods and computer-readable media are configured to be executable within a device which comprises a processor and a computer-readable medium as part of a computer subsystem of the device. As indicated above, the device may comprise any of the innumerable components for culturing cells, analyzing cells, and otherwise processing cells, including, without limitation, mechanical, fluidic, and robotic components useful for implementing the methods described herein—as would be readily apparent to one of ordinary skill in the art. The processor executes instructions for implementing the method, namely an in silico model as described herein. The model comprises according to one non-limiting embodiment, an intracellular space and an extracellular space. The intracellular space comprises steric (volume, spatial or molecular crowding) limitations attributable to cellular components, including without limitation: organelles, cytoskeleton, and other intracellular structures within the subcellular compartment, such as nucleus, mitochondria, microtubules, microfilaments, intermediate filaments, and further comprises enzymes and enzyme structures such as ribosomes as well as other constituents, including sugars, metabolites, and nucleic acids. Components in the intracellular space have one or more size (spatial constraint, e.g., volume) and/or kinetic parameters associated with them, and the components interact within the model according to those size and/or kinetic parameters. The extracellular compartment may include such influences as waste accumulation, temperature, pH, extracellular compositions, such as sugars, waste materials, buffers, cytokines, growth factors, extracellular matrix and/or cell growth scaffold, cell wall, cell culture vessel characteristics, etc., each of which can be assigned a kinetic relationship with the modeled cells and the constituents thereof.

The following examples are provided as non-limiting examples of the invention described herein.

EXAMPLES

The following is a table of abbreviations used in this example and throughout.

TABLE 1

List of abbreviations used herein

| Substrates | Abbreviations | Genes | Encoded enzyme |
| --- | --- | --- | --- |
| G6P | GLUCOSE-6-PHOSPHATE | ptsG | Glucose:PEP phosphotransferase |
| F6P | FRUCTOSE-6-PHOSPHATE | pfk | Phosphofructokinase |
| FDP | FRUCTOSE-1,6-DIPHOSPHATE | gapA | Glyceraldehyde-3-phosphate dehydrogenase |
| DHAP | DIHYDROXY ACETONE PHOAPHATE | tpiA | Triosephosphate isomerase |
| GAP | HLYCERALDEHYDE PHOSPHATE | pgk | Phosphoglycerate kinase |
| 1,3-DPG | 1,3-DIPHOSPHO GLYCERATE | pykA | Pyruvate kinase |
| 3-PG | 3-PHOSPHOGLYCERATE | sucA | a-Ketoglutarate dehydrogenase |
| 2-PG | 2-PHOSPHOGLYCERATE | fumA | Fumarase |
| PEP | PHOSPHOENOL PYRUVATE | mdh | Malate dehydrogenase |
| PYR | PYRUVATE | pta | Phosphotransacetylase |
| AC | ACETATE | ackA | Acetate kinase |
| ACCOA | ACETYL COENZYME A | gltA | Citrate synthase |
| ACTP | ACETYL PHOSPHATE | zwf | Glucose-6-phosphate dehydrogenase |
| OAA | OXALOACETATE | ppc | PEP carboxylase |
| CIT | CITRATE | aceE | Pyruvate dehydrogenase |
| ICIT | ISOCITRATE | eno | Enolase |
| AKG | ALPHA-KETOGLUTARATE | pgi | Phosphoglucose isomerase |
| SUCCoA | SUCCINYL COENZYME A | fba | Fructose-1,6-bisphosphate aldolase |
| SUC | SUCCINATE | | |
| FUM | FUMARATE | | |
| MAL | MALATE | | |

Example 1

Here we study the impact of the limited solvent capacity on E. coli cell metabolism at different physiological growth conditions. We demonstrate that this constraint is relevant for fast growing cells, and predict the existence of a metabolic switch between cells growing at low and high nutrient abundance, respectively. We carry out flux measurements of several reactions in the E. coli central metabolism, observing a partial agreement with the model predictions. Moreover, to uncover the regulatory mechanisms that control the changes in flux rates, we perform gene expression and enzyme activity measurements, finding that the switch is controlled predominantly at the enzyme activity level implemented by changes in the activity of a few key enzymes in the E. coli central metabolism. Finally, we discuss the potential relevance of the limited solvent capacity constraint to experimental observations in other organisms.

Estimation of Crowding Coefficients:

The E. coli intracellular density is C=0.34 g/ml. The specific volume was estimated for several proteins using the molar volumes and masses reported in Lee B, *Proc Natl Acad Sci USA* 1983, 80:622-626, resulting in average of 0.73 ml/g and standard deviation of 0.02 ml/g. The enzymes' turnover rates were obtained from the BRENDA database (Schomburg I, et al. *Nucleic Acids Res* 2002, 30:47-49) for 102 E. coli enzymes.

Metabolic Flux Predictions:

The Flux Balance analysis with Molecular Crowding is implemented by solving the following optimization problem: maximize the biomass production rate subject to the constraints: balance in the production and consumption of each metabolite (flux balance), the maximum capacity constraint for the carbon source uptake rate and the solvent capacity constraint (Eq. 3). After expressing the reaction's stoichiometric coefficients in units of mol/dry biomass, the maximum growth rate corresponds to the biomass production rate, where biomass production is an auxiliary reaction containing as substrates the cellular components in their relative concentrations and as product the cell's biomass.

The crowding coefficients were modeled as noise, assigning them randomly selected values from a list of estimated values for about 700 E. coli enzymes. The predictions for all fluxes were calculated (not shown)

Following the same procedure as for glucose, we also made predictions for the E. coli metabolic fluxes when growing on glycerol, lactate and succinate. The increase of the carbon source concentration in the growth medium was modeled as an increase of the maximum capacity of the corresponding carbon source uptake flux. For each maximum capacity we computed the fluxes that maximize the biomass production rate, obtaining a prediction for the optimal flux of all reactions and the optimal biomass production rate. Because the biomass production rate equals the growth rate, using these predictions we can analyze the behavior of metabolic fluxes as a function of the growth rate.

Bacterial Strain and General Growth Conditions:

The E. coli K12 strain MG1655 (F$^-\lambda^-$ ilvG rfb50 rph1) was used throughout the work. In order to obtain biomass samples for flux measurements, 20-ml of the overnight grown culture (~8-10 h) of wild-type cells in LB-medium was inoculated in 980-ml M9 minimal medium (Sigma) containing 2 g/L glucose, where 90% was natural glucose and the remaining 10% was labeled glucose $[1,2-^{13}C_2]$ glucose (with >99% purity and 99% isotope enrichment for each position, [Cambridge Isotope Laboratories, Andover, Mass.]). Cells were grown in a continuous growth mode at 5 different dilution rates (0.1, 0.25, 0.4, 0.55, and 0.72 L h$^{-1}$) in a Labfors bioreactor (Infors, Switzerland). The growth of the bacterial culture was regularly monitored at $A_{600nm}$ to document steady state at all dilution rates. The dissolved oxygen was set at 100% initial value, and sterile air was continuously sparged into the medium. Growth parameters, such as pO$_2$, pH, temperature (37° C.) and agitation (~400 rpm) were continuously monitored using microprocessor probes. The pH of the medium was constant around 7.0 and was controlled with regular adjustments by automatic supply of acid (10% H$_3$PO$_4$) and base (2N NaOH) using two peristaltic pumps. For determining intracellular metabolic enzyme activities and global transcriptome profiles, the bacterium was grown under similar conditions (except only natural glucose was used as source of carbon) in three separate experiments, and biomass samples were collected at all five-dilution rates. Biomass samples for intracellular enzyme activity, gene expression and flux determination were harvested at the end of each major dilution rates indicated by constant $A_{600nm}$ (optical densities) and $pO_2$ concentrations in the growth medium.

Metabolic Enzyme Activity Assays:

30-ml samples for enzyme assays were collected for various dilution rates at the end of each dilution rate. The cell pellets for enzyme assays were harvested by centrifugation at 4,000×g at 4° C. for 10 min. These cell pellets were re-suspended and washed in 100 mM Tris-HCl (pH 7.0) sonication buffer containing 20 mM KCl, 5 mM $MnSO_4$, 2 mM DTT and 0.1 mM EDTA. The cells were disrupted by 3 sonication cycles of 30 sec each in a sonicator (Fisher Scientific) to recover maximum possible yield of enzyme. The cell debris was removed by centrifugation and the resulting cell extract (supernatant) was immediately used for enzyme assays or stored at −20° C. All operations were carried out on ice. The supernatant of this sample was used to determine total protein concentration in enzyme samples using standard Bradford's assay (Biorad, Richmond, Calif.). This sample was also used for estimation of quantitative assay of endogenous enzymes. The method of continuous spectrophotometric rate determination with time was followed for measurement of activities of the enzymes of metabolic pathways. All the enzyme assays were done at 30° C. in a thermostatically controlled UV/Vis spectrophotometer (Cary 500) with 1-cm light path. All components the reaction mixture and respective substrates were pipetted out in a quartz cuvette (Fisher Scientific) and blanks were adjusted. Reactions were initiated by adding supernatant from the sonicated enzyme samples to give a final volume of 1 ml. The millimolar extinction coefficients for $NAD^+$, NADH, $NADP^+$ and NADPH was 6.22 $cm^{-1}$ $mM^{-1}$ at 340 nm, and those of methyl viologen and benzyl viologen at 578 nm was 9.78 and 8.65 $cm^{-1} \cdot mM^{-1}$, respectively, whereas the millimolar extinction coefficient value for 5-mercapto-2-nitrobenzoic acid at 412 nm was 13.6 $cm^{-1}$ $mM^{-1}$. For all enzyme assays described below, we define 1 unit of enzyme as the amount of enzyme required to convert 1 μmol of substrate into specific products per minute per milligram of protein under defined conditions of pH and temperature. Most enzyme assay protocols used were the standard assay protocols from Sigma (St. Louis, Mo., USA), expect few, which were obtained from the published literature (Peng, L. et al. Appl Microbiol Biotechnol 61, 163-78; Van der Werf, M. J., et al., Arch Microbiol 167, 332-342; and Zhao, J., et al., (2004) Appl Microbiol Biotechnol 64, 91-98.).

The assay conditions for various enzymes were as follows (the gene names are listed in parenthesis against the enzyme name): Glucose:PEP phosphotransferase (pts): 0.1 M Tris-HCl (pH 8.4), 10 mM $MgCl_2$, 1 mM DTT, 1 mM $NADP^+$, 10 mM D-glucose, 3 U glucose-6-phosphate dehydrogenase, 10 mM PEP. Phosphofructose kinase (pfkA): 50 mM imidazol-HCl (pH 7.0), 0.05 mM ATP, 5 mM $MgCl_2$, 1 mM EDTA, 0.25 mM NADH, 0.25 mM fructose-6-phosphate (F6P), 0.5 U aldolase, 0.5 U glyceraldehyde phosphate dehydrogenase, 0.5 U triose phosphateisomerase. Fructose-1,6-bisphosphate aldolase (fbaA): 0.05 M Tris-HCl (pH 7.5), 0.1 mM cysteine-HCl, 0.1 M potassium acetate, 2 mM FDP, 0.7 mM CoC12, 0.25 mM NADH, 20 U triose phosphate isomerase, 2 U glycerol-3-phophate dehydrogenase. Glyceraldehyde-3-phosphate dehydrogenase (gapA): 0.1 mM Tricine-HCl (pH 8.1), 5 mM potassium phosphate, 20 mM neutralized sodium arsenate, 2 mM FDP, 2 mM DTT, 1 mM $NAD^+$, 1 U aldolase. Triosephosphate isomerase (tpiA): 300 mM triethanolamine buffer (pH 7.8), 0.2 mM NADH, 1 U glycerolphosphate dehydrogenase, 5 mM glyceraldehyde-3-phosphate. Phosphoglycerate kinase (pgk): 0.1 M triethanolamine buffer (pH 7.8), 1 mM EDTA, 2 mM $MgSO_4.7H_2O$, 1 U glyceraldehyde-phosphate dehydrogenase, 1 mM ATP, 10 mM 3-phosphoglycerate. Pyruvate kinase (pykA): 0.1 M Tris-HCl (pH 7.5), 5 mM ADP, 1 mM DTT, 10 mM KCl, 15 mM $MgCl_2$, 0.5 mM phosphoenol pyruvate, 0.25 mM NADH, 10 U lactate dehydrogenase. α-Ketoglutarate dehydrogenase (sucA): 0.2 M phosphate buffer (pH 7.2), 1 mM CoASH, 0.1 M cysteine-HCl (pH 7.2), 10 mM $NAD^+$ (pH 7.2), 3 mM α-ketoglutarate. Fumarase (fumA): (assay based on formation of fumarate at 240 nm) 0.1 M Tris-HCl buffer (pH 7.2), 50 mM L-malate. Malate dehydrogenase (mdh): 2.5 ml 0.1 M Tris-HCl (pH 8.8), 0.1 ml 0.1 mM sodium malate, 0.1 ml 10 mM $NAD^+$ and cell extract, and water to a final volume of 3 ml. Phosphotransacetylase (pta): 0.1 M Tris-HCl (pH 7.8), 0.2 mM CoA, 30 mM $NH_4Cl$, 1.0 mM DTT, 1.0 mM $NAD^+$, 5.0 mM L-malate, 4 U citrate synthase, 20 U malate dehydrogenase, 2.0 mM acetyl phosphate. Acetate kinase (ackA): 0.1 M Tris-HCl (pH 7.4), 0.8 M potassium acetate, 0.2 M KCl, 4 mM ATP, 4 mM $MgCl_2$, 1.6 mM PEP, 0.4 mM NADH, 4 U pyruvate kinase, 55 U lactate dehydrogenase; Citrate synthase (gltA): 100 mM Tris-HCl (pH 8.0), 8 mM Acetyl CoA, 10 mM sodium oxaloacetate, 10 mM 5,5'-dithiobios-2-notrobenzoate; Glucose-6-phosphate dehydrogenase (zwf): 100 mM Tris-HCl (pH 7.5), 2.5 mM $MnCl_2$, 2 mM glucose-6-phosphate, 1 mM DTT, 1 mM $NADP^+$; PEP carboxylase (ppc): 66 mM Tris-HCl (pH 9.0), 10 mM $MgCl_2$, 10 mM sodium bicarbonate, 0.15 mM NADH, 2 U malate dehydrogenase, 5 mM phosphoenolpyruvate; Pyruvate dehydrogenase (aceE): 100 mM Tris-acetate (pH 7.8), 5 mM pyruvate, 0.1 mM CoA, 7 mM sodium arsenate, 2 mM methyl viologen; Enolase (eno): 100 mM Triethalomine buffer (pH 7.4), 5.6 mM phosphoglycerate, 0.35 mM β-NADH, 75 mM $MgSO_4$, 300 mM KCl, 1 mM ADP, 0.1 ml solution of 15 mM Tris-HCl (pH 7.4) mixed with 0.2% BSA. Phosphoglucose isomerase (pgi): 100 mM Tris-HCl (pH 7.8), 10 mM $MgCl_2$, 0.5 mM $NADP^+$, 10 U glucose-6-phosphate dehydrogenase, 2 mM fructose-6-phosphate.

The following equation was used for calculating enzyme activities for most of the enzyme (unless specified)

$$\text{Units/ml of enzyme} = \frac{\Delta A_{340nm}/\min(\text{Test}) - \Delta A_{340nm}/\min(\text{Blank})}{E.C. \times V_e} \times V_a \times DF$$

where, $V_a$: total volume (ml) of assay; DF: Dilution factor; E.C.: millimolar extinction coefficient of $NAD^+$, NADH, $NADP^+$ or NADPH at 340 nm was 6.22 $cm^{-1} \cdot mM^{-1}$, and those of methyl viologen and benzyl viologen at 578 nm was 9.78 and 8.65 $cm^{-1} \cdot mM^{-1}$, respectively, whereas it was 13.6 $cm^{-1} \cdot mM^{-1}$ for 5-mercapto-2-nitrobenzoic acid at 412 nm. $V_e$: Volume of enzyme $$\text{Units/mg protein} = \frac{\text{Units/ml enzyme}}{\text{mg protein/ml}}$$

Supernatants of the samples were also used for determining total protein concentrations using standard Bradford's assay (BioRad).

Flux Measurements and Analyses:

For flux analysis, biomass (from ~100 ml culture) and supernatant samples were collected at all five dilution rates. These samples were immediately flash frozen in liquid nitrogen and stored at −80° C. until further analysis. Flux rates were determined using a tracer-substrate based GC-MS and NMR metabolome mapping platform. The analyses included determining positional $^{13}$C tracer enrichment in multiple intermediary metabolites of glycolysis, glycogen synthesis, tricarboxylic acid cycle and their intracellular products from [1,2-$^{13}$C$_2$]-D-glucose, as described in detail below. The retention times and mass-to-charge (m/z) ion clusters of selected ions of bacterial and culture media metabolites were determined using mass isotopomer analysis (MIDA) (See, e.g., Lee W N, et al. *Anal Biochem* 1995, 226:100-112 and Lee W N et al., *Dev Neurosci* 1996, 18:469-477), and expressed as net fluxes by subtracting reverse fluxes from forward tracer incorporation patterns via reversible metabolic steps (Xu J, et al., *Anal Biochem* 2003, 315:238-246). Results were expressed as mmol/hr/g dry biomass glucose. Each experiment was carried out using triplicate cell cultures for each condition within each experiment, and the experiments were repeated once. Mass spectroscopic analyses were carried out by three independent automatic injections of 1 µl samples by the automatic sampler and accepted only if the standard sample deviation was less than 1% of the normalized peak intensity. Statistical analysis was performed using the Student's t-test for unpaired samples. Two-tailed significance at the 99% confidence interval (µ+/−2.58σ), P<0.01 indicated significant differences in glucose derived fluxes. For some reversible reactions, we measured both forward and reverse fluxes and calculated net fluxes towards product synthesis.

Glycogen Glucose and RNA Ribose Stable Isotope Studies:

RNA ribose and glycogen glucose were isolated by acid hydrolysis of cellular RNA after Trizol purification of cell extracts. Total RNA amounts were assessed by spectrophotometric determination, in triplicate cultures. Ribose and glycogen glucose were derivatized to their aldonitrile acetate form using hydroxylamine in pyridine with acetic anhydride (Supelco, Bellefonte, Pa.) before mass spectral analyses. We monitored the ion cluster around the m/z256 (carbons 1-5 of ribose) (chemical ionization, CI) and m/z217 (carbons 3-5 of ribose) and m/z242 (carbons 1-4 of ribose) (electron impact ionization, EI) to determine molar enrichment and the positional distribution of $^{13}$C in ribose. For glycogen glucose we monitored m/z327-332 using CI. By convention, the base mass of $^{12}$C-compounds (with their derivatization agents) is given as $m_0$ as measured by mass spectrometry as described elsewhere (Boros L G, et al., (2002) Drug Discov Today 7: 364-372). Ribose or glucose molecules labeled with a single $^{13}$C atom on the first carbon position (m1) recovered from RNA or glycogen, respectively, were used to gauge the ribose fraction produced by direct oxidation of glucose through the G6PD pathway. Ribose molecules labeled with $^{13}$C on the first two carbon positions (m2) were used to measure the fraction produced by transketolase. Doubly labeled ribose molecules ($m_2$ and $m_4$) on the fourth and fifth carbon positions were used to measure molar fraction produced by triose phosphate isomerase and transketolase.

Lactate:

Lactate from the cell culture media (0.2 ml) was extracted by ethylene chloride after acidification with HCl. Lactate was derivatized to its propylaminehepta-fluorobutyrate ester form and the m/z328 (carbons 1-3 of lactate) (chemical ionization, CI) was monitored for the detection of $m_1$ (recycled lactate through the PC) and $m_2$ (lactate produced by the Embden-Meyerhof-Parnas pathway) for the estimation of pentose cycle activity. In this study we recorded the $m_1/m_2$ ratios in lactate produced and released by bacterial cells in order to determine pentose cycle activity versus anaerobic glycolysis.

Glutamate:

Glutamate label distribution from glucose is suitable for determining glucose oxidation versus anabolic glucose use within the TCA cycle, also known as anaplerotic flux. Tissue culture medium was first treated with 6% perchloric acid and the supernatant was passed through a 3 cm$^3$ Dowex-50 (H+) column. Amino acids were eluted with 15 ml 2N ammonium hydroxide. To further separate glutamate from glutamine, the amino acid mixture was passed through a 3 cm$^3$ Dowex-1 (acetate) column, and then collected with 15 ml 0.5 N acetic acid. The glutamate fraction from the culture medium was converted to its trifluoroacetyl butyl ester (TAB). Under EI conditions, ionization of TAB-glutamate produces two fragments, m/z198 and m/z 152, corresponding to C2-O5 and C2-C4 of glutamate. Glutamate labeled on the 4-5 carbon positions indicates pyruvate dehydrogenase activity while glutamate labeled on the 2-3 carbon positions indicates pyruvate carboxylase activity for the entry of glucose carbons to the TCA cycle. TCA cycle anabolic glucose utilization is calculated based on the $m_1/m_2$ ratios of glutamate.

Fatty Acids:

Palmitate, stearate, cholesterol and oleate were extracted after saponification of cell pellets in 30% KOH and 100% ethanol using petroleum ether. Fatty acids were converted to their methylated derivative using 0.5N methanolic-HCL. Palmitate, stearate and oleate were monitored at m/z270, m/z 298 and m/z264, respectively, with the enrichment of $^{13}$C labeled acetyl units which reflect synthesis, elongation and desaturation of the new lipid fraction as determined by mass isotopomer distribution analysis (MIDA) of different isotopomers.

Gas Chromatography/Mass Spectrometry (GC/MS):

Mass spectral data were obtained on the HP5973 mass selective detector connected to an HP6890 gas chromatograph. The settings were as follows: GC inlet 250° C., transfer line 280° C., MS source 230° C., MS Quad 150° C. An HP-5 capillary column (30 m length, 250 µm diameter, 0.25 µm film thickness) was used for glucose, ribose and lactate analyses.

$^{13}$C, $^{1}$H and $^{31}$P Nuclear Magnetic Resonance studies of intracellular metabolites: Nuclear Magnetic Resonance (NMR) studies included acetate, alanine, betaine, cholines creatine, glucose, glutamate, glutamine, total glutathion (GSH), glycine, 3-hydroxybutyrate, myo-inositol, lactate, phosphocreatine, pyruvate, valine, hosphocreatine, creatine, ATP, ADP, AMP, NAD+, and total phosphomonoesters (PME) and phosphodiesters (PDE) extracted by ice-cold 0.9% NaCl, 12% PCA and 8 M KOH. The procedure included the transferring of 5 mL medium into a 15-mL tube (ice-bath), removing the rest of the medium thoroughly, washing cells with 6 mL of ice-cold NaCl, adding 2 mL ice-cold 12% PCA to the frozen cells or media and spinning at 1300 g for 20 min at 4° C. After transferring the supernatant into a new 50 mL tube and resuspending the pellet in 2 mL ice-cold 12% PCA in the old 50 mL tube we placed the tubes in an ultrasound ice bath for 5 min. We collected the supernatants, and lyophilized them in a freezedry system overnight. After re-suspending $^{13}$C, $^{1}$H and $^{31}$P spectra were obtained on a 9T Brucker vertical bore instrument for quantitative and $^{13}$C positional analyses.

Tricarboxylic Acid Cycle Analysis Using Trimethylsilyl (TMS) Derivatives:

Frozen pellets (−80° C.; wet 0.5 g) were powderized and extracted with 2:1 (volume) of chloroform-methanol using Omni-TH homogenizer. The slurry was centrifuged at 670 g for 20 min and the upper methanol-water phase was collected and treated with 200 µl of methoxylamine-HCl to protect keto and aldehyde groups. The lower chloroform phase is vortexed for 5 min with 10 mL of methanol-water 3:2 by volume. After 20 min centrifugation the two upper methanol-water phases were combined. The combined methanol-water phase was adjusted to pH 8.0 and evaporated under constant flow of Nitrogen gas in an exhaust fume hood. The residue was reacted with 100 µL of bis(trimethylsilyl) trifluoroacetamide with 10% trimethylchlorosilane (Regisil) at 70° C. for 70 minutes to form the TMS and MOX-TMS derivatives of TCA cycle metabolites. GC-MS analyses were carried out on an Agilent 5975 mass spectrometer, equipped with a model 6890 gas chromatograph and a Varian VF-5MS capillary column (60 m, 0.25 mm i.d., 0.25 mm film thickness.

Flux Data Analysis and Statistical Methods:

Each experiment was carried out using triplicate cell cultures for each condition within each experiment and experiments were repeated once. Mass spectroscopic analyses were carried out by three independent automatic injections of 1 µl samples by the automatic sampler and accepted only if the standard sample deviation was less than 1% of the normalized peak intensity. Statistical analysis was performed using the Student's t-test for unpaired samples. Two-tailed significance at the 99% confidence interval (µ+/−2.58σ), p<0.01 indicated significant differences in glucose-derived fluxes. For some reversible reactions, we measured both forward and reverse fluxes and calculated net fluxes RNA Preparation for Microarray Analysis:

At all five dilution rates, 10-20 ml of the cell culture was collected, mixed with 10% (v/v) of ice cold stop-solution (5% water-saturated phenol in absolute ethanol), and cell pellets were obtained by centrifugation at 4,500×g for 5 min at 4° C., followed by flash-freezing of pellets with liquid nitrogen. Cell pellets were stored at −80° C. until further use. RNA was isolated from the frozen cell pellets using Masterpure RNA isolation kit (Epicentre Biotechnologies, Madison, Wis.) and RNA samples were processed for transcriptome analysis using *E. coli* Affymetrix microarray chips, as described previously (Beg Q K, et al., *Proc Natl Acad Sci USA* 2007, 104:12663-1266.). Dchip method was used to analyze all microarray data as described in detail below.

The culture samples for microarray analysis were collected at all five dilution rates. Approximately, 10 ml of the cell culture was obtained and rapidly mixed with $\frac{1}{10}^{th}$ volume of the ice-cold stop-solution (5% water-saturated phenol in absolute ethanol) to inhibit any further transcriptional activity. The tubes were capped, and the sample and stop solution were mixed by inversion. The cell pellets were obtained by centrifugation at 4,500×g for 5 min at 4° C., were immediately flash frozen in liquid nitrogen, and were stored at −80° C. until further use. RNA was isolated from the frozen cell pellets using Epicenter's Masterpure RNA isolation kit (using manufacturer's product manual). The samples were also treated with DNAse for 1 hr at 37° C. to remove any DNA contamination in the RNA samples. 10 µg of all RNA samples were processed for transcriptome analysis using *E. coli* Affymetrix microarray chips by the Microarray Resource Centre, Department of Genetics and Genomics at Boston University School of Medicine as described previously (Beg Q K, et al., *Proc Natl Acad Sci USA* 104: 12663-12668). The microarray data was normalized using dChip (Li, C et al. *Genome Biology* 2001, 2: research0032.1-0032.11). The detailed microarray data from five dilution rates is extensive and is not shown.

Figure 7:
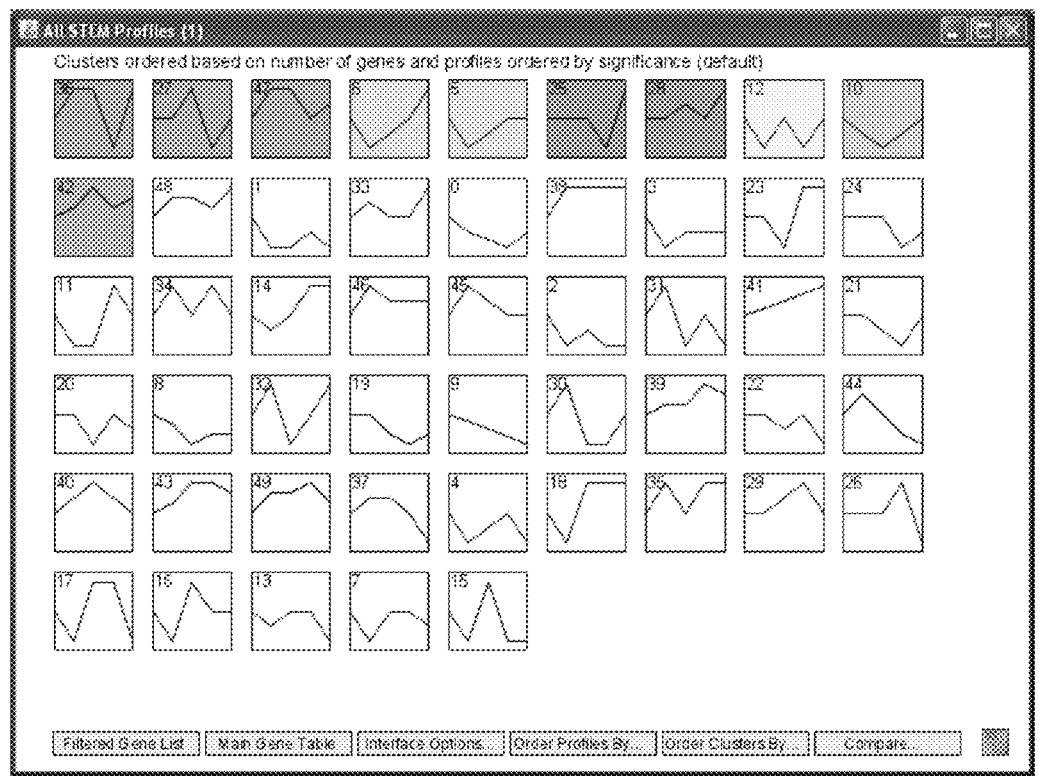
FIG. 7—Overview of STEM analysis showing all profiles considered. The profiles that are colored had a significant number of genes assigned, and similar profiles that were significant have the same color.
Figure 8A:
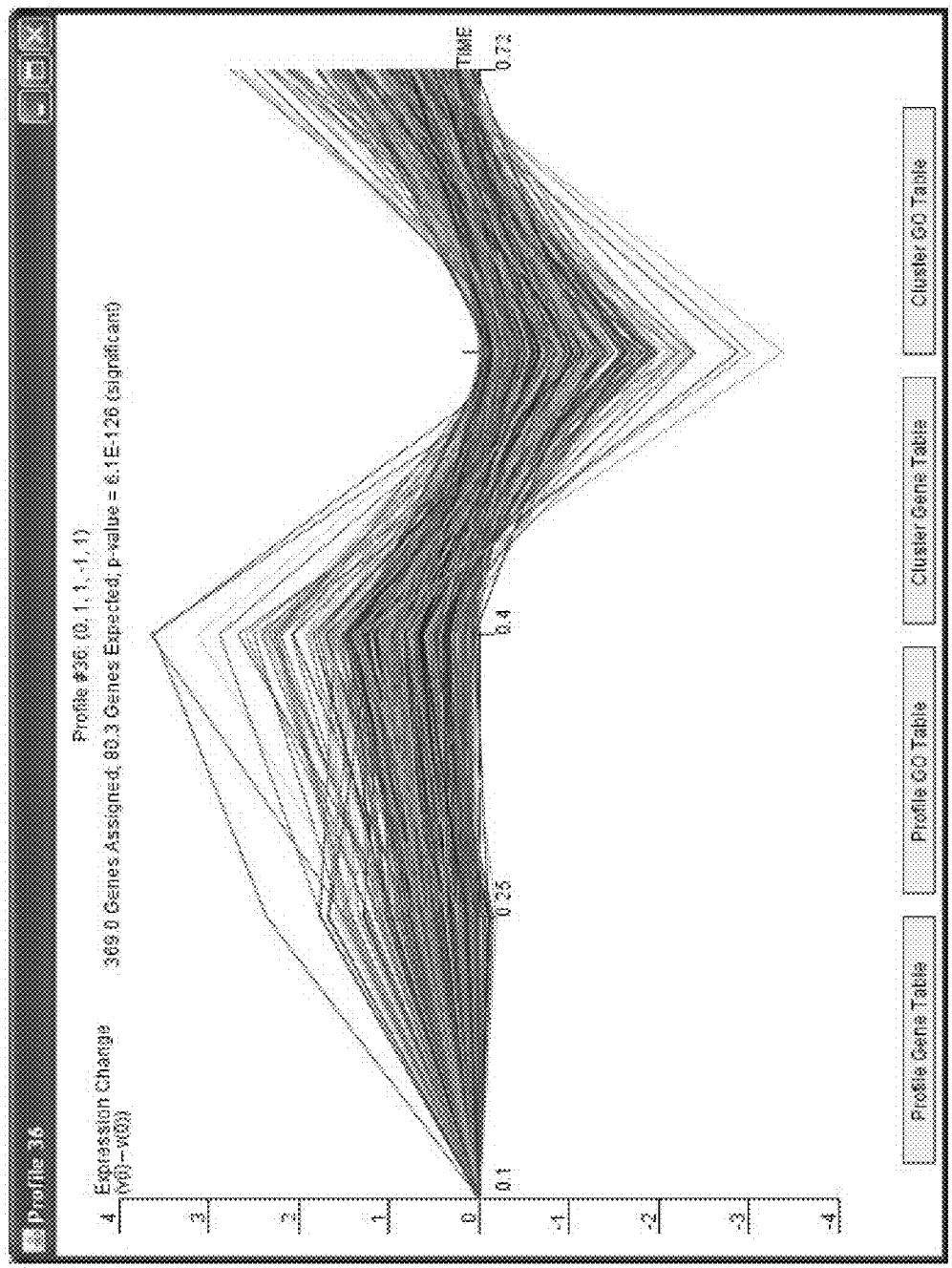
FIG. 8—FIGS. 8A-8C show Cluster 1 (Profiles 27, 36, and 47 from FIG. 7)
Figure 8B:
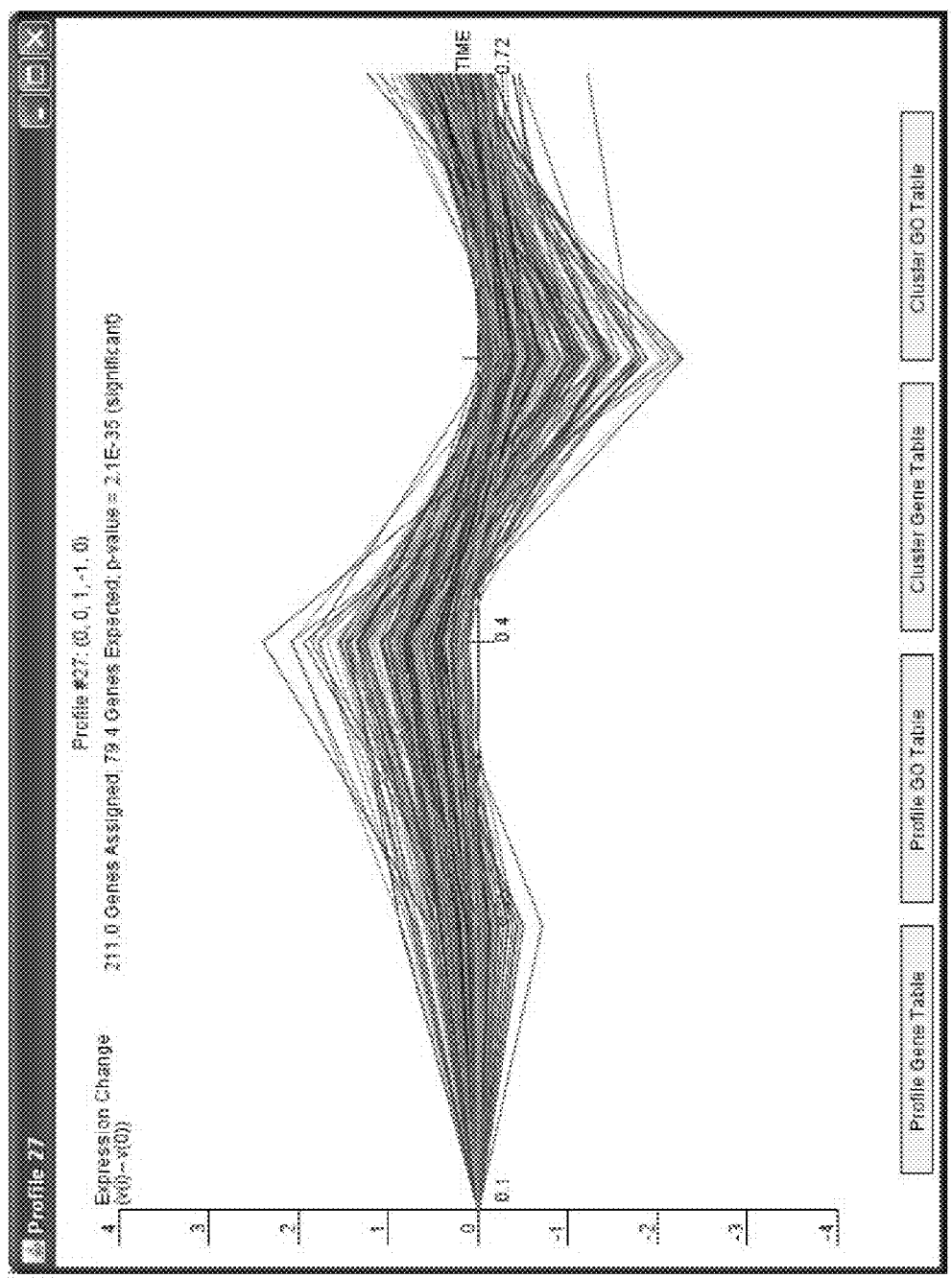
FIG. 8D shows GO results.
Figure 8C:
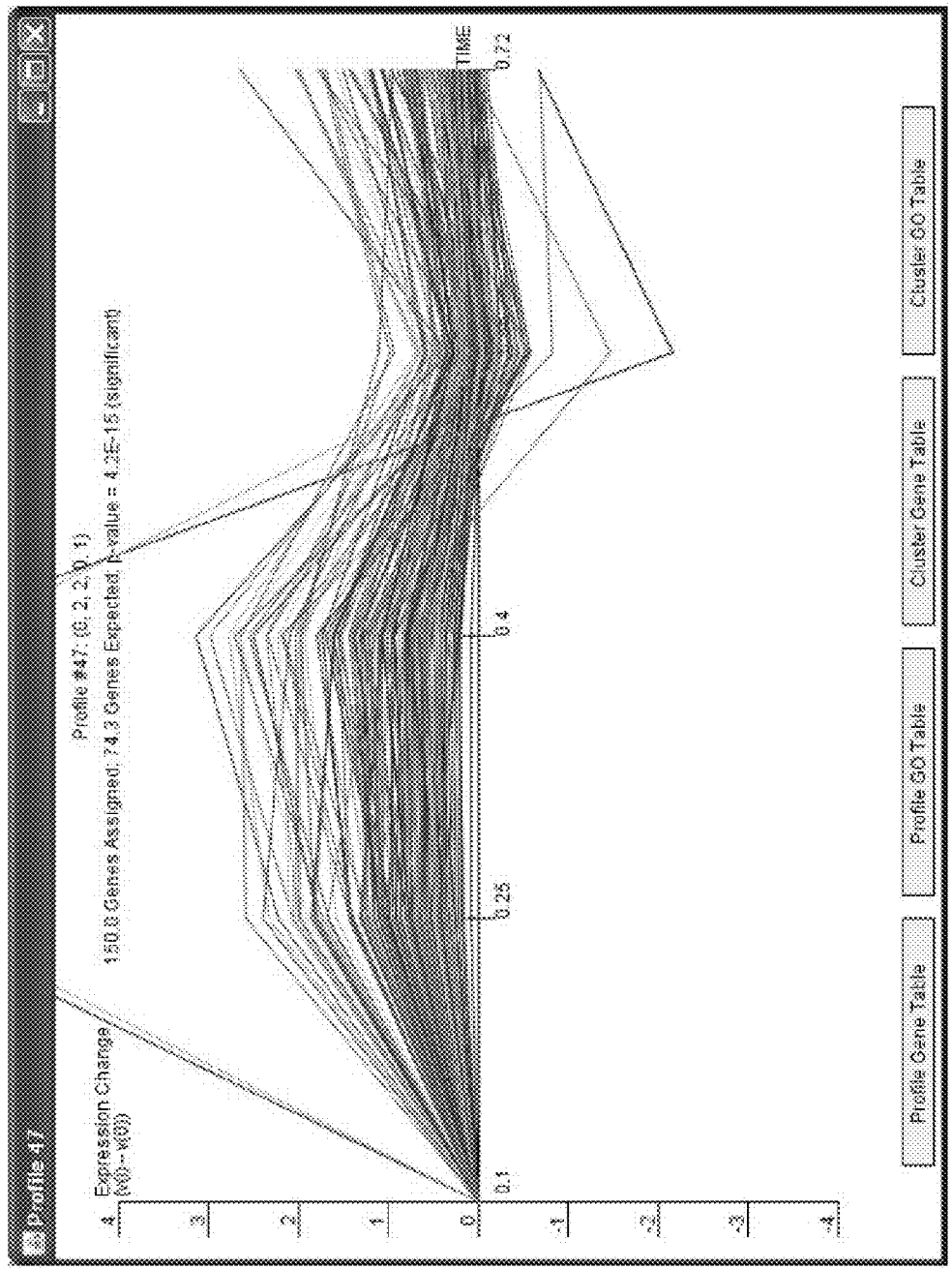
Figure 9A:
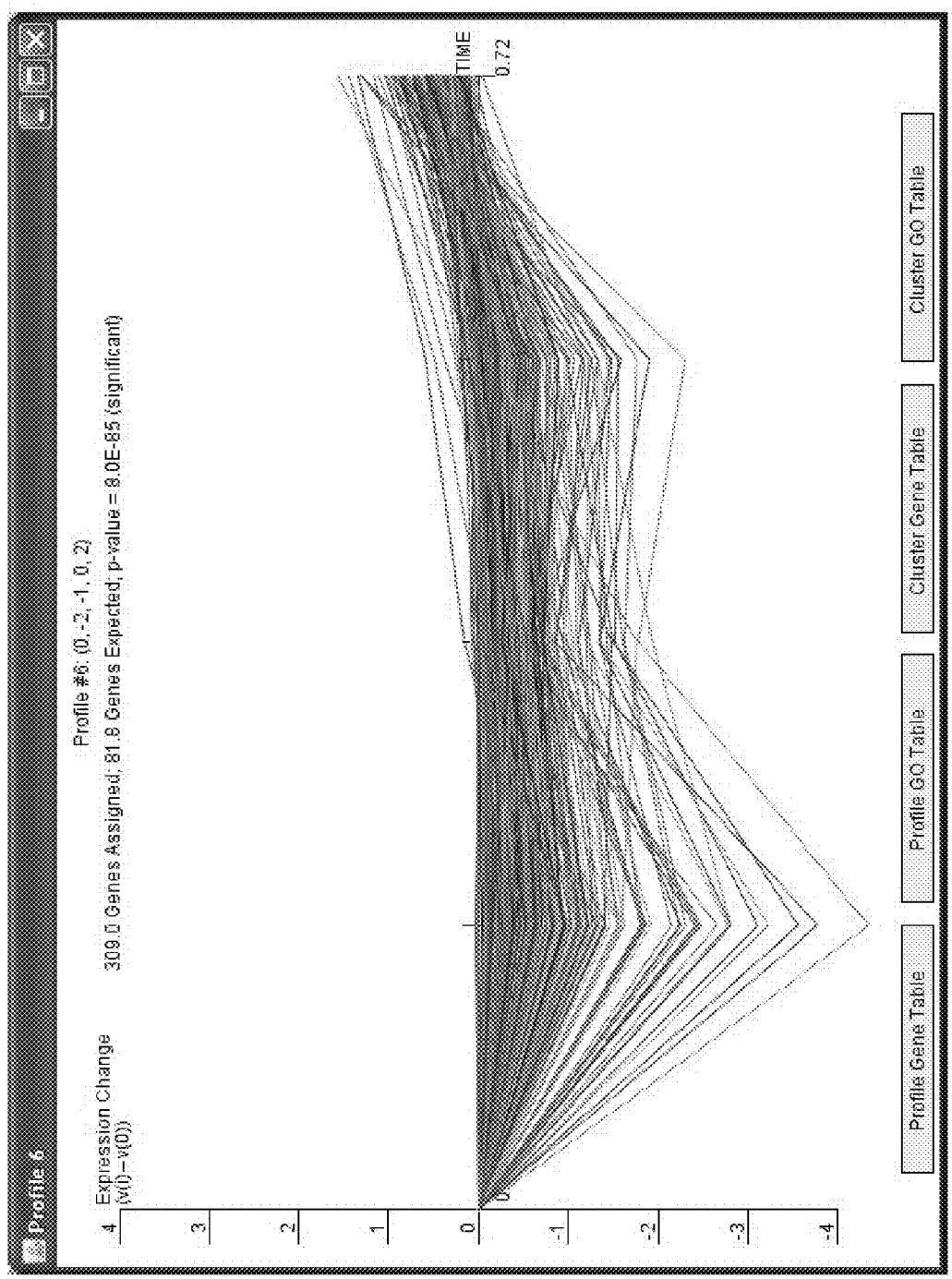
Figure 9B:
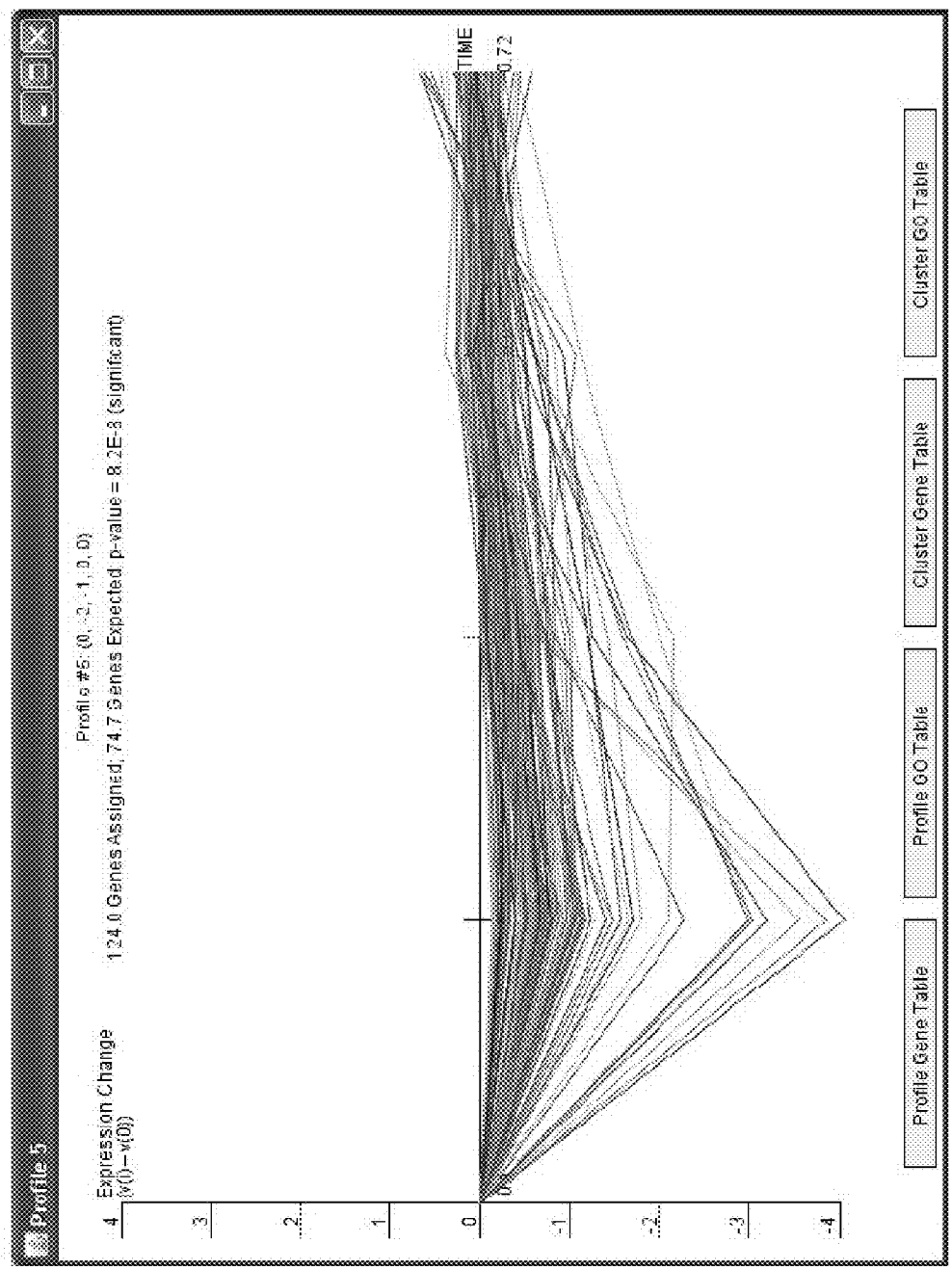
Figure 10A:
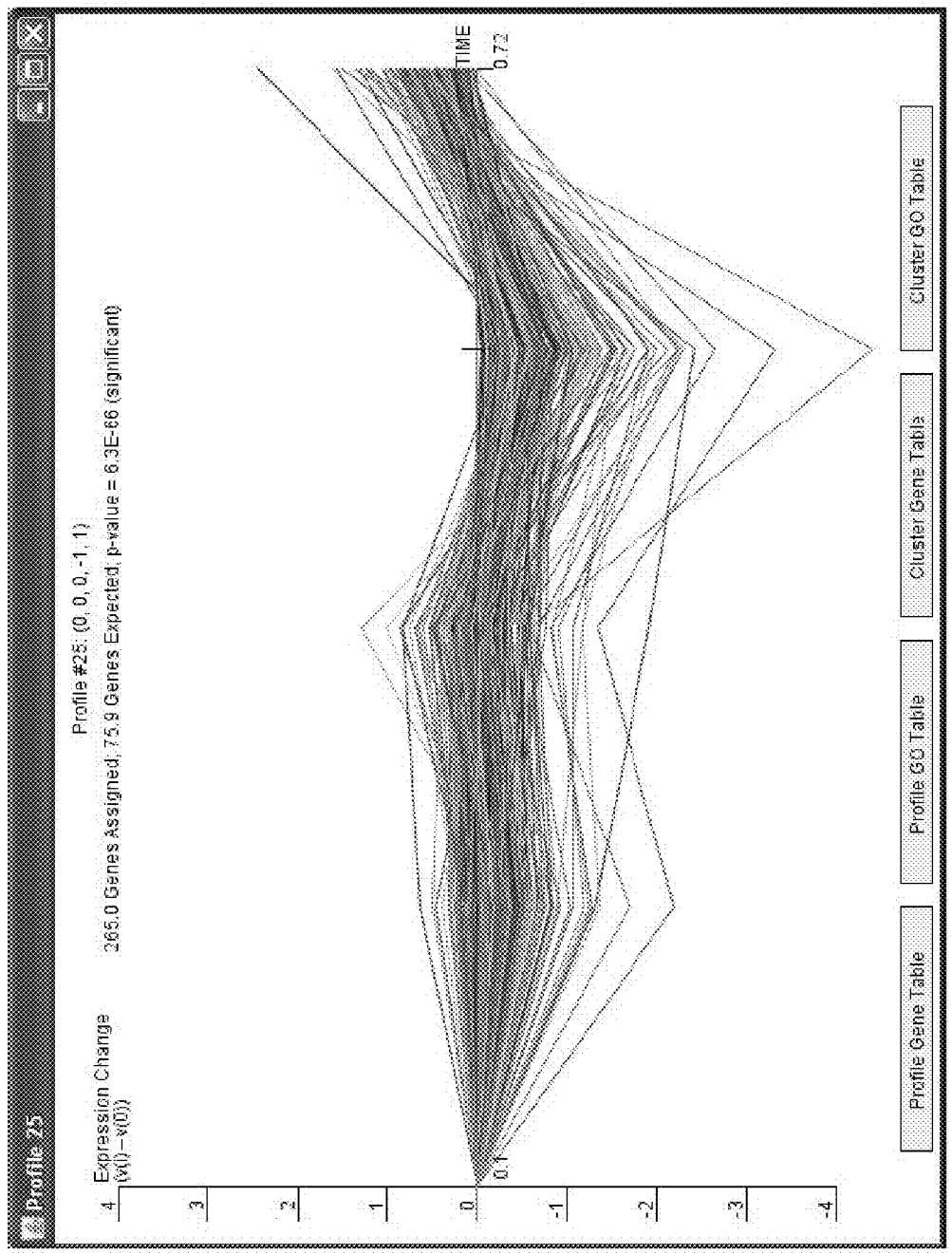
Figure 10B:
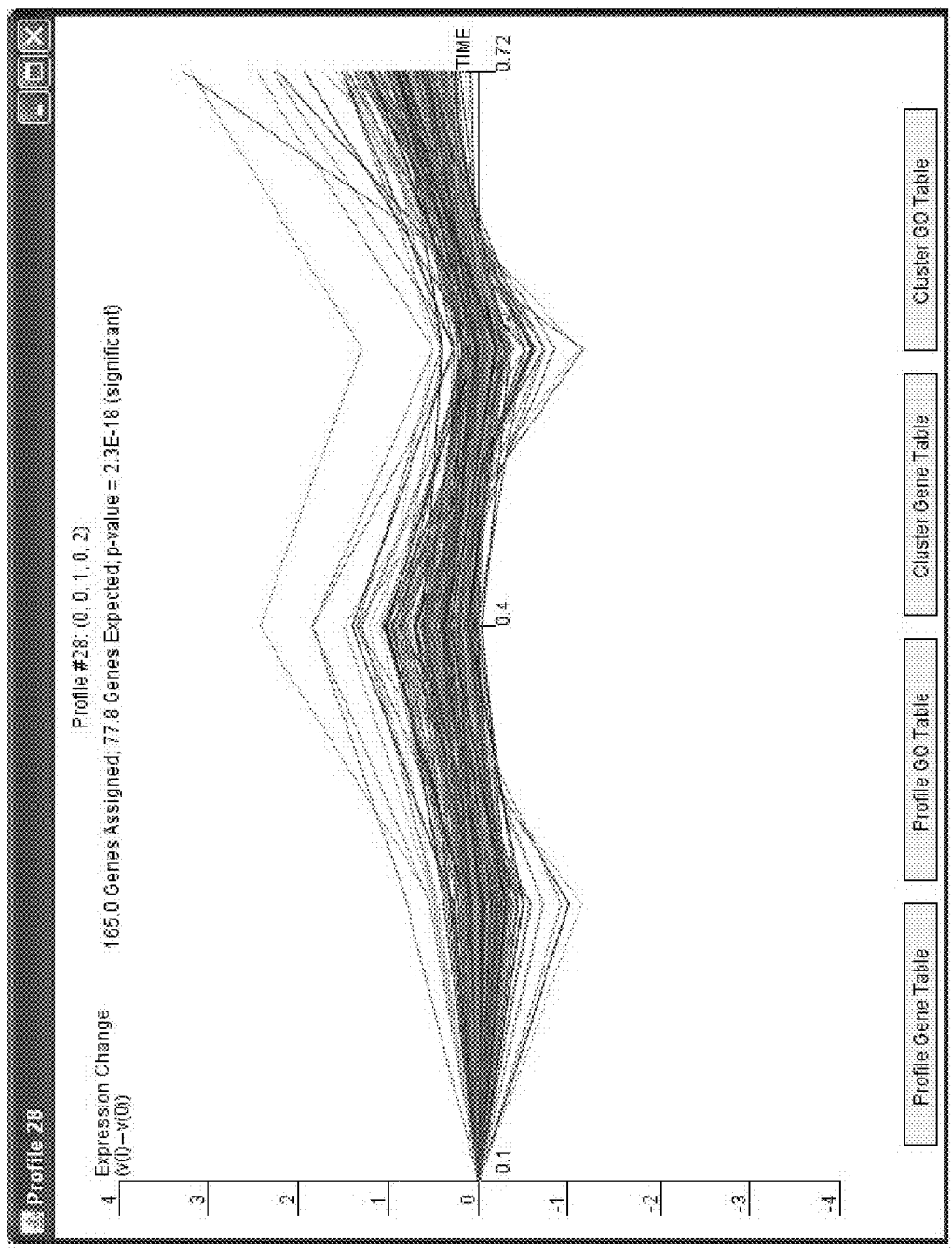
Figure 11A:
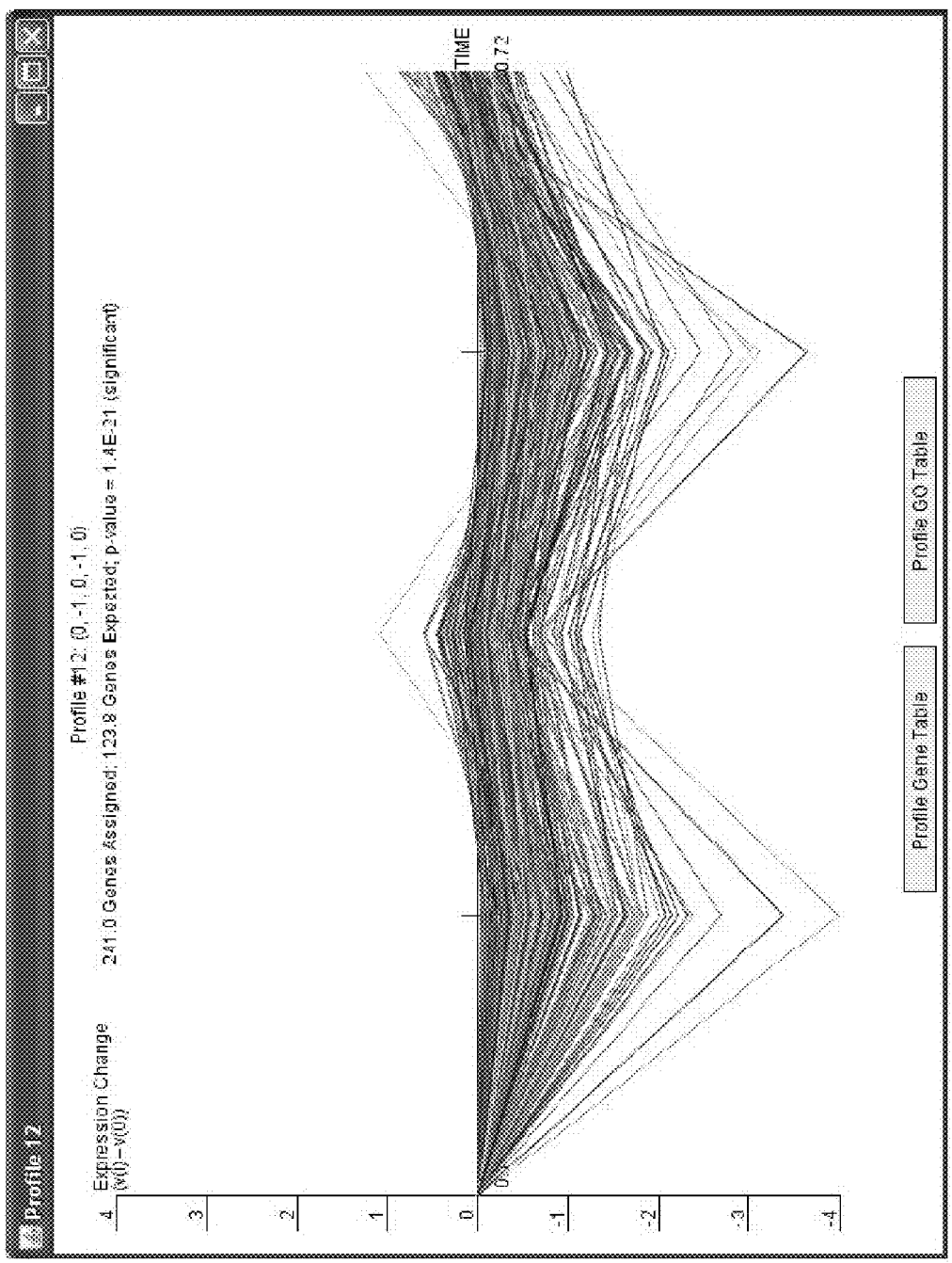
Figure 12A:
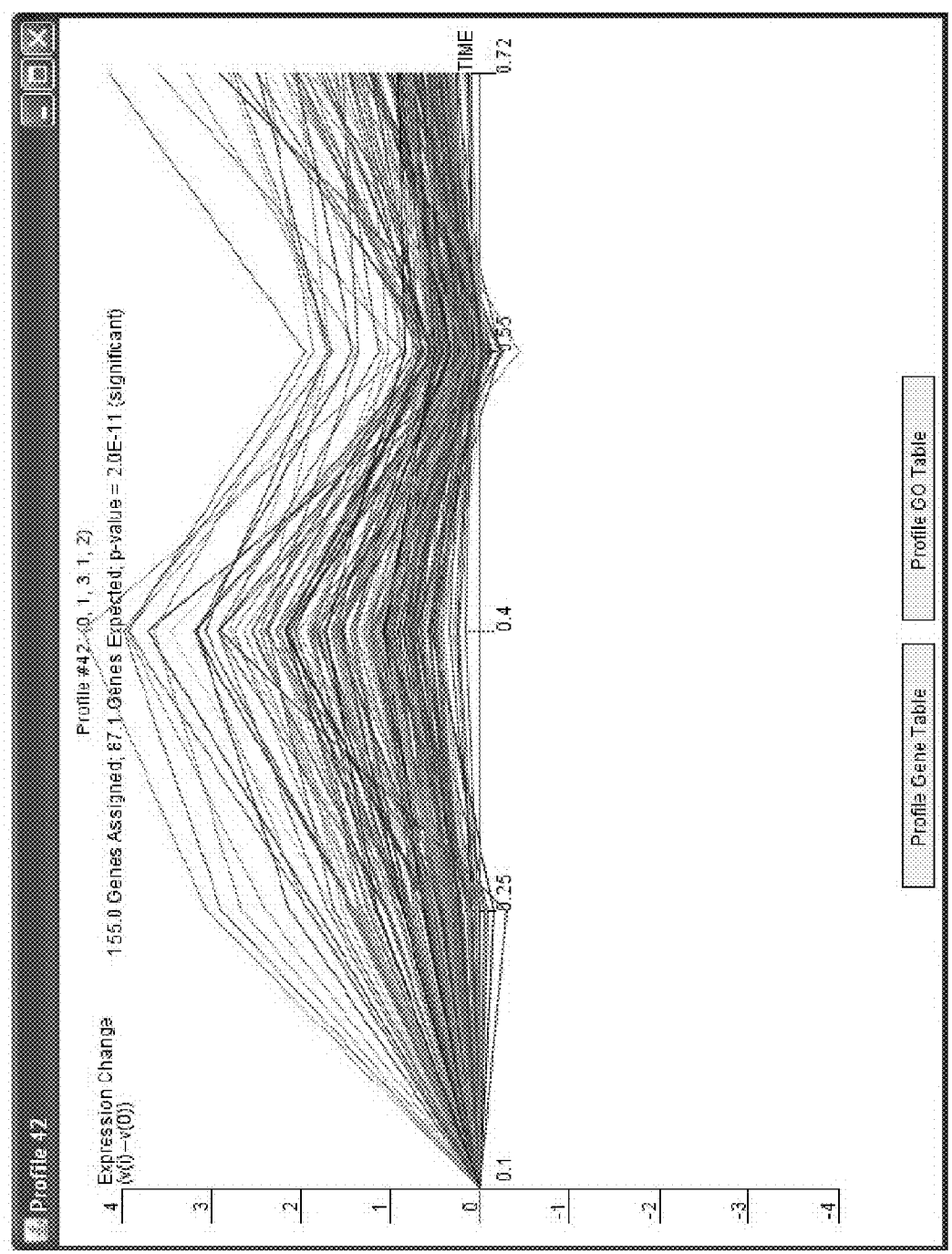

STEM Clustering Analysis:

We used the Short Time-series Expression Miner (STEM) (Ernst and Bar-Joseph, 2006) to identify significant patterns in gene expression profiles in response to the increasing dilution rates. The gene expression profiles were transformed so that they represent the log ratio change in expression from the first sample. The STEM clustering method identifies from a comprehensive library of distinct profiles those with a statistically significant number of genes most closely matching the shape of the profile. Significant profiles are then grouped together such that all profiles in the same group are similar within a threshold. The clusters of significant profiles are then analyzed with a Gene Ontology (GO) enrichment analysis. FIG. 7 shows the library of profiles considered and the significant profiles at a 0.05 Bonferroni corrected level in color. Significant profiles that were grouped together are in the same color.

In FIGS. 8-12, we show genes from significant profiles organized by their clustering group. We also show a GO enrichment table for the set of genes assigned to each of the clusters. The GO categories assigned to various clusters in FIGS. 8-12 reveal important results with respect to the changing gene expression profile at the five dilution rates. We found that the expression profiles for most of the genes in Cluster 1 (FIG. 8) are very similar to the expression profiles for the genes related to the TCA cycle (FIG. 5). For this cluster of genes we see that the GO categories cellular biosynthetic and metabolic processes have significant p-values. In Cluster 2 (FIG. 9) we see that genes for other cellular processes such as flagella, fimbrium development, cell adhesion, and activities in the outer membrane-bound periplasmic are down-regulated at all dilution rates until 0.55 h$^{-1}$; and the genes for most of these processes were up-regulated at the highest measured dilution rate of 0.72 h$^{-}$. Analysis of Cluster 3 (FIG. 10) reveals that activities of most of the genes responsible for part of cell membrane and porin activities are up regulated at intermediate dilution rates of 0.4 h$^{-1}$ followed by a down regulation at 0.55 h$^{-1}$ and up-regulation again at 0.72 h$^{-1}$. In Cluster 4 (FIG. 11) we see that the genes responsible for synthesis and metabolism of various kinds of polysaccharides, biopolymers and lipids, and DNA-mediated transposition were always down-regulated during the course of intermediate growth rates, except at the highest growth rates (0.72 h$^{-1}$), which means that *E. coli* never had the requirement of synthesizing or metabolizing polysaccharides at intermediate growth rates. Analysis of Cluster 5 (FIG. 12) reveals that the genes responsible for biosynthesis and metabolism of various amino acids, (such as glutamine, histidine, arginine etc.), urea cycle, and metabolism of various carboxylic acids are always up regulated throughout the growth of the bacterium at all dilution rates.

Querying Expression Data to Identify Specific Expression Profiles:

To assess the quality of the microarray profiles and to identify genes with expression patterns that are similar to genes encoding enzymes of the central carbon metabolism, we used TimeSearcher (Hochheiser, H., et al., Dynamic Querying for Pattern Identification in Microarray and Genomic Data. In *Proceedings IEEE Multimedia Confer-* ence and Expo 2003, (IEEE, Piscataway, N.J.), Vol. 3, pp. III-453-111-456.) to identify genes having similar expression profiles to any of the 23 genes corresponding to the 18 enzymes of FIG. 4. TimeSearcher displays a set of genes satisfying constraints imposed by visual query boxes. The input is a set of known genes and a set of constraint boxes around these genes, and the output is these genes plus all the other genes that also satisfy the constraint boxes.

Querying Gene Expression of Operons in the Central Carbon Metabolism:

We also examined the expression profile obtained at five-dilution rates growth of *E. coli* organized in the operons in the central carbon metabolism. In addition to the genes already listed in FIG. 5, we identified additional genes that are organized in operons (eg. frdABCD, sdhABCD, ace-ABK) for several more reactions in the central carbon metabolism, for which we don't have measured flux value. Plots (not shown, indicated a good agreement in the expression pattern of genes from the same operon.

Results

Limited Solvent Capacity Constrains the Metabolic Rate of Fast Growing *E. Coli* Cells The cell's cytoplasm is characterized by a high concentration of macromolecules resulting in a limited solvent capacity for the allocation of metabolic enzymes. See, Equations 2-4 (Eq. 2-4) above.

To understand the relevance of the constraint (Eq. 4) at physiological growth conditions we first estimate the crowding coefficients (where $a_i=Cv_i/b_i$) using data from experimental reports. The *E. coli* cytoplasmic density of macromolecules is C=0.34 g/ml (Zimmerman S B, et al. *J Mol Biol* 1991, 222:599-620), while the molar volumes of proteins are proportional to their molar masses (Lee B, *Proc Natl Acad Sci USA* 1983, 80:622-626). The coefficient of proportionality represents the specific volume and it is about 0.73 ml/g. This empirical law allows us to compute the molar volumes of *E. coli* enzymes from their molar masses. As a first approximation we estimate $b_i$, the coefficient of proportionality between reaction rate and enzyme concentration, from the enzyme's turnover numbers. Data obtained from the BRENDA data base for about hundred *E. coli* enzymes (Additional file 1) shows that the turnover numbers vary over five orders of magnitude (FIG. 1a), from $10^{-2}$ to $10^2$ 1/s. Using these parameter estimates we compute the crowding coefficients a, for about a hundred *E. coli* enzymes (FIG. 1b), resulting in an average and standard deviation of 0.014 and 0.009 1/[mmol/g/h], respectively. Because of the large enzyme turnover variations the crowding coefficients are distributed over a wide range as well, from $10^{-6}$ to $10^0$ 1/[mmol/g/h] (FIG. 1b).

Figure 2:
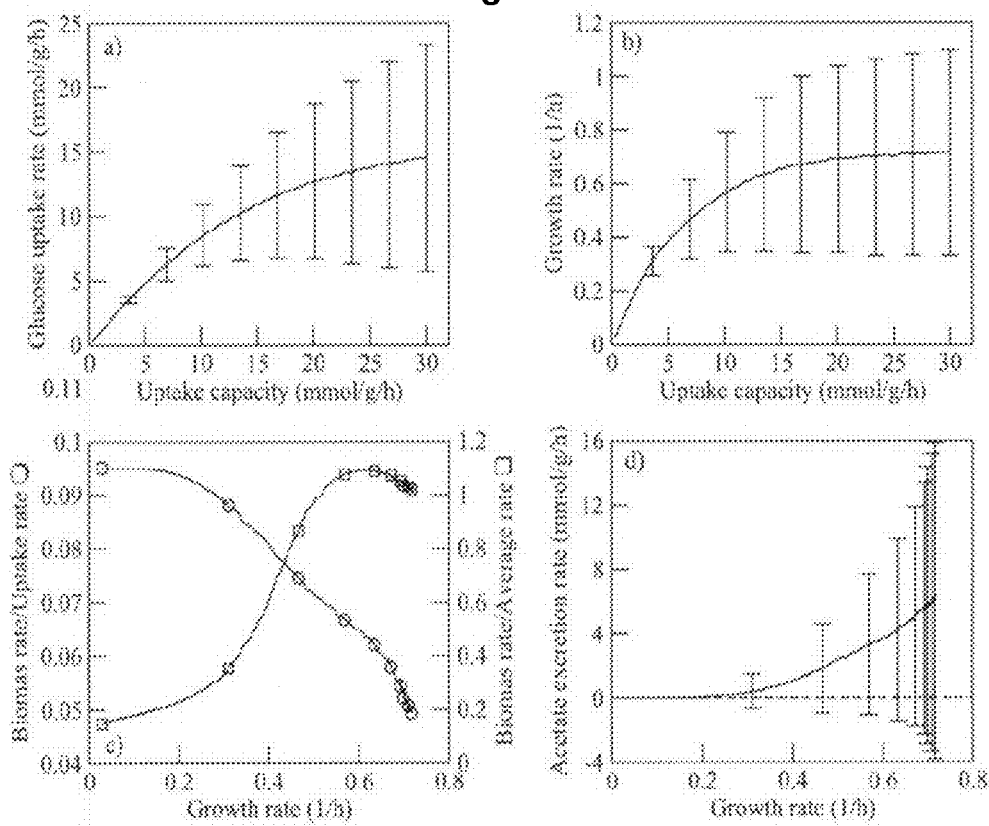
FIG. 2—The signatures of the predicted metabolic switch: The glucose uptake rate (a) and growth rate (b) as a function of the glucose uptake capacity, as obtained from the FBAwMC model. The line represents the average behavior and the error bars represent the standard deviation over 1,000 choices of crowding coefficients. (c) Flux ratios illustrating the switch in metabolic efficiency objective from low to high growth rates. At low growth the biomass rate per unit of uptake rate (circles) is at a maximum, while the biomass rate per unit of average rate is at a maximum at high growth rates (squares). (d) Acetate excretion rate as a function of the growth rate. At high growth rates the prediction for acetate excretion is sensitive to the crowding coefficients uncertainty, resulting in the large error bars.

FBAwMC Predicts a Change of Effective Metabolic Efficiency Objective:

Having estimated the crowding coefficients we next evaluate the relevance of the solvent capacity constraint (Eq. 4) at physiological growth conditions. To this end we utilize a FBA model of *E. coli* MG 1655 metabolic network that takes into account this constraint referred to as "flux balance analysis with molecular crowding" (FBAwMC). Under conditions of aerobic growth in a glucose-limited medium, FBAwMC predicts a saturation of the glucose uptake rate and the growth rate (FIG. 2a,b) with increasing the glucose uptake capacity. The predicted maximum glucose uptake rate (~15 mmol/g/h) and maximum growth rate (~0.7 h$^{-1}$ are within the range of experimentally determined values (Fischer E, et al., *Anal Biochem* 2004, 325:308-316), corroborating our previous report (Beg Q K, et al., *Proc Natl Acad Sci USA* 2007, 104:12663-12668) that the solvent capacity constraint (Eq. 4) is relevant at physiological conditions.

Associated with the predicted saturation of *E. coli* metabolic rates, FBAwMC predicts a metabolic switch characterized by a change in the effective criteria of metabolic efficiency. At low growth rates the ratio between the biomass production rate and the glucose uptake rate is at a maximum but decreases with increasing the growth rate. In contrast, the ratio between the biomass production rate and the average reaction rate increases with increasing the growth rate, reaching a maximum at high growth rates. In agreement with our expectations, at low growth rates nutrients are scarce and the best strategy for a cell is to maximize the biomass production rate per unit of limiting nutrient (in this case, glucose) uptake rate. In contrast, at high growth rates the nutrients are abundant, the predicted metabolic rate is limited by the solvent capacity constraint (Eq. 4) and, therefore, the maximum growth rate is achieved by maximizing the biomass production rate per average reaction rate (FIG. 2c). The predicted change in metabolic efficiency objective is accompanied by a redistribution of the metabolic fluxes, including those of exchange fluxes. Indeed, a characteristic example is the predicted excretion of acetate at high growth rates (FIG. 2d) that is well-supported by experimental observations (El-Mansi E M, et al., *J Gen Microbiol* 1989, 135:2875-2883; Reiling H E, et al., *J Biotechnol* 1985, 2:191-206; and Wolfe A J, *Microbiol Mol Biol Rev* 2005, 69:12-50)

FBAwMC-Predicted Metabolic Fluxes are within the Range of Experimental Values:

FBAwMC is also able to predict internal metabolic fluxes as a function of the growth rate. A subset of the FBAwMC derived flux predictions in the central carbon metabolism are shown in FIG. 3. In most cases the FBAwMC predicted fluxes are within the range of experimentally determined values. This is a striking result given that this implementation of FBAwMC does not contain any free parameters. The only model parameters are the crowding coefficients, which were determined above using independent experimental results. We should also note that the observed wide variability around the average behavior. Further testing of our predictions will be necessary upon availability of better estimates for the crowding coefficients.

Limiting our analysis to the expected behavior, we observe a slope change for several fluxes when reaching the highest growth rates. The reactions of the glycolytic pathway, the flux towards the pentose-phosphate pathway via the reaction catalyzed by the gene product of zwf, and the acetate pathway switch at high growth rates to a faster flux increase with increasing the growth rate. The experimental values corroborate this qualitative behavior, but the change is bigger for the ptsG-catalyzed reaction and even qualitatively different for the pykA-catalyzed reaction, both being part of the glycolytic pathway. A second noticeable effect is the predicted saturation of the TCA cycle flux at high growth rates. The experimentally measured values of the TCA cycle flux exhibit, however, a stronger effect characterized by a decreasing tendency at high growth rates (FIG. 3). Taken together these results indicate that while for most reactions the FBAwMC predictions are within the range of experimental measurements, a method for a more accurate estimate of the crowding coefficients on a network scale will be required to provide more precise predictions.

Identifying the Regulatory Mechanism(s) that Control the Action of the Metabolic Switch:

To examine if the changes in growth conditions and the corresponding adjustments in cellular metabolism can be traced by distinct molecular signatures we next measured the in vitro activity of eighteen selected enzymes that catalyze reactions in the central carbon metabolism of *E. coli* MG1655, and correlate their changes with those observed for the measured flux rates (FIG. 4). For several enzymes there is a good correlation between the measured enzyme- and flux activities (Pearson Correlation Coefficient, PCC, close to- or larger than 0.8). For example, with an increasing growth rate the enzyme activity of the ptsG and pfkA gene products follow the same increasing tendency as the fluxes of the corresponding metabolic reactions (PCC=0.79 and 0.85, respectively). The glycolytic flux is known to be controlled by the activity of these two enzymes while other reactions adjust their fluxes through changes in metabolite concentrations. In contrast, we found no significant correlation between the measured fluxes and enzyme activities of the TCA reactions (PCC=0.64, 0.35, −0.03 and −0.28 for enzymes associated with gitA, sucA. fumA and mdh, respectively), implying that the TCA flux is controlled by the activity of enzymes catalyzing reactions outside this pathway. A possible candidate to exert this action is the acetate pathway. Indeed, an increase of the flux on the acetate pathway towards the production of acetate can balance both the increase in the flux originating from the glycolytic pathway through aceE and a decrease in the flux from Acetyl-CoA to the TCA cycle. This hypothesis is supported by the increase in the enzyme activity of phosphotransacetylase (pta) when the growth rate increases beyond 0.4 $h^{-1}$ (PCC=0.98), which is exactly the growth rate threshold where the switch is taking place.

In parallel with the enzyme activity measurements we also prepared mRNA from samples obtained at all five dilution rates and processed them for microarray analysis. In contrast to the observed overall correlation between measured fluxes and in vitro enzyme activities we do not observe a significant correlation between the measured metabolic fluxes and the relative changes in mRNA levels of enzyme-encoding genes (FIG. 5), implying that the switch and corresponding enzymatic functions are not predominantly controlled at the transcriptional level. Correspondingly, no significant correlation between the in vitro enzyme activities and the relative changes in mRNA levels of enzyme-encoding genes can be seen (FIG. 5) Taken together these results indicate that the metabolic switch is predominantly controlled by an increase in the enzyme activities of the end products of ptsG and pfkA controlling the glycolysis flux, and pta controlling the acetate pathway flux, respectively.
Discussion Developing a modeling framework that can describe and predict in a quantitative manner the experimentally observed behavior of an organism is a significant challenge for systems biology. One prerequisite of this goal is to uncover the physicochemical constraints exerting the main influences on cellular metabolism (Price N D, Reed J L, Palsson B O: Genome-scale models of microbial cells: evaluating the consequences of constraints. *Nat Rev Microbiol* 2004, 2:886-897). Our results here and in Beg Q K, et al. (Intracellular crowding defines the mode and sequence of substrate uptake by *Escherichia coli* and constrains its metabolic activity. *Proc Natl Acad Sci USA* 2007, 104:12663-12668) indicate that the limited solvent capacity represents a physiologically relevant constraint for fast growing *E. coli* cells. The incorporation of this constraint to the FBA modeling framework leads to the FBAwMC model whose predictions indicate that the solvent capacity constraint results in a maximum glucose uptake rate and growth rate that are within the range of experimentally determined values. The flux predictions for several reactions of the *E. coli* metabolism are within the range of our measurements, as well.

From the perspective of quantitative modeling using flux balance approximations, the solvent capacity constraint forces us to consider reaction kinetics via the crowding coefficients, at least for fast growing cells. At low metabolic rates the solvent capacity constraint is less relevant and flux balance alone is sufficient to obtain satisfactory predictions. In contrast, at high metabolic rates a precise knowledge of the crowding coefficients is required to obtain accurate predictions. In the absence of kinetic information we can still obtain a good approximation by sampling the crowding coefficients from a list of estimated values and then focus on the resulting general trend.

More importantly, the solvent capacity constraint allows the interpretation of the metabolic switch taking place between slow and fast growing *E. coli* cells. A recent study of FBA models with different objectives demonstrates that under nutrient scarcity a FBA model with the maximization of the biomass yield objective achieve the highest predictive accuracy, while maximizing the ATP or biomass yield per average flux unit is the best objective for unlimited growth on glucose under aerobic conditions (Schuetz R, et al., *Mol Syst Biol* 2007, 3:119). In contrast, by considering the solvent capacity constraint we obtain the same results using the maximization of biomass production rate objective alone (FIG. 2c). This is more consistent with the expectation that cells achieving the fastest growth rates outgrow cells growing at a slower rate, but how the highest growth rate is achieved is determined by both the availability of substrates and internal metabolic constraints, such as the solvent capacity. Furthermore, the well-known acetate excretion (El-Mansi E M, et al., *J Gen Microbiol* 1989, 135:2875-2883. Reiling H E, et al. *J Biotechnol* 1985, 2:191-206; and Wolfe A J, *Microbiol Mol Biol Rev* 2005, 69:12-50) is explained by the solvent capacity constraint as well. We should note, however, that this does not exclude the possibility that under certain physiological conditions acetate excretion may result from a limited availability of oxygen in the culture medium (Varma A, et al., *Appl Environ Microbiol* 1994, 60:3724-3731).

Example 2

Here, we develop a modified FBA model that incorporates a solvent capacity constraint for the attainable enzyme concentrations within the crowded cytoplasm. Using this model, we predict the maximum growth rate of *E. coli* MG1655 wild-type and mutant strains on single carbon sources and for the dynamic patterns of substrate utilization from a mixed-substrate growth medium. We test the model predictions by using growth rate measurements and microarray and substrate concentration temporal profiles, and we obtain a good agreement between model predictions and experimental measurements. Taken together, these results suggest that macromolecular crowding indeed imposes a physiologically relevant constraint on bacterial metabolic activity and that incorporating this constraint allows for improved modeling of cell metabolism from system-level principles.

Mathematical Framework:

The flux balance analysis with molecular crowding (FBAwMC) modeling framework is implemented by solving the following optimization problem: maximize the growth rate subject to the constraints described above. The maximum growth rate corresponds to the biomass production rate, where biomass production is an auxiliary reaction containing as substrates the cellular components in their relative concentrations and as product the cell's biomass.

We model the crowding coefficients ai as noise. The reported results were obtained by assigning a random value to them from the gamma distribution $$P(a) = \frac{\beta}{\langle a \rangle}\left(\frac{\beta}{\langle a \rangle}a\right)^{\beta-1}\exp\left(-\frac{\beta}{\langle a \rangle}a\right) \quad [6]$$

where $\beta > 0$ and $\langle a \rangle$ is the average crowding coefficient. There is no particular reason for this choice other than by changing $\beta$ we can explore different scenarios. For instance, for $\beta = 1$ we obtain an exponential distribution, whereas for $\beta \gg 1$ we obtain a distribution that is almost concentrated around $a = \langle \alpha \rangle$. The results reported in FIGS. 13-15 were obtained by using $\beta = 3$ and running the simulations 1,000 times to test the sensitivity of the results with respect to the specific $a_i$ values. Similar results are obtained by using other P(a) distributions.

The maximum growth rate μ for each carbon source was obtained assuming an unbound uptake rate for that carbon source and zero for all other carbon sources. The average crowding coefficient $\langle a \rangle$ was fitted to obtain the minimum square deviation between the measured and model predicted growth rates, resulting $\langle a \rangle = 0.0040 \pm 0.0005$ h·g/mmol, in which g is grams dry weight. However, the maximum growth rates on glucose and glycerol are more consistent with $\langle a \rangle = 0.0031 \pm 0.0001$ h·g/mmol and $\langle a \rangle = 0.0053 \pm 0.0001$ h·g/mmol, respectively.

To model the temporal order of substrate uptake we considered an initial concentration of 0.4 g/liter for glucose, galactose, lactate, maltose, and glycerol, zero concentration for acetate, and cell's dry weight DW=0.00675 g. The progression of the dry weight and the external substrate concentrations were obtained from the integration of the differential equations where m is restricted to external metabolites, μm is the molar mass of metabolite m, and V is the working volume. The maximum growth rate μ(t) and the fluxes $f_i(t)$ are obtained by solving the FBAwMC model for the substrate concentration profile at time t. The value of $\langle a \rangle$ is smaller if glucose alone is consumed and larger if glycerol is consumed. Therefore, we solve three FBAwMC problems corresponding to the consumption of glucose alone ($\langle a \rangle = 0.0031$ h·g/mmol), consumption of all substrates except glycerol ($\langle a \rangle = 0.004$ h·g/mmol), and consumption of all substrates ($\langle a \rangle = 0.0053$ h·g/mmol), and selected the condition resulting in the maximum growth rate.

Figure 17:
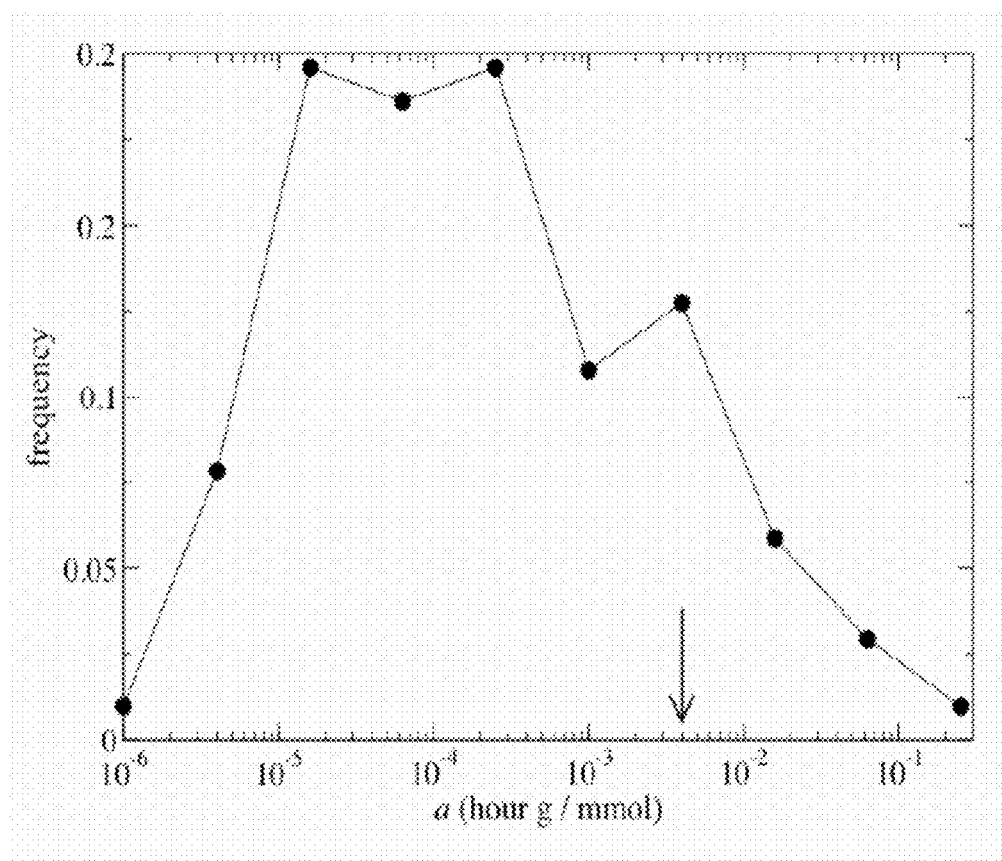
FIG. 17—Distribution of the a, coefficients as obtained from an independent estimate for about 100 *E. coli* enzymes. The arrow indicates the value of <a> obtained from the fit to the growth rate data.

Estimation of the Crowding Coefficients:

The crowding coefficients play a key role in our model. Therefore, it is important to estimate their values from experimental measurements. However, this is a challenging task, as it requires knowledge of the kinetic parameters associated with the *E. coli* enzymes, which are not available in all cases. Yet we can obtain an estimate for the crowding coefficients by making use of the known turnover rate of several *E. coli* enzymes. The crowding coefficients (units of time X mass/mole) are defined by Eq. 5 (see above), where C (units of mass/volume) is the density of the *E. coli* cytoplasm, vi (units of volume/mole) is the molar volume of enzyme i, and $b_i$ (units of 1/time) is the proportionality factor between the flux [units of mole/(mass X time)], and the enzyme concentration (units of mole/mass), i.e., $f_i = b_i E_i$. In general bi is decomposed into $$b_i = x_i k_i, \quad [7]$$

where $k_i$ (units of 1/time) is the enzyme turnover number, and $0 \le x_i \le 1$ (no units) is determined by the concentration of substrates, products, and activators/inhibitors associated with the ith reaction. For example, if reaction i is a single substrate irreversible reaction and it is characterized by Michaelis-Menten kinetics, then $$x_i = \frac{S}{S + K_i}, \quad [8]$$

where S is the substrate concentration and $K_i$ is the Michaelis-Menten or half-saturation constant. Thus, xi≈0 at small substrate concentrations ($S \ll K_i$), whereas at saturation ($S \gg K_i$) $x_i \approx 1$. Substituting Eq. 7 into Eq. 6 and assuming that enzymes are working near saturation ($x_i \approx 1$), we obtain $$a_i \sim \frac{Cv_i}{k_i} \quad [9]$$

where the symbol ~indicates that this is an estimate and some variation is expected for enzymes that are not working at saturation. The magnitudes on the right-hand side can be estimated by using different sources of experimental data. The *E. coli* cytoplasmatic concentration is $C \approx 0.34$ g/ml). The enzymes' molar volumes can be estimated from the equation $v_i^{(molar)} = M_i v_i^{(specific)}$, [10], where $M_i$ is the molar mass of enzyme i (units of mass/mole) and $v_i^{(specific)}$ is its specific volume (units of volume/mass). We estimate the specific volume from measurements of this magnitude for globular proteins. These data indicate that the specific volume has small variations among enzymes relative to the molar mass variations. Therefore, we take the same specific volume for all enzymes and equal to the reported average specific volume for the proteins, resulting in $v_i^{(specific)} \approx 0.73$ ml/g. Finally, we consider the molar mass and the turnover number of several *E. coli* enzymes reported in BRENDA. Using these data and Eqs. 9 and 10, we computed a, for several *E. coli* enzymes, resulting in the distribution shown in FIG. 17.

Growth Experiments, Carbon Substrate, and Microarray Analyses:

The *E. coli* K12 strain MG1655 (F$^-$ λ$^-$ ilvG rfb50 rph1) was used throughout the work. Isogenic *E. coli* mutants (pgk, atpC, gpmA, nuoA, gdhA, and pfkA) were obtained from F. Blattner (University of Wisconsin, Madison, Kang Y, et al., (2004) *J Bacteriol* 186:4921-4930.). The experimental details of the growth rate measurements, substrate concentration assays and microarray analyses are detailed below.

Bacterial Strains and Growth Conditions:

The *E. coli* K12 strain MG1655 (F-λ-ilvG rfb50 rph1) was used throughout the work. Isogenic *E. coli* mutants (pgk, atpC, gpmA, nuoA, gdhA, and pfkA) were obtained from F. Blattner (University of Wisconsin, Madison). Chemicals and reagents used in the growth experiments were from Sigma (St. Louis, Mo.) or Fisher Scientific (Pittsburgh, Pa.). The growth experiments using M9 minimal medium containing mixture of five carbon sources (glucose, maltose, galactose, L-lactate, and glycerol) were carried out in a 2-liter Labfors bioreactor with 1.2-liter working volume (Infors, Switzerland). All the carbon sources (used in equal ratios) were filter sterilized and added to the growth medium at a final concentration equivalent to 0.2% sugar. For these growth experiments, the dissolved oxygen was set at 100% initial value, and sterile air was continuously sparged into the medium. Growth parameters, such as pH, pO$_2$, temperature, and agitation were continuously monitored through microprocessor probes. Samples were collected at 30-min intervals to document various growth phases and extracellular substrate concentrations and to assess the transcriptome state. For assessing the exponential-phase transcriptome states in individual carbon-limited (glucose, galactose, maltose, glycerol, lactate, or acetate) M9 minimal medium, the carbon source concentration in the M9 minimal medium was adjusted to the number of carbon atoms equivalent to that present in 0.2% glucose. Fifty microliters of the overnight inoculum of E. coli MG 1655 (prepared in the same medium used for the experiment) was inoculated in 50 ml of growth medium in a 250-ml Erlenmeyer flask supplemented with the appropriate carbon source. The growth profile of OD600 was documented at regular intervals.

Experimental Determination of Maximum Growth Rates:

When determining maximum growth rates in different carbon sources, we used a 12- to 15-h-old E. coli culture (prepared in the same substrate to be used for the final medium) to inoculate a Sixfors bioreactor (Infors, Switzerland) containing M9 minimal medium (400 ml working volume) supplemented with various carbon sources, and monitored the growth profile at regular intervals by optical density at 600 nm. A method of continuous cultivation of bacterial cells with smooth changes in growth rate was used for determining the maximum growth rate in various substrates. This method has been shown to be more precise to determine growth rate in E. coli than batch culture (Paalme T, et al. (1997) Antonie Van Leeuwenhoek 71:217-230 and Paalme T, et al., (1995) J Microbiol Methods 24:145-153). When the cells reached stationary phase (also indicated by constant OD and sudden increase in dissolved oxygen value), the flow of fresh growth medium was started at a dilution rate slightly below their maximum growth rate calculated from their growth profile in the exponential phase. The cells were allowed to grow at this dilution rate until they reached a steady state. Once the cells were found to be growing well in the steady state, the washout of cells was started at a dilution rate that was above their maximum growth rate. The washout was done for the next 6 h, and the OD$_{600}$ data obtained (OD readings were converted into log) during the washout period were used to calculate the maximum growth rate for all the cultures.

$$\text{Growth rate} = D - \left(\frac{\ln_f - \ln_i}{3}\right) \quad [11]$$

where D is the dilution rate during washout of cells, lnf is the natural log of the final OD$_{600}$, and lni is the natural log of an OD$_{600}$ 3 h before the final OD$_{600}$.

Substrate Concentration Assays:

For determining the residual concentration of individual carbon sources in the growth medium, samples of cell culture were centrifuged for 2 min at 13,000 g at 4° C. The supernatant was filtered through a 0.22-µm filter and stored at −80° C. until further use. Concentrations of D-galactose, D-glucose, glycerol, L-lactate, maltose, and acetate in the cell-free supernatant were determined by using corresponding Enzymatic BioAnalysis kits (R-Biopharm, South Marshall, Mich.) according to the manufacturers' instructions. Before analysis, all the samples were placed in a water-bath at 80° C. to stop any background enzymatic activity. For maltose analysis, the samples were treated with glucose oxidase and hydrogen peroxide and passing air current for 1 hr to remove residual glucose (which might impair the precision of the maltose assay) as per the manufacturer's instructions.

Microarray Sample Collection:

For the shake-flask exponential-phase experiments using individual carbon sources, at OD$_{600}$≈0.2, the whole cell culture volume (50 ml) was mixed with 5 ml of ice-cold stop-solution (5% water-saturated phenol in absolute ethanol), and a cell pellet was obtained by centrifugation at 4,500 g for 5 min at 4° C., followed by flash freezing of pellets with liquid nitrogen. The pellets were stored at −80° C. until further use. For the time series experiments using a mixture of five carbon sources in M9 minimal medium, culture samples for microarray analysis were collected at 30-min interval between 2 and 8 h of growth. Approximately 5-50 ml of the cell culture (depending on the stage the cells were growing) was obtained and rapidly mixed with ¹/₁₀th vol of the ice-cold stop-solution (5% water-saturated phenol in absolute ethanol) to inhibit any further transcription. The tubes were capped, and the sample and stop-solution were mixed by inversion. The cell pellets were obtained by centrifugation at 4,500 g for 5 min at 4° C., immediately flash frozen in liquid nitrogen, and stored at −80° C. until further use. RNA was isolated from the frozen cell pellets by using Epicenter's Masterpure RNA isolation kit (using the manufacturer's product manual). The samples were also treated with DNase for 1 h at 37° C. to remove DNA contamination in the RNA samples. Ten micrograms of all RNA samples was processed for transcriptome analysis using E. coli Affymetrix microarray chips by the Microarray Resource Centre, Department of Genetics and Genomics at Boston University School of Medicine (www.gg.bu.edu/microarray/index.htm).

Microarray Analysis of Samples from Individual Carbon Source-Limited Media (Glucose, Maltose, Galactose, Glycerol, Lactate, and Acetate):

The Dataset for this analysis is not shown as it is too large. Details are summarized herein. To perform the data analyses, we first identified genes for which there is no evidence of sequence-specific hybridization intensity in any of the five samples. If there was no sequence-specific hybridization, that gene was not analyzed any further. We searched for genes that vary between the five arrays much more than genes with similar hybridization intensity. The idea here is that the observed difference for a gene that varies much more than its neighbors is probably not due to technical noise and thus the variability could be due to underlying biological differences between the samples. The ratio of the variability of a particular gene to the average variability of its 50 closest neighbors was determined. When analyzing these data, we chose an arbitrary threshold of 2.5 for this variability ratio and identified the top 150 genes that had a ratio larger than 2.5 (i.e., the 150 genes that are probably the most dramatically affected by the given growth conditions).

Examination of the top 150 genes reveals that glucose-, maltose-, and galactose-limited growth results in the condition-specific up-regulation of genes involved with the transport and catalysis of the specific carbon source (e.g., of those of the maltose regulon in the maltose-limited growth condition), whereas glycerol and acetate display similarities in the expression program, but the "acetate signature" is stronger and more expanded compared to glycerol's. This observation suggests the appearance and subsequent expansion of a foraging program as the quality of the carbon source decreases, as previously suggested (Liu M, et al. (2005) J

Figure 16:
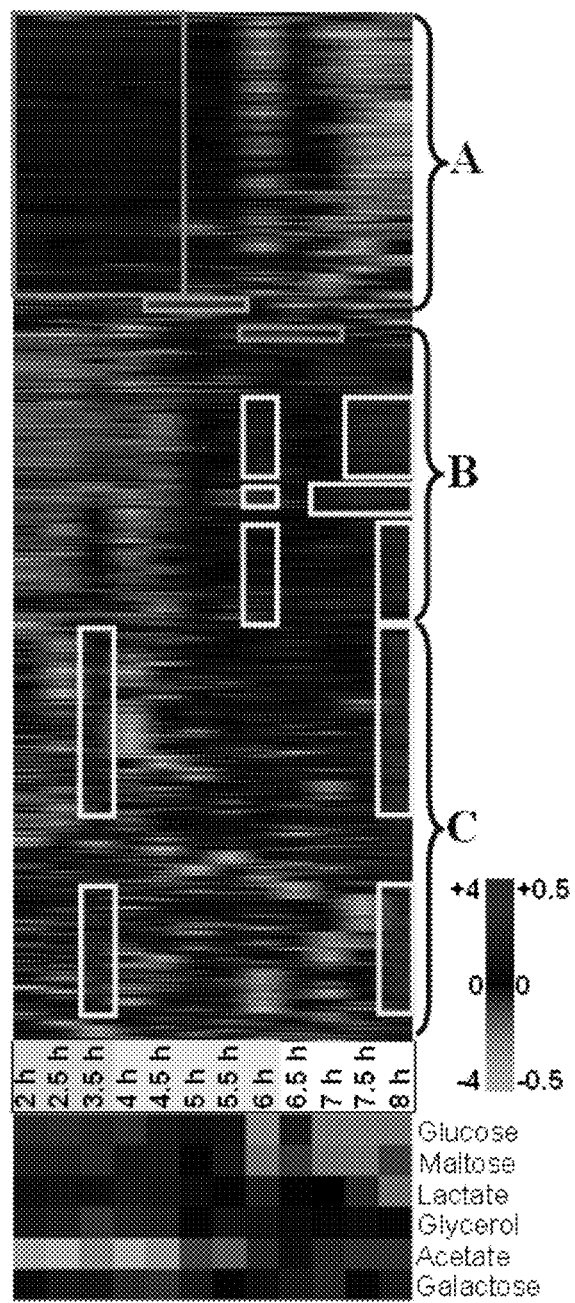
FIG. 16—Analysis of microarray expression data. Hierarchical clustering with optimal leaf ordering identifies three major expression modes. Relative gene expression values from the highest (dark gray) to the lowest (light gray) are shown, as indicated by the left side of the color scale bar (+4 to −4). Expression mode A: genes that are upregulated until 4.5 hrs; Expression mode B: genes with peak expression at 6 hr and after 7.5 hr; and Expression mode C: genes with peaks at 3.5 hr and after 7.5 hrs. Other boxes indicate upregulation of maltose and glycerol regulons. The temporal order of the three phases of substrate utilization is shown (as in FIG. 14). In the bottom matrix the overall correlation of expression profiles at the given time points are compared to that of obtained in mid-log batch cultures of the indicated single carbon-limited media, as indicated by the right side of the color scale bar (+0.5 (dark gray-high) and −0.5 (light gray-low)).

*Biol Chem* 280:15921-15927). As the mid-logphase growth experiment using lactate as sole carbon source was done separately then other five carbon source experiments, we compared the expression of the genes expressed under lactate-limiting conditions with those of glucose on a different Affymetrix chip (dataset not shown). Those genes that failed to exhibit sequence-specific hybridization signal in either sample were removed from consideration. As random variability due to system noise is generally inversely related to hybridization intensity, we compared the relative difference between the glucose and lactate samples for each gene to the average difference between the two samples for genes with similar hybridization intensity. The idea is that if a gene is in a hybridization intensity neighborhood of noisy signals, the observed difference between the two samples is less likely to be due to a biological cause than if other genes with similar hybridization intensity show little change. This idea was reduced to a number. Genes with a "surplus variability" were identified. Other genes were identified that were more likely to be differentially expressed than those genes with a surplus variability <4. Finally, we calculated the log 2-fold change between the lactate and glucose samples and identified those that are more than 2-fold higher in the lactate sample and in the glucose (GLC) sample. To have all the information after using two different microarray platforms, we scaled the raw values from the second glucose experiment so that the total sum of raw intensities of common genes would be the same as the first. The two glucose experiments were then averaged together. Then we scaled the lactate array by the same factor as used to make the two glucose sums the same. Then for each gene and condition we took the log 2 of the intensity value over the geometric mean of the intensity values across all six experiments. The glucose data in the correlation matrix shown in the bottom panel of FIG. 16 are the average of the two glucose values from the datasets after this normalization.

Figure 18:
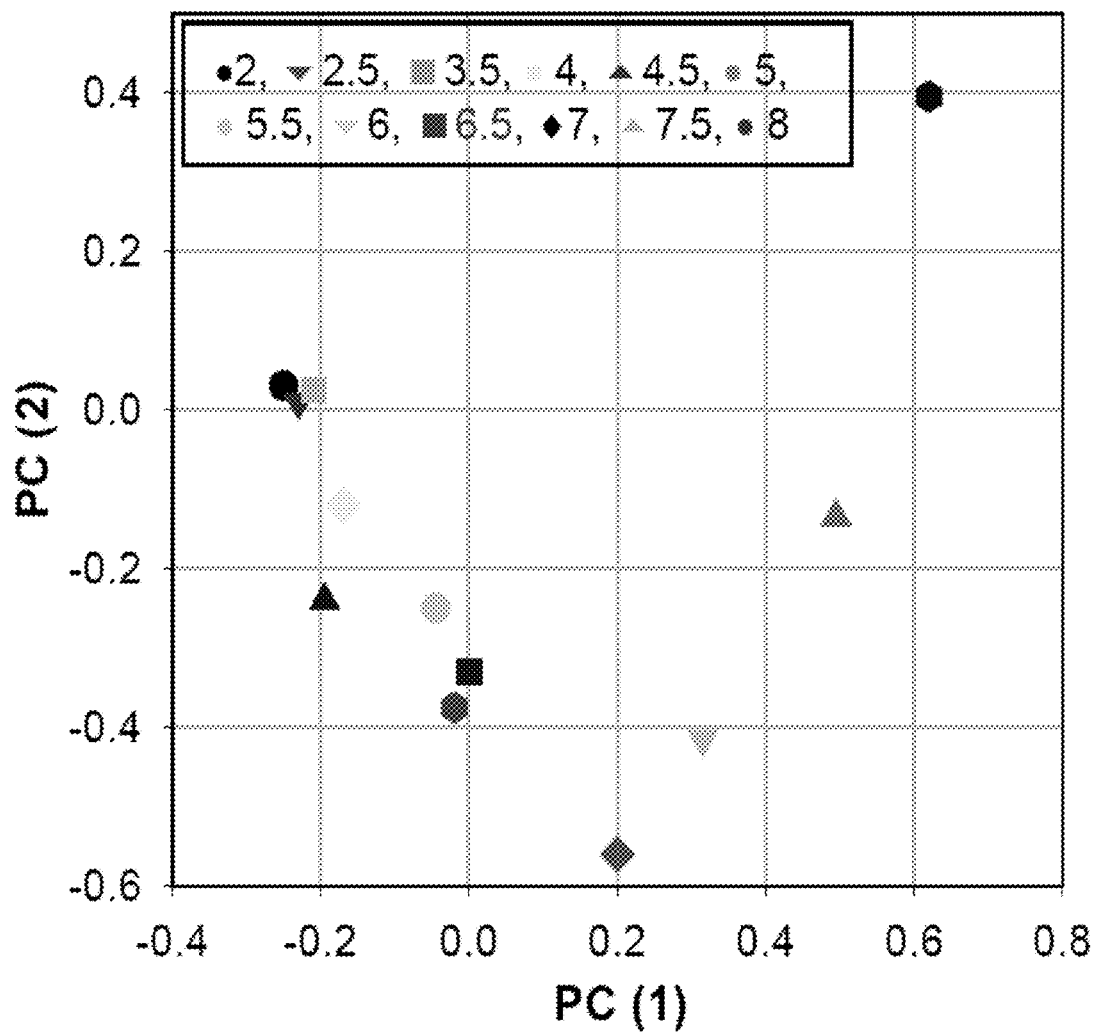
FIG. 18—Principal component analysis of the microarray data from time-series experiment on mixed-substrate medium.

Microarray Analysis of Samples from Time Series Mixed-Substrate Experiment:

To analyze the dataset, first we removed those expression measurements that were not sequence-specific in any of the samples in the dataset. This filter removes expression measurements for genes that are probably not expressed under the growth conditions. Then we calculated the fold change for each time point relative to the geometric mean of the hybridization intensity of all time points for each gene. Then we organized the expression measurements from top to bottom so that genes that show similar changes between the samples are near each other. The Principal Component Analysis (Peterson LE (2003) *Comput Methods Programs Biomed* 70:107-119.) (FIG. 18), which globally assesses the similarity of transcriptome profiles to each other by considering all the genes on the array, displays that there are similar expression profiles in all samples collected between 2 and 3.5 h (exclusive glucose utilization phase). This was followed by transition in the transcriptome state at the beginning of the mixed-utilization phase between 4 and 4.5 h. The 5- to 5.5-h (mixed substrate utilization phase) and 6.5-h samples (late carbon utilization phase) display similar global expression profiles, interrupted by a significant alteration in the expression profile at 6 h (which is indicating the switch from acetate secretion to acetate utilization).

Querying Expression Data to Identify Specific Expression Profiles:

TimeSearcher was used to identify genes having expression profiles similar to those of genes that are known to participate in specific uptake pathways. TimeSearcher displays a set of genes satisfying constraints imposed by visual query boxes. The input is a set of known genes and a set of constraint boxes around these genes, and the output is these genes plus all the other genes that also satisfy the constraint boxes. Genes with similar expression pattern identified for each profile were identified. These individual figures for glucose, lactate, maltose, galactose, glycerol, and acetate uptake clearly showed that several other genes that do not directly take part in substrate uptake of these individual carbon sources are also up-regulated along with the substrate uptake genes. Many of these genes take part in the intermediate steps of metabolism after substrate uptake.

Hierarchical Clustering of Time-Series Gene Expression Data:

To further study the clusters determined by TimeSearcher we performed hierarchical clustering with optimal leaf ordering (Bar-Joseph Z, et al. (2001) *Bioinformatics* 17:S22-S29 and Eisen M B, et al. (1998) *Proc Natl Acad Sci USA* 95:14863-14868). Next, we examined the enrichment of different clusters for different Gene Ontology (GO) category annotations by using the hypergeometric distribution to compute P values. Corrected P values for multiple hypothesis testing were computed by using a randomization procedure. We observed three major expression clusters, denoted as A, B, and C (see FIG. 16). The details of GO analysis of genes in each cluster about these expression clusters were identified.

Probabilistic Clustering of Time-Series Data:

While hierarchical clustering is useful for visualizing and analyzing complete datasets, it is less appropriate for studying specific clusters because it is a greedy method that is sensitive to noise. To complement the hierarchical clustering results we have used a Hidden Markov Model (HMM) to cluster the data (Ernst J, Vainas O, et al. (2007) *Mol Syst Biol* 3:74). Unlike in that reference, static transcription factor-gene association data were not used as part of the clustering model. The HMM model was restricted such that each state of the model was associated with one time point, and every state had a transition to at least one state in the next time point and no more than three states. Output distributions of each state were associated with a Gaussian distribution. Genes were grouped into clusters such that each gene in the same cluster had the same most probable path through the HMM model. A total of 16 clusters were identified.

Stress Response:

We also examined the expression profiles of stress-response genes during stationary phase, when the stationary phase σ factor RpoS controls the cellular physiology and complex gene regulatory network. In addition to the up-regulation of genes responsible for glycerol and acetate uptake (FIG. 15), several other known genes for the stress response were also up-regulated. For this we selected several genes which are shown to be up-regulated during stationary-phase stress response, and compared their expression profiles in our microarray data. Our results (FIG. 19) on mixed-substrate microarray analysis also showed that several known genes during various stationary-phase stress responses (osmotic stress, periplasmic shock, genes that help cell for long-term survival, universal stress) also show a high expression pattern after the cell reaches stationary phase; the expression pattern of these genes come down between 6 and 6.5 h and then go up again after 6.5 h. Thus, it can be concluded that *E. coli* cells display a dual stress response, a mild response prior to switching to the utilization of glycerol and acetate and a major one at the complete exhaustion of all substrates.

Figure 19:
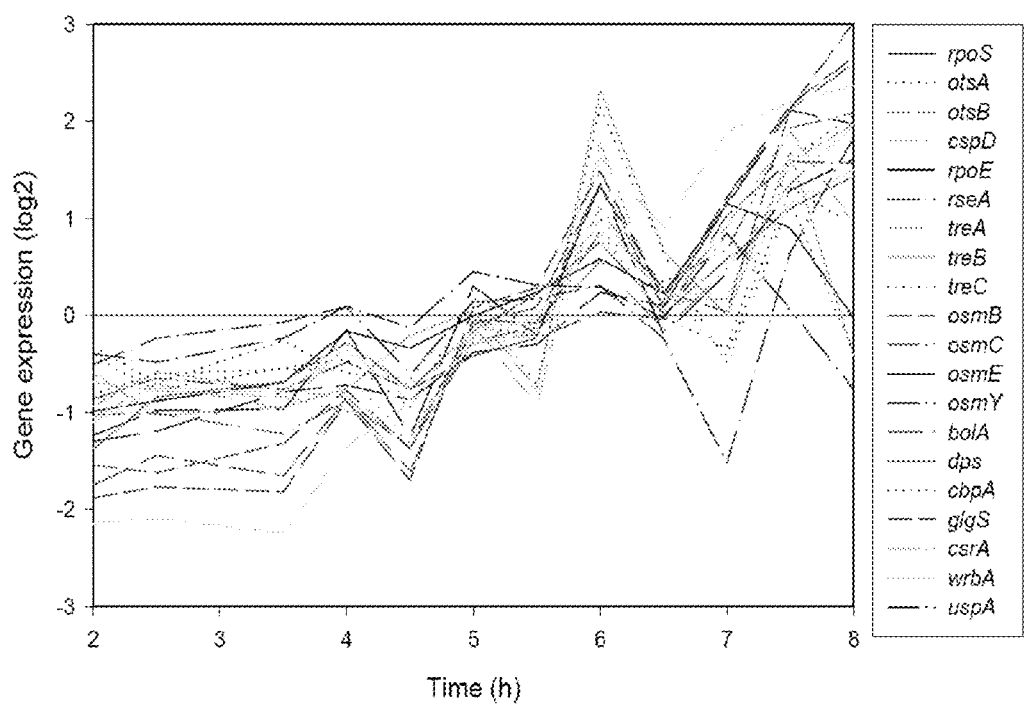
FIG. 19—Gene expression profiles of various genes known to be up-regulated during stationary phase stress response.

Biological functions of various genes shown in FIG. 19—rpoS: RNA polymerase, σS (σ38) factor; synthesis of many growth phase related proteins. Upon entry into stationary phase, the major adjustments in cellular physiology are controlled by complex regulatory network involving stationary-phase a factor RpoS.

The following genes are involved in survival of osmotic stress: otsA and otsB: trehalose-6-phosphate synthase and trehalose-6-phosphate phophatase; respectively; treC: trehalose-6-phosphate hydrolase; treB: PTS system enzyme II, trehalose specific; treA: trehalase, periplasmic; osmY: hyperosmotically inducible periplasmic protein; osmC: osmotically inducible protein; osmB: osmotically inducible lipoprotein; osmE: osmotically inducible protein. The following genes help cells for long-term survival: bolA: possible regulator of murein genes; dps: global regulator, starvation conditions; cbpA: curved DNA-binding protein; functions closely related to DnaJ; glgS: glycogen biosynthesis, rpoS dependent. Other genes induced during various stress responses: cspD: stress-induced DNA replication inhibitor; rpoE: RNA polymerase, σE factor; heat shock and oxidative stress; rseA: σE factor, negative regulatory protein (induced during periplasmic shock); csrA: carbon storage regulator; controls glycogen synthesis, gluconeogenesis, cell size; and surface properties; wrbA: flavoprotein WrbA (Trp repressor binding protein); uspA: universal stress protein.

Results

FBA with Molecular Crowding Predicts the Relative Maximum Growth of *E. coli* Growing on Single Carbon Sources:

FBAwMC is described above. To examine the validity of macromolecular crowding as a constraint on a cell's metabolic activity, and to test the predictive capability of the FBAwMC framework, we first examined the phenotypic consequences of extracellular substrate availability during growth in single carbon-limited medium with oxygen being in abundance, focusing on the maximum growth rate. The FBAwMC contains as a free parameter the average crowding coefficient <a>, and the model predictions for the maximum growth rate are proportional to <a>. We first assumed that <a> is a constant independent of the substrates. In this case it is possible to make predictions for the maximum growth rate in different substrates in arbitrary units. To obtain the maximum growth rates in specific units we fit <a> to minimize the mean-square deviation between the predicted and measured growth rates, resulting in <a>=0.0040±0.0005 h·g/mmol, in which g is grams of dry weight. We have obtained an independent estimate of $a_i$ for ≈100 *E. coli* enzymes as well, resulting in values between $10^{-6}$ and $10^{-1}$ and most probable values between $10^{-5}$ and $10^{-2}$ (in units of h·g/mmol). The obtained <a> is, therefore, within the expected range.

Using the reconstructed *E. coli* MG1655 metabolic network, we first tested the maximal growth rate of *E. coli* MG1655 cells in various single carbon-limited media and compared the results with the theoretically predicted growth rates (FIG. 13a). In most cases the line of perfect agreement falls within the standard deviation, implying an overall good agreement between the model predictions and the measured maximum growth rates. For glucose and glycerol, the line of perfect agreement is outside the standard deviation, indicating that our assumption of a substrate-independent <a> is not valid for these two substrates. *E. coli* is better adapted to growth on glucose, suggesting a smaller average crowding coefficient than in any of the other carbon sources. Indeed, the average crowding coefficient necessary to obtain a perfect agreement for glucose is smaller: <a>=0.0031±0.0001 h·g/mmol. In contrast, in some carbon-limited media *E. coli* reaches its predicted maximal growth rate only after a period of adaptive evolution (Fong S S, et al., (2004) *Nat Genet* 36:1056-1058; Ibarra R U, et al., (2002) *Nature* 420:186-189), suggesting a higher average crowding coefficient before metabolic adaptation. Indeed, the average crowding coefficient necessary to obtain a perfect agreement for glycerol is larger: <a>=0.0053±0.0001 h·g/mmol.

The FBAwMC framework also allows us to predict the maximal growth rate of microbial strains with deleted metabolic enzymes, by simply removing the corresponding metabolic reaction from the FBAwMC model and recomputing the maximal growth rate. To test the power of this predictive capability we experimentally determined the maximal growth rate of several *E. coli* MG1655 single gene deletion mutants grown in glucose-limited medium. As shown in FIG. 13b, the agreement between predicted and measured maximal growth rates is remarkably good for various *E. coli* mutants, providing further evidence for the validity of our approach. It is worth noting that, as with FBA alone, this analysis is not limited to single-enzyme mutants, but can be carried out for any combination of two or more enzyme deletions as well.

Substrate Hierarchy Utilization by *E. coli* Cells Growing in Mixed Substrates

Figure 13:
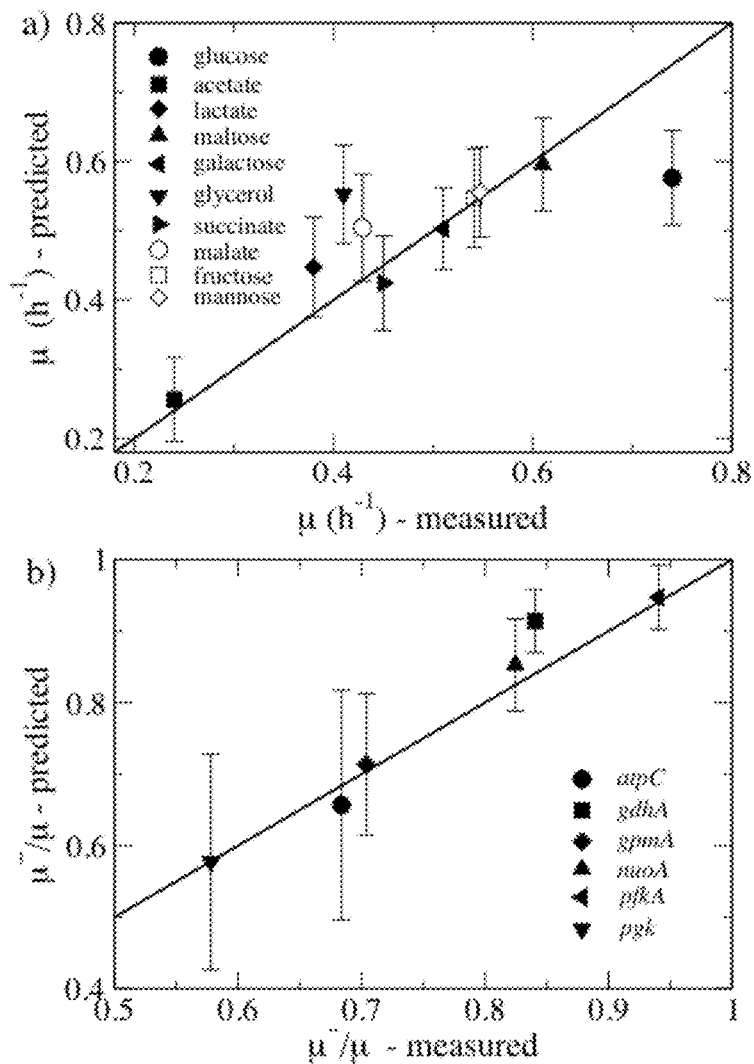
FIG. 13—Predicted and measured maximum growth rates comparison. (a) Comparison between the predicted- (Y-axis) and measured (X-axis) growth rates p of *E. coli* MG 1655 grown in M9 minimal medium with different carbon sources. For a perfect match between experiments and theory the symbols should fall on the black diagonal. The symbols indicate the carbon substrate identified in the legend. The predicted growth rates were obtained using <a>=0.0040 hour DW/mmol. The error bars represent standard deviation over 1000 sets of specific a, parameters. (b) Same plot for single gene deletion *E. coli* mutants growing in glucose, the deleted genes being indicated in the legend. The mutant growth rates μ⁻ are given relative to the predicted and measured maximum growth rate p of wild type *E. coli* cells growing in glucose-limited medium.
Figure 14:
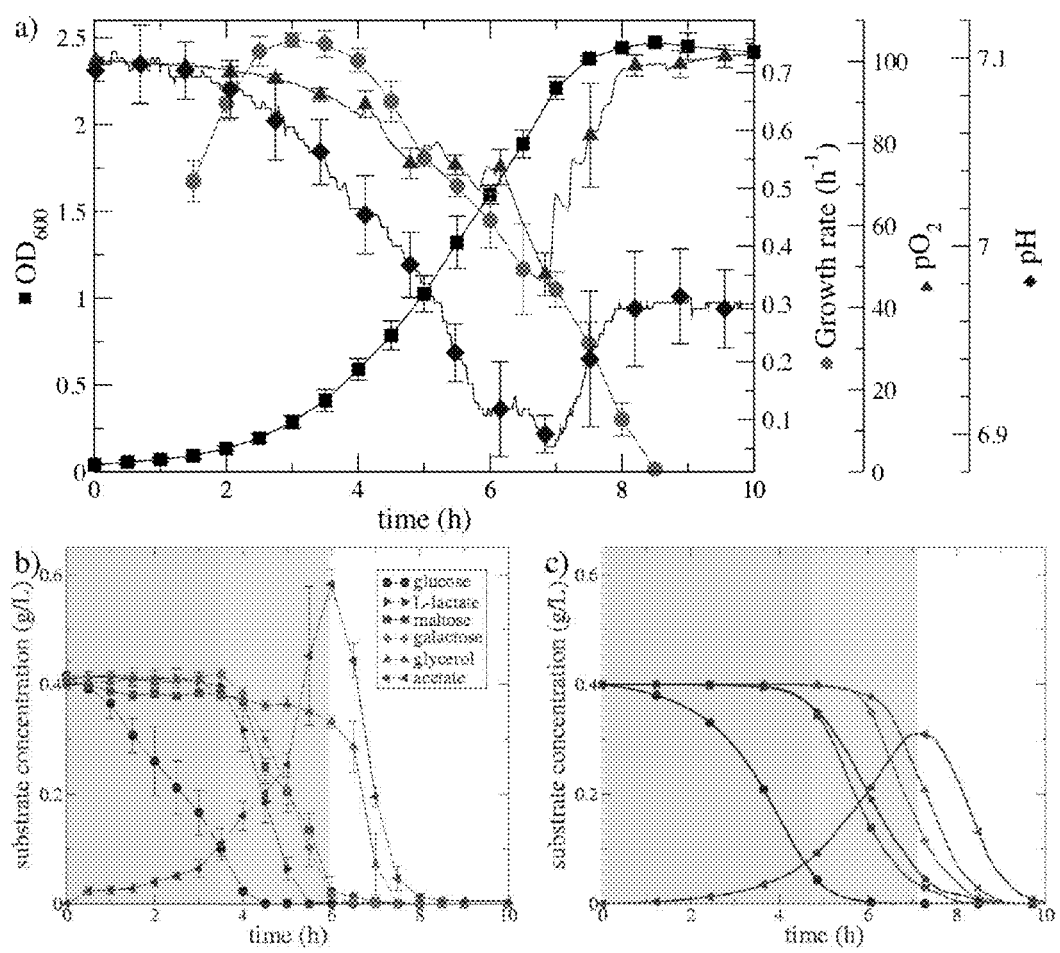
FIG. 14—*E. coli* growth profile, and predicted vs. measured hierarchy of substrate utilization (a) the absolute concentration and maximal growth rates of a batch culture of *E. coli* cells grown in M9-minimal medium containing an equal ratio of glucose, maltose, galactose, glycerol, and lactate is shown, together with the pH and oxygen concentration level. (b) The measured concentration of the indicated carbon sources in the growth medium. The growth experiments were performed in triplicate and averages and standard deviations are shown here. The three substrate utilization phases, phase 1 (exclusive glucose), phase 2 (mixed substrate) and phase 3 (glycerol and acetate) are indicated. (c) Predicted substrate uptakes from the growth medium based on the FBAwMC model. The color coding for substrate utilization curves is identical in panels b and c, and the error bars represent the standard deviations of the data analyzed from the samples collected from three individual bioreactor runs.
Figure 15A:
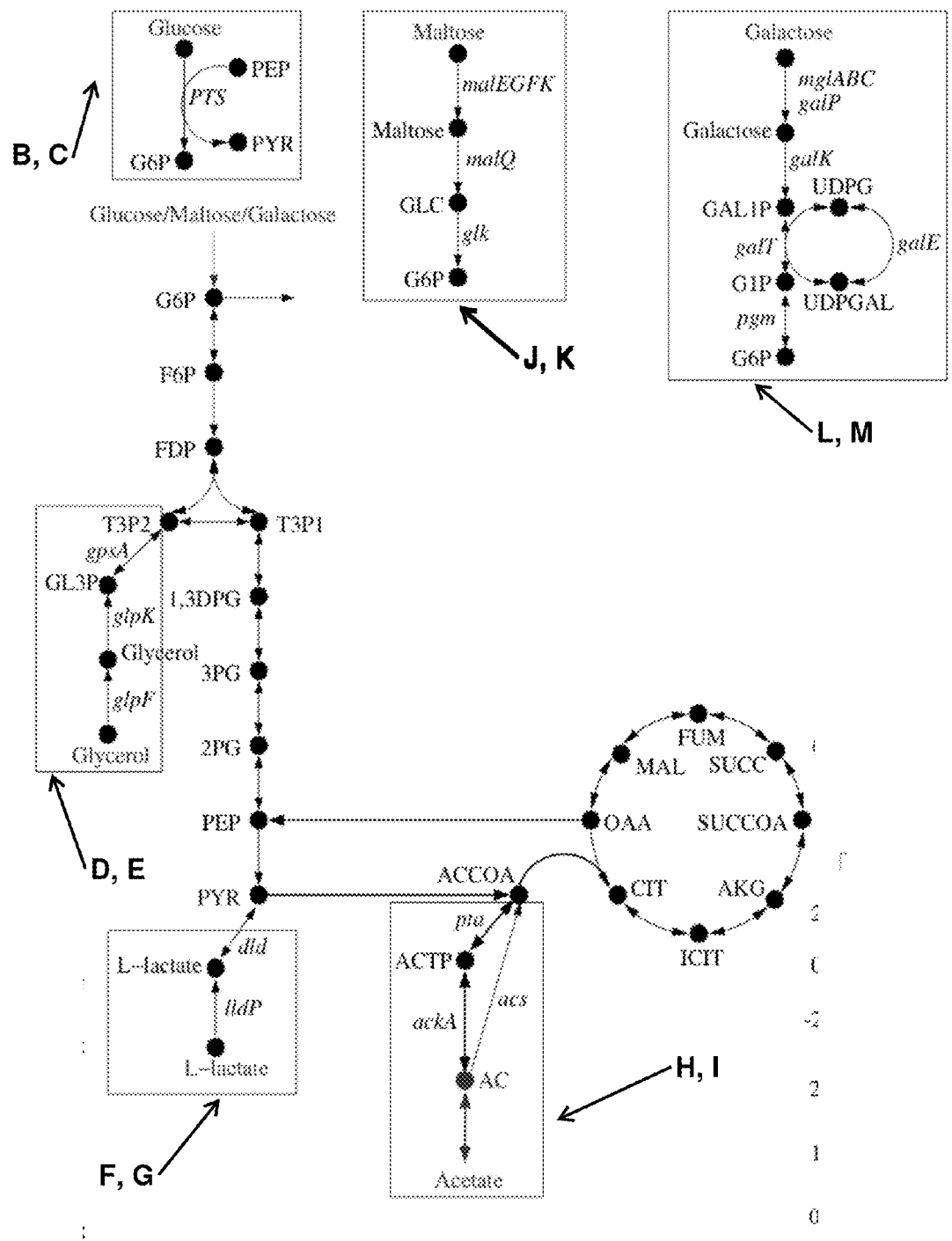
FIG. 15A shows a schematic of the central metabolism pathways for substrate uptake. Labels B to M in FIG. 15A denote the profiles in FIGS. 15B-15M, respectively.
Figure 15B:
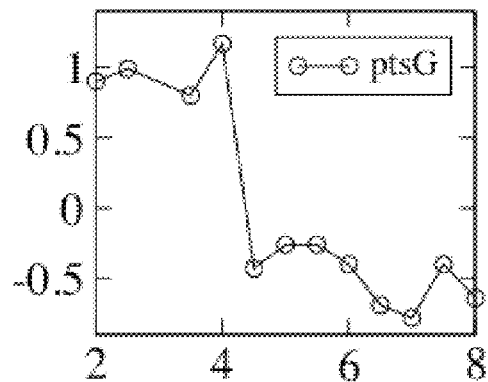
FIGS. 15B, 15D, 15F, 15H, 15J and 15L represent the measured relative gene expression profiles as a function of time (in hrs).
Figure 15C:
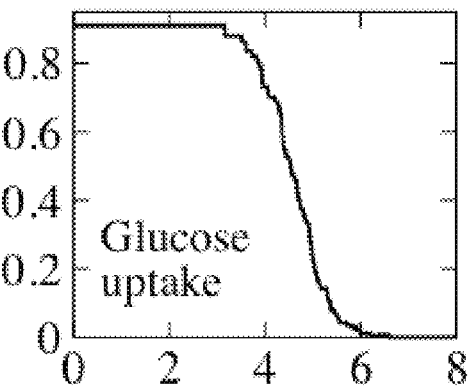
FIGS. 15C, 15E, 15G, 15I, 15K and 15M represent the predicted substrate uptake profiles (mmol/min g DW) also as a function of time (in hrs). Of the carbon sources present in the original growth medium, the uptake and entry points of glucose, maltose, galactose, glycerol, and lactate into the *E. coli* glycolytic pathway and citric acid cycle are shown. Acetate is initially produced and later consumed by *E. coli* cells growing in batch culture. All other substrates are shown in black and the genes encoding for various enzymes catalyzing the transport and degradation of intermediary substrates are also italicized. The description of genes responsible for uptake and utilization of listed carbon sources, their biological roles, and description of substrate entry mechanisms are detailed in FIG. 20. mRNA expression profiles of genes encoding metabolic transporters and enzymes specifically involved in galactose-, glucose-, glycerol-, lactate-, acetate- and maltose metabolism are shown. Gene expression values (on y-axis) in the time series microarray data are the calculated fold-changes for each time point relative to the geometric mean of the hybridization intensity of all time points for each gene and are expressed as log 2. The low values represent lower gene expression, while higher values represent higher gene expression.
Figure 15D:
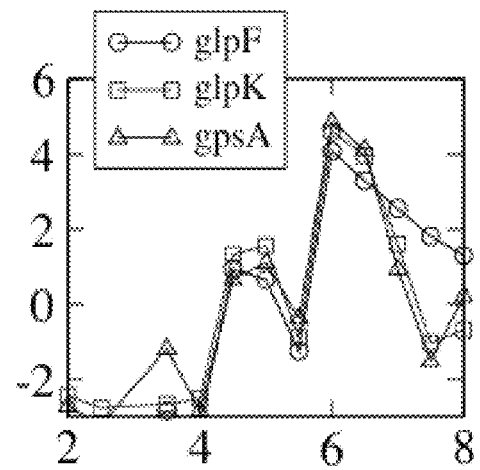
Figure 15E:
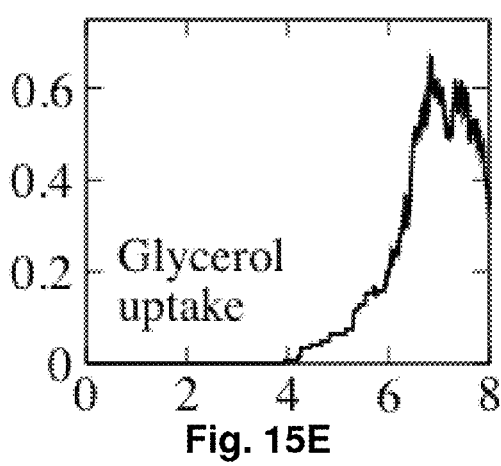
Figure 15F:
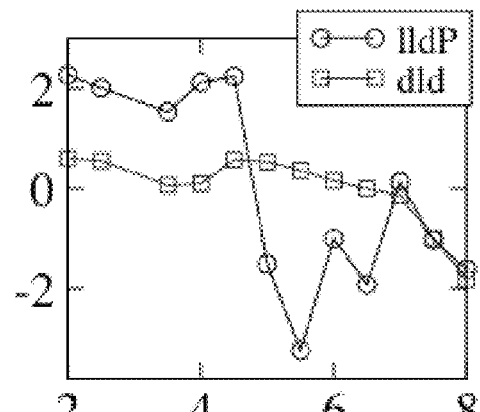
Figure 15G:
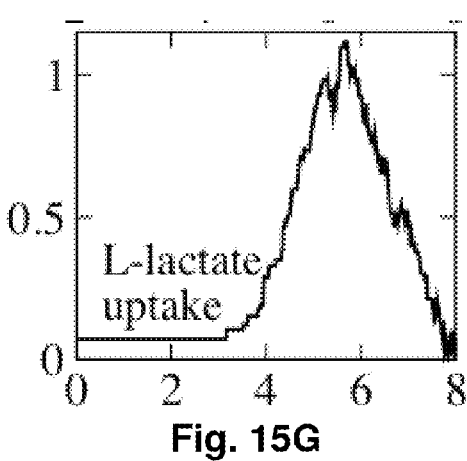
Figure 15H:
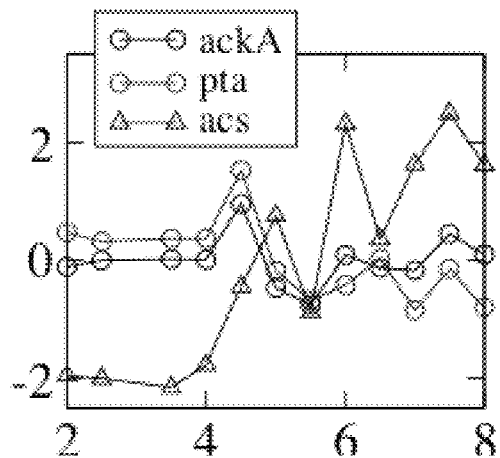
Figure 15I:
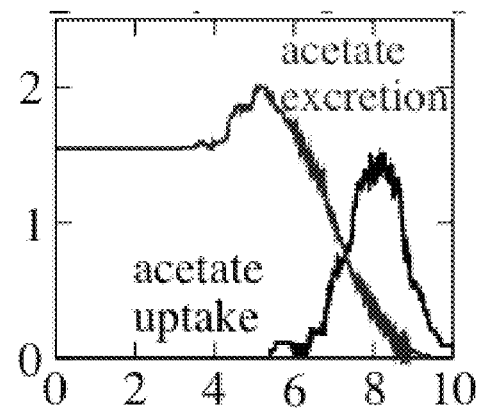
Figure 15J:
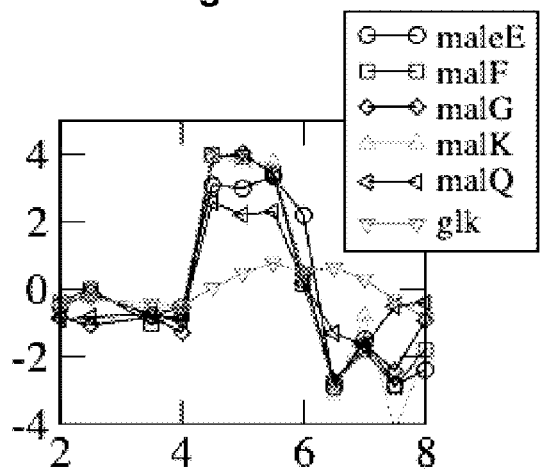
Figure 15K:
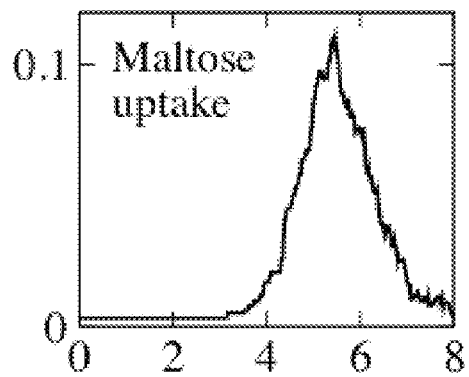
Figure 15L:
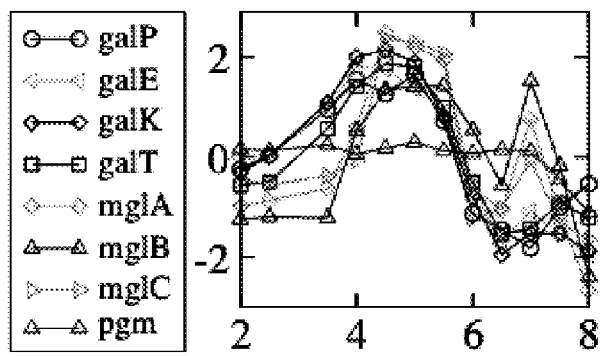
Figure 15M:
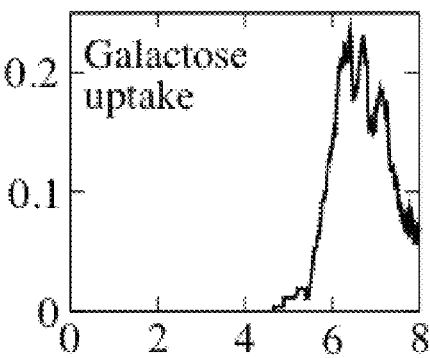

Extensive experimental data indicate that when grown in complex media bacterial cells use the available substrates either preferentially or simultaneously depending on the growth conditions. To further assess the role of an enzyme concentration limit on cellular metabolism we next examined the substrate utilization of *E. coli* cells in a mixed carbon-limited medium, and we compared the results to the FBAwMC *E. coli* model-predicted substrate uptake and utilization (FIG. 14). We grew *E. coli* MG1655 for 12 h in a batch culture containing an equal concentration (0.04% each) of five different carbon sources (galactose, glucose, maltose, glycerol, and lactate) (FIG. 14a). These substrates are taken up by *E. coli* through substrate-specific transport mechanisms and enter the central carbon metabolism through various substrate intermediates (FIG. 15 metabolic pathways). Note, that in single carbon-limited medium, maximum growth rates of *E. coli* in glucose (0.74 $h^{-1}$) was higher; whereas the experimentally measured maximal growth rates in glycerol (0.41 $h^{-1}$) and lactate (0.38 $h^{-1}$) were lower than the model predictions (FIG. 13a). In contrast, the maximal growth rates obtained on maltose (0.61 $h^{-1}$) and galactose (0.51 $h^{-1}$) were in good agreement with the FBAwMC-predicted values (FIG. 13a).

As typically seen in batch culture, initially *E. coli* cells showed minimal growth (lag phase) followed by rapid population expansion between 2 and 8 h (exponential growth phase) with no further growth afterward (stationary phase) (FIG. 14a). Parallel with this, the growth rate rapidly increased with the start of the logarithmic growth phase, reaching its maximum between 3 and 3.5 h. Thereafter the growth rate steadily declined, becoming negligible to zero after 8 h (FIG. 14a).

Of the five supplied carbon sources, in the first 3.5 h of growth only glucose was used (phase 1); it was depleted from the medium within the first 4 h (FIG. 14a). This "exclusive glucose use" phase coincided with the initial explosive growth and the maximal attained growth rate of the culture (FIG. 14a). At 3.5-4 h *E. coli* cells started to use all four remaining carbon sources, albeit at different rates. Galactose, lactate, and maltose were preferentially used during the next 2 h (phase 2), all three of them being depleted from the growth medium by the sixth hour (FIG. 14b). During this "mixed carbon utilization" phase lactate was used up at the fastest rate, followed by maltose and galactose. A small amount of glycerol was also taken up during this time interval, but its predominant utilization occurred only after 6 h, and it was completely depleted from the medium by 7.5 h (FIG. 14b). The concentration of acetate, a well known byproduct of rapid E. coli aerobic growth, increased steadily, reaching its peak concentration in the growth medium at 6 h of growth. Thereafter, the process was reversed, and acetate, along with glycerol, was rapidly consumed and was depleted from the medium by 8 h (FIG. 14b), denoting a "late carbon utilization" phase in the culture (phase 3). Of note, as single carbon source, acetate provides a lower maximal growth rate (0.24 $h^{-1}$) than any of the five supplied carbon sources (FIG. 13a). Taken together, the sequential order of carbon substrates' uptake in the batch culture experiment only partially correlates with the maximal growth rate they individually provide: it appears earlier for lactate and later for maltose and glycerol.

Subsequently, we tested FBAwMC E. coli model on the mixed-substrate conditions. In contrast with FBA, which predicts the simultaneous utilization of all carbon sources, we find a remarkably good correlation between the mode and sequence of FBAwMC-predicted and measured substrate uptake and consumption (FIGS. 14b and 14c). There are, however, two notable differences. First the FBAwMC predicts a lesser excretion of acetate. In turn the substrates are consumed faster in vivo (FIG. 14b) because a larger fraction of the carbon source is diverted toward the excretion of acetate. As a consequence the different phases of substrate consumption are shifted to the right (longer times) for the model predictions. The second major discrepancy is the delayed consumption of galactose in the model predictions (FIG. 14c). Yet, overall FBAwMC correctly predicts the existence of the three experimentally observed phases of substrate consumption: initial consumption of glucose, intermediate mixed-substrate consumption, and late consumption of glycerol and acetate.

As surrogate markers of cellular metabolism, during the batch culture experiments we also traced the changes in pH and oxygen concentrations in the growth medium. We observed a steady decline in pH during the first 6 h, followed by a slight increase then decrease between 6 and 7 h, and finally an increase between 7 and 8 h (FIG. 14a). There was also an accelerating decline in the dissolved oxygen concentration ($pO_2$) in the medium during the first 7 h, followed by a rapid stepwise increase during the next 30 min. However, the decline phase (indicating aerobic respiration in an increasingly acidic environment because of acetate excretion) was consistently interrupted by rapid upswings in $pO_2$ concentration (FIG. 14a). These spikes indicate brief pauses in aerobic metabolism likely due to switches in predominant substrate use. Indeed, the first of these spikes, at ≈4 h, correlates with the depletion of glucose and initiation of mixed-substrate utilization; the second, at ≈5 h, with the depletion of lactate and increased utilization of maltose; and the third, at ≈6 h, with the start of joint glycerol and acetate utilization. Similarly, the first rapid increase in oxygen concentration at ≈7 h correlates with the near-depletion of glycerol, followed by a final increase after 30 min corresponding with the depletion of acetate from the medium (FIG. 14b).

The Mode and Sequence of Substrate Utilization Correlate with the Expression of Genes Participating in the Uptake Modules:

We also prepared mRNA from samples obtained at 30-min intervals between 2 and 8 h and processed them for microarray analysis. At the level of substrate uptake pathways (FIG. 15) it is evident that the expression of ptsG, the gene encoding the glucose transporter PtsG/Crr, was at a high level from the first time point up until the depletion of glucose from the growth medium, and ptsG expression was rapidly turned off afterward. Similarly, the expression of the gene (lldP) encoding the lactate transporter, LldP, was high during the first 4.5 h of growth and was turned off rapidly thereafter, in agreement with the earlier than predicted utilization of lactate. In contrast, the expression of gene products responsible for maltose and galactose uptake and utilization were turned on much later and peaked at 4.5-5.5 h, corresponding with the period of their maximal uptake. The expression of gene products responsible for glycerol uptake and utilization peaked in two waves, the smaller one between 4.5 and 5 h and the larger one at 6.5-7 h, the latter corresponding to maximal glycerol consumption from the medium (FIG. 14b). Finally, the expression of acs, whose gene product catalyzes acetate uptake toward the citric acid cycle, peaked between 6 and 8 h of growth, corresponding to the maximal uptake of previously secreted acetate from the growth medium. We note that all these changes are in good agreement with the FBAwMC model-predicted uptake of the corresponding substrates (FIG. 15, black tracings).

To assess the quality of the microarray profiles and to identify genes with expression patterns that are similar to those of genes encoding enzymes of the uptake pathways we used TimeSearcher. We find that most genes displaying expression patterns similar to those of the query genes are colocalized with them in the same operon. For example, for the maltose uptake module genes (malEFGK, malQ, and glk), TimeSearcher identified several other genes (lamB, malM, malP, malS, and malZ) with similar expression profiles. These genes are part of various operons within the maltose regulon, although not all of them directly participate in maltose uptake. Similarly, for glycerol metabolism several related glycerol utilization genes (glpA, glpB, glpC, gipD, glpQ, and glpT) displayed expression patterns that were similar to those of the three genes responsible for glycerol uptake (glpF, glpK, and gpsA). The products of these genes are part of the pathway for glycerol catabolism after its uptake.

Activation of Stress Programs Upon Switching Metabolic Phases

To assess the global state of E. coli transcriptome during the various metabolic phases of the time course experiment, we used three different data analysis methods to analyze the full microarray data. These methods included hierarchical clustering with optimal leaf ordering (Bar-Joseph Z, et al., (1998) Proc Natl Acad Sci USA.) (FIG. 16), principal component analysis (PCA) (Peterson LE (2003) Comput Methods Programs Biomed 70:107-119.) (FIG. 18), and a probabilistic clustering method based on hidden Markov models (HMMs) (Ernst J, Vainas O, Harbison C T, Simon I, Bar-Joseph Z (2007) Mol Syst Biol 3:74.) (not shown). It was evident that during the exclusive glucose utilization phase there are similar expression profiles in all samples collected between 2 and 3.5 h, followed by transition in the transcriptome state at the beginning of mixed utilization phase after 4 h (FIG. 16). Within the latter phase, the up-regulation of, e.g., the genes of the maltose regulon are clearly evident (FIG. 16).

Samples obtained during the mixed-substrate utilization phase (5 and 5.5 h) and the late carbon utilization phase (6.5 h) display similar global expression profiles (FIG. 16), interrupted by a significant alteration in the expression profile at 6 h that denotes the switch from acetate secretion to acetate utilization (FIG. 15). Interestingly, the transcriptome at 6 h displays substantial similarity to that characterizing E. coli cells at the (near) exhaustion of all substrates from the medium (7-8 h), a phase that is characterized by generic stress response (FIG. 16 and FIG. 19). Similarly, many of the genes up-regulated at the end of the last phase are also up-regulated to a lesser extent at 3.5 h, the stage of switching from exclusive glucose utilization to a mixed-substrate utilization phase.

To further characterize the time-point-specific expression profiles, we also prepared mRNA samples from individual mid-logarithmic batch culture E. coli cells ($OD_{600} \approx 0.2$) grown in glucose-, maltose-, glycerol-, acetate-, lactate-, or galactose-limited medium, processed them for microarray analysis, and compared the obtained transcriptome profiles with those of the individual time points (FIG. 16 Lower) from mixed-substrate experiment. It is evident that the transcriptome profiles during the glucose-only and mixed-substrate utilization phases display the highest correlation to that of glucose- and maltose-limited cultures, especially at the initial time points, whereas the late carbon utilization profiles are most similar to that of glycerol- and, especially, acetate-limited cultures. Highly notable is the transcriptome profile of galactose-limited cultures, which shows some similarity to that of cells at the stage of switching from exclusive glucose utilization to a mixed-substrate-utilization phase (3.5 h), and an even higher similarity to the transcriptome profiles of cells when all carbon sources are depleted (8 h). Thus, E. coli cells display a partial adaptation/stress response at each major metabolic transition, followed by a generic stress response (FIG. 19) and implementation of a foraging program (Liu M, et al., (2005) J Biol Chem 280:15921-15927.) at complete exhaustion of all extracellular substrates that seems to be most primed for acetate and galactose catabolism.

Discussion

A key aim of systems biology is the identification of the organizing principles and fundamental constraints that characterize the function of molecular interaction networks, including those that define cellular metabolism. In the present work we have focused on the identification of principles that define the growth and substrate utilization mode of bacterial cells in complex environments. Our experimental results indicate the occurrence of three major metabolic phases during the growth of E. coli on one type of mixed-substrate medium. Glucose, which by itself provides the highest growth rate, is preferentially used by E. coli, followed by simultaneous utilization of maltose, 1-lactate, and galactose. Glycerol and (secreted) acetate are used at a third and final stage of growth. In addition, global mRNA expression data indicate that the organism-level integration of cellular functions in part involves the appearance of partial stress response by E. coli at the boundaries of major metabolic phases, and, as previously shown (Liu M, et al., (2005) J Biol Chem 280:15921-15927), the activation of a foraging program upon exhaustion of substrates from the growth medium (FIG. 16).

The simulation results show that the FBAwMC model introduced here successfully captures all main features of the examined metabolic activities. First, there is a significant correlation between in vivo relative maximal growth rates of E. coli in different carbon-limited media and the in silico predictions of the FBAwMC (FIG. 13). Second, the FBAwMC model predicts remarkably well the existence of three metabolic phases and hierarchical mode (i.e., single- or mixed-substrate utilization) of substrate utilization in mixed-substrate growth medium (FIGS. 14-16). In essence, our modeling approach indicates that when E. coli cells grow in conditions of substrate abundance their growth rate is determined by the solvent capacity of the cytoplasm; vice versa, the solvent capacity should be saturated at the maximal growth rate. Therefore, when growing in a mixture of abundant carbon sources E. coli cells should preferentially consume the carbon source resulting in the highest growth rate. At solvent capacity saturation, the synthesis of metabolic enzymes for the utilization of a second, less efficient, carbon source can take place only at the expenses of degrading metabolic enzymes involved in the consumption of the more efficient carbon source. However, this would result in a growth rate reduction and, therefore, cells preferentially using the more efficient carbon source would outgrow those that allow the simultaneous utilization of other carbon sources.

We observe, however, two discrepancies of the FBAwMC model predictions: (i) a higher than predicted amount of secreted acetate in the growth medium, and (ii) a somewhat earlier uptake and consumption of various substrates from the medium compared with that predicted by the model. The first discrepancy is likely rooted on the contribution of other cell components apart from metabolic enzymes. With increasing growth rate higher concentrations of ribosomal proteins, mRNA, and DNA are required in addition to metabolic enzymes (Neidhardt F C, et al., (1990) Physiology of the Bacterial Cell: A Molecular Approach (Sinauer, Sunderland, Mass.). This observation indicates that the FBAwMC model may underestimate the impact of macromolecular crowding and the resulting excretion of acetate. The second discrepancy is quite likely a consequence of the first one, as acetate secretion is generally correlated with an increased carbon source uptake rate (El-Mansi E M, et al., (1989) J Gen Microbiol 135:2875-2883).

Taken together, our results show that in silico models incorporating flux balance and other physicochemical constraints can capture increasingly well the metabolic activity of bacterial cells, and that the maximum enzyme concentration is a key constraint shaping the hierarchy of substrate utilization in mixed-substrate growth conditions. Yet, while the metabolic capabilities of a cell are limited by such constraints, in reality any change in metabolic activity is controlled by regulatory mechanisms evolved in the context of these constraints. Therefore, constrained optimization approaches are also expected to help us better understand and/or uncover regulatory mechanisms acting in E. coli and other organisms.

Example 3

Flux Balance in S. Cerevisiae with Molecular Crowding and Kinetic Modeling

During cellular metabolism the concentration of enzymes and metabolites are continuously adjusted in order to achieve specific metabolic demands. It is highly likely that during evolution global metabolic regulation has evolved such as to achieve a given metabolic demand with an optimal use of intracellular resources. However, the size of enzymes and intermediate metabolites are dramatically different. Enzymes are macromolecules that occupy a relatively large amount of space within a cell's crowded cytoplasm, while metabolites are much smaller. This implies that metabolite concentrations are likely to be adjusted to minimize the overall 'enzymatic cost' (in terms of space cost).

Here we study the validity of this hypothesis by focusing on the glycolysis pathway of the yeast, Saccharomyces cerevisiae, for which a kinetic model is available. We show that the maximum glycolysis rate determined by the limited solvent capacity is close to the values measured in vivo. Furthermore, the measured concentration of intermediate metabolites and enzyme activities of glycolysis are in agreement with the predicted values necessary to achieve this maximum glycolysis rate. Taken together these results indicate that the limited solvent capacity constraint is relevant for *S. cerevisiae* at physiological conditions. From the modeling point of view, this work demonstrates that a full kinetic model together with the limited solvent capacity constraint can be used to predict not only the metabolite concentrations, but in vivo enzyme activities as well.

Methods

Kinetic Model of Glycolysis:

We use the *S. cerevisiae* glycolysis model reported in Hynne F, Dano S, Sorensen PG (2001) Full-scale model of glycolysis in *Saccharomyces cerevisiae*. Biophys Chem 94: 121-163 (see below for details). The only modification is the extension of the phsophofructokinase (Pik) kinetic model from an irreversible to a reversible model.

Figure 21:
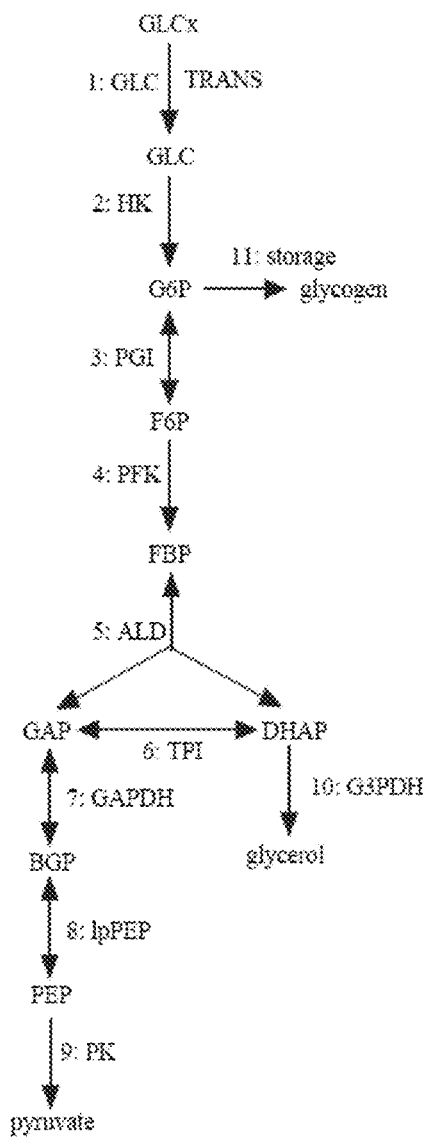
FIG. 21 is a schematic representation of *Saccharomyces cerevisiae* glycolysis.

FIG. 21 is a schematic representation of *saccharomyces cerevisiae* glycolysis.

The optimization objective is the glycolysis rate $$\frac{R}{1-\phi} = \frac{1}{\sum_{i=2}^{10} a_i r_i} \quad [12]$$

where $\Phi$ is the fraction of cell volume occupied by cell components other than glycolysis enzymes, $r_i$ is the rate of the i-th reaction relative to the glycolysis rate, $$a_i = \frac{v_{spec}\mu_i\rho}{x_i k_i} \quad [13]$$

is the crowding coefficient associated with the i-th reaction, $v_{spec}$ is the specific volume, and $\mu_i$ and $k_i$ are the molar mass and catalytic constant of the enzyme catalyzing the i-th reaction. Note that the transport (3) and storage (11) reactions have been excluded. The former does not contribute to the cytoplasm crowding and the latter is considered and step outside glycolysis.

Given the storage rate and the concentration of ATP, the rate equation [24] below determines the concentration of G6P. Furthermore, given this G6P concentration, and the concentration of extracellular glucose, ATP and ADP, the rate equation [14] determines the concentration of intracellular glucose. The remaining metabolite concentrations are obtained such that to maximize [12].

The following are rate equation models, as reported in Hynne F, et al., (2001) *Biophys Chem* 94: 121-163.

Glucose Transport (TRANS):

$$v_1 = \frac{\dfrac{P_1 \dfrac{[GLCx]}{K_{1GLC}} + 1}{P_1 \dfrac{[GLC]}{K_{1GLC}} + 1}\left(1 + \dfrac{[GLC]}{K_{1GLC}} + \dfrac{[G6P]}{K_{1GLC}} + \dfrac{[GLC][G6P]}{K_{1GLC}K_{1IIGLC}}\right)}{\dfrac{[GLCx] - [GLC]}{K_{1GLC}}} V_{1,max} \quad [14]$$

Hexokinase (HK):

$$x_2 = \frac{K_{2DGLC}K_{2ATP} + K_{2GLC}[ATP] + K_{2ATP}[GLC] + [GLC][ATP]}{[ATP][GLC]} \quad [15]$$

Phosphoglucoisomerase (PGI):

$$x_3 = \frac{K_{3G6P} + [G6P] + \dfrac{K_{3G6P}}{K_{3F6P}}[F6P]}{[G6P] - \dfrac{[F6P]}{K_{3eq}}} \quad [16]$$

Phosphofructokinase-1 (PFK):

$$x_4 = \frac{K_{5F6P}\left(1 + \kappa_4 \dfrac{[ATP]^2}{[ADP]^2}\right) + \left([F6P] + \dfrac{K_{4F6P}}{K_{4FBP}}[FBP]\right)^2}{\left([F6P] + \dfrac{[FBP]}{K_{4eq}}\right)\left([F6P] + \dfrac{K_{4F6P}}{K_{4FBP}}[FBP]\right)} \quad [17]$$

This reaction is generally considered as irreversible. Ignoring its reversibility would result, however, in infinitely large values for FBP. Therefore, we have made the reversible extension of this model following Hofmeyr J-H et al., (1997) The reversible Hill equation: how to incorporate cooperative enzymes into metabolic models. Compt Appl Biosci 13: 377-385.

Aldolase (ALD):

$$x_5 = \frac{K_{5FBP} + [FBP] + \dfrac{[GAP]K_{5DHAP}V_{5f}}{K_{5eq}V_{5r}} + \dfrac{[DHAP]K_{5GAP}V_{5f}}{K_{5eq}V_{5r}} + \dfrac{[FBP][GAP]}{K_{5IGAP}} + \dfrac{[GAP][DHAP]V_{5f}}{K_{5eq}V_{5r}}}{[FBP] - \dfrac{[GAP][DHAP]}{K_{5eq}}} \quad [18]$$

Triosephosphate Isomerase (TPI):

$$x_6 = \frac{K_{6DHAP} + [DHAP] + \dfrac{K_{6DHAP}}{K_{6GAP}}[GAP]}{[DHAP] - \dfrac{[GAP]}{K_{6eq}}} \quad [19]$$

Glyceraldehyde 3-phosphate dehydrogenase (GAPDH):

$$x_7 = \frac{K_{7GAP}K_{7NAD}\left(1 + \dfrac{[GAP]}{K_{7GAP}} + \dfrac{[BGP]}{K_{7BGP}}\right)\left(1 + \dfrac{[NAD]}{K_{7NAD}} + \dfrac{[NADH]}{K_{7NADH}}\right)}{[GAP][NAD] - \dfrac{[BGP][NADH]}{K_{7eq}}} \quad [20]$$

(1pPEP):

$$v_8 = k_{8f}[BGP][ADP] - k_{8r}[PEP][ATP] \quad [21]$$

Pyruvate Kinase (PK):

$$x_9 = \frac{(K_{9PEP} + [PEP])(K_{9ADP} + [ADP])}{[ADP][PEP]} \quad [22]$$

Glycerol 3-Phosphate Dehydrogenase (G3PDH):

$$x_{10} = \frac{K_{10DHAP}\left(1 + \frac{K_{15INADH}}{[NADH]}\left(1 + \frac{[NAD]}{K_{10INAD}}\right)\right)[DHAP]\left(1 + \frac{K_{15NADH}}{[NADH]}\left(1 + \frac{[NAD]}{K_{10INAD}}\right)\right)}{[DHAP]} \quad [23]$$

Storage $$v_{11} = k_{11}[ATP][G6P] \quad [24]$$

TABLE 2

Kinetic constants (as reported in Hynne F, et al. (2001) Biophys Chem 94: 121-163):

| Reaction | Parameter | Value |
|---|---|---|
| 1: TRANS | $K_{1GLC}$ | 1.7 |
|  | $K_{1IG0P}$ | 1.2 |
|  | $K_{1IIG0P}$ | 7.2 |
|  | $P_1$ | 1 |
|  | $V_{1,max}$ | 1015 mM/min |
| 2: HK | $K_{2ATP}$ | 0.1 |
|  | $K_{3GLC}$ | 0 |
|  | $K_{3DGLC}$ | 0.37 |
| 3: PGI | $K_{3G6P}$ | 0.8 |
|  | $K_{3F6P}$ | 0.15 |
|  | $K_{3eq}$ | 0.13 |
| 4: PFK | $K_{4P6P}$ | 0.021 |
|  | $K_{4FBP}$ | 0.003[a] |
|  | $\kappa_4$ | 0.15 |
|  | $K_{4eq}$ | 800.0[b] |
| 5: ALD | $V_{5f}/V_{5r}$ | 0.2 |
|  | $K_{5FBP}$ | 0.3 |
|  | $K_{5GAP}$ | 4.0 |
|  | $K_{5DHAP}$ | 2.0 |
|  | $K_{5IGAP}$ | 10.0 |
|  | $K_{5eq}$ | 0.081 |
| 6: TPI | $K_{6DHAP}$ | 1.23 |
|  | $K_{6GAP}$ | 1.27 |
|  | $K_{6eq}$ | 0.055 |
| 7: GAPDH | $K_{7GAP}$ | 0.6 |
|  | $K_{7BGP}$ | 0.01 |
|  | $K_{7NAD}$ | 0.1 |
|  | $K_{7NADH}$ | 0.06 |
|  | $K_{7eq}$ | 0.0055 |
| 8: lpPEP | $k_{8f}$ | 443900 |
|  | $k_{8r}$ | 1529 |
| 9: PK | $K_{9ADP}$ | 0.17 |
|  | $K_{9PEP}$ | 0.2 |
| 10: G3PDH | $K_{10NADH}$ | 0.13 |
|  | $K_{10DHAP}$ | 25 |
|  | $K_{10INADH}$ | 0.034 |
|  | $K_{10INAD}$ | 0.13 |
| 11: storage | $k_{11}$ | 2.26 |

[a]This parameter was fitted to obtain the best agreement between the measured FBP concentration and the value predicted by the maximization of [12] with all other metabolite concentrations fixed to their experimentally determined values.
[b]From Teusink B et al., (2000) Eur J Biochem 267: 5113-5329.

TABLE 3

Enzyme molar masses and catalytic constants

| Nomanclature | Enzyme | Molar mass (g/mol) | Catalytic constant (1/s) |
|---|---|---|---|
| hk | hexokinase | 53738.7 | 96 |
| pgi | phosphogluco isomerase | 61299.5 | 120 |
| pfk | phospho-fructokinase | 107971 | 376 |
| ald | fructose 1,6-bisphosphate aldolase | 39620.9 | 142 |
| tpi | triosephosphate isomerase | 26795.6 | 3580 |
| gapdh | D-glyceraldehyde 3-phosphate dehydrogenase | 35750 | 144 |
| pk | pyruvate kinase | 55195.5 | 632 |
| g3pdh | glycerol 3-phosphate dehydrogenase | 42869.1 | 33.3 |

The catalytic constants were obtained from experimental estimates for *Saccharomyces carlsbergensis* (Boiteux et al., Design of glycolysis, Phil Trans R Soc Lond B, 1981, 293, pgs. 5-22), except for g3pdh that was obtained from an estimate for *Eidolon helvum*.

TABLE 4

Specific volume and cell density

| Parameter | Name | Value | Source |
|---|---|---|---|
| $v_{spec}$ | Specific volume | 0.73 ml/g | globular protein [6] |
| $\rho$ | Cell density | 0.34 g/ml | *E. coli* [7] |

TABLE 5

Reaction rates (Hynne F, et al. (2001) Biophys Chem 94: 121-163):

| Reaction/pathway | nomenclature | relative rate |
|---|---|---|
| glycolysis | $v_0$ | 27 mM/min |
| fermentation | $r_{ferm}$ | 0.12 |
| glycerol production | $r_{glyc}$ | 0.13 |
| lactonitrile formation | $r_{lact}$ | 0.04 |
| glycogen buildup | $r_{stor}$ | 0.71 |
| HK | $r_2$ | $r_{ferm} + r_{glyc} + r_{lact} + 2r_{stor}$ |
| PGI | $r_3$ | $r_{ferm} + r_{glyc} + r_{lact} + r_{stor}$ |
| PFK | $r_4$ | $r_{ferm} + r_{glyc} + r_{lact} + r_{stor}$ |
| ALD | $r_5$ | $r_{ferm} + r_{glyc} + r_{lact} + r_{stor}$ |
| TPI | $r_6$ | $r_{ferm} + r_{stor}$ |
| GAPDH | $r_7$ | $2r_{ferm} + r_{glyc} + r_{lact} + 2r_{stor}$ |
| lpPEP | $r_8$ | $2r_{ferm} + r_{glyc} + r_{lact} + 2r_{stor}$ |
| PK | $r_9$ | $2r_{ferm} + r_{glyc} + r_{lact} + 2r_{stor}$ |
| G3PDH | $r_{10}$ | $r_{glyc} + r_{lact}$ |

TABLE 6

Fixed metabolite concentrations (Hynne F, et al. (2001) Biophys Chem 94: 121-163):

| Nomenclature | Metabolite | Experiment (mM) |
|---|---|---|
| GLCx | External glucose | 1.6 |
| ATP | Adenosine 5'-triphosphate | 2.1 |
| ADP | Adenosine 5'-biphosphate | 1.5 |
| AMP | Adenosine 5'-monophosphate | 0.33 |
| NADH | Nicotinamide adenine dinucleotide (reduced form) | 0.33 |
| NAD | Nicotinamide adenine dinucleotide (oxidized form) | 0.65 |

III. Experimental Data Used in the Comparison with the Theoretical Predictions

TABLE 7

Metabolite concentrations, as reported in Hynne F, et al. (2001) Biophys Chem 94: 121-163.

| Nomenclature | Metabolite | Concentration (mM) |
|---|---|---|
| G6P | Glucose 6-phosphate | 4.1 |
| F6P | Fructose 6-phosphate | 0.5 |
| FBP | Fructose 1,6-biphosphate | 5.1 |
| GAP | Glyceraldehyde 3-phosphate | 0.12 |
| DHAP | Dihydroxyacetone phosphate | 2.5 |
| PEP | Phosphoenol pyruvate | 0.04 |

TABLE 8

Enzyme activities A relative to the glycolysis rate R (Teusink B et al. (2000), Eur J Biochem 267: 5113-5329)

| Nomenclature | Enzyme | Activity (A/R) |
|---|---|---|
| pgi | phosphogluco isomerase | 3.15 |
| pfk | phospho-fructokinase | 1.7 |
| ald | fructose 1,6-biphosphate aldolase | 2.98 |
| tpi | triosephosphate isomerase | 21.0 |
| gapdh | D-glyceraldehyde 3-phosphate dehydrogenase | 11.0-00.0[a] |
| pk | pyruvate kinase | 10.1 |

[a] For the forward and reverse reaction. In this case we used the average, 35.5, to make the comparison with the theoretical predictions.

Catalytic Constants, Cell Density, Specific Volume:

The catalytic constants were obtained from experimental estimates for *Saccharomyces carlsbergensis* (Boiteux et al., Design of glycolysis, Phil Trans R Soc Lond B, 1981, 293, pgs. 5-22), except for glycerol 3-phosphate dehydrogenase that was obtained from an estimate for *Eidolon helvum* (Schomburg I, Nucleic Acids Res 30: 47-49). For the cell density we use an estimate reported for *E. coli*, p=0.34 g/ml (Zimmerman S B, et al. (1991) J Mol Biol 222: 599-620.). The specific volume was estimated for several proteins using the molar volumes and masses reported in (Lee B (1983) Proc Natl Acad Sci USA 80: 622-626), resulting in average of 0.73 ml/g, and a standard deviation of 0.02 ml/g.

Figure 3A:
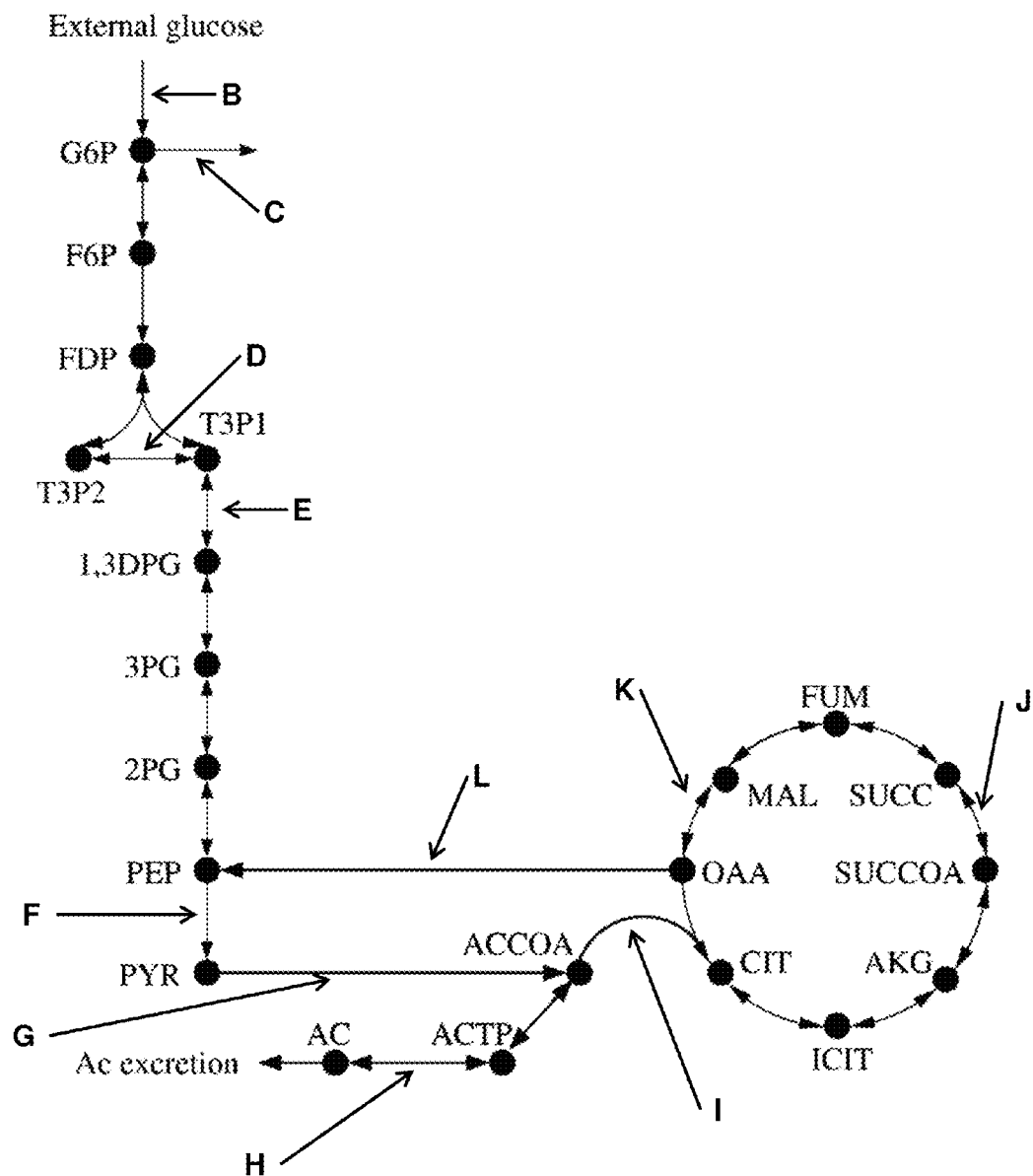
FIG. 3A shows a schematic of the central metabolism pathways. Labels B to L in FIG. 3A denote the experimental flux measurements shown in FIGS. 3B-3L, respectively. The experimental flux measurements were performed at dilution rates 0.1, 0.25, 0.4, 0.55 and 0.72 $h^{-1}$. Selected reactions of glycolysis, the first reaction of the pentose phosphate pathway (zwf), the TCA cycle, acetate excretion pathway and the reactions catalyzed by ppc and aceE connecting the glycolytic- and TCA pathways are shown. The solid black circles represent the denoted metabolites while the black arrows represent metabolic reactions labeled by the genes encoding the enzymes catalyzing the respective reactions (see Table 1 in Example 1 for the list of abbreviations and information on enzymes encoded by listed genes). The error bars for predicted fluxes indicate the standard deviation over 1,000 choices of the crowding coefficients among the list of values estimated for ~100 *E. coli* enzymes, whereas the error bars for the experimental fluxes represent the standard deviations for three independent measurements.
Figure 3B:
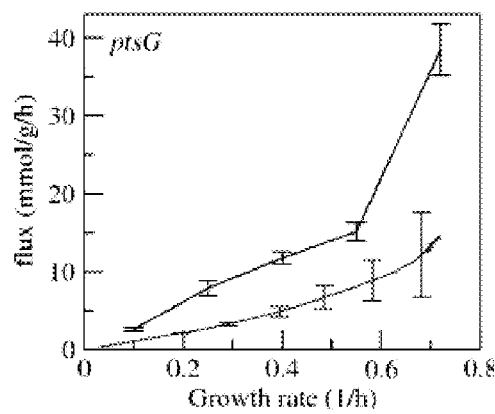
FIG. 3—Predicted vs. measured metabolic fluxes in the *E. coli* central metabolism. Comparisons between the FBAwMC-predicted and measured fluxes as a function of growth/dilution rates for selected reactions in the central carbon metabolism of *E. coli*.
Figure 3C:
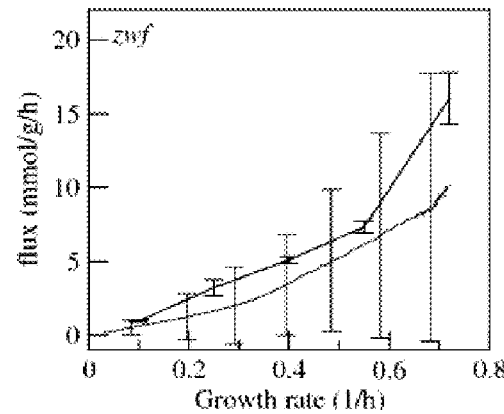
Figure 3D:
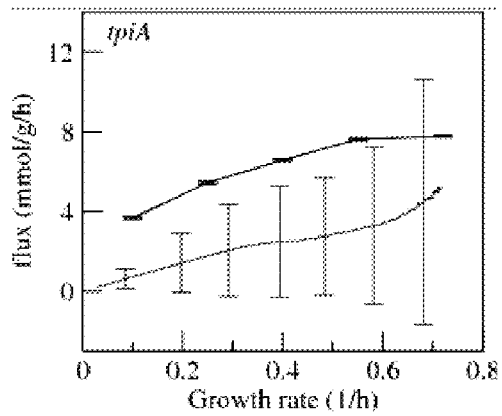
Figure 3E:
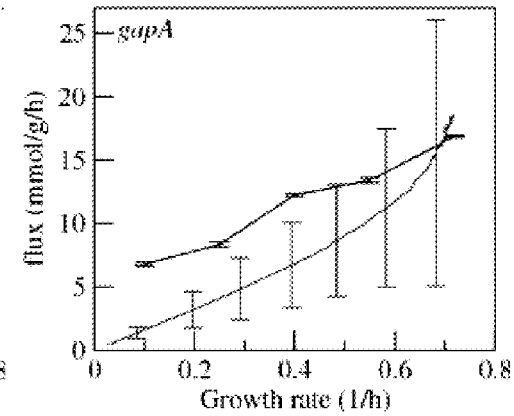
Figure 3F:
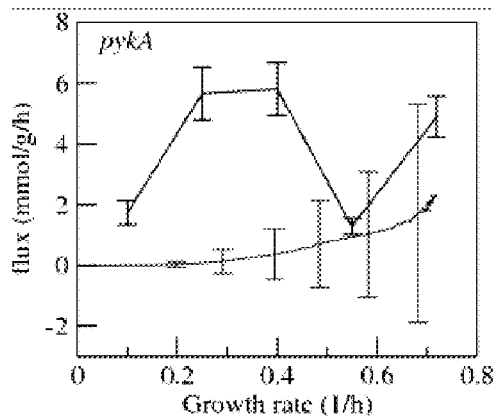
Figure 3G:
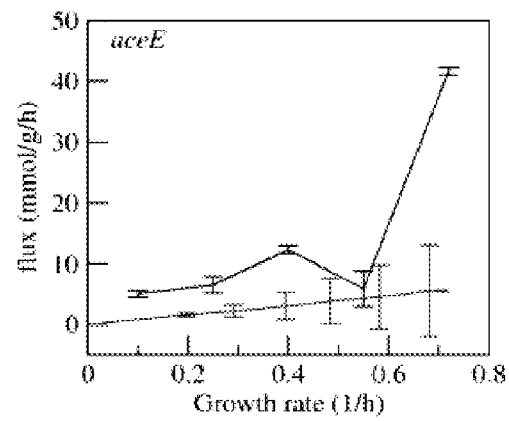
Figure 3H:
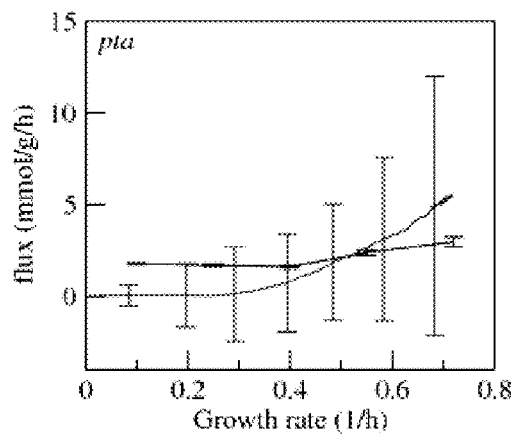
Figure 3I:
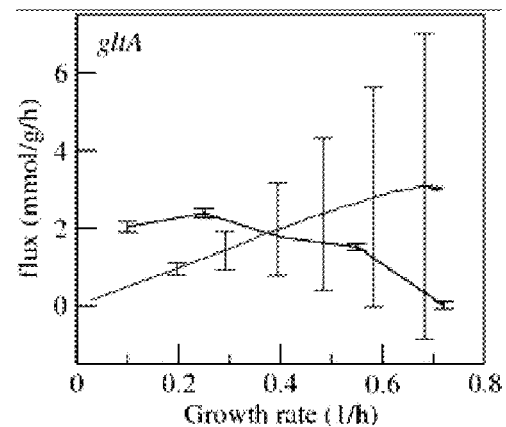
Figure 3J:
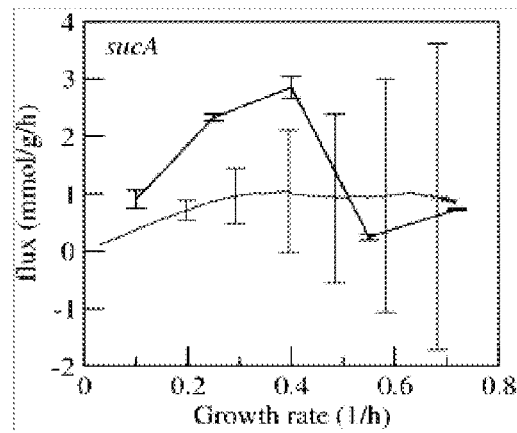
Figure 3K:
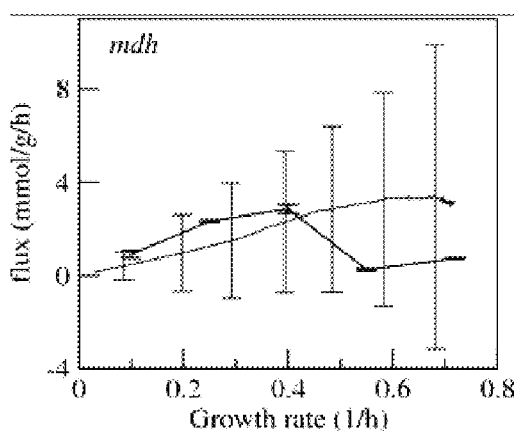
Figure 3L:
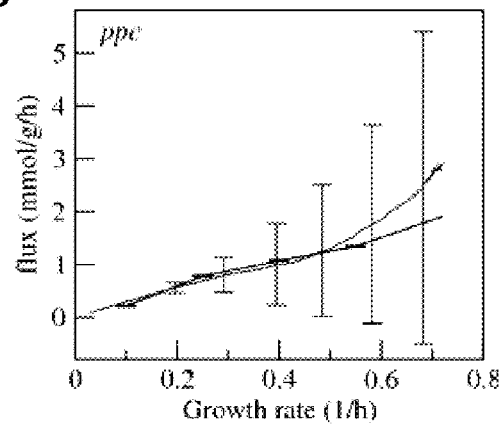

Optimal Metabolite Concentrations:

The optimal metabolite concentrations are obtained maximizing [15] with respect to the free metabolite concentrations. In the case of FIG. 2b,c,d, all metabolite concentrations are fixed to their experimental values, except for the metabolite indicated by the X-axis. In the case of FIG. 3a,b, all intermediate metabolite concentrations are optimized, keeping fixed the concentration of external glucose and co factors (ATP, ADP, AMP, NADH, NAD). In both cases the reaction rates relative to the glycolysis rate (r) were taken as input parameters, using the values reported in Hynne F, et al. Biophys Chem 94: 121-163. The maximization was performed using simulated annealing (Press W H, et al. (1993) Numerical recipes in C: The art of scientific computing. Cambridge: Cambridge University Press).

Figure 24:
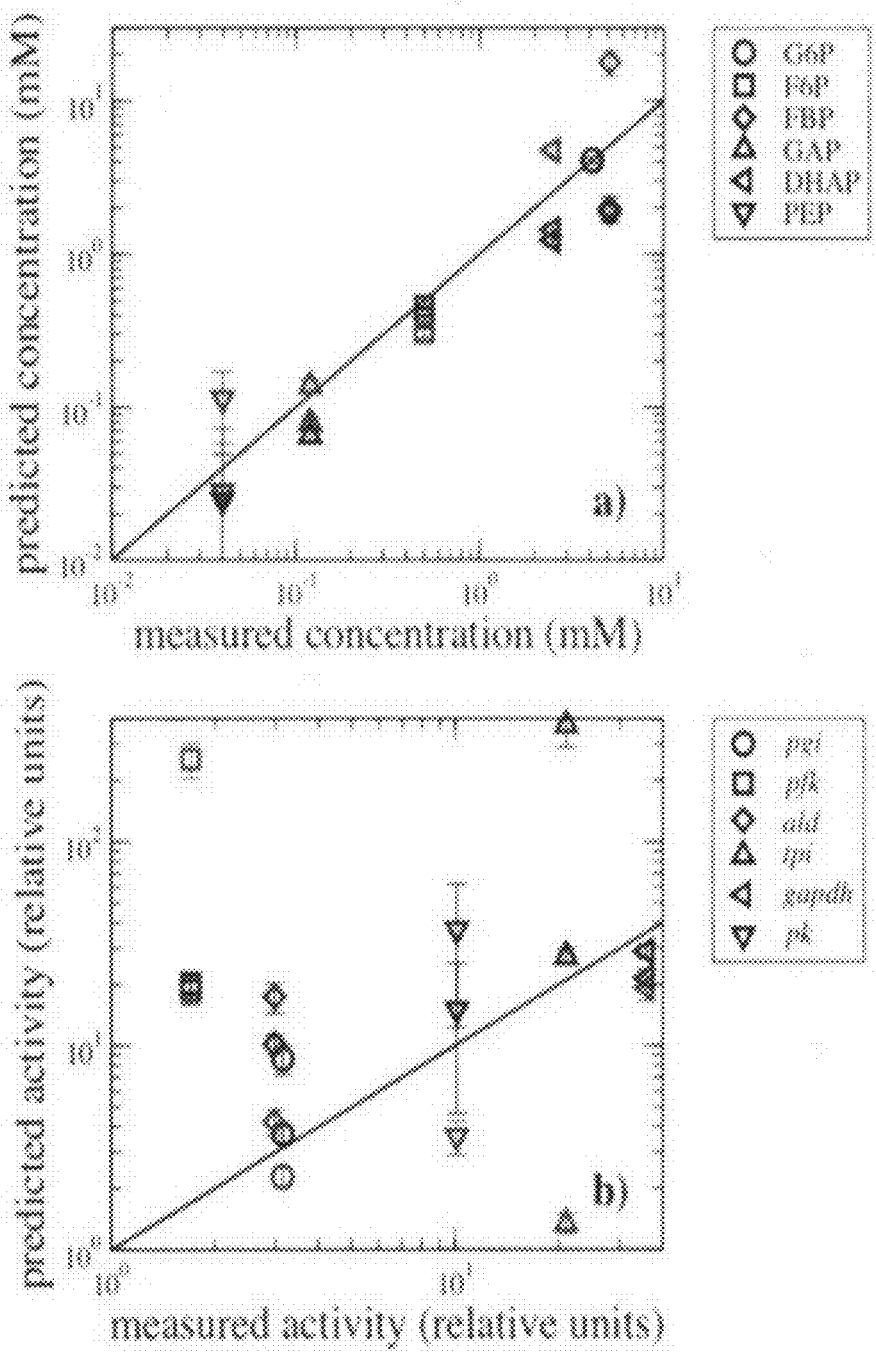
FIG. 24—Correlation between predictions vs. experimental data: (A) The predicted metabolite concentrations are plotted as a function of the experimentally determined values (black symbols). The error bars represent the standard deviations, upon generating 100 random sets of kinetic parameters. The solid line corresponds with the coincidence of measured and predicted values, indicating a strong correlation between them. (B) The predicted enzyme activities are plotted as a function of the experimentally determined values, measured in units of the glycolysis rate. The error bars represent the standard deviations, upon generating 100 random sets of kinetic parameters. The solid line corresponds with the coincidence of measured and predicted values, indicating a strong correlation between them. In both cases the red and blue symbols were obtained using the more general optimization objective $R=(1-\phi)/\Sigma_{i=1}^{N}(a_i r_i)^H$, with H=0.1 and 10, respectively.

Parameter Sensitivity:

To analyze the sensitivity of our predictions to the model parameters we have generated random sets of kinetic parameters, assuming a 10% variation of the fixed metabolite concentrations and all kinetic constants except for the catalytic activities. For the latter we assumed a larger variation of 50%, because they were estimated from a different organism. For each set of parameters we make predictions for the metabolite concentrations and enzyme activities. FIG. 24 reports the mean values and standard deviations.

Results

Limited Solvent Capacity Constraint:

The cell's cytoplasm is characterized by a high concentration of macromolecules resulting in a limited solvent capacity for the allocation of metabolic enzymes. More precisely, given that enzyme molecules have a finite molar volume $v_i$ only a finite number of them fit in a given cell volume V. Indeed, if $n_i$ is the number of moles of the $i^{th}$ enzyme, then $$\Sigma_{i=1}^N v_i n_i + V_0 = V, \quad [25]$$

where $V_o$ accounts for the volume of other cell components and the free volume necessary for cellular transport as well. Equation (14) can be also rewritten as $$v_{spec} \Sigma_{i=1}^N \rho_i = 1 - \phi, \quad [26]$$

where $\rho_i = n_i \mu_i / V$ is the enzyme density (enzyme mass/volume), $\mu_i$ is the molar mass $v_{spec}$ is the specific volume, and $\Phi = V_o/V$ is the fraction of cell volume occupied by cell components other than the enzymes catalyzing the reactions of the pathway under consideration, including the free volume necessary for diffusion. The specific volume has been assumed to be constant for all enzymes, an approximation that has been shown to be realistic at least for globular proteins. In this new form we can clearly identify the enzyme density (or mass, given that the volume is constant) as the enzyme associated variable contributing to the solvent capacity constraint. This choice is more appropriate than the enzyme concentration $C_i = n_i/V$ (moles/volume) because the specific volume is approximately constant across enzymes, while the molar volume can exhibit significant variations. For example, according to experimental data for several globular proteins the molar volume exhibits a 70% variation while the specific volume is almost constant, with a small 2% variation.

The solvent capacity constraint thus imposes a limit to the amount of catalytic units (i.e., enzymes) that can be allocated in the cell cytoplasm. In the following we show that this in turn leads to a constraint for the maximum metabolic rate. The rate of the $i^{th}$ reaction per unit of cell dry weight (mol/time/mass) is given by $$R_i = x_i A_i = \frac{x_i k_i C_i}{M} = \frac{x_i k_i \mu_i \rho_i}{M}, \quad [27]$$

where $A_i$ is the specific enzyme activity, $C_i$ is the enzyme concentration in molar units, $k_i$ is the catalytic constant and M is the cell mass. The coefficient $x_i$ is determined by the specific kinetic model: it takes values in the range of $0 \leq x_i \leq 1$, and it is a function of metabolite concentrations. For example, if the reaction is described by Michaelis-Menten kinetics with one substrate then $x_i = S_i/(K_i + S_i)$, where Si is the substrate concentration and $k_i$ is the equilibrium constant. More generally, $x_i$ is a function of the concentration of substrates, products and other metabolites regulating the enzyme activity. The fact that the reaction rates are roughly proportional to the enzyme concentrations [27] suggests that the limited solvent capacity constraint [26] has an impact on the reaction rates as well. Indeed, from equations [26 and 27], we obtain $$R = \frac{1-\phi}{\sum_{i=1}^N a_i r_i}, \quad [28]$$

where R is the cell metabolic rate (or pathway rate), $r_i=R_i/lR$ is the rate of reaction i relative to the metabolic rate, and $$a_i = \frac{v_{spec}\mu_i\rho}{x_i k_i}, \quad [29]$$

where $\rho=M/V$ is the cell density. We refer to $a_i$ as the crowding coefficients because they quantify the contribution of each reaction rate to molecular crowding. The crowding coefficient of a reaction i increases with increasing the enzyme's molar mass $\mu_i$ and decreases with increasing catalytic activity $k_i$. It is also a function of the metabolite concentrations through $x_i$.

Hypothetical Three Metabolites Pathway:

To illustrate the impact of the limited solvent capacity constraint, we first analyze a hypothetical example, in which we use the relative reaction rates as input parameters, and the metabolite concentrations are the variables to be optimized. Given the reaction rates and the "optimal" metabolite concentrations, the enzyme activities are determined by equation [27]. Finally, the maximum metabolic rate is computed using equation [28].

Figure 22:
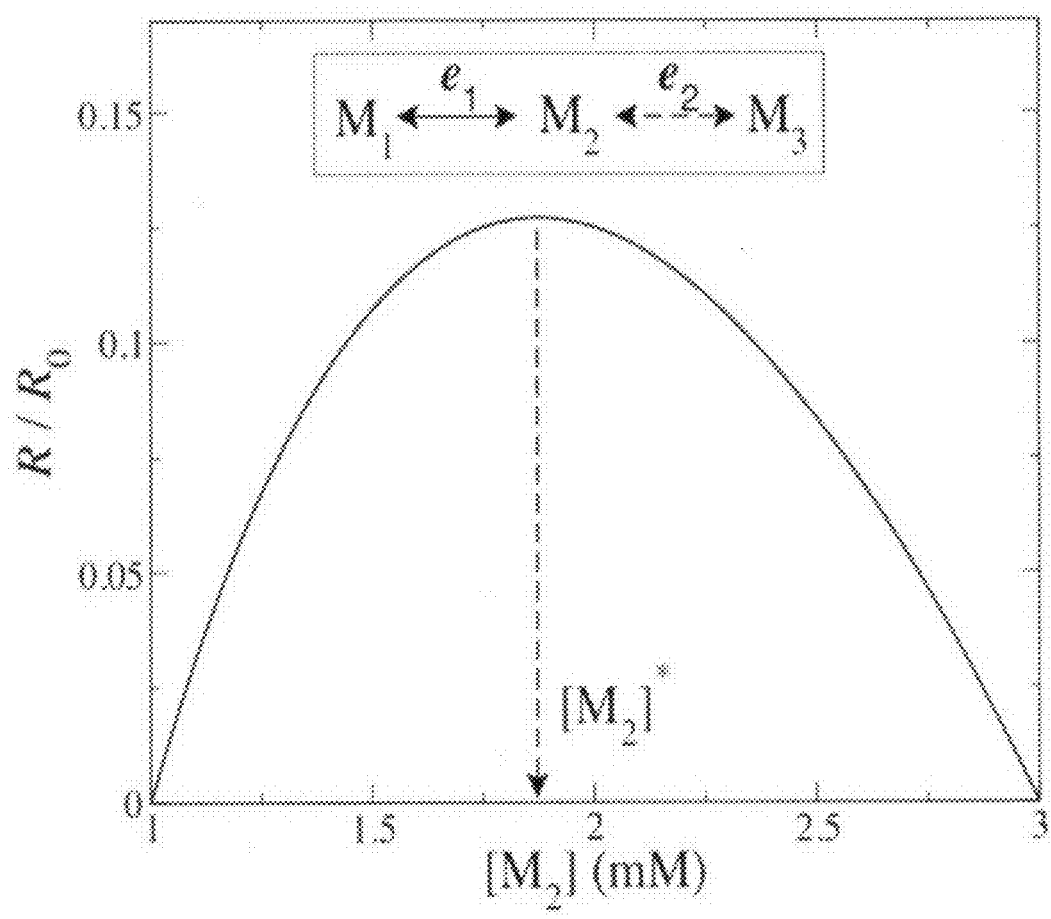
FIG. 22—Hypothetical three metabolite pathway: The inset shows a hypothetical three metabolite-containing pathway with two reactions. The main panel displays the pathway rate as a function of the concentration of the intermediate metabolite, relative to Ro (defined in the text). Of note, at an intermediate metabolite concentration [M2]* the pathway rate achieves a maximum. The plot was obtained using the kinetic parameters indicated in the text.

Consider a metabolic pathway consisting of two reversible reactions converting metabolite $M_1$ into $M_2$ (reaction 1) and $M_2$ into $M_3$ (reaction 2), catalyzed by enzymes $e_1$ and $e_2$, respectively (FIG. 22, inset). The reaction rates per unit of cell mass, $R_1$ and $R_2$, are modeled by reversible Michaelis-Menten rate equations $$R_1 = \frac{[M_1] - [M_2]/K_{1eq}}{K_{11} + [M_1] + K_{11}[M_2]/K_{12}} K_1 C_1 \frac{1}{M}, \quad [30]$$

$$R_2 = \frac{[M_2] - [M_3]/K_{2eq}}{K_{22} + [M_2] + K_{22}[M_1]/K_{23}} K_2 C_2 \frac{1}{M} \quad [31]$$

where $K_{1eq}$ and $K_{2eq}$ are the equilibrium constants of reaction 1 and 2, respectively, $K_{im}$ is the Michaelis-Menten constant of metabolite m in reaction i, M is the cell mass and $C_i$ is the concentration of the $i_{th}$ enzyme. For the purpose of illustration, we assume that the kinetic parameters associated with both reactions are the same, all Michaelis constants equal to 1 mM, and fixed pathway ends metabolite concentrations $[M_1]=3$ mM and $[M_2]=1$ mM. Furthermore, mass conservation for $M_2$ implies that $R_1=R_2=R$ ($r_1=r_2=1$) in the steady state, where R is the pathway rate. Under these approximations the pathway rate [28] is given by $$\frac{R}{R_0} = \left[ \frac{K_{11} + [M_1] + K_{11}[M_2]/K_{12}}{[M_1] - [M_2]/K_{1eq}} + \frac{K_{22} + [M_2] + K_{22}[M_3]/K_{23}}{[M_2] - [M_3]/K_{2eq}} \right]^{-1}, \quad [32]$$

where $R_o=(1-\Phi)k_i l v_{spec}\mu_1\rho$. At this point the value of $R_o$ is not needed and we focus on the relative pathway rate $R/R_o$. When reaction 1 is close to equilibrium $[M_2] \approx [M_1]K_{1eq}=3$ mM, the first term in the right hand side becomes very large, resulting in a small pathway rate (FIG. 22). When reaction 2 is close to equilibrium $[M_2] \approx [M_3]/K_{2eq}=1$ mM, the second term in the right hand side becomes very large, again resulting in a small pathway rate (FIG. 22). At an intermediate $[M_2]^*$ between these two extremes the pathway rate achieves its maximum. Therefore, given the solvent capacity constraint, there is an optimal metabolite concentration resulting in a maximum pathway rate.

S. cerevisiae Glycolysis:

Next, we investigated whether the observation of an optimal metabolite concentration for maximum pathway rate extrapolates to a more realistic scenario. For this purpose we use the glycolysis pathway of the yeast S. cerevisiae (FIG. 23A) as a case study. Glycolysis represents a universal pathway for energy production in all domains of life. In S. cerevisiae it has been studied extensively resulting in the description of a rate equation model for each of its reactions. In particular, we consider the kinetic model developed in Hynne F, et al. (2001) (see Methods). To compare our predictions with experimentally determined values we consider the glycolysis reaction rates and metabolite concentrations reported in Hynne F et al. (2001) and the enzyme activities reported in (Teusink B, et al. (2000).

Figure 23:
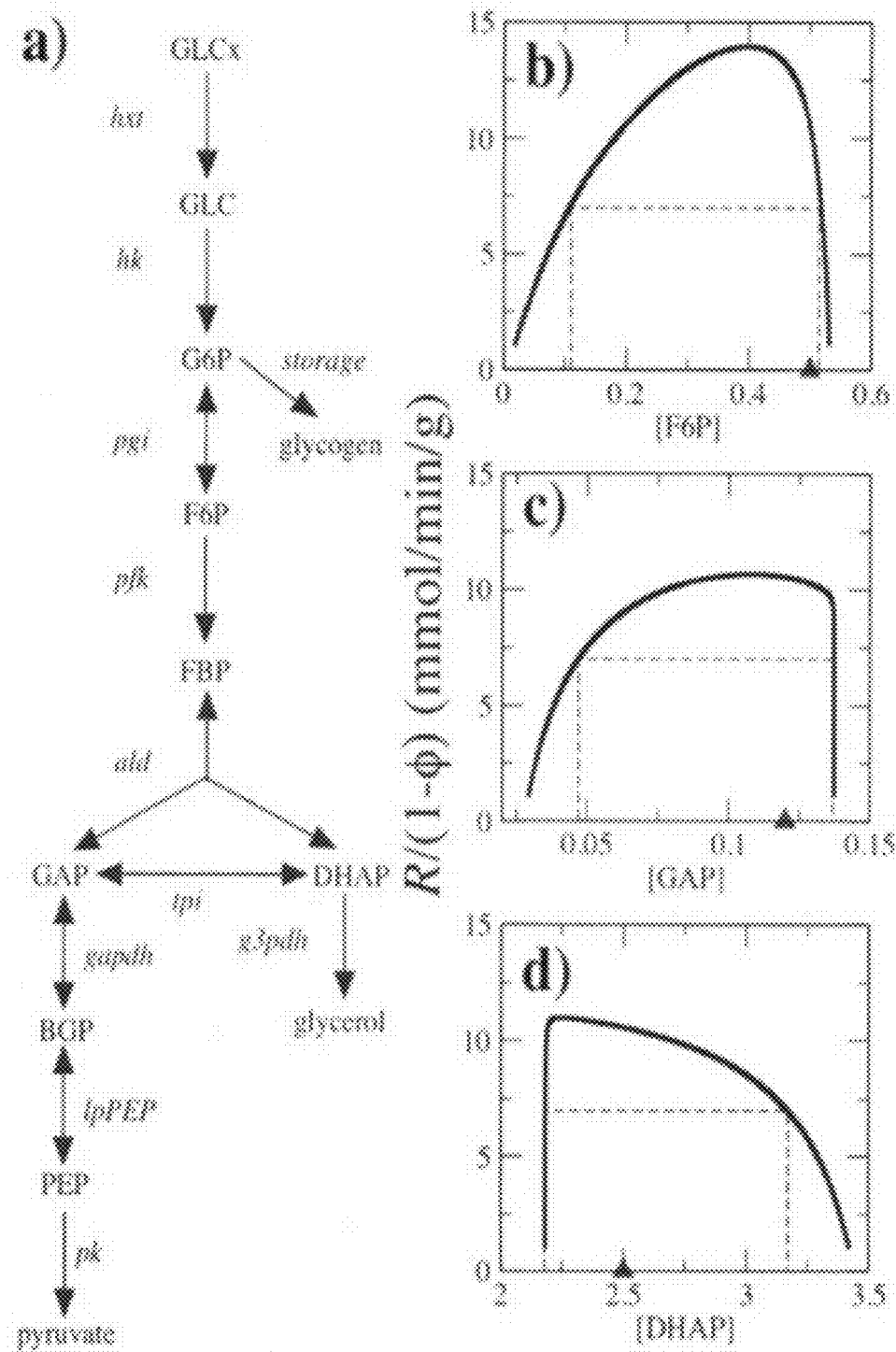
FIG. 23—*S. cerevisiae* glycolysis: (A) Schematic representation of glycolysis in *S. cerevisiae*. Metabolites: GLCx, external glucose; GLC, glucose; G6P, glucose 6-phosphate; F6P, fructose 6-phosphate; FBP, fructose 1,6-bisphosphate; DHAP, glycerone phosphate; GAP, D-glyceraldehyde 3phosphate; BPG, 1,3-bisphosphoglycerate; and PEP, phospho-enol-pyruvate. Reactions: hxt, glucose transport; hk, hexokinase; pgi, phosphogluco isomerase; pjk, phosphofructokinase; aid, fructose 1,6-bisphosphate aldolase; tpi, triosephosphate isomerase; gapdh, D-glyceraldehyde 3-phosphate dehydrogenase; IpPEP, reactions from BGP to PEP; pk, pyruvate kinase; and g3pdh, glycerol 3-phosphate dehydrogenase. (B,C,D) The predicted glycolysis rates as a function of the concentrations of intermediary metabolites in the *S. cerevisiae* glycolysis pathway (in mM). The experimentally determined metabolite levels (from Hynne F, Dano S, Sorensen P G (2001) Full-scale model of glycolysis in *Saccharomyces cerevisiae*. Biophys Chem 94: 121-163) are indicated by the triangles. The dashed lines indicate the concentration intervals resulting in 50% or more of the maximum rate. Measured concentration (mM), measured activity (relative units)

In analogy with the three metabolites case study (FIG. 22), first we investigate the dependency of the glycolysis rate R on the concentration of a given metabolite. In this case we fix all other metabolite concentrations and all relative reaction rates to their experimentally determined values. By doing so the predicted glycolysis rate is an implicit function of the free metabolite concentration alone, through equation [28]. For example, FIG. 23B displays the maximum metabolic rate R as a function of the concentration of fructose-6-phosphate (F6P). R is predicted to achieve a maximum around a F6P concentration of 0.4 mM, close to its experimentally determined value of 0.5 mM (red triangle in FIG. 23B). Similar conclusions are obtained for D-glyceraldehyde-3phosphate (GAP) (FIG. 23C) and glycerone-phosphate (DHAP) (FIG. 23D). This analysis corroborates that there is an optimal metabolite concentration maximizing R and, more importantly, that this concentration is very close to the experimentally determined metabolite concentrations. In all cases the measured metabolite concentrations are within the range of 50% or more of the maximum glycolysis rate.

To further test the optimal metabolite concentration hypothesis, we perform a global optimization and simultaneously compute the optimal concentrations of the glycolysis intermediate metabolites. In this case we fix the concentrations of external glucose and co-factors and all relative reaction rates to their experimentally determined values. By doing so the predicted glycolysis rate is an implicit function of the glycolysis intermediate metabolite concentrations, through Equation [28]. The optimal intermediate metabolite concentrations are those maximizing Equation [28]. FIG. 24A displays the predicted optimal metabolite concentrations as a function of their experimentally determined values (black symbols), the line representing a perfect match. The agreement is remarkably good given the wide range of metabolite concentrations. For phospho-enolpyruvate (PEP), the predicted value is very sensitive to the model parameters, as indicated by the wide error bars. For fructose 1,6-biphosphate (FBP) the predicted value is smaller by a factor of five than the experimental value, but it is still within range. Taken together, these results indicate that the measured concentrations of intermediate metabolites in the S. cerevisiae glycolysis are close to the predicted optimal values maximizing the glycolysis rate given the limited solvent capacity constraint.

Using the optimal intermediate metabolite concentrations we can make predictions for the enzyme activities as well. Indeed, from the first equality in [27] it follows that $$\frac{A_i}{R} = \frac{r_i}{x_i}..\quad [33]$$

The reaction rates relative to the glycolysis rate $r_i$ are obtained from experimental data, while $x_i$ are obtained after substituting the predicted optimal metabolite concentrations on the reaction's kinetic models. FIG. 24B displays the predicted enzyme activities (in units of the glycolysis rate) as a function of the experimentally determined values (black symbols), the line representing a perfect match. In most cases we obtain a relatively good agreement between experimentally measured and predicted values, with the exception of phosphofructokinase (Pfk), for which the measured enzyme activities are significantly overestimated. Of note, for pyruvate kinase (pk) the predictions are significantly affected by the model parameters, as indicated by the wide error bars.

The preceeding analysis does not exclude the possibility that other constraints could result in a good agreement as well. To address this point we consider the more general optimization objective $R=(1-\phi)/\Sigma_{i=}^N (a_i r_i)^H$ [34], parametrized by the exponent H. Although this objective is not inspired by some biological intuition, it allows to explore other possibilites beyond the original case H=1. FIG. 24 shows our predictions for the case H=0.1 (red symbols) and H=10 (blue symbols), representing a milder and a stronger dependency with the crowding coefficient $a_i$, respectively. For H=0.1, 1.0 and 10 the predicted metabolite concentrations are in good agreement with the experimental values. These results indicate that it is sufficient that the optimization objective is a monotonic decreasing function of the crowding coefficients. When the latter is satisfied the metabolite concentrations are up to a great extent constrained by the kinetic model. This is not, however, the case for the enzyme activities. For H=0.1 and the enzymes pfk, tpi and pk, there is a large deviation from the perfect match line. For H=0 and the enzymes (tpi and pk, there is a large deviation from the perfect match line as well. Overall, H=1 gives the better agreement between enzyme activity predictions and their measured values. In addition, it provides a clear biophysical interpretation of the solvent capacity constraint (H=1).

Finally, we use equation [28] to compute the maximum glycolysis rate as determined by the limited solvent capacity constraint. The global optimization predicts the glycolysis rate $R=(1-\Phi)\times 12.5$ mmol/min/g dry weight. Taking into account that about 30% of the cell is occupied by cell components excluding water, that proteins account for ~45% of the dry weight, and that of these glycolysic enzymes account for ~22% of the protein mass we obtain $1-\Phi 0.03$. Therefore, given that glycolysis enzymes occupy only 3% of the cell volume, we obtain R~0.38 mmol/min/g dry weight. This prediction is in very good agreement with the experimentally determined glycolysis rate of S. cerevisiae, ranging between 0.1 to 0.4 mmol/min/g dry weight.

The successful modeling of cell metabolism requires the understanding of the physicochemical constraints that are relevant at physiological growth conditions. In our previous work focusing on E. coli we have reported results indicating that the limited solvent capacity is an important constraint on cell metabolism, especially under nutrient rich growth conditions. Using a flux balance approach that incorporates this constraint we predicted the maximum growth rate in different carbon sources, the sequence and mode of substrate uptake and utilization from a complex medium, and the changes in intracellular flux rates upon varying E. coli cells' growth rate. More importantly, these predictions were in good agreement with experimentally determined values.

Here we have extended the study of the impact of the limited solvent capacity by (i) considering a different organism (S. cerevisiae), and (ii) a full kinetic model of glycolysis. Using the full kinetic model of S. cerevisiae glycolysis, we have demonstrated that the predicted optimal intermediate metabolite concentrations and enzyme activites are in good agreement with the corresponding experimental values. Discrepancies were only observed in association with two different steps in the glycolysis pathway, namely the reaction catalyzed by pjk and the reactions between BPG and PEP. It cannot be excluded that these discrepancies are associated with deficiencies of the kinetic model. Furthermore, the glycolysis rate achieved at the optimal metabolite concentrations is in the range of the experimentally measured values.

From the quantitative modeling point of view our results indicate that a full kinetic model together with the solvent capacity constraint can be used to make predictions for the metabolite concentrations and enzyme activities. Thus, we propose the simultaneous optimization of intermediate metabolite concentrations, maximizing the metabolic rate given the solvent capacity, as a method to computationally predict the concentrations of a metabolic pathway's intermediate metabolites and enzyme activities. We have demonstrated the applicability of this method by computing the concentration of S. cerevisiae glycolysis intermediate metabolites, resulting in a good agreement with published data.

The high concentration of macromolecules in the cell's cytoplasm imposes a global constraint on the metabolic capacity of an organism. No clear explanation has been provided to support that choice. Our starting postulate is an undeniable physical constraint, the total cell volume. Under this constraint, the enzyme molar volumes are the primary magnitude quantifying the enzymatic cost. In turn, since the enzyme-specific volumes are approximately constant, we can use the enzyme density (mass/volume) as an alternative measure of enzymatic cost. This modeling framework has advantages and disadvantages with respect to more traditional approaches based on dynamical systems modeling. As an advantage, our method does not require as input parameters the enzyme activities but rather make quantitative predictions for them. On the other hand, our method is based on a steady state approximation. Therefore, in its present form, it cannot be used to understand dynamical processes, such as the observed metabolite concentration oscillations in S. cerevisiae cells when growing at high glucose concentrations.

Example 4

Serine Biosynthesis with One Carbon Catabolism and the Glycine Cleavage System Represents a Novel Pathway for ATP Generation Previous experimental evidence indicates that some cancer cells have an alternative glycolysis pathway with net zero ATP production, implying that upregulation of glycolysis in these cells may not be related to the generation of ATP. Here we use a genome-scale model of human cell metabolism to investigate the potential metabolic alterations in cells using net zero ATP glycolysis. We uncover a novel pathway for ATP generation that involves reactions from the serine biosynthesis, one-carbon metabolism and glycine cleavage systems, and show that the pathway is transcriptionally upregulated in an inducible murine model of Myc-driven liver tumorigenesis. This pathway has a predicted two-fold higher flux rate in cells using net zero ATP glycolysis than those using standard glycolysis and generates twice as much ATP with significantly lower rate of lactate, but a higher rate of alanine secretion. Thus, in cells using the standard- or the net zero ATP glycolysis pathways a significant portion of the glycolysis flux is always associated with ATP generation, and the ratio between the flux rates of the two pathways determines the rate of ATP generation and lactate and alanine secretion during glycolysis.

Oxidative phosphorylation (OxPhos) in the mitochondria is the major pathway for ATP generation in normal cells under normal oxygen conditions (normoxia), generating 32 mole of ATP per mole of glucose. In contrast, under conditions of oxygen limitation (hypoxia), the mitochondrial activity is down-regulated and cells switch to glycolysis for ATP generation that yields only 2 mole of ATP per mole of glucose. Surprisingly, as first observed by Warburg, the metabolism of cancer cells is frequently characterized by a significant upregulation of glycolysis even under normoxic conditions, with both an increased glucose uptake and excretion of lactate (Warburg effect, aerobic glycolysis). More recently, it became evident that the Warburg effect is not unique to cancer cells alone. Indeed, both rapidly proliferating normal cells and non-proliferating cells with high metabolic activity display high levels of glycolysis with lactate excretion under normoxic conditions. Despite the importance of OxPhos and aerobic glycolysis in ATP generation, previous empirical evidence indicates that some cancer cells also utilize an alternative glycolysis pathway with net zero ATP generation. This striking observation implies a physiological role for aerobic glycolysis other than ATP generation. One such role may be the capacity of glycolysis to fulfill the need of rapidly proliferating cells for precursor metabolites. However, it has been shown previously that the need for precursor metabolites in itself is not sufficient to explain the high glycolysis rates observed in proliferating cells. Instead, molecular crowding and its resulting constraint on macromolecular concentrations is the key factor determining the Warburg effect. The high density of macromolecules in the cell imposes limits on the total mitochondrial content per unit of cell volume and the total content of ribosomes and metabolic enzymes as well. In turn, the inherent limitation in mitochondrial density results in an upper bound on the maximum achievable OxPhos capacity. We have shown previously that this maximum is achieved at physiological conditions and that it results in a metabolic switch involving an upregulation of glycolysis and lactate excretion. Yet, all these results were obtained making use of the standard glycolysis pathway, with a yield of 2 moles of ATP per mole of glucose.

Here we investigate the metabolic flux redistributions in proliferating cells that utilize the alternative glycolysis pathway with net zero ATP production. To this end we improve on our previous flux balance model of human cell metabolism by more precisely accounting for protein synthesis, including a self-consistent constraint that all ribosomal-, enzyme associated-, and non-metabolic proteins need to be accounted for by the rate of protein synthesis, which is proportional to the ribosomal density. We also make a more precise accounting of the molecular crowding constraint by considering mitochondria as a subcellular compartment independent from the cytosol. Using this model we uncover a novel pathway for ATP generation that involves reactions in the serine biosynthesis, one-carbon metabolism and the glycine cleavage system, and show that the pathway is transcriptionally upregulated in an inducible murine model of Myc driven liver tumorigenesis. The flux rate of this pathway is predicted to be two-fold higher in cells with net zero ATP glycolysis relative to cells with the standard glycolysis. Furthermore, it accounts for most of the glycolysis rate in cells with net zero ATP glycolysis.

Results

As a starting point, we utilize a genome-scale metabolic reconstruction of a generic human cell that includes most biochemical reactions catalyzed by enzymes encoded in the human genome essentially as described in Mo M L, et al. ((2007) A genome-scale, constraint-based approach to systems biology of human metabolism. *Mol Biosyst* 3: 598-60). We add auxiliary reactions to represent nutrient uptake, excretion of metabolic byproducts, basal ATP demand needed for cell maintenance, basal rate of protein degradation, synthesis of cell biomass components (proteins, lipids, RNA and DNA) and cell proliferation (biomass components→cell). We assume that the cell is in a steady state where the production and consumption of every metabolite and macromolecules balances, known as the flux balance constraint. We use $S_{mi}$ to denote the stoichiometric coefficient of metabolite m in reaction i. We use $f_i$ to denote the steady state reaction rate (flux) of the $i^{th}$ reaction in the metabolic network, where all reversible reactions are represented by a forward and backward rate, respectively. Reactions are divided into nutrient import reactions (RI), reactions taking place outside the mitochondria (RnM) and reactions taking place in the mitochondria (RM). We use $\phi_c$ to denote the relative cell volume fraction occupied by the cth cellular compartment, where a compartment represents the overall contribution of macromolecules of certain type (e.g., ribosomes) or of certain cell organelle (e.g., mitochondria). Specifically, here we consider proteins that do not form part of enzyme complexes or ribosomes ($P_0$), all metabolic enzymes catalyzing reactions outside the mitochondria (EnM), all metabolic enzymes catalyzing reactions in the mitochondria (EM), ribosomes (R), and mitochondria (M). We assume the proliferation rate ($\mu$) and the total relative volume fraction occupied by macromolecules and organelles ($\phi_{max}$) are known and are given as input parameters of the model. Finally, we estimate the metabolic fluxes and compartment densities as the solution of the following optimization problem:

find the $f_i$ and $\phi_c$ that minimize the sum of nutrient import costs:

$$\sum_{i \in RI} c_i f_i \quad [35]$$

subject to the metabolic constraints: flux balance constraints:

$$\sum_i S_{mi} f_i = 0 \quad [36]$$

minimum/maximum flux constraints:

$$v_{i,min} \leq f_i \leq v_{i,max} \quad [37]$$

minimum/maximum volume fraction constraints:

$$0 \leq \phi_c \leq \phi_{max} \qquad [38]$$

molecular crowding constraints:

$$\sum_{i \in RnM} a_i f_i \leq \phi_{EnM} \qquad [39]$$

$$\sum_{i \in RM} a_i f_i \leq \phi_M$$

$$a_{M,ATP} f_{ATP\_synthase} \leq \phi_M$$

$$a_R f_{protein\_synthesis} \leq \phi_R$$

$$\phi_{P0} + \phi_{EnM} + \phi_R + \phi_M \leq \phi_{max}$$

where $c_i$ is the nutrient import cost associated with the uptake reaction i, $ai=vi/keff,i$ are the crowding coefficients of metabolic enzymes (enzyme molar volume/enzyme effective turnover), $aR=vR/kR$ is the ribosome crowding coefficient (ribosome molar volume/protein synthesis rate per ribosome), and $a_{M,ATP}=v_{s,M}/r_M$ the crowding coefficient of mitochondria ATP generation (ATP synthesis rate per mitochondria mass/mitochondria specific volume).

The estimation of all the model parameters is presented in the Methods section. Here we discuss some of them that deserve particular attention. The cost of importing molecules is in general determined by their size, charge and hydrophilic properties. In a first approximation we assume that the cost of importing molecules is proportional to their size and use the molecular weight as a surrogate for size. Within this approximation the import cost ci is equal to the molecular weight of the molecule imported in the auxiliary uptake reaction i. The effective turnover numbers keff,i, quantify the reaction rate per enzyme molecule. For example, for an irreversible single substrate reaction satisfying Michaelis-Menten kinetics, $keff=kS/(K+S)$, where k is the enzyme turnover number, K the half-saturation concentration and S the substrate concentration.

The turnover numbers of some human enzymes are reported in the BRENDA database. They have a typical value of 10 see and a significant variation from 1 to 100 $sec^{-1}$. However, for most reactions we do not know the turnover number, the kinetic model, or the metabolite concentrations, impeding us to estimate keff. To cope with this indeterminacy we performed a sampling strategy, whereby the keff,i were sampled from a reasonable range of values, and then focused on the predicted average behavior and 90% confidence intervals (see Methods for additional details). The typical enzyme crowding coefficient is about ai~0.00013 $(mM/min)^{-1}$, which is interpreted as follows: to maintain a reaction rate of 1 mM/min we need to allocate a relative cell volume of 0.00013 (0.013%) for the corresponding enzyme. The crowding coefficients are significantly larger for ribosomes and the mitochondria: $a_R=3.6$ $(mM/min)^{-1}$ and $a_{M,ATP}=0.017$ $(mM/min)^{-1}$, respectively.

The flux balance equation for proteins (equation 36) with m=proteins) is formulated more generally than before. Previous models have assumed a constant protein concentration and have not taken into account the self-consistent need to synthesize all the proteins in enzyme complexes and ribosomes. In contrast, here we account for three major categories, proteins not associated with metabolism, proteins that are components of enzyme complexes, and ribosomal proteins, with their concentrations (moles/cell volume) denoted by $P_0$, $P_E$, and $P_R$, respectively. In proliferating cells, these concentrations will decrease at a rate $(\mu+k_D)(P_0+P_E+P_R)$, where μ denotes the proliferation rate and kD the basal rate of protein turnover. The total concentration of proteins in enzyme complexes can be estimated as $P_E=n_{PE}E=n_{PE}\Sigma_i f_i/k_{eff,i}$, where $n_{PE}$ is the average number of proteins in an enzyme complex (about 2.4) and E is the total concentration of metabolic enzymes. Similarly, $P_R=n_{PR}\phi_R/v_R$, where $n_{PR}$ is the number of proteins in a ribosome (82 for the 80S ribosomes) and $\phi_R/v_R$ is the concentration of ribosomes. Putting all these elements together, the balance between protein turnover and synthesis implies fProtein_sysnthesis= $(\mu+kD)[P0+nPE\Sigma ifi/keff,i+(nPR/vR)\phi R]$, where the term $(\mu+kD)P0$ is the only one considered in previous models. In an effective manner, each metabolic reaction contributes to a component of protein synthesis, with a stoichiometric coefficient $(\mu+k_D)n_{PE}/k_{eff,i}$ quantifying the amount of protein necessary to keep the concentration of the corresponding enzyme constant. Similarly, a constant ribosome volume fraction also accounts for a component of protein synthesis, with a stoichiometric coefficient $(\mu+k_D)n_{PR}/v_R$ quantifying the amount of protein necessary to keep the ribosomes concentration constant. The rate of protein synthesis accounting for this effective protein dilution/degradation thus models the autocatalytic nature of cell metabolism, whereby the macromolecular complexes catalyzing the metabolic reactions ultimately are themselves a product of metabolism.

To model the alternative glycolysis pathway we replaced the pyruvate kinase catalyzed reaction: Phosphoenolpyruvate+ADP+$H^+$→Pyruvate+ATP, by the ATP independent reaction: Phosphoenolpyruvate+$H^+$→Pyruvate+Phosphate. In the latter reaction phosphoglycerate mutase (PGM1) is a candidate phosphate acceptor, which is then dephosphorylated by a yet unknown mechanism.

Figure 25:
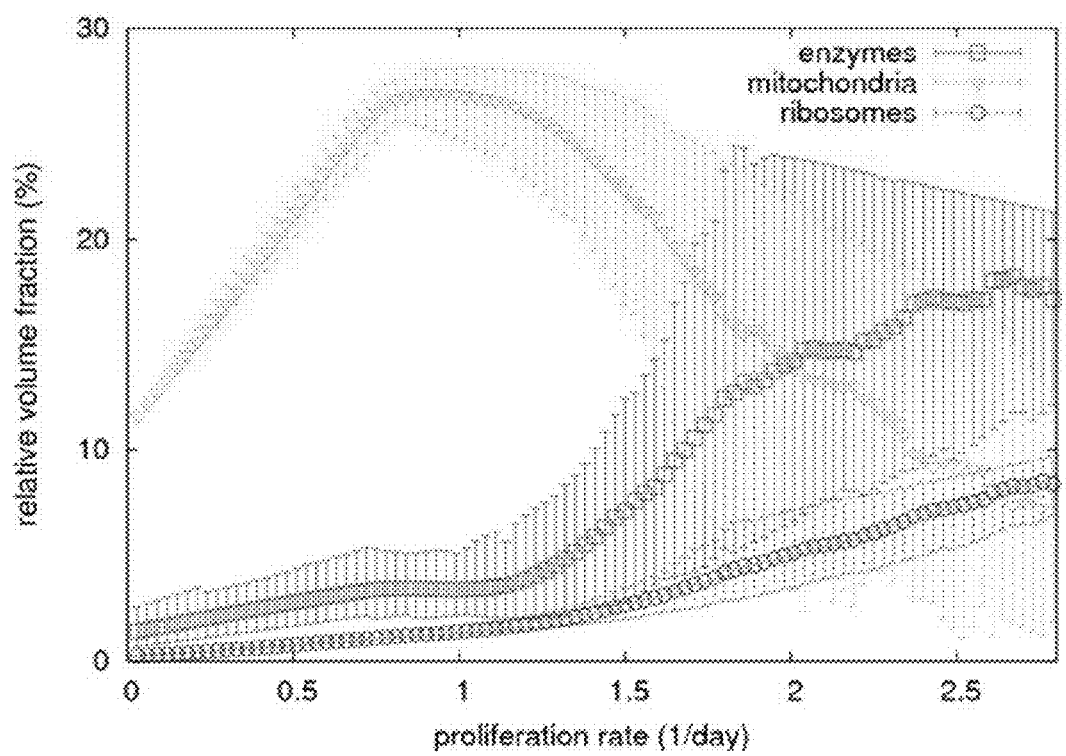
FIG. 25: A graph showing cell component densities at different proliferation rates
Figure 26A:
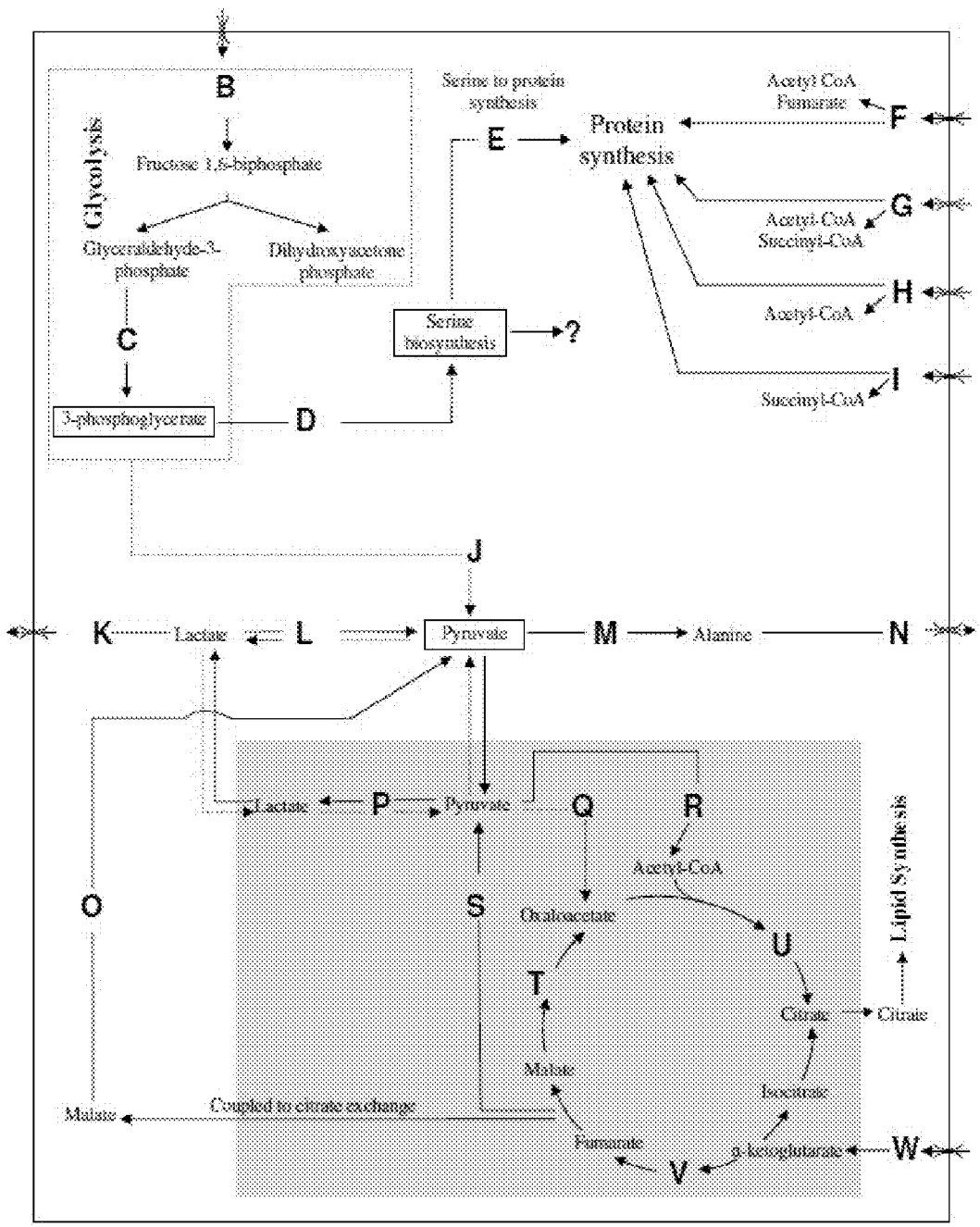
FIG. 26A is a representation of the flux of selected metabolic reactions and pathways at different proliferation rates, in cells utilizing glycolysis with net zero ATP production. Labels B to W in FIG. 26A denote the rate of the indicated reactions (vertical axis, in units of mM/min=mmol/min/L) as a function of the proliferation rate (horizontal axis, in units of 1/day) shown in FIGS. 26B-26W, respectively. The gray shadow background contains reactions taking place in the mitochondria.
Figure 26B:
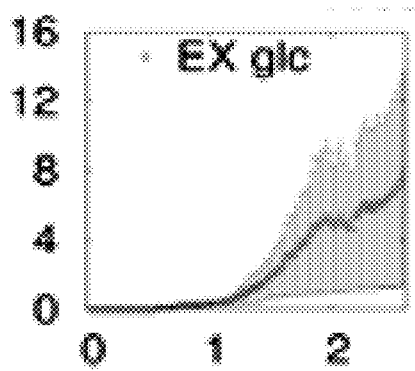
FIG. 26: Metabolic switch with increasing proliferation rate.
Figure 26C:
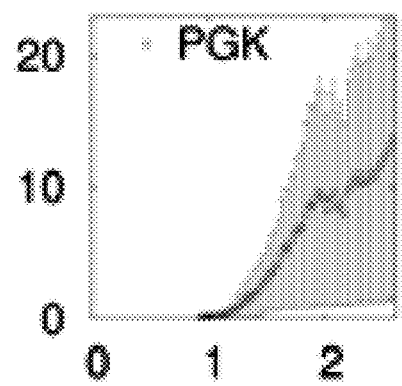
Figure 26D:
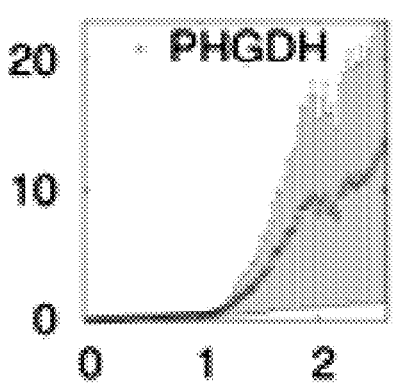
Figure 26E:
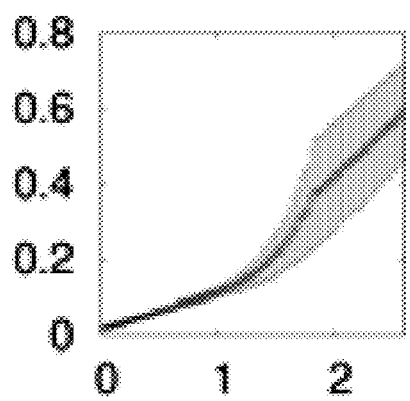
Figure 26F:
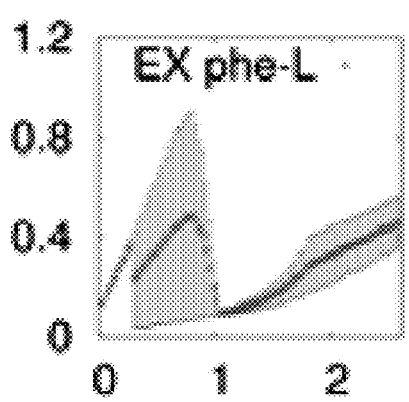
Figure 26G:
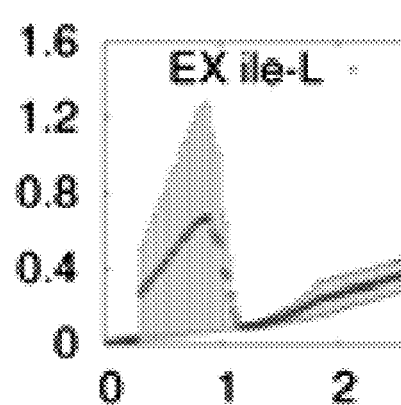
Figure 26H:
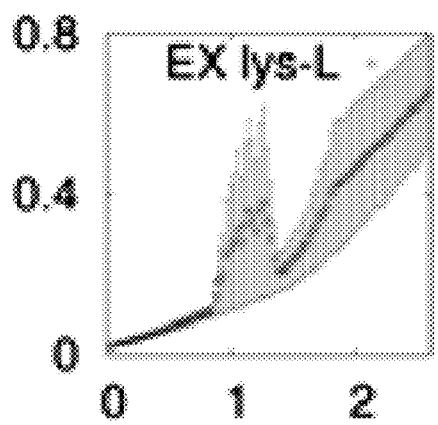
Figure 26I:
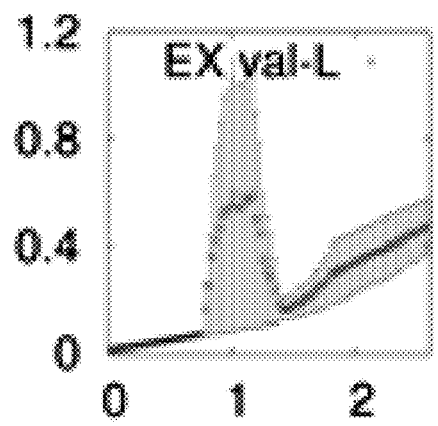
Figure 26J:
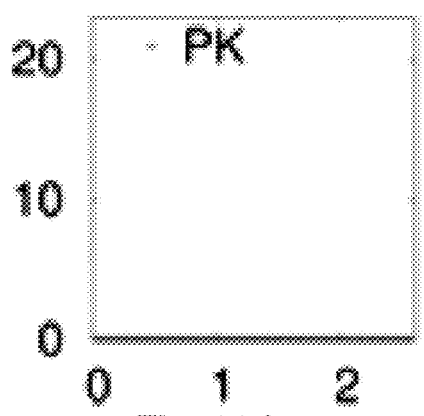
Figure 26K:
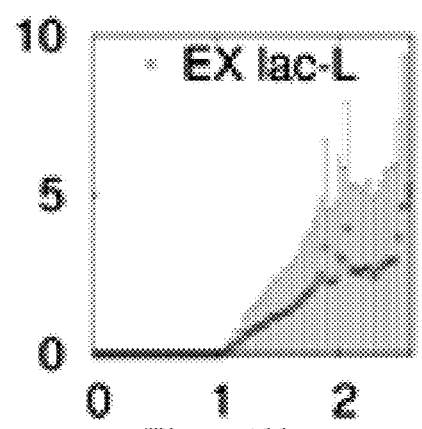
Figure 26L:
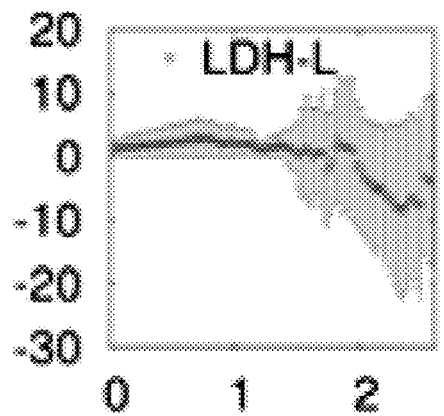
Figure 26M:
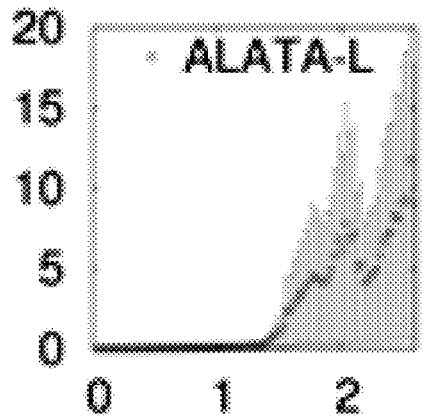
Figure 26N:
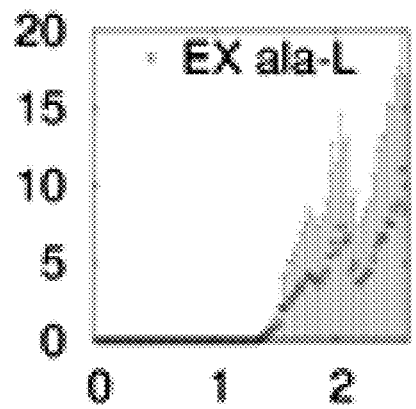
Figure 26O:
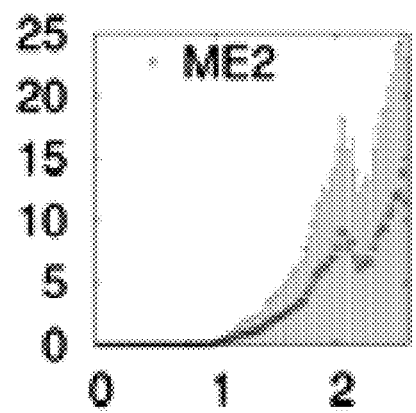
Figure 26P:
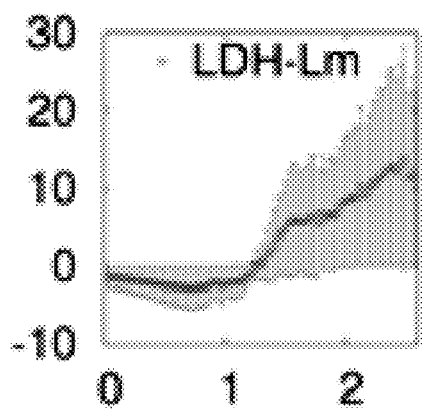
Figure 26Q:
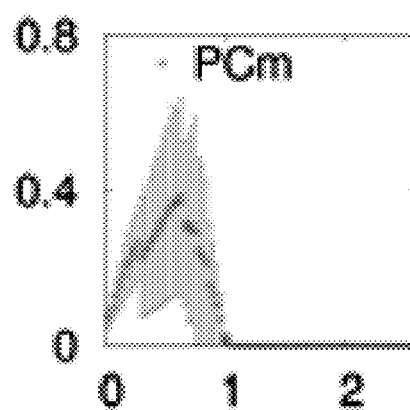
Figure 26R:
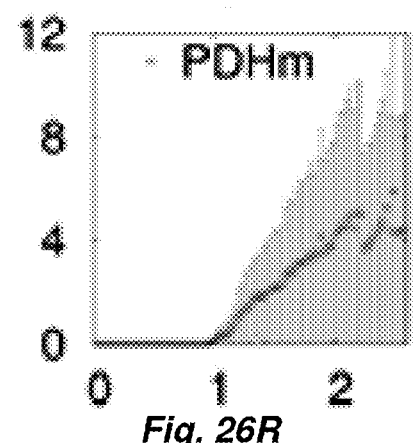
Figure 26S:
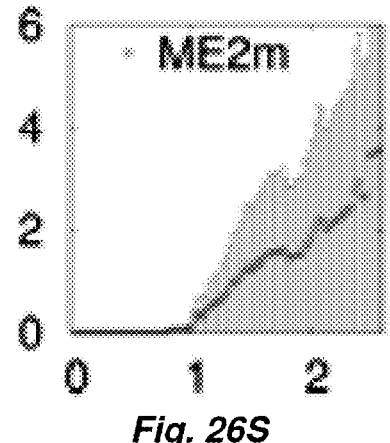
Figure 26T:
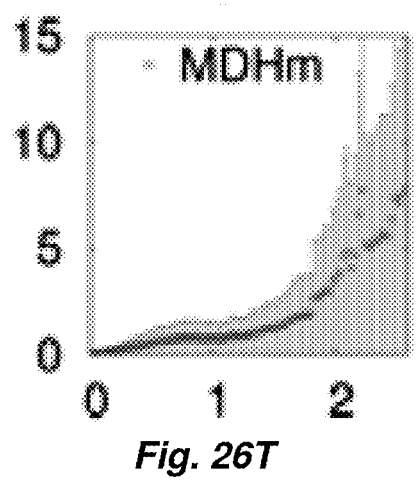
Figure 26U:
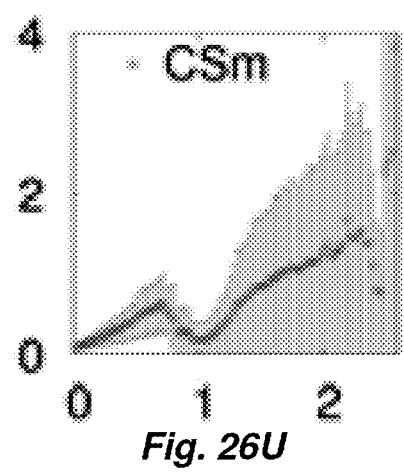
Figure 26V:
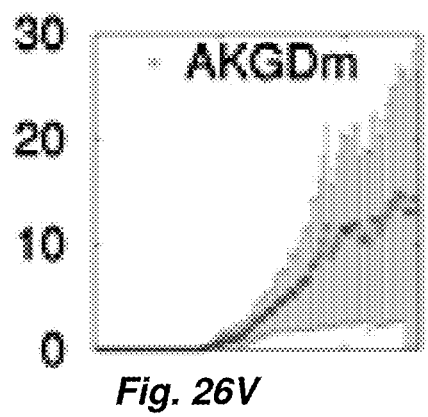
Figure 26W:
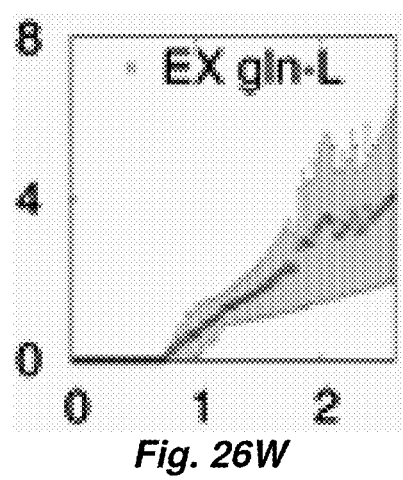

Changes in the Relative Macromolecular Densities with Increased Cell Proliferation FIG. 25 shows the predicted relative volume fraction occupied by non-mitochondrial Enzymes ($\phi_{EnM}=\Sigma_i|_{EnM}a_i f_i$), mitochondria ($\phi_M$), and ribosomes ($\phi_R$) as a function of the proliferation rate for cells growing in a medium containing glucose, glutamine, essential amino acids, and oxygen. The ribosomal density increases monotonically with increasing the proliferation rate in a nonlinear fashion, reaching a maximum of 10% of the cell volume at the highest proliferation rate of approximately 2.79/day (minimum doubling time of $\ln(2)/\mu_{max}$=6 hours) (FIG. 25, circles). At low proliferation rates the mitochondrial density increases with increasing the proliferation rate from 10% to about 30% of the cell volume (FIG. 25, triangles). However, beyond a proliferation rate of about 0.8/day (doubling time 21 hours), the mitochondrial density decreases with increasing the proliferation rate. This is in turn accompanied by a dramatic increase in the density of metabolic enzymes (FIG. 25, squares). Our model thus predicts that when switching from low to high proliferation rates, the cell makes a transition from a mitochondria dominated molecular crowding regime to one dominated by enzymes+ribosomes (FIG. 25).

The impact of altering the different model parameters on the behavior of the model can also be tested. Larger values of the mitochondrial crowding coefficient $a_M$, e.g., due to a decrease in mitochondrial efficiency for ATP generation, will cause a decrease of mitochondrial density at lower proliferation rates. Larger ribosome crowding coefficient $a_R$, e.g., due to a decrease in protein synthesis efficiency, will result in a faster increase of the ribosome density with increasing the proliferation rate, and a consequently faster decrease of the mitochondria density. Similarly, an increase in the average crowding coefficient of metabolic enzymes will cause a faster increase of the total enzyme concentration with increasing the proliferation, resulting in a faster decrease of the mitochondrial density as well. Cancer cells are characterized by partial alterations in all of these components, potentially resulting in a more dramatic effect than that depicted in FIG. 25. In particular, mutations leading to damaged mitochondria will enhance the effect, as originally hypothesized by Warburg.

Metabolic Switch from Low- to High Proliferation Rates

The predicted transition in the macromolecular composition of the cell is accompanied by a global switch in the cell's metabolic state (FIG. 26). At the proliferation rate of about 0.8/day (doubling time 21 hours) the model predicts a substantial increase in glucose uptake, sudden activation of glutamine uptake and α-ketoglutarate dehydrogenase activity, complete deactivation of pyruvate decarboxylase (PCm) and activation of pyruvate dehydrogenase (PDHm). The activity of pyruvate carboxylase in the low proliferation regime, where there is no glutamine uptake, is consistent with recent experimental data showing that pyruvate carboxylase is needed for growth without glutamine. The activation of glutamine uptake at high proliferation rates is also in agreement with what have been observed experimentally. We also observe activation of lactate excretion at high proliferation rates, the hallmark of the Warburg effect. Several notable changes take place around the pyruvate branching point (FIG. 26). Most noticeably, the glycolysis pathway (FIG. 26) is truncated at 3-phosphoglycerate and the flux over the ATP-decoupled pyruvate kinase-catalyzed reaction is zero at all proliferation rates. We emphasize that we have not imposed a zero flux over this reaction, and the zero flux is a prediction of the model itself. Phenylalanine, isoleucine, lysine and valine are the major sources of TCA cycle intermediates and pyruvate (via malate) at low proliferation rates. However, at high proliferation rates the TCA cycle intermediates and pyruvate are instead generated from glutamine. The cytosolic- (LDH-L) and mitochondrial L-lactate dehydrogenases (LDH-Lm) form a cycle between pyruvate and lactate. At low proliferation rates, LDH-L converts pyruvate to lactate and LDH-Lm converts lactate back to pyruvate, both reactions working at the same rate (FIG. 26, pyruvate-lactate loop, dashed lines). At high proliferation rates the cycle is reverted, LDH-L converting lactate to pyruvate and LDH-Lm pyruvate back to lactate (FIG. 26, pyruvate-lactate loop, solid lines). In the latter case the LDH-Lm catalyzed reaction has a higher rate, resulting in the net production of lactate, which is then excreted. Finally, at high proliferation alanine is produced from pyruvate and is then excreted. We note the amino acid selectivity for pyruvate and TCA cycle intermediates at low proliferation rates depends on the specific choice of nutrient import cost in equation (1). For example, assuming that the cost of nutrient uptake is equal for all nutrients, we obtain that tryptophan is utilized as a source of pyruvate at low proliferation rates (data not shown). However, the high fluxes of glutamine uptake, the 3-phosphoglycerate shift towards serine biosynthesis, and alanine excretion at high proliferation rates, and the results described below are independent of the choice of nutrient cost coefficients.

Novel Pathway for ATP Generation

Figure 27A:
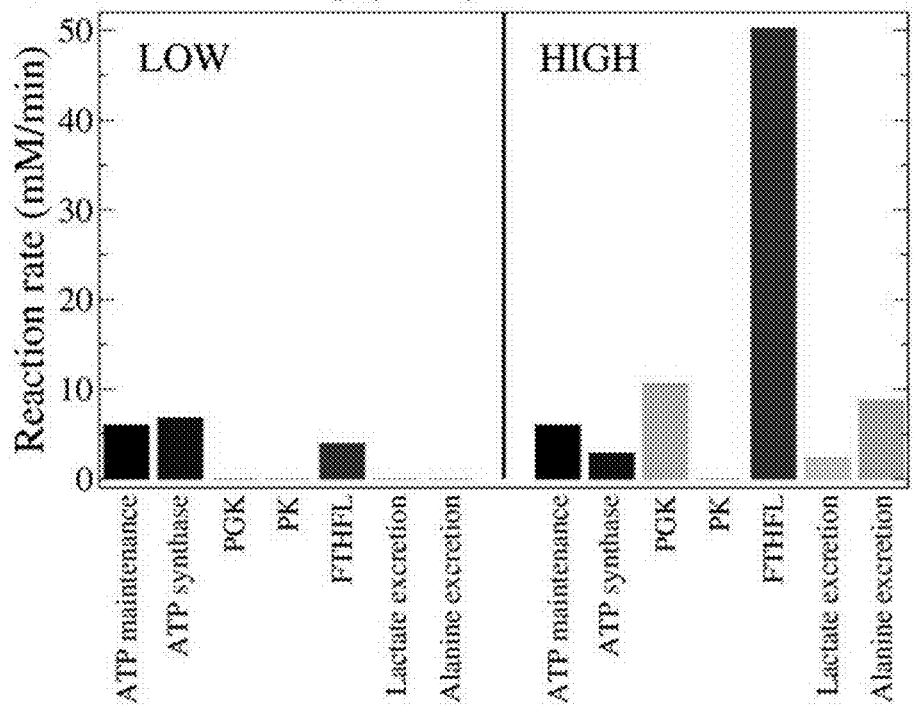
FIG. 27A: cells using the alternative glycolysis pathway with net zero ATP production.
Figure 27B:
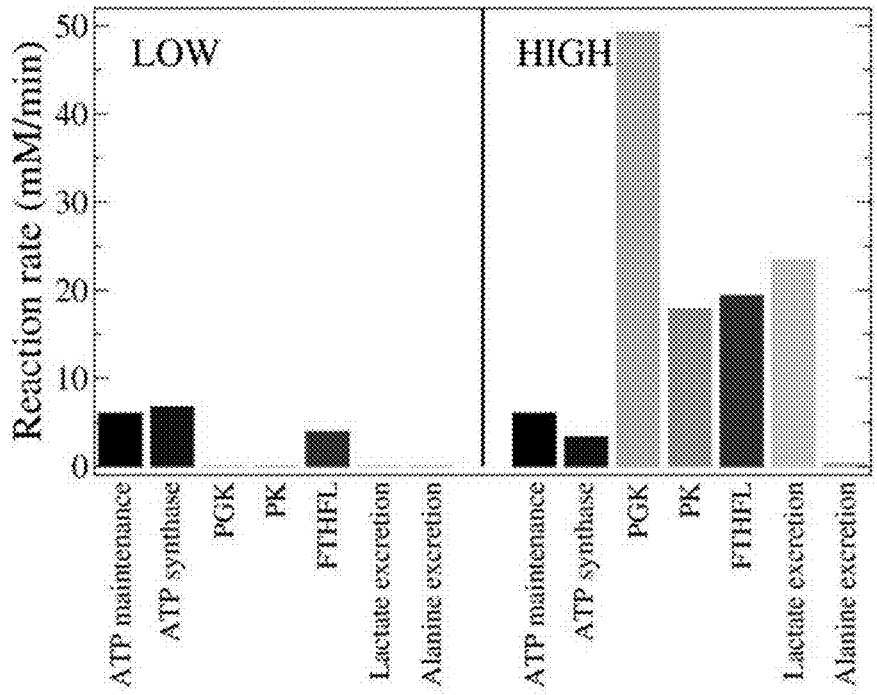
FIG. 27B: cells using the standard glycolysis.
Figure 28:
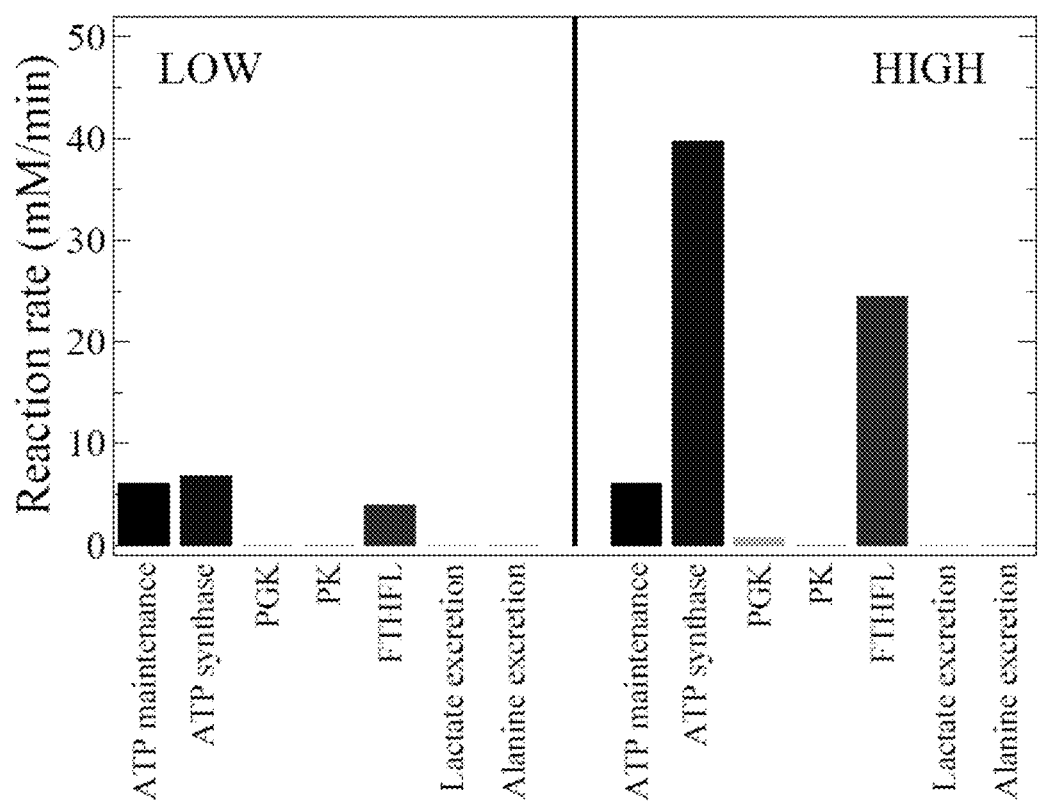
FIG. 28: Selected reactions contributing to ATP generation at different proliferation rates in cells using the alternative glycolysis pathway with net zero ATP production, after removing the molecular crowding constraint. Contribution of ATP synthase, phosphoglycerate kinase (PGK), pyruvate kinase (PK) and formate-tetrahydrofolate ligase (FTHFL) to ATP generation in cells at low (0.03/day, left) and high (2.52/day, right) proliferation rates. The ATP consumed for cell maintenance (black) is shown as a reference.

When considering the molecular crowding constraint, our simulations show that at high proliferation rates most of the glycolysis rate is diverted towards the biosynthesis of serine (FIG. 26). However, this flux rate exceeds by more than 10 fold the serine requirements for protein synthesis (FIG. 26, serine to protein synthesis, top center panel). Therefore, we hypothesized that cells utilizing the net zero ATP glycolysis may overexpress some alternative pathway for ATP generation. To test this hypothesis we inspected the genome-scale reaction rate predictions, focusing on reactions producing ATP. Following this approach we identified the reactions with high rates of ATP production in cells with a net zero ATP glycolysis at different proliferation rates. At low proliferation rates (0.03/day, doubling time 24 days) ATP synthase was the dominant reaction, supplying most of the ATP required for cell maintenance (FIGS. 27A and 27B, left panels). On the other hand, at high proliferations rates (2.79/day, doubling time 6 hours) the formate-tetrahydrofolate ligase (FTHFL), working in the reverse direction to form ATP, is the dominant reaction (FIG. 27A, right panel). Formate-tetrahydrofolate ligase is also active in cells with the standard glycolysis (FIG. 27B, right panel). However, in the case of standard glycolysis phosphoglycerate kinase and pyruvate kinase are the dominant reactions at high proliferation rates (FIG. 27B, right panel). Finally, we note that the molecular crowding constraint is determinant in the differential utilization of ATP synthase and FTHFL at high proliferation rates (FIG. 27B, HIGH), because its removal from the model (which mathematically is equivalent to Setting ϕmax=∞ in equation (39)) results in a dramatic increase in the ATP synthase rate and a decrease of the FTHFL rate at high proliferation rates (FIG. 28, HIGH).

By tracking back the flux from the formate-tetrahydrofolate ligase-catalyzed reaction to glycolysis we uncovered a novel pathway for ATP generation (FIG. 29). The pathway is composed of three main steps. First, synthesis of L-serine from the glycolysis intermediate metabolite 3-phosphoglycerate, using NAD and L-glutamate as cofactors (FIG. 29B), with the overall reaction (40) 3-phosphoglycerate+L-glutamate+NAD$^+$+H$_2$O→L-Serine+α-Ketoglutarate+H$^+$+NADH+Phosphate Second, the conversion of L-serine to glycine with a concomitant one-carbon metabolism cycle, resulting in the net generation of 1 mole of ATP per mole of serine transformed, using NADP+ as a cofactor (FIG. 4b), with the overall reaction L-Serine+NADP$^+$+H$_2$O+ADP+Phosphate→Glycine+NADPH+2 H$^+$+ATP Finally, the conversion glycine to ammonium (NH4) in the mitochondria with a concomitant one-carbon metabolism cycle, using NAD$^+$ and NADP$^+$ as cofactors (FIG. 29D or 29E), with the overall reaction:

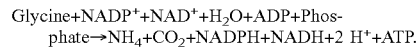

Glycine+NADP$^+$+NAD$^+$+H$_2$O+ADP+Phosphate→NH$_4$+CO$_2$+NADPH+NADH+2 H$^+$+ATP.

This pathway has a net yield of 2 mole of ATP per mole of 3-phosphoglycerate, therefore 4 mole of ATP per mole of glucose. Furthermore, when compared to the standard glycolysis, the net zero ATP glycolysis manifests a significant decrease in lactate excretion while increasing the alanine excretion (FIGS. 27A AND 27B, right panel).

Figure 29A:
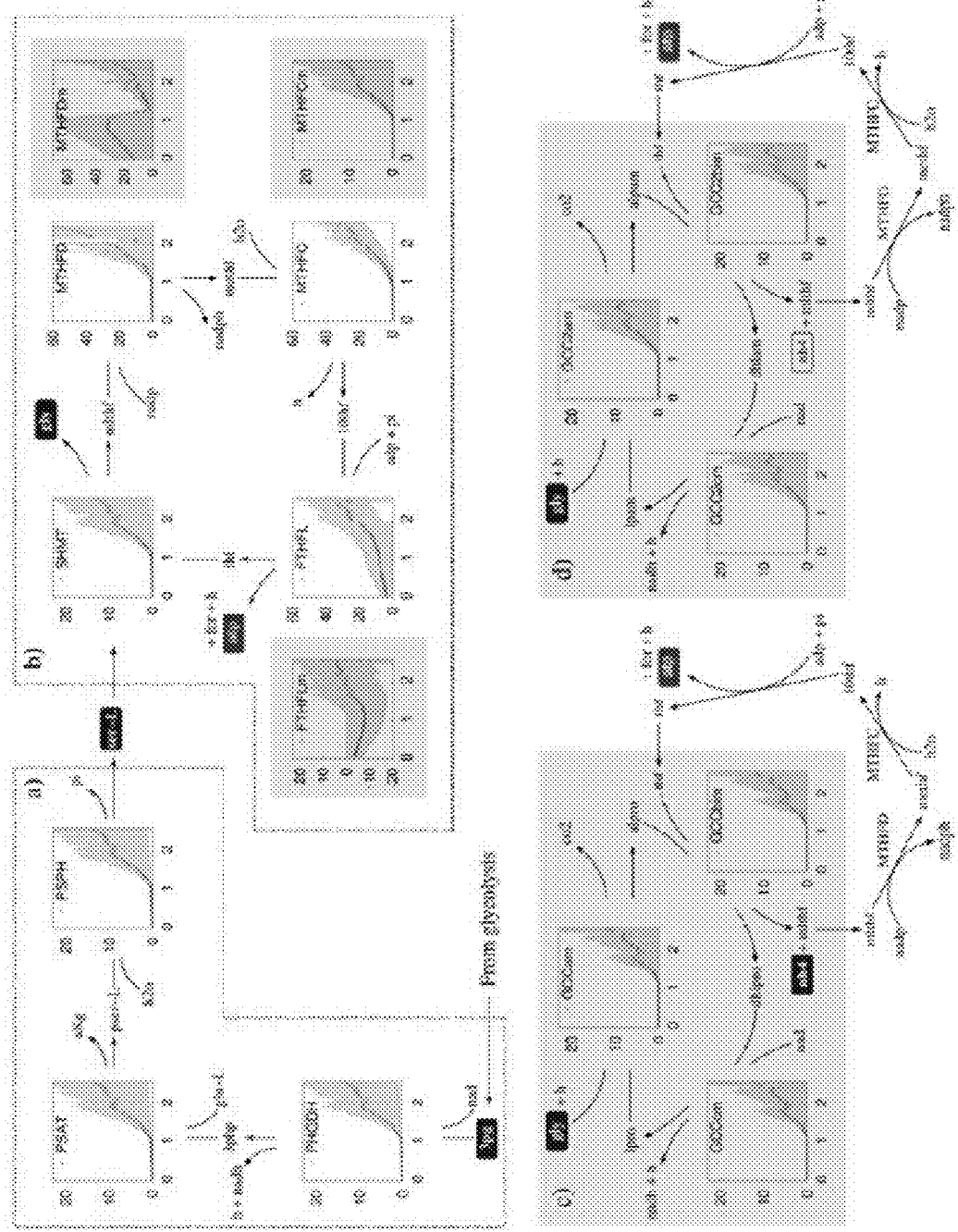
FIG. 29A is a schematic diagram of the ATP producing pathways described herein.
Figure 29B:
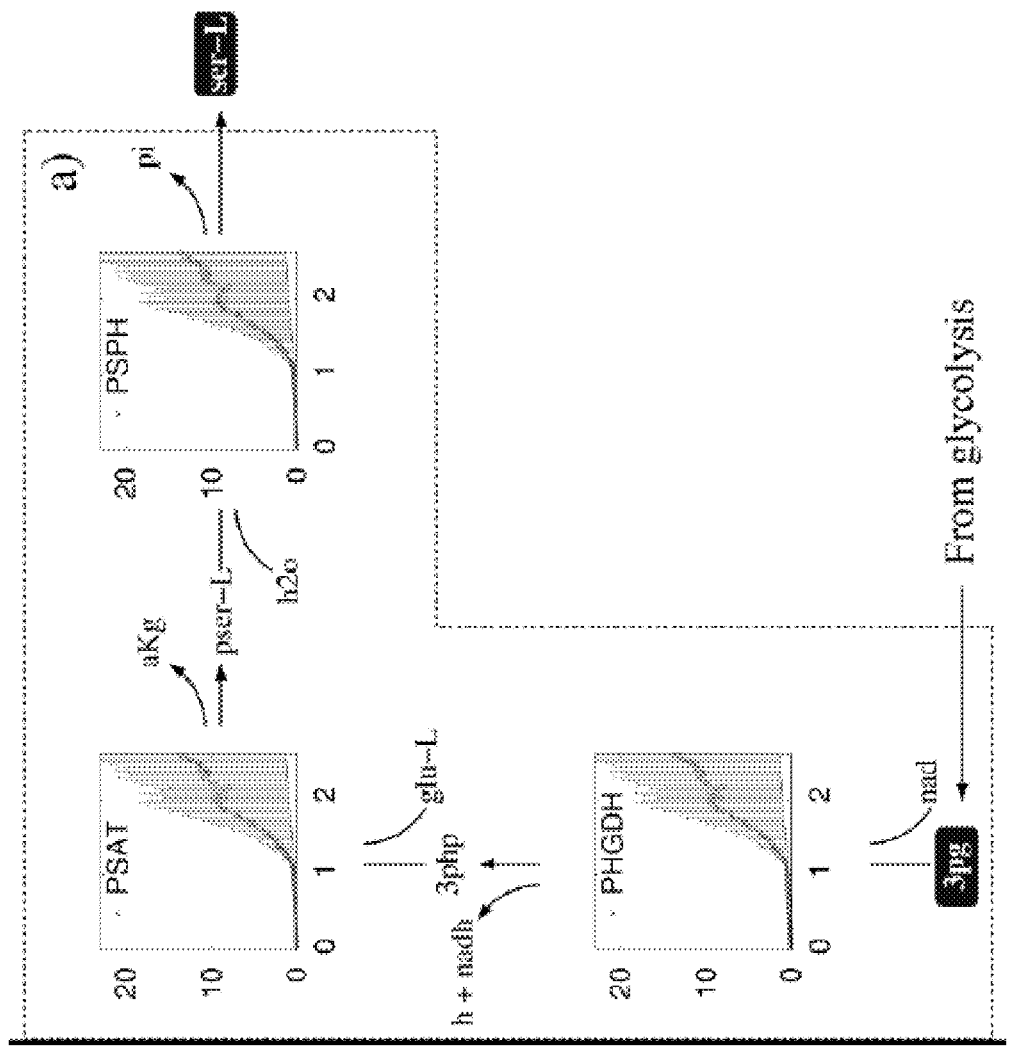
FIG. 29: Novel ATP producing pathway.
Figure 29C:
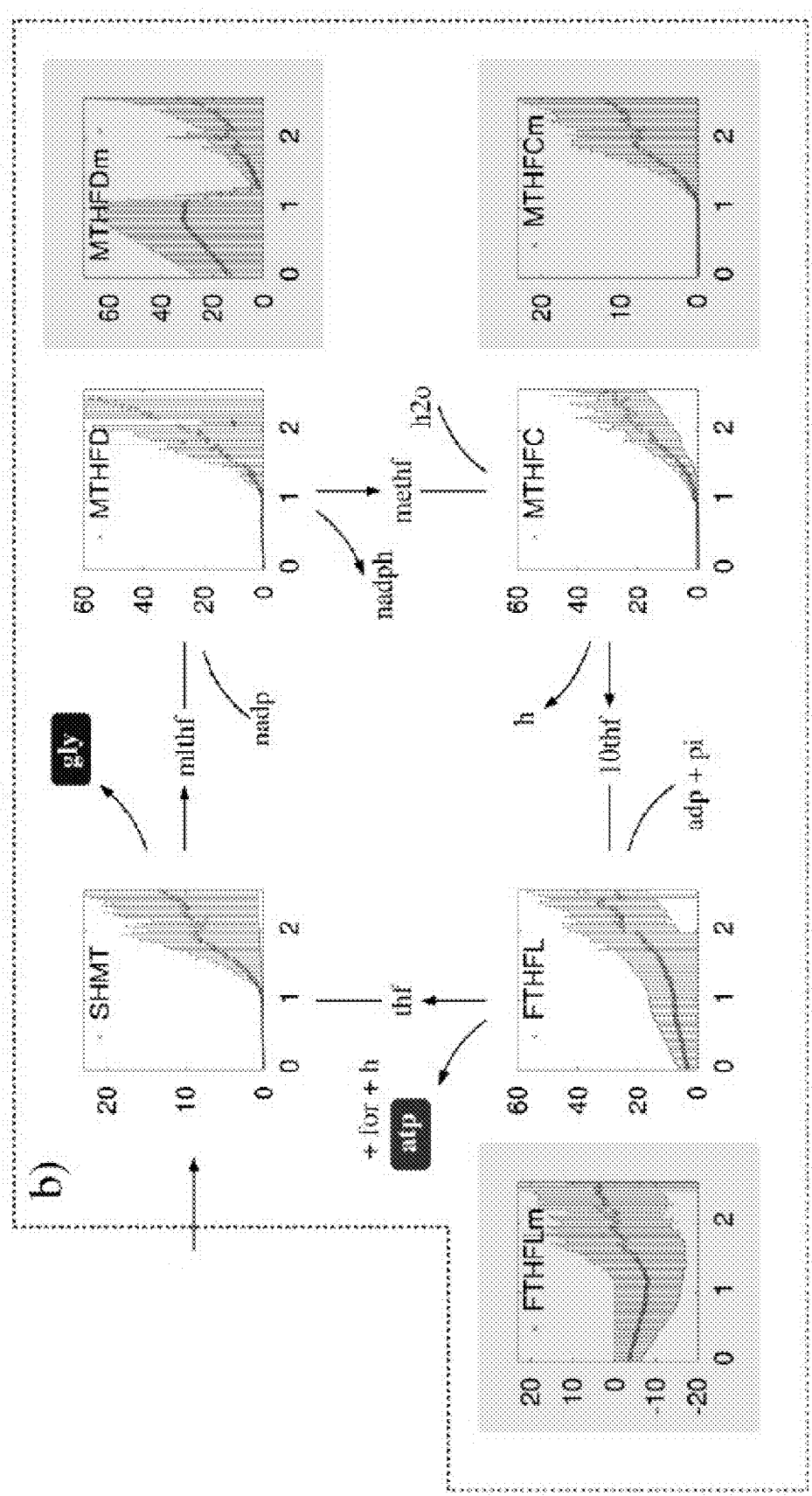
Figure 29D:
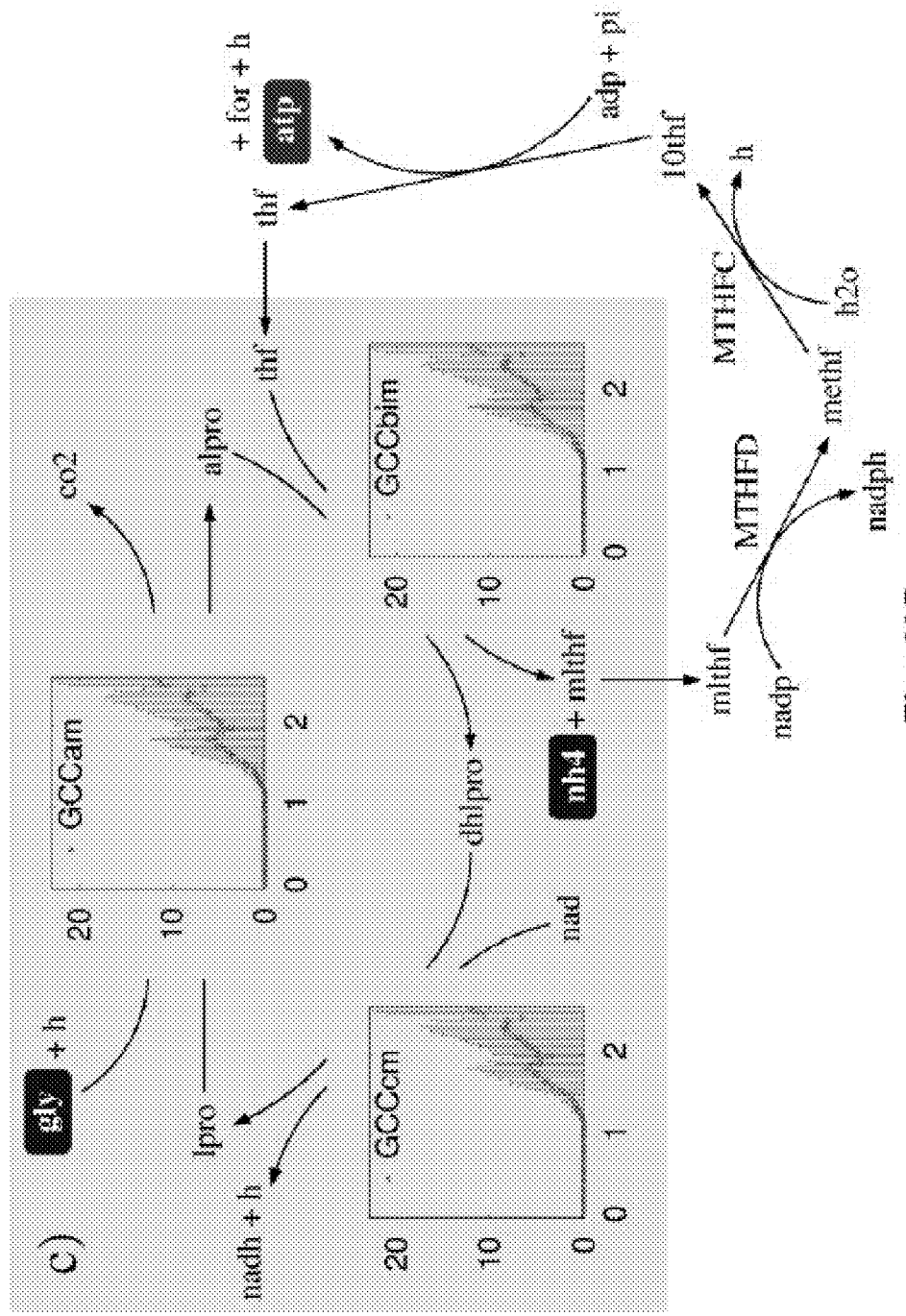
Figure 29E:
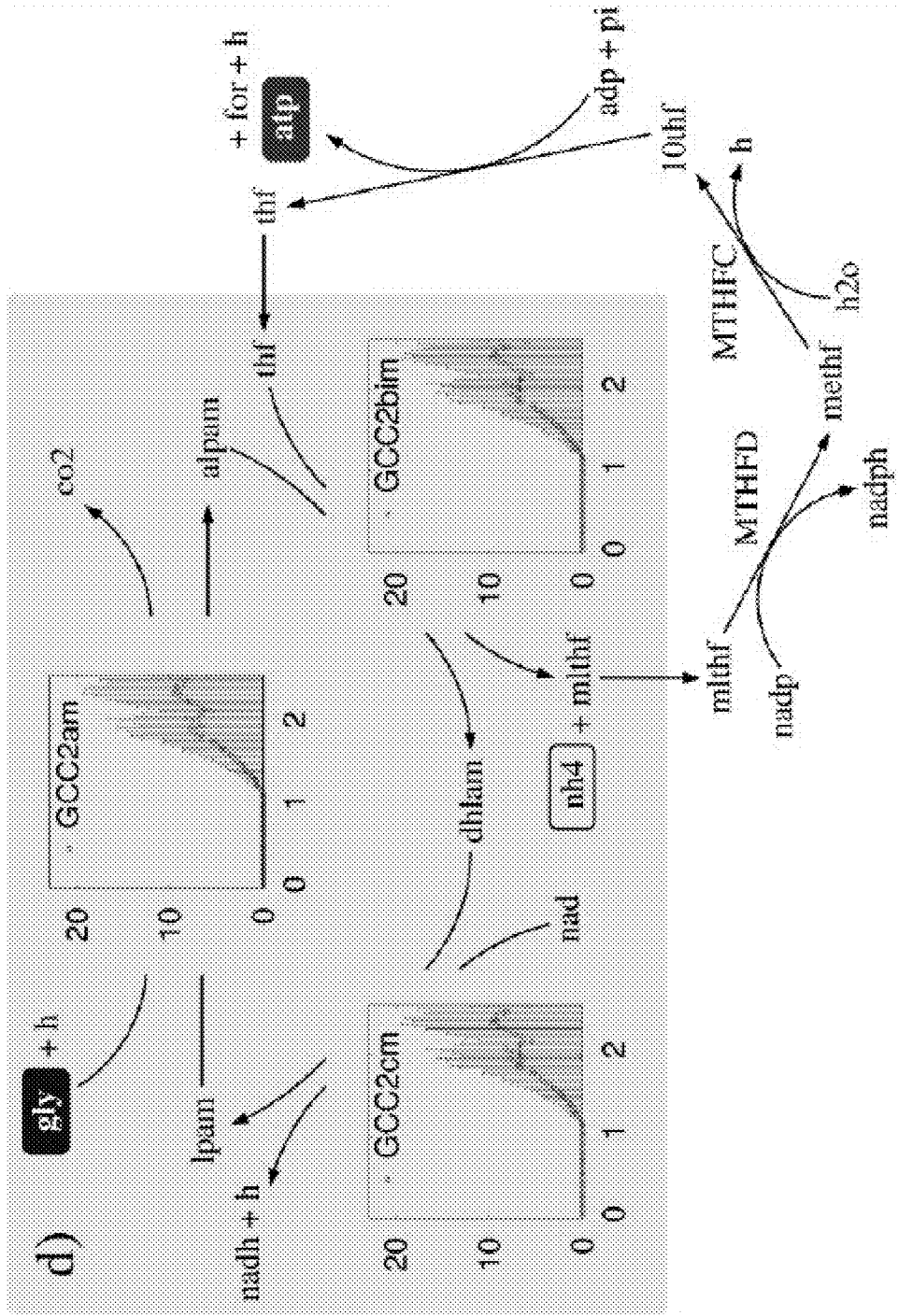

Although the reactions in the reaction cycle shown in FIG. 29C are all annotated as reversible in the human metabolic network reconstruction (Schellenberger J, et al. (2010) *BMC Bioinformatics* 11: 213), the cycle may not work in the direction of ATP production due to thermodynamic constraints. FTHFL can efficiently catalyze the synthesis of ATP in the bacterium *Clostridium cylindrosporum*. However, it remains to be elucidated whether this is also feasible in human cells, where the tri-functional enzyme C1-tetrahydrofolate synthase is responsible for the methylene-tetrahydrofolate dehydrogenase, methenyl-tetrahydrofolate cyclohydrolase and FTHFL activities. To address this issue, we have analyzed a kinetic model of the reaction cycle shown in FIG. 29C, focusing on the cytosolic enzymes alone. The model is described below and is based on a previous model of folate metabolism. We demonstrate that the kinetic model has a stable steady state in the direction of ATP production, indicating that the novel pathway is thermodynamically feasible.

Although the reactions in the reaction cycle shown in FIG. 29C are all annotated as reversible, the cycle may not work in the direction of ATP production due to thermodynamic constraints. As indicated above, to address this issue, we analyze a kinetic model of the reaction cycle shown in FIG. 4b, focusing on the cytosolic enzymes alone. The four reactions in FIG. 29C are modeled as reversible random multimolecular reactions:

$$f_{SHMT} = \left\{ k_{SHMT,f} \frac{[thf]}{K_{SHMT,thf} + [thf]} \frac{[ser-L]}{K_{SHMT,ser-L} + [ser-L]} - k_{SHMT,r} \frac{[mlthf]}{K_{SHMT,mlthf} + [mlthf]} \frac{[gly]}{K_{SHMT,gly} + [gly]} \right\} E_{SHMT} \quad (43)$$

$$f_{MTHFD} = \left\{ k_{MTHFD,f} \frac{[mlthf]}{K_{MTHFD,mlthf} + [mlthf]} \frac{[nadp]}{K_{MTHFD,nadp} + [nadp]} - k_{MTHFD,r} \frac{[methf]}{K_{MTHFD,methf} + [methf]} \frac{[nadph]}{K_{MTHFD,nadph} + [nadph]} \right\} E_{MTHFD1} \quad (44)$$

$$f_{MTHFC} = \left\{ k_{MTHFC,f} \frac{[methf]}{K_{MTHFC,methf} + [methf]} - k_{MTHFC,r} \frac{[10fthf]}{K_{MTHFC,10fthf} + [10fthf]} \right\} E_{MTHFD1} \quad (45)$$

$$f_{FTHFL} = \left\{ k_{FTHFL,f} \frac{[10fthf]}{K_{FTHFL,10fthf} + [10fthf]} \frac{[adp]}{K_{FTHFL,adp} + [adp]} \frac{[pi]}{K_{FTHFL,pi} + [pi]} - k_{FTHFL,r} \frac{[thf]}{K_{FTHFL,thf} + [thf]} \frac{[atp]}{K_{FTHFL,atp} + [atp]} \frac{[for]}{K_{FTHFL,for} + [for]} \right\} E_{MTHFD1} \quad (46)$$

where $f_{reaction}$ denotes the net reaction rate, $k_{reaction,f}$ and $k_{reaction,r}$ forward and backward turnover numbers, $K_{reaction,metabolite}$ the half-saturation constant, [metabolite] the corresponding metabolite concentration, and $E_{enzyme}$ the concentration of the corresponding enzyme. Here the following abbreviations have been used: tetrahydrofolate (thf), 5,10-methylene hydrofolate (mlthf), 5,10-methenyltetrahydrofolate (methf), 10-formyltetrahydrofolate (10fthf), L-serine (ser-L), glycine (gly), formate (for), serine hydroxymethyltransferase (SHMT), methylenetetrahydrofolate dehydrogenase (MTHFD), methenyltetrahydrofolate cyclohydrolase (MTHFC), and 5-formethyltetrahydrofolate cycloligase (FTHFL). We note in human cells the MTHFD, MTHFC and FTHFL activities are carried on by a tri-functional enzyme encoded by the MTHD1. The kinetic parameter values are reported in Table S3, below. These parameters where obtained from Nijhout H F, et al. ((2004) J Biol Chem 279:55008-16) or through references cited in the BRENDA database (Scheer M, et al. (2011) Nucleic Acids Res 39:D670-6). In humans the cytosolic enzyme activities of MTHFD, MTHFC and FTHFL are carried by the tri-functional enzyme C1-tetrahydrofolate synthase, encoded by the SMTHFD1 gene. Therefore, the reaction cycle shown in FIG. 29C is regulated by the activity of two enzymes, serine hydroxymethyltransferase (SHMT) and C1-tetrahydrofolate synthase (SMTHFD1). The total concentration of these two enzymes ESHMT+SMTHFD1 determines how fast the system evolves to a steady state and the absolute rate at steady state, but it has no impact on the metabolite concentrations at steady state. Taking this fact into consideration we focus on the system behavior as a function of the relative concentration of one of the enzymes, SHMT for example $E_{SMTHFD1}/(E_{SHMT}+E_{SMTHFD1})$.

TABLE 9

Model parameters. All half-saturation constants $K_{reaction, metabolite}$ and metabolite concentrations [metabolite] are expressed in mM and all turnover numbers $k_{reaction,direction}$ in 1/sec.

| Parameter | Value | Source |
|---|---|---|
| SHMT | | |
| $k_{SHMT,f}$ | 9.58 | [3] |
| $k_{SHMT,r}$ | 0.60 | Estimated as $k_{SHMT,f} V_{max,r}/V_{max,f}$ |
| $V_{max,f}$ | 40,000 | [1] |
| $V_{max,r}$ | 25,000 | [1] |
| $K_{SHMT,thf}$ | 0.05 | [1] |
| $K_{SHMT,ser-L}$ | 0.6 | [1] |
| $K_{SHMT,mlthf}$ | 3.2 | [1] |
| $K_{SHMT,gly}$ | 10 | [1] |
| MTHFD | | |
| $k_{MTHFD,f}$ | 10 | [4] |
| $k_{MTHFD,r}$ | | $k_{MTHFD,f} V_{max,r}/V_{max,f}$ |
| $V_{max,f}$ | 200,000 | [1] |
| $V_{max,r}$ | 594,000 | [1] |
| $K_{MTHFD,mlthf}$ | 0.002 | [1] |
| $K_{MTHFD,nadp}$ | 0.022 | [4] |
| $K_{MTHFD,methf}$ | 0.01 | [1] |
| $K_{MTHFD,nadph}$ | 0.022 | Estimated as $K_{MTHFD,nadph}$ |
| [nadp] | 0.02 | [5] |
| [nadph] | 0.01 | [5] |
| MTHFC | | |
| $k_{MTHFC,f}$ | 134 | [6] |
| $k_{MTHFC,r}$ | 3.35 | Estimated as $k_{MTHFC,f} V_{max,r}/V_{max,f}$ |
| $V_{max,f}$ | 800,000 | [1] |
| $V_{max,r}$ | 20,000 | [1] |
| $K_{MTHFC,methf}$ | 250 | [1] |
| $K_{MTHFC,10fthf}$ | 100 | [1] |
| FTHFL | | |
| $k_{FTHFL,f}$ | 0.23 | Estimated from (4) at equilibrium ($f_{FTHFL} = 0$) |
| $[10fthf]_{eq}$ | 4 | Clostridium cylindrosporum [7] |
| $[adp]_{eq}$ | 4 | Clostridium cylindrosporum [7] |
| $[pi]_{eq}$ | 4 | Clostridium cylindrosporum [7] |
| $[thf]_{eq}$ | 0.9 | Clostridium cylindrosporum [7] |
| $[atp]_{eq}$ | 0.8 | Clostridium cylindrosporum [7] |
| $[for]_{eq}$ | 2.3 | Clostridium cylindrosporum [7] |
| $k_{FTHFL,r}$ | 0.0364 | [8] |
| $K_{FTHFL,10fthf}$ | 10 | Clostridium cylindrosporum [9] |
| $K_{FTHFL,adp}$ | 0.0364 | [8] |
| $K_{FTHFL,pi}$ | 4 | [8] |
| $K_{FTHFL,thf}$ | 0.364 | [8] |
| $K_{FTHFL,atp}$ | 0.0302 | [8] |
| $K_{FTHFL,for}$ | 0.0367 | [8] |
| [adp] | 0.011 | [10] |
| [pi] | 6 | [10] |
| [atp] | 5 | [10] |
| [for] | 0.9 | [1] |

[1] Nijhout H F, et al. (2004) J Biol Chem 279: 55008-16;
[2] Scheer M, et al. (2011) Nucleic Acids Res 39: D670-6;
[3] Kruschwitz H, et al. (1995) Protein Expr Purif 6: 411-6;
[4] Pawelek P D, et al. (1998) Biochemistry 37: 1109-15;
[5] Pinkas-Sarafova A, et al. (2005) Biochem Biophys Res Commun 336: 554-64;
[6] Pawelek P D, et al. (2000) Biochim Biophys Acta 1479: 59-68;
[7] Himes R H, et al. (1962) J Biol Chem 237: 2903-14;
[8] Christensen K E, et al. (2009) Hum Mutat: 212-20;
[9] Buttlaire DH (1980) Methods Enzymol 66: 585-99; and
[10] Kushmerick M J, et al. (1992) Proc Natl Acad Sci USA 897521-5.

We focus our analysis on the concentrations of the intermediate metabolites thf, mlthf, methf and 10fthf, assuming the concentration of ser-L, glyc, formate, co-factors and enzymes constant, and given as input parameters of the model (Table 9, above). The concentration of intermediate metabolites evolve in time following the first order differential equations $$\frac{d[thf]}{dt} = f_{FTHFL}([thf],[10fthf]) - f_{SHMT}([mlthf],[thf]) \quad (47)$$

$$\frac{d[mlthf]}{dt} = f_{SHMT}([mlthf],[thf]) - f_{MTHFC}([mlthf],[methf]) \quad (48)$$

$$\frac{d[methf]}{dt} = f_{MTHFC}([mlthf],[methf]) - f_{MTHFD}([methf],[10fthf]) \quad (49)$$

$$\frac{d[thf]}{dt} = f_{MTHFD}([methf],[10fthf]) - f_{FTHFL}([10fthf],[thf]) \quad (50)$$

Our aim is to determine whether this dynamical system has a steady state with in the direction of producing ATP. To this end we numerically determined the fixed point of (47)-(50) that resulted in the highest steady state flux with ATP production. This was accomplished solving the optimization problem:

$$\text{Maximize } f_{FTHFL}([\text{mlthf}],[thf]) \quad (51)$$

subject to the fixed point constraints $$\frac{d[thf]}{dt} = \frac{d[mlthf]}{dt} = \frac{d[methf]}{dt} = \frac{d[thf]}{dt} = 0 \quad (52)$$

and the metabolite concentration bounds $$0 \leq [thf] \leq [thf]_{max}$$

$$0 \leq [\text{mlthf}] \leq [\text{mlthf}]_{max}$$

$$0 \leq [\text{methf}] \leq [\text{methf}]_{max}$$

$$0 \leq [10fthf] \leq [10fthf]_{max}. \quad (53)$$

The problem was solved in Matlab using the function fmicon, with all upper bounds equal to 1 mM.

Figure 4A:
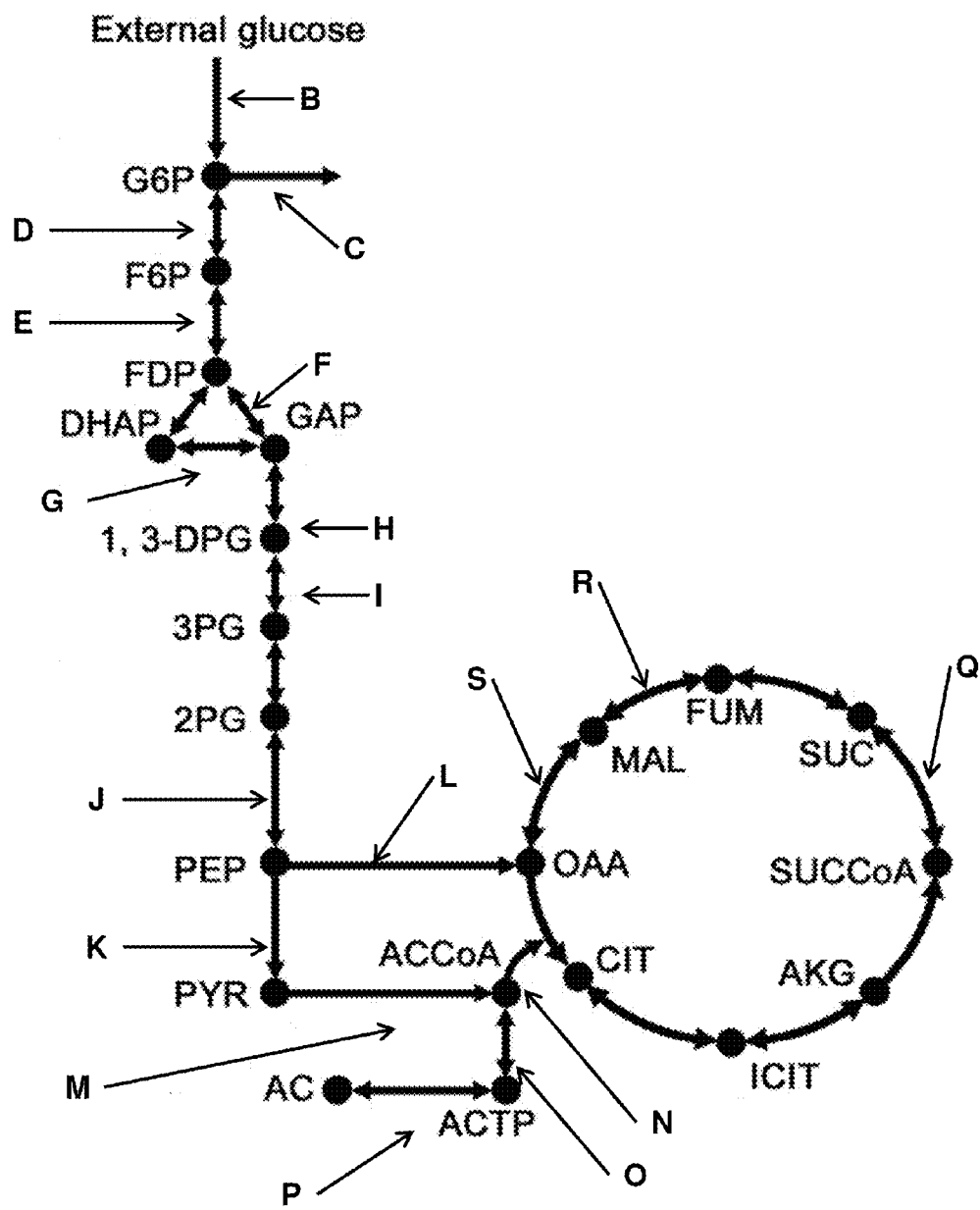
FIG. 4A shows a schematic of the central metabolism pathways. Labels B to S in FIG. 4A denote the measured flux rates shown in FIGS. 4B-4S, respectively. Measured flux rates (mmol/h/g dry biomass) and in vitro enzyme activities (U/mg protein) on two separate Y-axes of selected reactions in the central metabolism of *E. coli* are shown as a function of growth/dilution rates (X-axis). All labels are as in FIG. 3. The error bars for the experimental flux and enzyme activity plots are a result of three independent measurements.
Figure 4B:
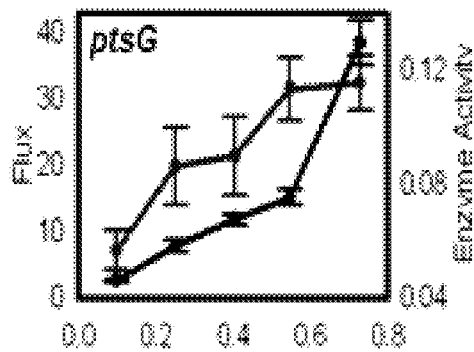
Figure 4C:
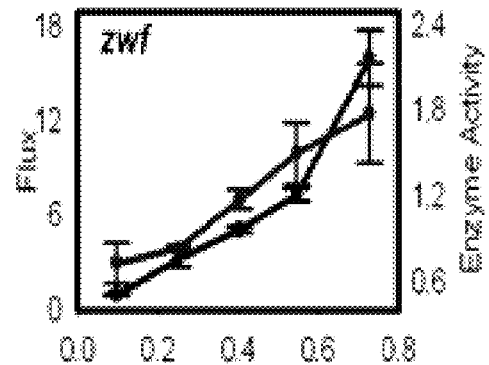
Figure 4D:
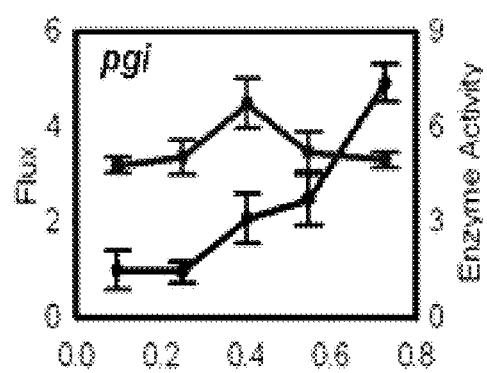
Figure 4E:
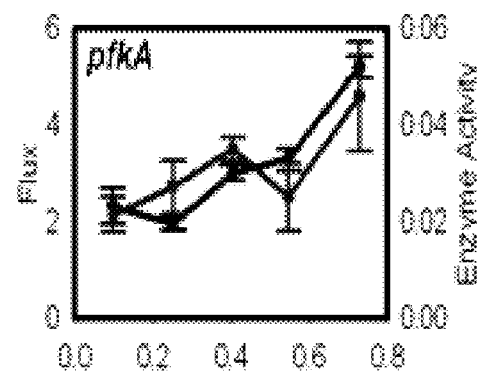
Figure 4F:
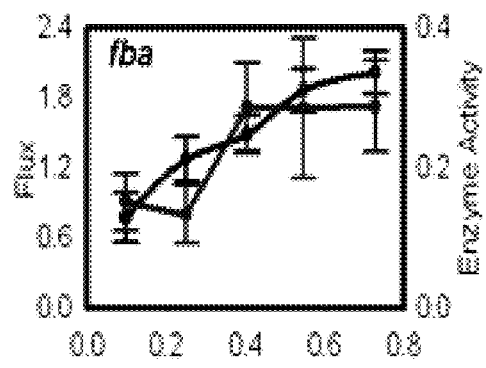
Figure 4G:
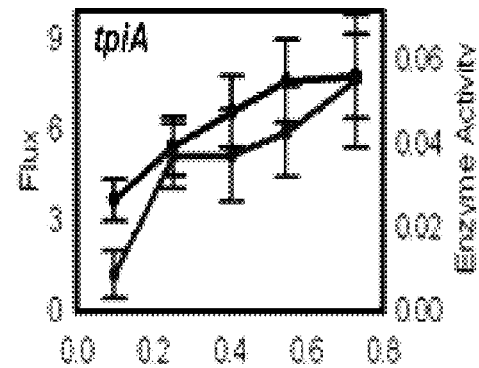
Figure 4H:
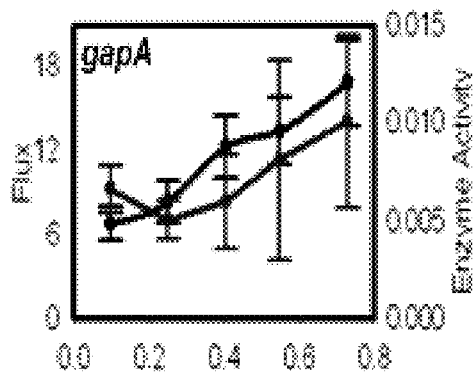
Figure 4I:
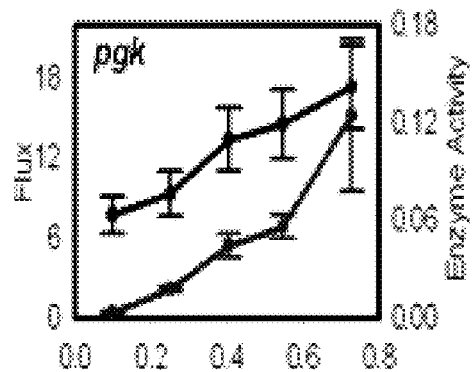
Figure 4J:
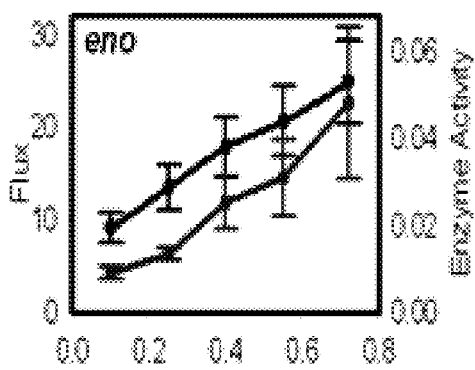
Figure 4K:
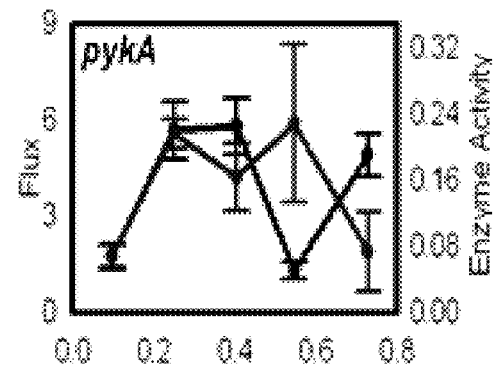
Figure 4L:
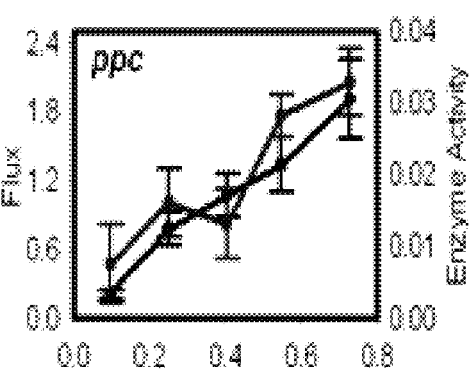
Figure 4M:
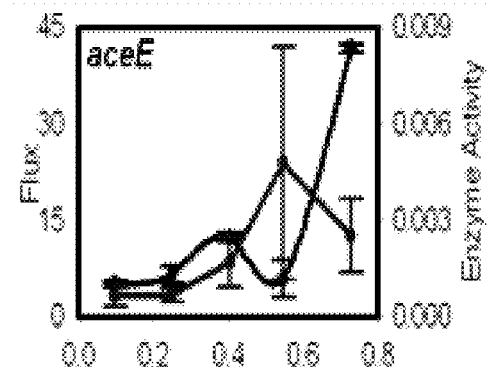
Figure 4N:
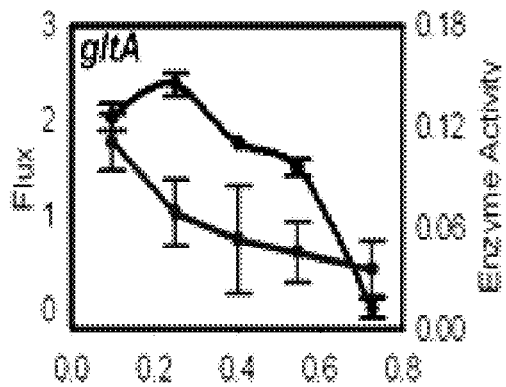
Figure 4O:
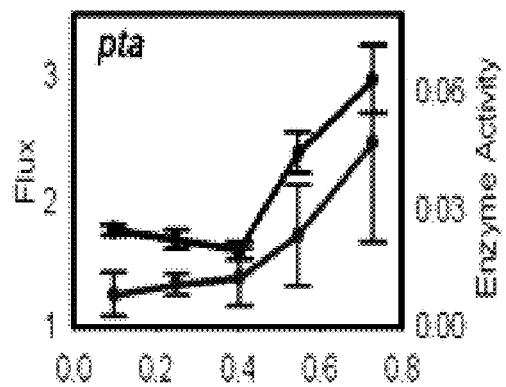
Figure 4P:
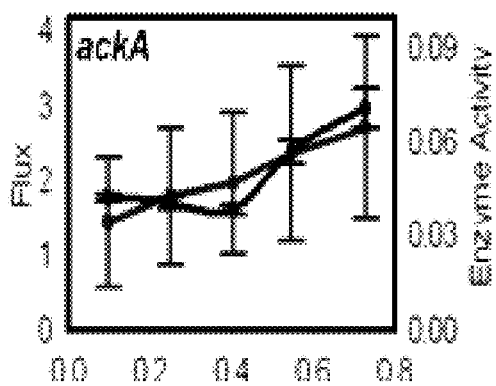
Figure 4Q:
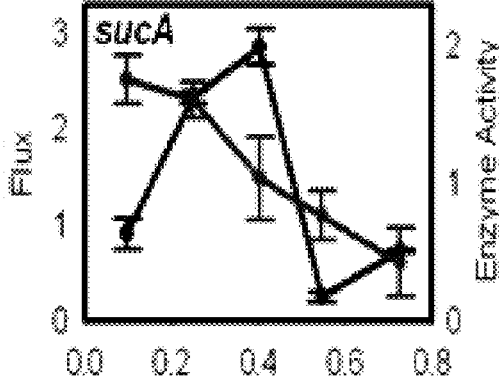
Figure 4R:
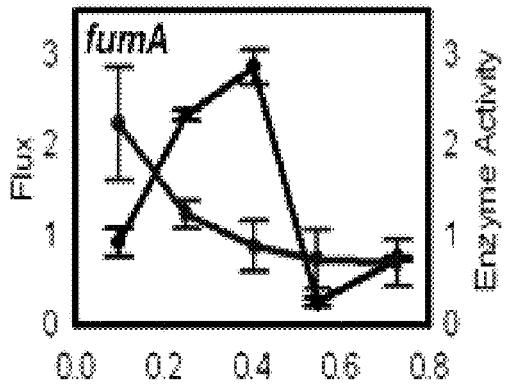
Figure 4S:
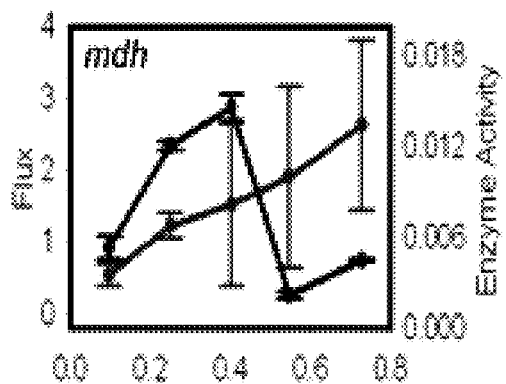
Figure 5A:
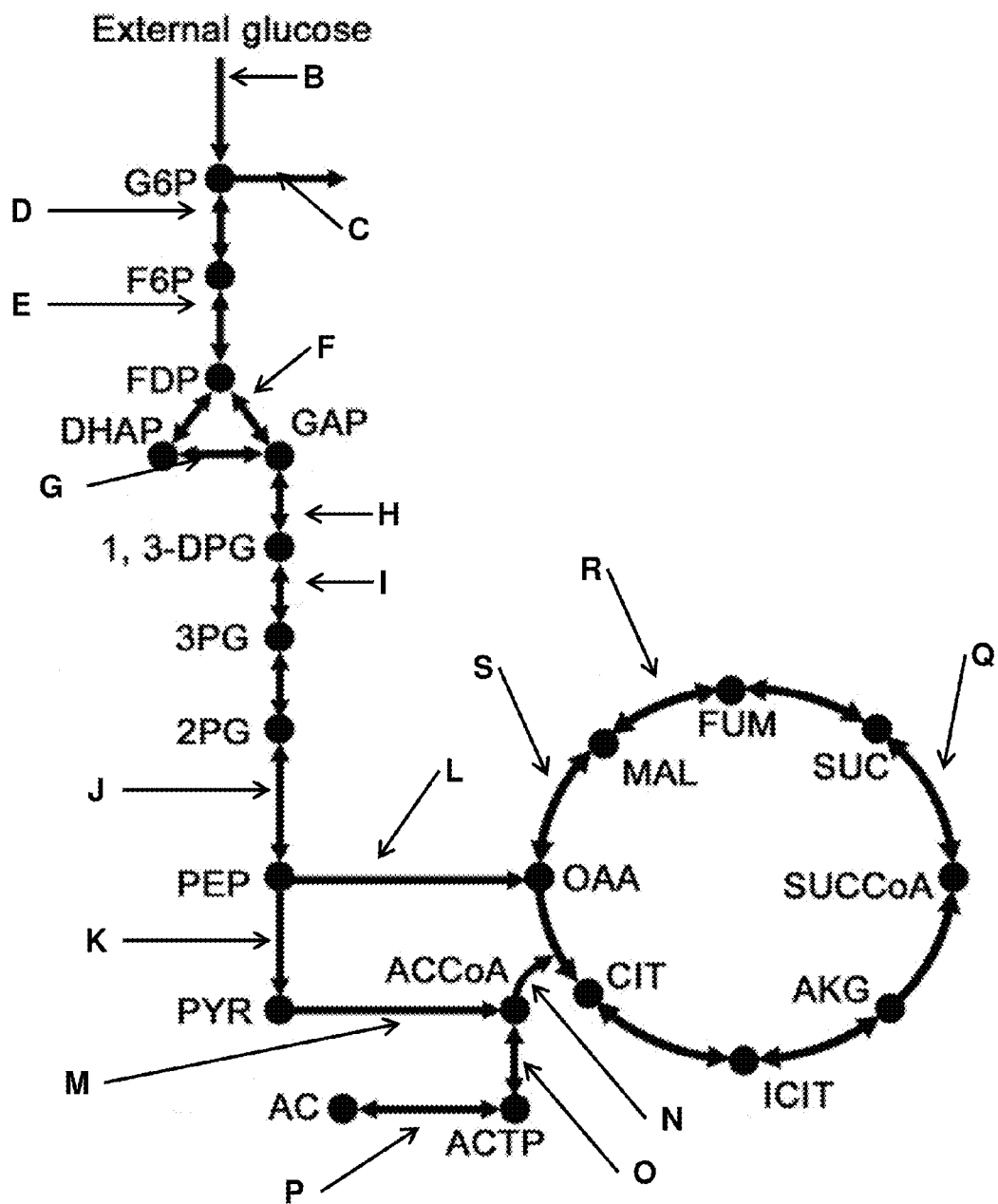
FIG. 5A shows a schematic of the central metabolism pathways. Labels B to S in FIG. 5A denote the measured flux rates shown in FIGS. 5B-5S, respectively. Measured flux rates (mmol/h/g dry biomass), in vitro enzyme activities (U/mg protein), and gene expression levels (log ratio) on three separate Y-axis of selected reactions in the central metabolism of *E. coli* are shown as a function of growth/dilution rates (X-axis). All labels are as in FIG. 4. The error bars for the experimental flux and enzyme activity plots are a result of three independent measurements. For enzymes encoded by more than one gene (isozymes or enzyme complexes) we report the mRNA levels of more than one gene: pfkA and pfkB; pykA and pykF; aceE and aceF; sucABCD; and fumA and fumC.
Figure 5B:
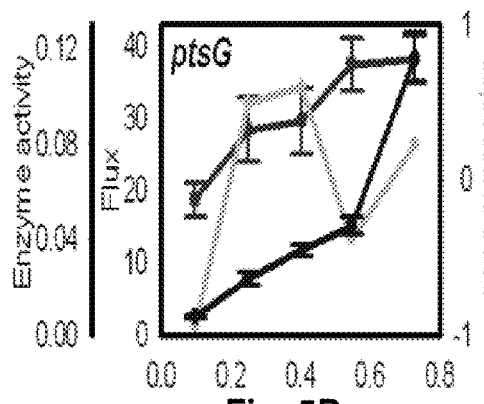
FIG. 5—Comparison of measured metabolic fluxes, enzyme activities, and relative mRNA levels.
Figure 5C:
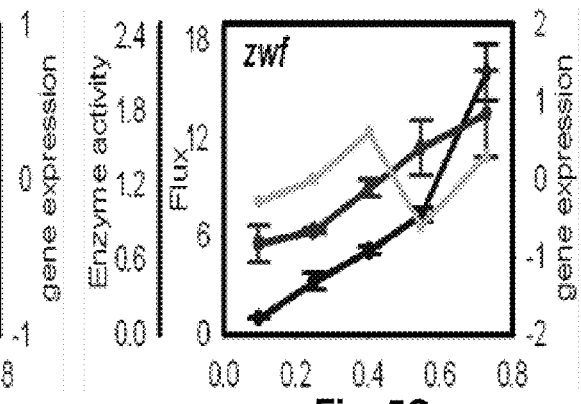
Figure 5D:
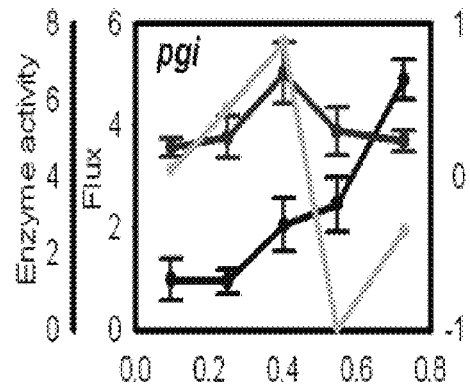
Figure 5E:
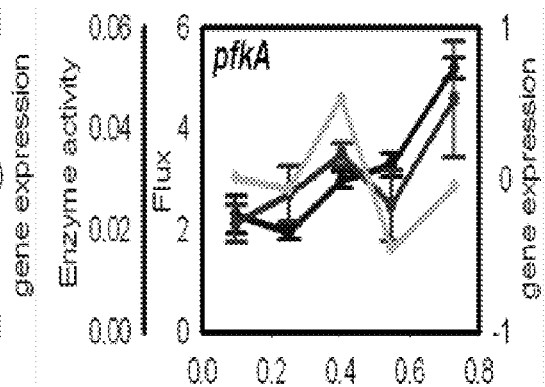
Figure 5F:
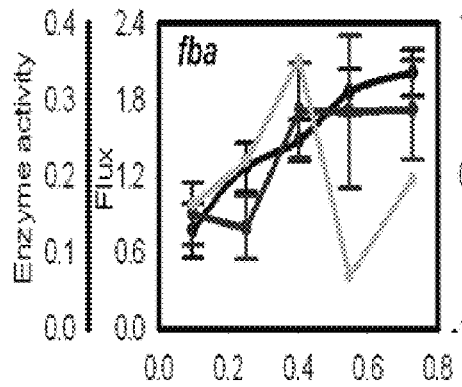
Figure 5G:
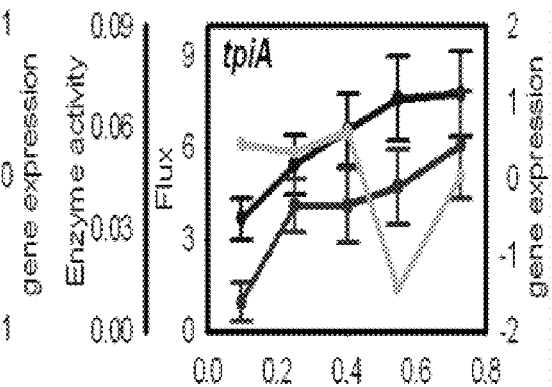
Figure 5H:
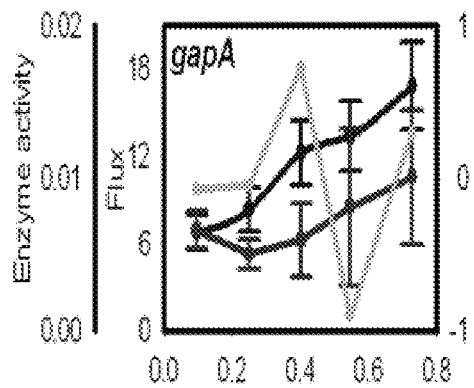
Figure 5I:
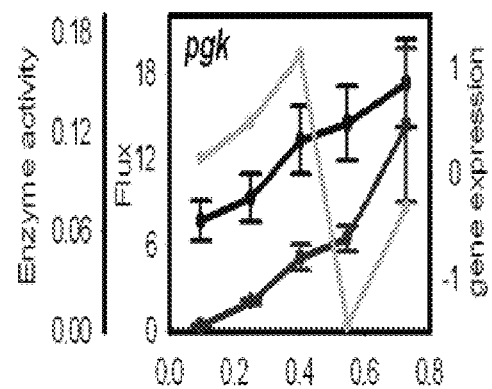
Figure 5J:
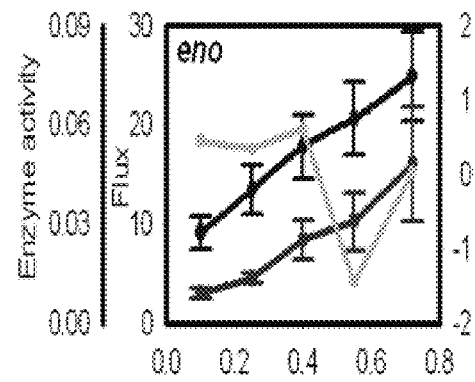
Figure 5K:
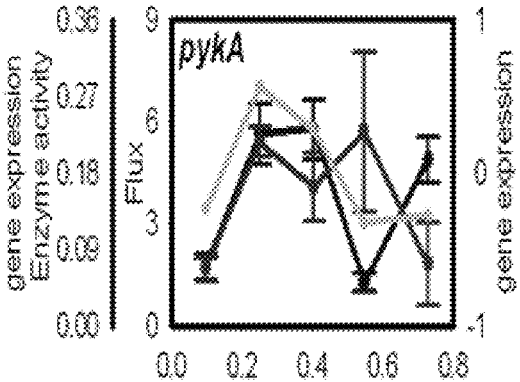
Figure 5L:
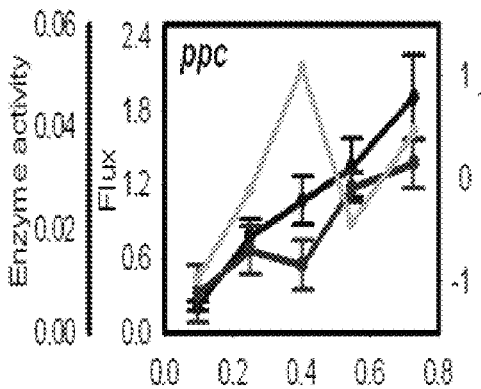
Figure 5M:
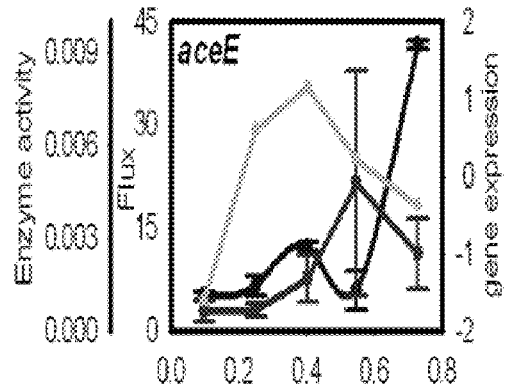
Figure 5N:
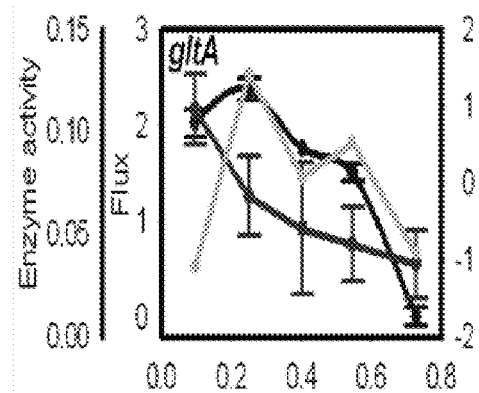
Figure 5O:
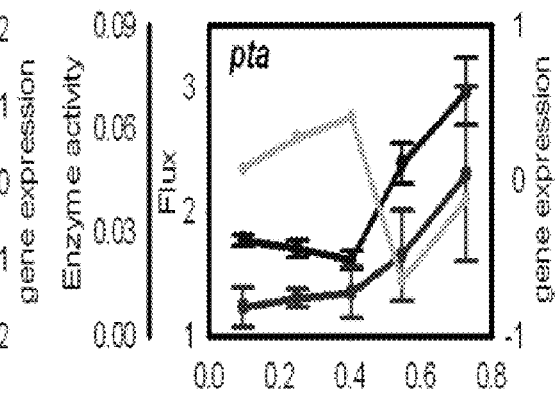
Figure 5P:
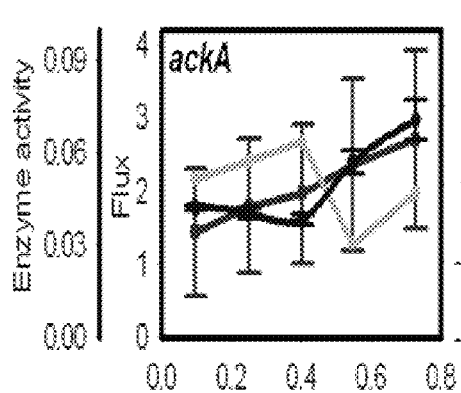
Figure 5Q:
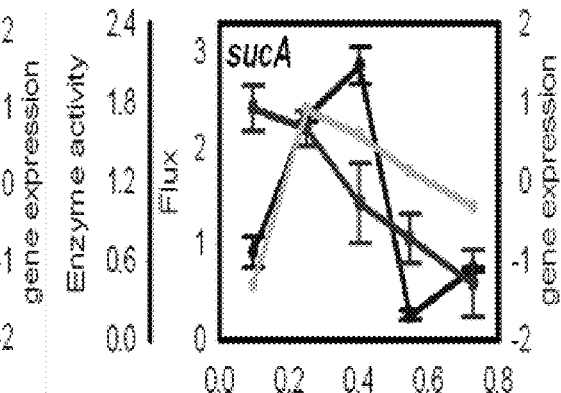
Figure 5R:
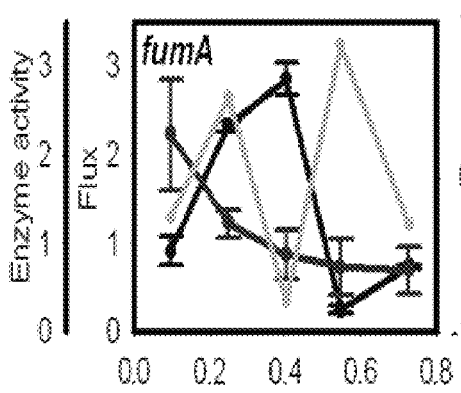
Figure 5S:
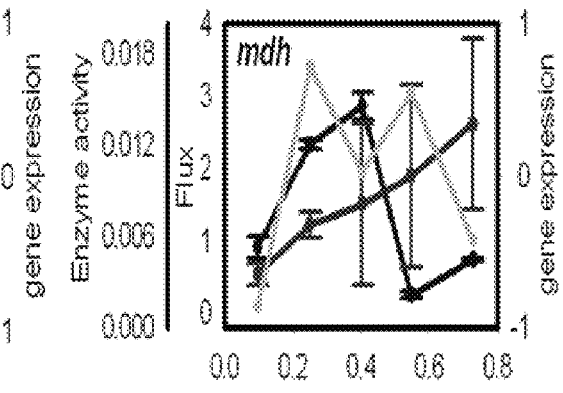
Figure 6:
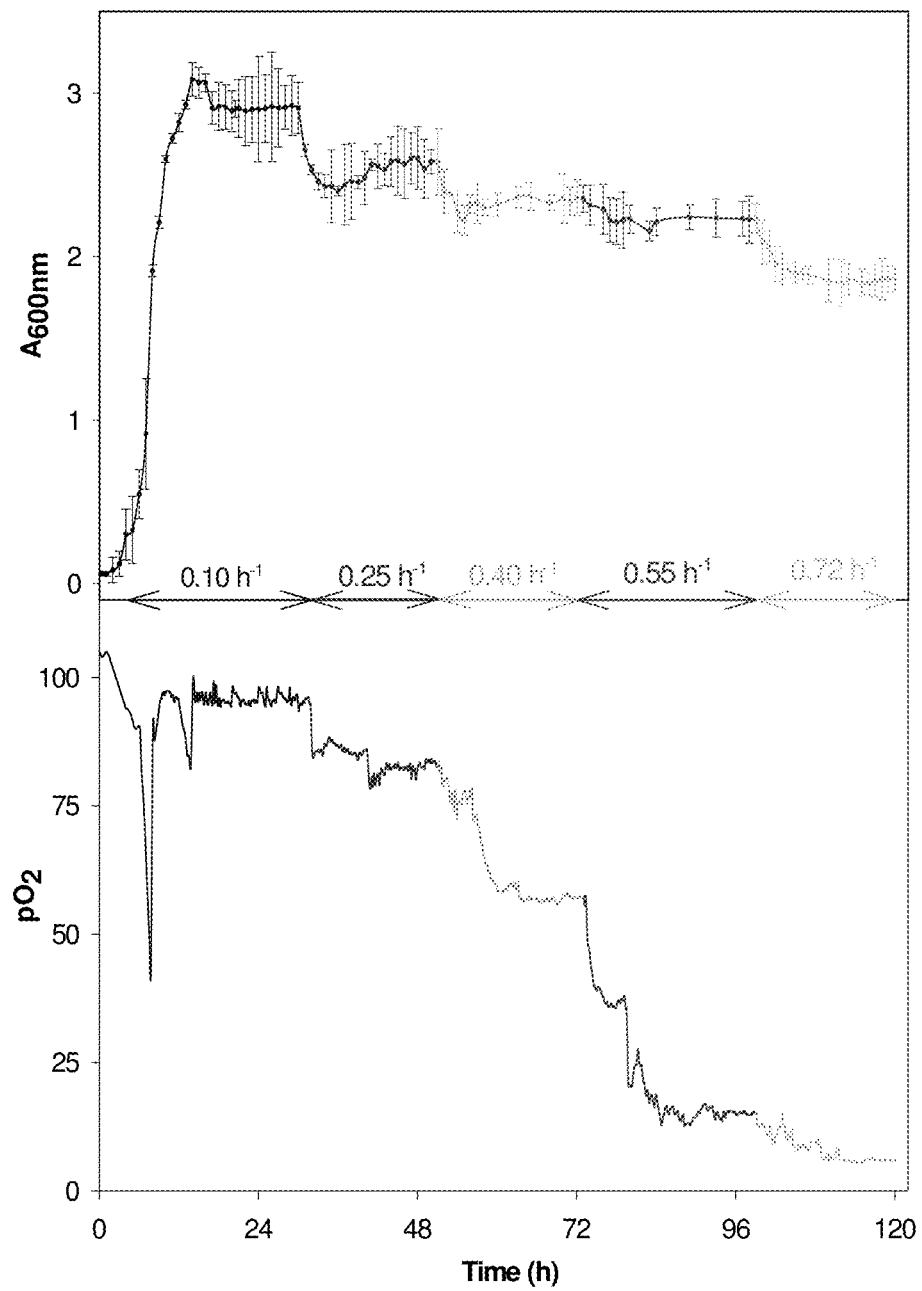
FIG. 6—Growth ($A_{600nm}$) and residual pO2 concentrations profile of *E. coli* MG 1655 at various dilution rates in M9 minimal medium supplemented with 0.2% glucose. Biomass samples for intracellular enzyme activity, gene expression and flux determination were harvested at the end of each major dilution rates indicated by constant $A_{600nm}$ (optical densities) and $pO_2$ concentrations in the growth medium.
Figure 30:
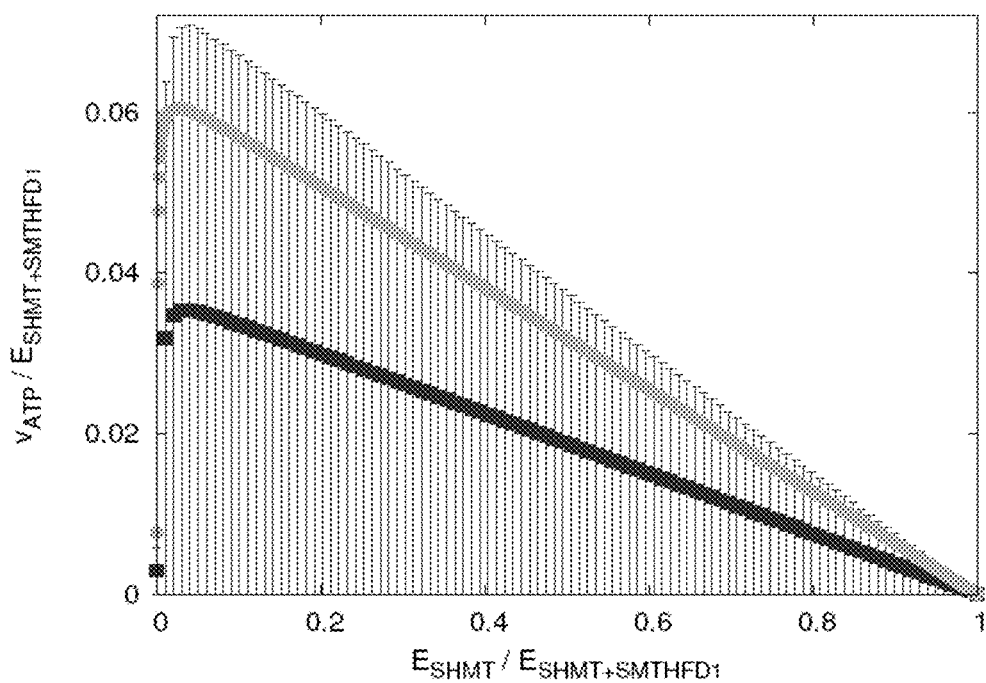
FIG. 30: Kinetic properties of the reaction cycle shown in FIG. 29C. Maximum ATP production rate of cycle in FIG. 29C as a function of $E_{SHMT}(E_{SHMT}+E_{MTHFD1})$. The gray circles were obtained using reported kinetic parameters. The black squares and error bars represent the median and 90% confidence interval over 100 simulated kinetic parameters, where the logarithm of each kinetic parameter was sampled uniformly from a value two fold lower to a value two fold higher than the reported values.

For all $0 < E_{SMTHFD1}/(E_{SHMT}+E_{SMTHFD1}) < 1$ the steady state with maximum rate is characterized by a positive rate of ATP production (FIG. 30, gray circles), indicating that the reaction cycle shown in FIG. 4b is thermodynamically feasible in the direction of ATP production. The maximum rate is achieved at a relative concentration $E_{SMTHFD1}/(E_{SHMT}+E_{SMTHFD1})$ around 0.05. Hence, the cycle achieves higher rates when the relative concentration of SMTHFD1 is much higher than that of SHMT. We also note the maximum rate calculated from the specified kinetic parameters is much higher than the median obtained from simulations applying a two-fold change in the model kinetic parameters (FIG. 30, black squares). This could indicate that the kinetic parameters in this pathway have been selected for maximum ATP production. However, since the curve for the observed kinetic parameters is still within the 90% confidence intervals (FIG. 30, black error bars) we cannot exclude this is just coincidence.

The Novel ATP Producing Pathway is Regulated by Myc

Figure 31A:
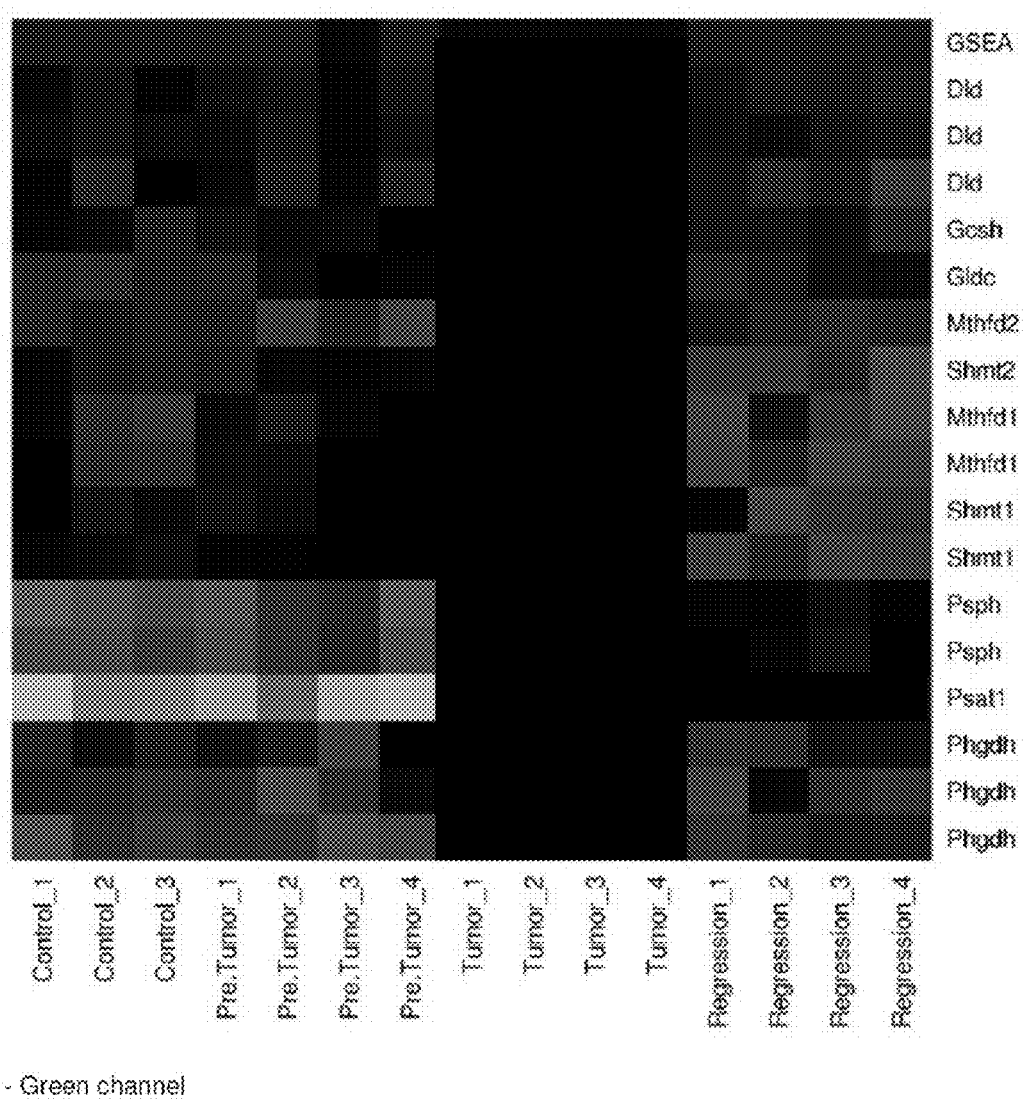
FIG. 31A shows green colors and FIG. 31B shows red colors. Gene expression profiles of genes in the novel ATP producing pathway at different stages of a doxycycline-inducible Myc driven liver cancer. Controls are samples from adjacent normal tissue, "Pre.Tumor" are tumor samples taken 4-5 weeks after Myc induction, "Tumor" are tumor samples taken 8-10 weeks after Myc induction and "Regression" are tumor samples taken 3 days after removal of Myc induction. Color intensity is proportional to change in expression relative to the average across all samples, with red color indicating increased- and green color indicating decreased gene expression. Repeated gene names represent different microarray probes for the same gene.
Figure 31B:
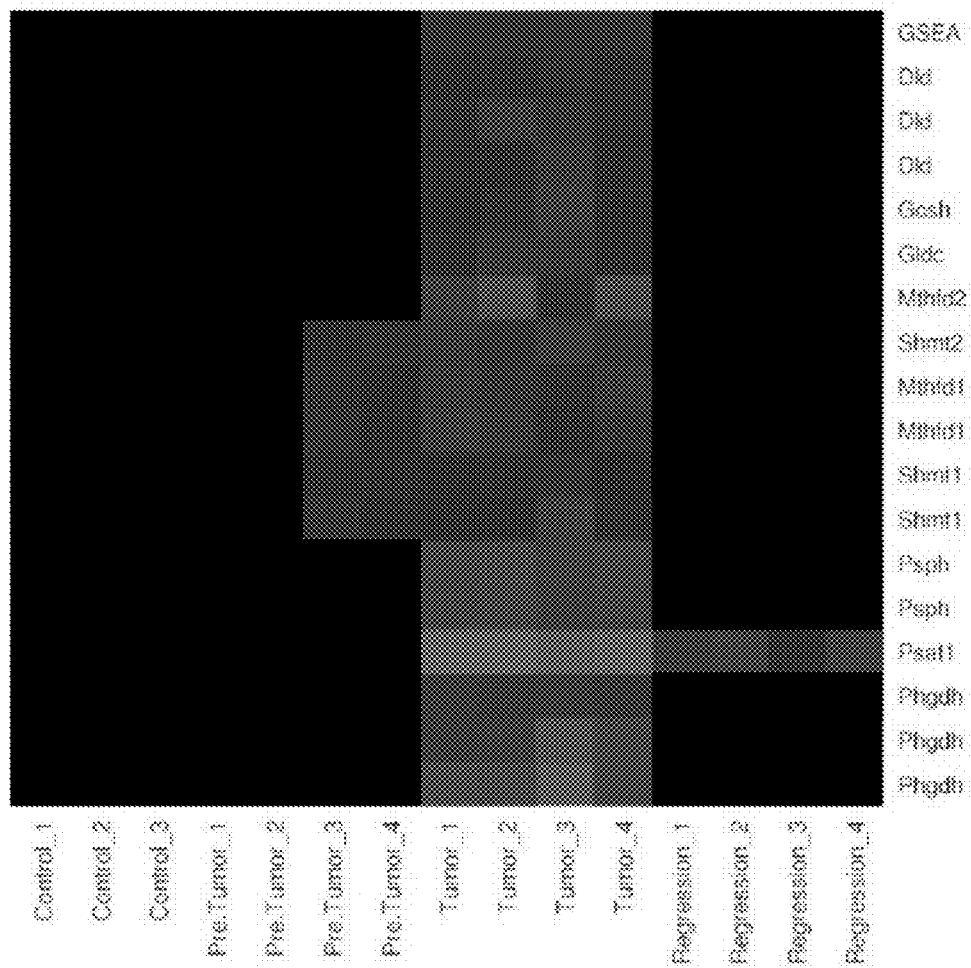

Consistent with our modeling results, the upregulation of serine and glycine biosynthesis have been observed in some tumor types before. To start to gain insight into this pathway's regulation, we next aimed to identify transcription factors regulating the novel ATP-producing pathway. We performed a search of several transcription factor signatures annotated in the Molecular Signatures Database (MSigDB, Subramanian A, et al. (2005) *Proc Natl Acad Sci USA* 102: 15545-15550). We identified Myc as a transcriptional regulator of six out of the 11 genes in the pathway: PHGDH, PSPH, SHMT1, MTHFD1, MTHFD2 and GCSH (Myc Target Gene Database, (Zeller K1, et al. (2003) *Genome Biol* 4: R69)), indicating that Myc-induced tumorigenesis may be intimately linked to the activation of this pathway. To test this hypothesis, we have analyzed data from a doxycycline-inducible murine model of Myc-driven liver cancer (Hu S, et al. (2011) *Cell Metab* 14: 131-142), reporting gene expression microarrays at different tumor stages. We find that the genes coding for the enzymes in the novel ATP-producing pathway are induced following Myc induction, and all, but two (Psat1 and Psph), return to their control levels upon Myc downregulation-induced tumor regression (FIG. 31). Thus, activation of the novel ATP-producing pathway is evident upon Myc-induced tumorigenesis.

Discussion

The existence of an alternative glycolysis pathway with net zero ATP production in rapidly proliferating cells challenges the general notion that the production of ATP is a major function of glycolysis. Instead, an alternative hypothesis suggests that the increased rate of glycolysis in rapidly proliferating cells is present to support the increased demand for precursor metabolites by anabolic processes involved in cell growth and proliferation. However, based on a partial- or full genome-scale reconstruction of human cell metabolism containing the standard glycolysis pathway, we and others have shown that the anabolic requirements can be satisfied without the need for a dramatic upregulation of glycolysis and the excretion of lactate. We have recapitulated this result here, now using the alternative glycolysis pathway with net zero ATP production, providing in silico evidence that the demand for precursor metabolites can be satisfied without upregulation of the alternative glycolysis pathway (FIG. 26).

We have shown previously that molecular crowding is a major determinant of the metabolic changes observed in highly proliferating mammalian and prokaryotic cells and in quiescent cells with high energy demands. In essence, the high density of macromolecules in the intracellular millieu results in a "competition" among mitochondria, ribosomes, metabolic enzymes and structural protein for the available intracellular space. At low metabolic rates this constraint is less pronounced, and therefore the density of the required organelles and macromolecules can increase to accommodate the increasing metabolic rate. However, just as a finite number of people can be placed in a room, only a finite amount of mitochondria can be present in the cell, resulting in an upper bound for OxPhos capacity. To satisfy its energetic needs beyond this maximum OxPhos capacity the cell need to switch to other pathways that are less costly in terms of the required cell volume fraction to allocate the corresponding enzymes, such as the classic glycolysis pathway. However, this hypothesis has been challenged by the observation that highly proliferating cells utilize an alternative glycolysis pathway with net zero ATP production. To resolve this contradiction we have improved our genome-scale metabolic model of a human cell to be able to investigate the consequences of a net zero ATP production glycolysis.

The results of our in silico analyses yield several surprising observations. The glycolysis flux is upregulated in highly proliferating cells and it is routed from 3-phosphoglycerate toward serine biosynthesis. This prediction is supported by experimental observations in both cancer cells and highly proliferating normal cells. Rapidly proliferating normal cells (including embryonic cells) and cancer cells express the M2 isoenzyme of pyruvate kinase (PKM2). The PKM2 isoform can be present either as a tetramer with high PK catalytic activity or as a dimer with low catalytic activity, in the latter case greatly reducing the rate over the last step of standard glycolysis. The upregulation of serine and glycine biosynthesis were observed both in various tumor types and mitogen-activated normal lymphocytes, and serum stimulation of Rat1A fibroblast proliferation resulted in an increased $^{13}$C-labeled glycine derived from 3-phosphoglycerate, in a myc dependent manner. Also, when found upregulated, the serine biosynthesis pathway's enzymes are individually essential both for the growth of a subset of breast cancer and melanoma cell lines and for tumorigenesis in 3-dimensional in vitro and in vivo breast cancer models. More importantly, we provided evidence that the expression of genes in this pathway correlates with Myc overexpression in a Myc-driven murine tumor model (FIG. 31). These observations support the activity of the novel ATP-producing pathway in a subset of tumors and, in particular, in Myc driven tumors.

Our in silico approach allow us to investigate the fate of the high rate of the serine biosynthesis pathway. We discover that its final endpoint is a novel pathway for ATP generation, starting from the biosynthesis of serine and involving reactions in the one carbon metabolism pathway and the serine cleavage system (FIG. 29). The reaction responsible for the net ATP generation is catalyzed by formate-tetrahydrofolate ligase (EC 6.3.4.3), working in the ATP production direction. This pathway has a yield of 2 mole of ATP per mole of 3-phosphoglycerate, or 4 moles of ATP per mole of glucose. Taken together our in silico evidence indicates that, even in the context of an alternative glycolysis pathway with net zero ATP production, glycolysis is upregulated to satisfy the high energy demand of highly proliferating cells, during conditions where molecular crowding imposes a bound or a reduction in the mitochondrial density.

The novel pathway doubles the ATP yield from 2 to 4 mole of ATP per mole of glucose (See, Table 10).

TABLE 10

A. Glycolysis:

Glucose + 2 ADP + 2 Phosphate → 2 Lactate + 2ATP + 2H$_2$O + 2H$^+$

B. Novel ATP generating Pathway

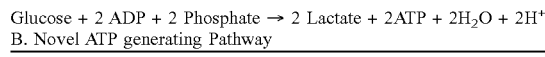
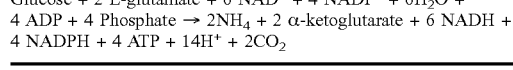

Glucose + 2 L-glutamate + 6 NAD$^+$ + 4 NADP$^+$ + 6H$_2$O + 4 ADP + 4 Phosphate → 2NH$_4$ + 2 α-ketoglutarate + 6 NADH + 4 NADPH + 4 ATP + 14H$^+$ + 2CO$_2$ The novel pathway requires, however, the balance of several co-factors and thus it is coupled to several other reactions. Yet, it remains to be elucidated what the potential evolutionary advantage of having two alternative glycolysis pathways is (i.e., the net zero ATP and the standard pathways). As we show here, the novel pathway can generate two times more ATP, thus an energetic reason is probably likely. In contrast, the novel pathway involves 17 reactions, 7 more than the standard glycolysis, potentially contributing more to molecular crowding. Taken together with OxPhos, we obtain a hierarchy in terms of ATP yield: OxPhos>>net-zero-ATP-glycolysis>standard glycolysis, and the same hierarchy in terms of molecular crowding. Therefore, these pathways provide the cell with different alternatives to cope with competing efficiency principles, ATP yield per mole of substrate or ATP yield per occupied volume fraction. Concomitantly, other factors, such as the cellular lactate and alanine production also has several potential advantages on the population level that may enhance the invasiveness of tumor cells. Also, tumor cells frequently encounter fluctuating hypoxia levels within growing tumors requiring a capability to rapidly deploy alternative metabolic strategies. In any event, our model identifies several metabolic changes that can be subject to further theoretical and experimental investigations and delineates potential enzyme targets for treatment modalities attempting to interfere with cancer metabolism.

Materials and Methods

Metabolic Network Reconstruction:

The reactions annotated in *H. sapiens* metabolic reconstruction 1 were downloaded from the BiGG database (Schellenberger J, et al. (2010) BiGG: a Biochemical Genetic and Genomic knowledgebase of large scale metabolic reconstructions. BMC Bioinformatics 11: 213).

Crowding Coefficients:

Dividing the mitochondrium specific volume (3.15 mL/g in mammalian liver and 2.6 mL/g in muscle) by the rate of ATP production per mitochondrial mass (0.1-1.0 mmol ATP/min/g) we obtain am values between 0.0026 to 0.032 min/mM. Except when specified, we use the median 0.017 min/mM. Dividing the ribosome molar volume ($v_R$=4,000 nm$^3$ 6.02 10$^{23}$/mol=2.4 L/mmol) by the rate of protein synthesis per ribosome (0.67 proteins/min) we obtain $a_R$=3.6 min/mM. The enzyme crowding coefficients were estimated as $a_i = v_E/k_i$. Multiplying the median molecular weight of human enzymes (98,750 g/mol, BRENDA by the enzymes specific volume (approximated by the specific volume of spherical proteins, 0.79 mL/g) we obtain an estimated enzymes molar volume of $v_E$=0.078 L/mmol.

Sensitivity Analysis:

The turnover numbers of human enzymes k have significant variations from 1 to 100 sec$^{-1}$ and the distribution of log$_{10}$(k) is approximately uniform in this range (BRENDA). Based on this data we sampled the log$_{10}$(keff) values from a uniform distribution in the range between log$_{10}$(1) to log$_{10}$(100). At each proliferation rate we run 100 simulations. On each simulation, for each reaction, a value of k$_{eff,i}$ is extracted from the distribution described above. With this set of k$_{eff,i}$ parameters we then solve the optimization problem (1)-(5) and obtain estimates for the reaction rates. Based on the 100 simulations we finally estimate the median and 90% confident intervals for the rate of each reaction. This data is reported in FIGS. 2-4 for selected reactions. Macromolecular composition: Proteins were divided into three pools: ribosomal-, components of metabolic enzyme complexes-, and non-metabolic proteins. Each ribosome contributes to n$_{PR}$=82 proteins/ribosome (49 in the 60S and 33 in the 40S subunits). The ribosomal protein concentration was computed as P$_R$=n$_{PR}$φ$_R$/v$_R$. Each enzyme contributes with n$_{PE}$=2.4 proteins in average, estimated as median enzyme molecular weight (98,750 g/mol, reported above) divided by the median molecular weight of a human protein (40,835 g/mol). The median molecular weight of a human protein was estimated from the median protein length (355 amino acids) and the typical amino acid composition. The enzyme related protein concentration was computed as P$_E$=Σ$_i$nP$_E$f$_i$/k$_i$. The concentration of non-metabolic proteins was estimated as 85% (10% metabolic enzymes and 5% ribosomal protein) of the reported total protein content per cell dry weight (0.018 mmol/g DW), i.e. 0.015 mmol/g DW. The lipids, DNA and RNA composition were estimated by their relative abundance in a generic mammalian cell. The abundance per cell dry weight was converted to concentrations after dividing by the typical cell specific volume 4.3 mL/g. This resulted in a concentration of non-metabolic protein of $P_0$=3.59 mM. The maximum macromolecular density of human cells in the absence of osmotic stress is around $\phi_{max}$=40%.

Maintenance Parameters:

The ATP production rate necessary for cell maintenance is 1.55 mmol ATP/g DW/h. The basal protein degradation rate was estimated as $k_D(P_0+P_E+P_R)$, where $k_D$=0.01/h.

Simulations:

The optimization problem in equations (1)-(5) was solved in Matlab, using the linear programming function linprog. All reversible reactions were represented by an irreversible reaction on each direction with their own effective turnover number $k_{eff,i}$. Most flux bounds were set to $v_{i,min}$=0 and $v_{i,max}$=∞, unless specified otherwise.

Microarray Data Analysis:

The Gene expression dataset reported in Hu S, et al. ((2011) (13)C-Pyruvate Imaging Reveals Alterations in Glycolysis that Precede c-Myc-Induced Tumor Formation and Regression. Cell Metab 14: 131-142) was downloaded from the Gene Expression Omnibus (GEO:GSE28198)). RMA normalized signals were calculated and mean-centered across samples. Model predicted relative cell volume fraction occupied by metabolic enzymes (squares), ribosomes (circles) and mitochondria (triangles), respectively. The model-predicted median and 90% confidence intervals are shown. Note, that the predicted metabolic switch is lost if the molecular crowding constraint is removed from the model (see FIG. S1). Abbreviations: metabolite import/export (Ex metabolite: glc=glucose, gln=glutamine, Ala-L=L-alanine, phe-L=L-phenylalanine, ile-L=isoleucine, lys-L=L-lysine, val-L=L-valine, lac-L=L-lactate), phosphoglycerate kinase (PGK), pyruvate kinase (PK), phosphoglycerate dehydrogenase (PGCD), L-alanine transaminase (ALATA-L), malic enzyme (ME), malate dehydrogenase (MDH), pyruvate carboxylase (PC), pyruvate dehydrogenase (PDH), citrate synthase (CS), α-ketoglutarate dehydrogenase (AKGD).

Whereas particular embodiments of the one or more inventions described herein have been described above for purposes of illustration, it will be evident to those skilled in the art that numerous variations of the details of those one or more inventions may be made without departing from the embodiments defined in the appended claims.

This application is a Continuation-In-Part of U.S. patent application Ser. No. 12/170,852, filed Jul. 10, 2008, which claims the benefit under 35 U.S.C. §119(e) to U.S. Provisional Patent Application No. 60/959,024, filed Jul. 10, 2007, this application also claims the benefit under 35 U.S.C. §119(e) to U.S. Provisional Patent Application No. 61/540,770, filed Sep. 29, 2011, each of which is incorporated herein by reference in its entirety.

We claim:

1. A computer-implemented method for achieving an optimal function of a biochemical reaction network in cells in a cell culture, comprising:
   (a) calculating in a computer one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and
   (b) initiating or maintaining the optimal cell culture parameter in the cell culture to achieve the optimal function of the biochemical reaction network in the cells.

2. The method of claim 1, in which the optimization method further comprises calculating one or more of a maximum metabolic rate, an optimal metabolite concentration and an enzyme activity by applying a computational optimization method to a kinetic model of a metabolic pathway.

3. The method of claim 1, further comprising culturing a cell under culture conditions that favor achievement of the optimal function.

4. The method of claim 1, further comprising: (c) constructing the genetic makeup of a cell to contain the biochemical reactions (d) placing the cell constructed under (c) in culture under a specified environment to obtain a population of cells; and (e) cultivating the cells as in step (d) for a sufficient period of time and under conditions to allow the cells to evolve to the desired optimal function determined under (a), wherein the biochemical reaction network comprises a comprehensive biochemical reaction network.

5. The method of claim 1, wherein the optimal function is maximizing biomass production.

6. The method of claim 1, in which the optimal property is maximal internal yield of ATP.

7. The method of claim 1, in which the solvent capacity accounts for ribosome density in the cells in the cell culture as a measure of ribosomal-, enzyme associated-, and non-metabolic proteins in the cells.

8. The method of claim 1, in which the solvent capacity accounts for mitochondria as a subcellular compartment in the cells in the cell culture.

9. The method of claim 1, in which the cells are human cells.

10. The method of claim 1, in which the cells are cancer cells.

11. The method of claim 1 that comprises a model of a pathway for ATP generation that involves reactions in the serine biosynthesis, one-carbon metabolism and the glycine cleavage system.

12. A computer readable medium having stored thereon instructions which, when executed by a processor, cause the processor to implement a process implementing a computer model for achieving an optimal function of a biochemical reaction network in cells in a cell culture, comprising:
   (a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and
   (b) initiating or maintaining the optimal cell culture parameter in the cell culture to achieve the optimal function of the biochemical reaction network in the cells.

13. The computer readable medium of claim 12, in which the optimization method further comprises calculating one or more of a maximum metabolic rate, an optimal metabolite concentration and an enzyme activity by applying a computational optimization method to a kinetic model of a metabolic pathway.

14. The computer readable medium of claim 12, wherein the optimal function is maximizing biomass production.

15. The computer readable medium of claim 12, in which the optimal property is maximal internal yield of ATP.

16. The computer readable medium of claim 12, in which the solvent capacity accounts for ribosome density in the cells in the cell culture as a measure of ribosomal-, enzyme associated-, and non-metabolic-proteins in the cells.

17. The computer readable medium of claim 12, in which the solvent capacity accounts for mitochondria as a subcellular compartment in the cells in the cell culture.

18. The computer readable medium of claim 12, in which the cells are human cells.

19. The computer readable medium of claim 12, in which the cells are cancer cells.

20. The computer readable medium of claim 12, that comprises a model of a pathway for ATP generation that involves reactions in the serine biosynthesis, one-carbon metabolism and the glycine cleavage system.

21. A device comprising and the computer-readable medium of claim 12 and a processor for executing the instructions on the computer-readable medium for achieving an optimal function of a biochemical reaction network in cells in a cell culture, comprising:
(a) calculating one or more optimal cell culture parameters in a cell culture using a flux balance analysis constrained by a solvent capacity of cells in the cell culture, wherein the optimal cell culture parameter is calculated by determining an optimal property of a biochemical reaction network comprising a list of biochemical reactions by applying a computational optimization method to one or more of the biochemical reactions of the biochemical reaction network, the optimization method comprising (i) altering one or more elements of the one or more biochemical reactions in the biochemical reaction network and re-computing the optimal property, and (ii) repeating (i) until an optimal function is reached; and
(b) initiating or maintaining the optimal cell culture parameter in the cell culture to achieve the optimal function of the biochemical reaction network in the cells.

22. The device of claim 21, further comprising one or more additional components for implementation of the instructions, including, without limitation: a pH sensor; a gas sensor; a chemical sensor; a temperature sensor; one or more culture vessels; one or more heating elements; one or more cooling elements; one or more reservoirs for storing cell culture medium, cell culturing ingredients or an analytical composition; one or more mechanisms for dispensing cell culture medium, cell culturing ingredients or an analytical composition into a cell culture or other container or for taking and/or analyzing samples from one or more cell culture vessels; one or more analytical devices; a display and one or more communication subsystems for receiving or transmitting data.

* * * * *